US011752162B2

(12) United States Patent
Cooke et al.

(10) Patent No.: US 11,752,162 B2
(45) Date of Patent: Sep. 12, 2023

(54) COMPOUNDS AND COMPOSITIONS FOR TREATING SOLID TUMORS BY INTRATUMORAL ADMINISTRATION

(71) Applicant: Novartis AG, Basel (CH)

(72) Inventors: Michael Cooke, Brookline, MA (US); Shailaja Kasibhatla, San Diego, CA (US); Andrew T. Miller, San Diego, CA (US); Tom Yao-Hsiang Wu, San Diego, CA (US)

(73) Assignee: Novartis AG, Basel (CH)

( * ) Notice: Subject to any disclaimer, the term of this patent is extended or adjusted under 35 U.S.C. 154(b) by 34 days.

(21) Appl. No.: 16/614,280

(22) PCT Filed: May 17, 2018

(86) PCT No.: PCT/IB2018/053481
§ 371 (c)(1),
(2) Date: Nov. 15, 2019

(87) PCT Pub. No.: WO2018/211453
PCT Pub. Date: Nov. 22, 2018

(65) Prior Publication Data
US 2021/0154214 A1 May 27, 2021

Related U.S. Application Data

(60) Provisional application No. 62/508,474, filed on May 19, 2017.

(51) Int. Cl.
| A61P 35/04 | (2006.01) |
| A61K 31/675 | (2006.01) |
| A61K 9/00 | (2006.01) |
| A61K 9/10 | (2006.01) |
| A61K 9/19 | (2006.01) |
| A61K 47/02 | (2006.01) |
| A61K 47/26 | (2006.01) |
| C07K 16/28 | (2006.01) |

(52) U.S. Cl.
CPC .......... *A61K 31/675* (2013.01); *A61K 9/0019* (2013.01); *A61K 9/10* (2013.01); *A61K 9/19* (2013.01); *A61K 47/02* (2013.01); *A61K 47/26* (2013.01); *A61P 35/04* (2018.01); *C07K 16/2818* (2013.01)

(58) Field of Classification Search
CPC ....................................................... A61P 35/04
See application file for complete search history.

(56) References Cited

U.S. PATENT DOCUMENTS

| 9,045,470 B2 | 6/2015 | Wu |
| 9,801,947 B2 | 10/2017 | Miller |
| 9,980,956 B2 | 5/2018 | Vasilakos |
| 10,449,251 B2 | 10/2019 | Li et al. |
| 10,583,134 B2 | 3/2020 | Vasilakos |
| 2011/0053893 A1 | 3/2011 | Wu et al. |
| 2012/0237546 A1 | 9/2012 | Singh |

FOREIGN PATENT DOCUMENTS

| WO | WO 2005/026158 | 3/2005 | |
| WO | 2010144734 A1 | 12/2010 | |
| WO | 2011049677 A1 | 4/2011 | |
| WO | WO-2011049677 A1 * | 4/2011 | .............. A61P 11/00 |
| WO | 2011027222 A2 | 10/2011 | |
| WO | 2011121305 A2 | 10/2011 | |
| WO | 2011130379 A1 | 10/2011 | |
| WO | 2012031140 A1 | 3/2012 | |
| WO | WO-2012031140 A1 * | 3/2012 | .............. C07F 9/645 |
| WO | 2012168486 A1 | 12/2012 | |
| WO | 2013030378 A1 | 3/2013 | |
| WO | 2014118305 A1 | 8/2014 | |

(Continued)

OTHER PUBLICATIONS

Dine et al., "Immune Checkpoint Inhibitors: An Innovation in Immunotherapy for the Treatment and Management of Patients with Cancer", Asia-Pacific Journal of Oncology, Jan. 1, 2017, vol. 4, Issue 2, pp. 127-135, ISSN: 2347-5625, DOI: 10.4103/apjon.apjon_4_17.

Cortez et al., "Incorporation of Phosphonate into Benzonaphthyridine Toll-like Receptor 7 Agonists for Adsorption to Aluminum Hydroxide", Journal of Medicinal Chemistry, Jun. 13, 2016, vol. 59, No. 12, pp. 5868-5878.

Collin, Matthieu, "Immune checkpoint inhibitors: a patent review (2010-2015)", Expert Opinion on Therapeutic Patents, Apr. 18, 2016, vol. 26, No. 5, pp. 555-564, ISSN: 1354-3776, DOI: 10.1080./13543776.2016.1176150.

(Continued)

*Primary Examiner* — John S Kenyon
(74) *Attorney, Agent, or Firm* — Biospark Intellectual Property Law

(57) ABSTRACT

The invention provided herein includes pharmaceutical compositions comprising a TLR7 agonist having the structure of Formula (A), aluminum-containing particles, and one or more pharmaceutically acceptable excipient. The invention further provides the use of such compositions in the treatment of solid tumors either alone or in combination with one or more additional pharmaceutical compositions.

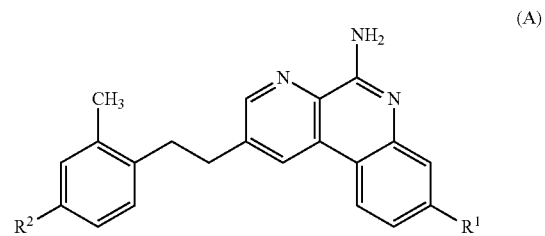

(A)

21 Claims, 11 Drawing Sheets

Specification includes a Sequence Listing.

(56) References Cited

FOREIGN PATENT DOCUMENTS

| WO | 2015144691 | A1 | 10/2015 |
| WO | 2017076873 | A1 | 5/2017 |

OTHER PUBLICATIONS

Smits et al., "The use of TLR7 and TLR8 Ligands for the Enhancement of Cancer Immunotherapy" Oncologist 13(8):859-75, Aug. 2008.

Lu, "TLR agonists for cancer immunotherapy: tipping the balance between the immune stimulatory and inhibitory effects" Frontiers in Immunology 5(83):1-4, Mar. 2014.

* cited by examiner

COMPOUNDS AND COMPOSITIONS FOR TREATING SOLID TUMORS BY INTRATUMORAL ADMINISTRATION

CROSS-REFERENCE TO RELATED APPLICATIONS

This application is a 35 U.S.C. 371 U.S. National Phase Application of International Application Serial No. PCT/IB2018/053481 filed 17 May 2018 and claims the benefit of U.S. Provisional Application No. 62/508,474, filed 19 May 2017, the disclosures of which are herein incorporated by reference in their entirety and for all purposes.

SEQUENCE LISTING

The instant application contains a Sequence Listing which has been submitted electronically in ASCII format and is hereby incorporated by reference in its entirety. Said ASCII copy, created on May 17, 2017, is named PAT057568-US-PSP_ST25.txt and is 73,200 bytes in size.

FIELD OF THE INVENTION

The invention provides methods of treating tumors by intratumoral administration of TLR7 agonistst and the use of such agonists for the treatment of tumors.

BACKGROUND OF THE INVENTION

Toll-like receptors (TLRs) are pattern recognition receptors which play an essential role in the innate immunity, by recognizing invasion of microbial pathogens and initiating intracellular signal transduction pathways to trigger expression of genes, the products of which can control innate immune responses. Specifically, Toll like receptor (TLR) agonists activate innate immune cells through the TLR-MyD88-NFkβ and IRF3/7 pathways. TLR7, TLR8, and TLR9 belong to a subfamily of TLRs based on their genomic structure, sequence similarities, and homology. TLR7, TLR8, and TLR9 are located in intracellular endolysosomal compartments and show a unique pattern of cell type-specific expression that is thought to be responsible for different pathogen response profiles.

Small molecule agonists of TLR7 and/or TLR8 have been reported and shown to activate innate immune responses by inducing selected cytokine biosynthesis, the induction of co-stimulatory molecules, and by increased antigen-presenting capacity. Such compounds include imidazoquinoline amine derivatives (U.S. Pat. No. 4,689,338), imidazopyridine amine derivative (U.S. Pat. No. 5,446,153), imidazonaphthyridine derivative (U.S. Pat. No. 6,194,425), oxazoloquinoline amine derivatives (U.S. Pat. No. 6,110,929); thiazoloquinoline amine derivatives (U.S. Pat. No. 6,110,929), selenazoloquinoline amine derivatives (U.S. Pat. No. 6,110,929), pyrazolopyridine derivatives (U.S. Pat. No. 9,145,410), and benzonaphthyridine amine derivatives (U.S. Pat. Nos. 8,466,167 and 9,045,470).

The synthetic TLR7 agonist, Imiquimod (1-(2-methylpropyl)-1H-imidazo[4,5-c]quinolin-4-amine) is FDA-approved in a cream formulation for the topical treatment of cutaneous basal cell carcinoma, actinic keratosis and genital warts, and has limited activity against cutaneous melanoma and breast tumors (J. Immunol. 2014, 193(9): 4722-4731). Systemic administration of Imiquimod, and structurally similar Resquimod, is limited by cytokine-mediated adverse effects including severe flu-like symptoms (Expert Opin. Emerging Drugs (2010), 15:544-555). Consequently, Imiquimod is used exclusively in topical applications and is not used to treat deep, non-cutaneous tumors such as melanoma or solid tumors.

An injectable lipid modified imidazoquinoline (TLR7/8 dual agonist) that forms a tissue depot with gradual, sustained release which allows for local TLR triggering activity without systemic cytokine release has been reported (J. Immunol. 2014, 193(9): 4722-4731). However, this compound was shown to be ineffective for large tumors and in addition the serum concentration of this compound 24 hours post subcutaneous administration decreased by approximately 50% (Journal for ImmunoTherapy of Cancer, 2014, 2:12). Therefore, there remains a need for intratumor administration of a TLR7 agonist with prolonged sustained release, which may benefit the treatment of large tumors.

SUMMARY OF THE INVENTION

There remains a need for new treatments and therapies for solid tumors and liquid tumors. The invention provides pharmaceutical compositions and pharmaceutical combinations comprising a TLR7 agonist and a suspension of particles comprising aluminum. The invention also provides pharmaceutical compositions and pharmaceutical combinations comprising a TLR7 agonist and a suspension of particles comprising aluminum for the use in treating solid tumors or liquid tumors. The invention further provides methods for treating a solid tumor or liquid tumor by administrating to a subject in need thereof such pharmaceutical compositions or pharmaceutical combinations, and the use such pharmaceutical compositions or pharmaceutical combinations in the treatment of a solid tumor or a liquid tumor.

The present invention provides the following aspects, advantageous features and specific embodiments, respectively alone or in combination, as listed in the following items:

The present invention provides the following aspects, advantageous features and specific embodiments, respectively alone or in combination, as listed in the following items:

Item 1: A pharmaceutical composition comprising a compound having the structure of Formula (A), or a pharmaceutically acceptable salt thereof, aluminum-containing particles, a buffering agent, and one or more pharmaceutically acceptable excipients:

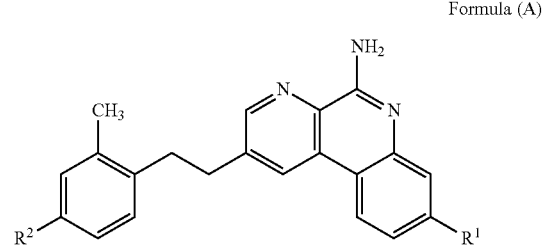

Formula (A)

wherein:
R$^1$ is -L$_1$R$^4$, -L$_1$R$^5$, —OL$_1$R$^4$, —OL$_1$R$^5$, CH$_3$, —C(=O)P(O)(OH)$_2$ or —C(=O)CF$_2$P(O)(OH)$_2$;
R$^2$ is -L$_2$R$^4$, -L$_2$R$^6$, -L$_2$L$_3$L$_2$R$^6$, -L$_2$L$_3$R$^4$, -L$_2$L$_3$L$_2$R$^4$, —OL$_2$R$^4$, —OL$_2$R$^6$, —OL$_2$L$_3$R$^6$, —OL$_2$L$_3$L$_2$R$^6$, —OL$_2$L$_{3R}$$^4$, —OL$_2$L$_3$L$_2$R$^4$ or —OCH$_3$;
each R$^3$ is independently selected from H and fluoro;

$R^4$ is —P(O)(OH)$_2$,
$R^5$ is —CF$_2$P(O)(OH)$_2$ or —C(O)OH;
$R^6$ is —CF$_2$P(O)(OH)$_2$ or —C(O)OH;
L$_1$ is C$_1$-C$_6$alkylene, C$_2$-C$_6$alkenylene or —((CR$^4$R$^4$)$_p$O)$_q$(CH$_2$)$_p$—, wherein the C$_1$-C$_6$alkylene and C$_2$-C$_6$alkenylene of L$_1$ are substituted with 0 to 4 fluoro groups;
each L$_2$ is independently selected from C$_1$-C$_6$alkylene and —((CR$^3$R$^3$)$_p$O)$_q$(CH$_2$)$_p$—, wherein the C$_1$-C$_6$alkylene of L$_2$ is substituted with 0 to 4 fluoro groups; L$_3$ is arylene or a 5-6 membered heteroarylene;
each p is independently selected from 1, 2, 3, 4, 5 and 6, and q is 1, 2, 3 or 4.

Item 2. The pharmaceutical composition of item 1, wherein the composition comprises a compound having the structure of Formula (A), or a pharmaceutically acceptable salt thereof, a buffering agent, a pharmaceutically acceptable excipient selected from mannitol and sucrose, wherein the composition has a pH in the range of 6.5 to 9.0, and the aluminum-containing particles are a suspension of aluminum-containing particles.

Item 3. The pharmaceutical composition of item 1 or item 2, wherein the composition comprises a compound having the structure of Formula (A), or a pharmaceutically acceptable salt thereof, a buffering agent, mannitol, wherein the composition has a pH in the range of 6.5 to 9.0, and the aluminum-containing particles are a suspension of aluminum-containing particles.

Item 4. The pharmaceutical composition of any one of items 1 to 3, wherein the composition has a pH in the range of 7.0 to 8.0.

Item 5. The pharmaceutical composition of any one of items 1 to 4, wherein the composition has a pH in the range of 7.2 to 7.8.

Item 6. The pharmaceutical composition of any one of items 1 to 5, wherein the aluminum-containing particles are aluminum hydroxide particles, aluminum oxyhydroxide particles or aluminum hydroxyphosphate particles and the suspension of aluminum-containing particles is a suspension of aluminum hydroxide particles, aluminum oxyhydroxide particles or aluminum hydroxyphosphate particles.

Item 7. The pharmaceutical composition of any one of items 1 to 6, wherein the aluminum-containing particles are aluminum hydroxide particles, and the suspension of aluminum-containing particles is a suspension of aluminum hydroxide particles.

Item 8. The pharmaceutical composition of any one of items 1 to 7, wherein the composition comprises a compound having the structure of Formula (A), or a pharmaceutically acceptable salt thereof, a suspension of aluminum hydroxide particles, Tris buffer and mannitol.

Item 9. The pharmaceutical composition of any one of items 1 to 8, wherein the composition comprises 0.5 to 2 mg/mL of a compound having the structure of Formula (A), or a pharmaceutically acceptable salt thereof, 5-100 mM Tris buffer, 5-10% (w/v) mannitol, and a suspension of aluminum hydroxide particles having an aluminum content of 1 to 4 mg/mL.

Item 10. The pharmaceutical composition of any one of items 1 to 9, wherein the composition comprises 0.5 to 2 mg/mL of a compound having the structure of Formula (A), or a pharmaceutically acceptable salt thereof, 5-50 mM Tris buffer, 5-10% (w/v) mannitol, and a suspension of aluminum hydroxide particles having an aluminum content of 1 to 4 mg/mL.

Item 11. The pharmaceutical composition of any one of items 1 to 10, wherein the composition comprises 0.5 to 2 mg/mL of a compound having the structure of Formula (A), or a pharmaceutically acceptable salt thereof, 5-20 mM Tris buffer, 5-10% (w/v) mannitol, and a suspension of aluminum hydroxide particles having an aluminum content of 1 to 4 mg/mL.

Item 12. The pharmaceutical composition of any one of items 1 to 11, wherein the composition comprises 1 mg/mL of a compound having the structure of Formula (A), or a pharmaceutically acceptable salt thereof, 5-20 mM Tris buffer, 5-10% (w/v) mannitol, and a suspension of aluminum hydroxide particles having an aluminum content of 2 mg/mL, and wherein the composition has a pH in the range of 7.0 to 8.0.

Item 13. The pharmaceutical composition of any one of items 1 to 12, wherein the composition comprises 1 mg/mL of a compound having the structure of Formula (A), or a pharmaceutically acceptable salt thereof, 16 mM Tris buffer, 7.5% (w/v) mannitol, and a suspension of aluminum hydroxide particles having an aluminum content of 2 mg/mL, and wherein the composition has a pH in the range of 7.0 to 8.0.

Item 14. The pharmaceutical composition of any one of items 1 to 12, wherein the composition comprises 1 mg/mL of a compound having the structure of Formula (A), or a pharmaceutically acceptable salt thereof, 5 mM Tris buffer, 8.25% (w/v) mannitol, and a suspension of aluminum hydroxide particles having an aluminum content of 2 mg/mL, and wherein the composition has a pH of in the range of 7.0 to 8.0.

Item 15. The pharmaceutical composition of any one of items 1 to 12, wherein the composition comprises 1 mg/mL of a compound having the structure of Formula (A), or a pharmaceutically acceptable salt thereof, 5 mM Tris buffer, 5.5% (w/v) mannitol, and a suspension of aluminum hydroxide particles having an aluminum content of 2 mg/mL, and wherein the composition has a pH of in the range of 7.0 to 8.0.

Item 16. The pharmaceutical composition of any one of items 1 to 7, wherein the composition comprises a compound having the structure of Formula (A), or a pharmaceutically acceptable salt thereof, a suspension of aluminum hydroxide particles, Tris buffer and sucrose.

Item 17. The pharmaceutical composition of any one of items 1 to 7 or 16, wherein the composition comprises 0.5 to 2 mg/mL of a compound having the structure of Formula (A), or a pharmaceutically acceptable salt thereof, 5-100 mM Tris buffer, 5-10% (w/v) sucrose, and a suspension of aluminum hydroxide particles having an aluminum content of 1 to 4 mg/mL.

Item 18. The pharmaceutical composition of any one of items 1 to 7 or 16 to 17, wherein the composition comprises 0.5 to 2 mg/mL of a compound having the structure of Formula (A), or a pharmaceutically acceptable salt thereof, 5-50 mM Tris buffer, 5-10% (w/v) sucrose, and a suspension of aluminum hydroxide particles having an aluminum content of 1 to 4 mg/mL.

Item 19. The pharmaceutical composition of any one of items 1 to 7 or 15 to 17, wherein the composition comprises 0.5 to 2 mg/mL of a compound having the structure of Formula (A), or a pharmaceutically acceptable salt thereof, 5-20 mM Tris buffer, 5-10% (w/v) sucrose, and a suspension of aluminum hydroxide particles having an aluminum content of 1 to 4 mg/mL.

Item 20. The pharmaceutical composition of any one of items 1 to 7 or 16 to 20, wherein the composition comprises 1 mg/mL of a compound having the structure of Formula (A), or a pharmaceutically acceptable salt thereof, 5-20 mM Tris buffer, 5-10% (w/v) sucrose, and a suspension of aluminum hydroxide particles having an aluminum content of 2 mg/mL, and wherein the composition has a pH in the range of 7.0 to 8.0.

Item 21. The pharmaceutical composition of any one of items 1 to 7 or 16 to 20, wherein the composition comprises 1 mg/mL of a compound having the structure of Formula (A), or a pharmaceutically acceptable salt thereof, 16 mM Tris buffer, 7.5% (w/v) sucrose, and a suspension of aluminum hydroxide particles having an aluminum content of 2 mg/mL, and wherein the composition has a pH in the range of 7.0 to 8.0.

Item 22. The pharmaceutical composition of any one of items 1 to 7 or 16 to 21, wherein the composition comprises 1 mg/mL of a compound having the structure of Formula (A), or a pharmaceutically acceptable salt thereof, 5 mM Tris buffer, 8.25% (w/v) sucrose, and a suspension of aluminum hydroxide particles having an aluminum content of 2 mg/mL, and wherein the composition has a pH in the range of 7.0 to 8.0.

Item 23. The pharmaceutical composition of any one of items 1 to 22, wherein the (w/w) ratio of the weight of compound of Formula A to the weight of aluminum in the suspension of aluminum-containing particles is in the range from 1:1 to 1:20.

Item 24. The pharmaceutical composition of any one of items 1 to 23, wherein the (w/w) ratio of the weight of compound of Formula A to the weight of aluminum in the suspension of aluminum-containing particles is in the range from 1:1.5 to 1:2.5.

Item 25. The pharmaceutical composition of any one of items 1 to 22, wherein the (w/w) ratio of the weight of compound of Formula A to the weight of aluminum in the suspension of aluminum-containing particles is 1:1.5.

Item 26. The pharmaceutical composition of any one of items 1 to 22, wherein the (w/w) ratio of the weight of compound of Formula A to the weight of aluminum in the suspension of aluminum-containing particles is 1:2.

Item 27. The pharmaceutical composition of any one of items 1 to 15 or 23, wherein the composition comprises a compound having the structure of Formula (A), or a pharmaceutically acceptable salt thereof, 5-20 mM Tris buffer, 5-10% (w/v) mannitol, and a suspension of aluminum hydroxide particles, and wherein the (w/w) ratio of the weight of compound of Formula A to the weight of aluminum in the suspension of particles is 1:20.

Item 28. The pharmaceutical composition of any one of items 1 to 15 or 23, wherein the composition comprises a compound having the structure of Formula (A), or a pharmaceutically acceptable salt thereof, 5-20 mM Tris buffer, 5-10% (w/v) mannitol, and a suspension of aluminum hydroxide particles, and wherein the (w/w) ratio of the weight of compound of Formula A to the weight of aluminum in the suspension of particles is 1:2 and the composition has a pH in the range of 7.0 to 8.0.

Item 29. The pharmaceutical composition of any one of items 1 to 15 or 23, wherein the composition comprises a compound having the structure of Formula (A), or a pharmaceutically acceptable salt thereof, 16 mM Tris buffer, 7.5 (w/v) mannitol, and a suspension of aluminum hydroxide particles, and wherein the (w/w) ratio of the weight of compound of Formula A to the weight of aluminum in the suspension of particles is 1:2 and the composition has a pH of in the range of 7.0 to 8.0.

Item 30. The pharmaceutical composition of any one of items 1 to 15 or 23, wherein the composition comprises a compound having the structure of Formula (A), or a pharmaceutically acceptable salt thereof, 5 mM Tris buffer, 8.25 (w/v) mannitol, and a suspension of aluminum hydroxide particles, and wherein the (w/w) ratio of the weight of compound of Formula A to the weight of aluminum in the suspension of particles is 1:2 and the composition has a pH of in the range of 7.0 to 8.0.

Item 31. The pharmaceutical composition of any one of items 1 to 15 or 23, wherein the composition comprises a compound having the structure of Formula (A), or a pharmaceutically acceptable salt thereof, 5 mM Tris buffer, 5.5 (w/v) mannitol, and a suspension of aluminum hydroxide particles, and wherein the (w/w) ratio of the weight of compound of Formula A to the weight of aluminum in the suspension of particles is 1:2 and the composition has a pH of in the range of 7.0 to 8.0.

Item 32. The pharmaceutical composition of any one of items 16 to 23, wherein the composition comprises a compound having the structure of Formula (A), or a pharmaceutically acceptable salt thereof, 5-20 mM Tris buffer, 5-10% (w/v) sucrose, and a suspension of aluminum hydroxide particles, and wherein the (w/w) ratio of the compound of Formula A to the aluminum in the suspension of particles is 1:20.

Item 33. The pharmaceutical composition of any one of items 16 to 23, wherein the composition comprises a compound having the structure of Formula (A), or a pharmaceutically acceptable salt thereof, 5-20 mM Tris buffer, 5-10% (w/v) sucrose, and a suspension of aluminum hydroxide particles, and wherein the (w/w) ratio of the compound of Formula A to the aluminum in the suspension of particles is 1:2 and the composition has a pH in the range of 7.0 to 8.0.

Item 34. The pharmaceutical composition of any one of items 16 to 23, wherein the composition comprises a compound having the structure of Formula (A), or a pharmaceutically acceptable salt thereof, 16 mM Tris buffer, 7.5 (w/v) sucrose, and a suspension of aluminum hydroxide particles, and wherein the (w/w) ratio of the compound of Formula A to the aluminum in the suspension of particles is 1:2 and the composition has a pH in the range of 7.0 to 8.0.

Item 35. The pharmaceutical composition of any one of items 16 to 23, wherein the composition comprises a compound having the structure of Formula (A), or a pharmaceutically acceptable salt thereof, 5 mM Tris buffer, 8.25 (w/v) sucrose, and a suspension of aluminum hydroxide particles, and wherein the (w/w) ratio of the compound of Formula A to the aluminum in the suspension of particles is 1:2 and the composition has a pH in the range of 7.0 to 8.0.

Item 36. The pharmaceutical composition of any one of items 1 to 34, wherein the compound having the structure of Formula (A) is:

3-(5-amino-2-(4-(2-(3,3-difluoro-3-phosphonopropoxy)ethoxy)-2-methylphenethyl)benzo[f][1,7]naphthyridin-8-yl)propanoic acid;

3-(5-amino-2-(2-methyl-4-(2-(2-(2-phosphonoethoxy)ethoxy)ethoxy)phenethyl)benzo[f][1,7]naphthyridin-8-yl)propanoic acid;

3-(5-amino-2-(4-(4,4-difluoro-4-phosphonobutoxy)-2-methylphenethyl)benzo[f][1,7]naphthyridin-8-yl)propanoic acid;

3-(5-amino-2-(2-methyl-4-(3-phosphonopropoxy)phenethyl)benzo[f][1,7]naphthyridin-8-yl)propanoic acid;

3-(5-amino-2-(4-(2-(2-(3,3-difluoro-3-phosphonopropoxy)
    ethoxy)ethoxy)-2-methylphenethyl)benzo[f][1,7]naph-
    thyridin-8-yl)propanoic acid;
3-(5-amino-2-(2-methyl-4-(2-(2-(2-phosphonoethoxy)
    ethoxy)ethoxy)phenethyl)benzo[f][1,7]naphthyri-
    din-8-yl)propanoic acid, and
3-(5-amino-2-(2-methyl-4-(2-(2-phosphonoethoxy)ethoxy)
    phenethyl)benzo[f][1,7]naphthyridin-8-yl)propanoic
    acid.
(3-(4-(2-(5-amino-8-methylbenzo[f][1,7]naphthyridin-2-yl)
    ethyl)-3-methylphenoxy)propyl)phosphonic acid;
4-(2-(5-amino-8-methylbenzo[f][1,7]naphthyridin-2-yl)
    ethyl)-3-methylphenyl dihydrogen phosphate;
((4-(2-(5-amino-8-methylbenzo[f][1,7]naphthyridin-2-yl)
    ethyl)-3-methylphenoxy)methyl)phosphonic acid;
5-(4-(2-(5-amino-8-methylbenzo[f][1,7]naphthyridin-2-yl)
    ethyl)-3-methylphenoxy)-1,1-difluoropentylphosphonic
    acid;
(4-(4-(2-(5-amino-8-methylbenzo[f][1,7]naphthyridin-2-yl)
    ethyl)-3-methylphenoxy)-1,1-difluorobutyl)phosphonic
    acid;
(3-(2-(2-(4-(2-(5-amino-8-methylbenzo[f][1,7]naphthyri-
    din-2-yl)ethyl)-3-methylphenoxy)ethoxy)ethoxy)-1,1-di-
    fluoropropyl)phosphonic acid;
3-(2-(4-(2-(5-amino-8-methylbenzo[f][1,7]naphthyridin-2-
    yl)ethyl)-3-methylphenoxy)ethoxy)-1,1-difluoropropy-
    lphosphonic acid;
2-(4-((4-(2-(5-amino-8-methylbenzo[f][1,7]naphthyridin-2-
    yl)ethyl)-3-methylphenoxy)methyl)phenyl)-1,1-difluoro-
    ethylphosphonic acid;
(3-((4-(2-(5-amino-8-methylbenzo[f][1,7]naphthyridin-2-
    yl)ethyl)-3-methylphenoxy)methyl)phenyl)phosphonic
    acid;
(2-(4-(2-(5-amino-8-methylbenzo[f][1,7]naphthyridin-2-yl)
    ethyl)-3-methylphenoxy)ethyl)phosphonic acid;
(6-(4-(2-(5-amino-8-methylbenzo[f][1,7]naphthyridin-2-yl)
    ethyl)-3-methylphenoxy)hexyl)phosphonic acid;
(6-(4-(2-(5-amino-8-methylbenzo[f][1,7]naphthyridin-2-yl)
    ethyl)-3-methylphenoxy)-1,1-difluorohexyl)phosphonic
    acid;
(4-((4-(2-(5-amino-8-methylbenzo[f][1,7]naphthyridin-2-
    yl)ethyl)-3-methylphenoxy)methyl)benzyl)phosphonic
    acid;
(2-(2-(2-(4-(2-(5-amino-8-methylbenzo[f][1,7]naphthyri-
    din-2-yl)ethyl)-3-methylphenoxy)ethoxy)ethoxy)ethyl)
    phosphonic acid;
(5-(4-(2-(5-amino-8-methylbenzo[f][1,7]naphthyridin-2-yl)
    ethyl)-3-methylphenoxy)pentyl)phosphonic acid, and
(4-(4-(2-(5-amino-8-methylbenzo[f][1,7]naphthyridin-2-yl)
    ethyl)-3-methylphenoxy)butyl)phosphonic acid.
2-(5-amino-2-(4-methoxy-2-methylphenethyl)benzo[f][1,7]
    naphthyridin-8-yl)-1,1-difluoro-2-oxoethylphosphonic
    acid;
(E)-(2-(5-amino-2-(4-methoxy-2-methylphenethyl)benzo[f]
    [1,7]naphthyridin-8-yl)vinyl)phosphonic acid;
2-(5-amino-2-(4-methoxy-2-methylphenethyl)benzo[f][1,7]
    naphthyridin-8-yl)ethylphosphonic acid;
(E)-(2-(5-amino-2-(4-methoxy-2-methylphenethyl)benzo[f]
    [1,7]naphthyridin-8-yl)-1-fluorovinyl)phosphonic acid,
    or
(5-amino-2-(4-methoxy-2-methylphenethyl)benzo[f][1,7]
    naphthyridine-8-carbonyl)phosphonic acid.
Item 37. The pharmaceutical composition of any one of
    items 1 to 36, wherein the compound is 3-(5-amino-2-(4-
    (2-(2-(3,3-difluoro-3-phosphonopropoxy)ethoxy)-2-meth-
    ylphenethyl)benzo[f][1,7]naphthyridin-8-yl)propanoic
    acid.

Item 38. The pharmaceutical composition of any one of
    items 1 to 36, wherein the compound is 3-(5-amino-2-(2-
    methyl-4-(2-(2-(2-phosphonoethoxy)ethoxy)ethoxy)
    phenethyl)benzo[f][1,7]naphthyridin-8-yl)propanoic
    acid.
Item 39. The pharmaceutical composition of any one of
    items 1 to 8, wherein the composition comprises 3-(5-
    amino-2-(4-(2-(3,3-difluoro-3-phosphonopropoxy)
    ethoxy)-2-methylphenethyl)benzo[f][1,7]naphthyridin-8-
    yl)propanoic acid, or a pharmaceutically acceptable salt
    thereof, a suspension of aluminum hydroxide particles,
    Tris buffer and mannitol.
Item 40. The pharmaceutical composition of any one of
    items 1 to 8 or 39, wherein the composition comprises 0.5
    to 2 mg/mL of 3-(5-amino-2-(4-(2-(3,3-difluoro-3-
    phosphonopropoxy)ethoxy)-2-methylphenethyl)benzo[f]
    [1,7]naphthyridin-8-yl)propanoic acid, or a pharmaceuti-
    cally acceptable salt thereof, 5-100 mM Tris buffer,
    5-10% (w/v) mannitol, and a suspension of aluminum
    hydroxide particles having an aluminum content of 1 to 4
    mg/mL.
Item 41. The pharmaceutical composition of any one of
    items 1 to 8 or 39 to 40, wherein the composition
    comprises 0.5 to 2 mg/mL of 3-(5-amino-2-(4-(2-(3,3-
    difluoro-3-phosphonopropoxy)ethoxy)-2-methylphen-
    ethyl)benzo[f][1,7]naphthyridin-8-yl)propanoic acid, or a
    pharmaceutically acceptable salt thereof, 5-50 mM Tris
    buffer, 5-10% (w/v) mannitol, and a suspension of alu-
    minum hydroxide particles having an aluminum content
    of 1 to 4 mg/mL.
Item 42. The pharmaceutical composition of any one of
    items 1 to 8 or 39 to 41, wherein the composition
    comprises 0.5 to 2 mg/mL of 3-(5-amino-2-(4-(2-(3,3-
    difluoro-3-phosphonopropoxy)ethoxy)-2-methylphen-
    ethyl)benzo[f][1,7]naphthyridin-8-yl)propanoic acid, or a
    pharmaceutically acceptable salt thereof, 5-20 mM Tris
    buffer, 5-10% (w/v) mannitol, and a suspension of alu-
    minum hydroxide particles having an aluminum content
    of 1 to 4 mg/mL.
Item 43. The pharmaceutical composition of any one of
    items 1 to 8 or 39 to 42, wherein the composition
    comprises 1 mg/mL of 3-(5-amino-2-(4-(2-(3,3-difluoro-
    3-phosphonopropoxy)ethoxy)-2-methylphenethyl)benzo
    [f][1,7]naphthyridin-8-yl)propanoic acid, or a pharma-
    ceutically acceptable salt thereof, 5-20 mM Tris buffer,
    5-10% (w/v) mannitol, and a suspension of aluminum
    hydroxide particles having an aluminum content of 2
    mg/mL, and wherein the composition has a pH in the
    range of 7.0 to 8.0.
Item 44. The pharmaceutical composition of any one of
    items 1 to 8 or 39 to 43, wherein the composition
    comprises 1 mg/mL of 3-(5-amino-2-(4-(2-(3,3-difluoro-
    3-phosphonopropoxy)ethoxy)-2-methylphenethyl)benzo
    [f][1,7]naphthyridin-8-yl)propanoic acid, or a pharma-
    ceutically acceptable salt thereof, 16 mM Tris buffer,
    7.5% (w/v) mannitol, and a suspension of aluminum
    hydroxide particles having an aluminum content of 2
    mg/mL, and wherein the composition has a pH in the
    range of 7.0 to 8.0.
Item 45. The pharmaceutical composition of any one of
    items 1 to 8 or 39 to 43, wherein the composition
    comprises 1 mg/mL of 3-(5-amino-2-(4-(2-(3,3-difluoro-
    3-phosphonopropoxy)ethoxy)-2-methylphenethyl)benzo
    [f][1,7]naphthyridin-8-yl)propanoic acid, or a pharma-
    ceutically acceptable salt thereof, 5 mM Tris buffer,
    8.25% (w/v) mannitol, and a suspension of aluminum hydroxide particles having an aluminum content of 2 mg/mL, and wherein the composition has a pH in the range of 7.0 to 8.0.

Item 46. The pharmaceutical composition of any one of items 1 to 8 or 39 to 43, wherein the composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 5.5% (w/v) mannitol, and a suspension of aluminum hydroxide particles having an aluminum content of 2 mg/mL, and wherein the composition has a pH in the range of 7.0 to 8.0.

Item 47. The pharmaceutical composition of any one of items 1 to 7, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles, Tris buffer and sucrose.

Item 48. The pharmaceutical composition of any one of items 1 to 7 or 47, wherein the composition comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) sucrose, and a suspension of aluminum hydroxide particles having an aluminum content of 1 to 4 mg/mL.

Item 49. The pharmaceutical composition of any one of items 1 to 7 or 47 to 48, wherein the composition comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-50 mM Tris buffer, 5-10% (w/v) sucrose, and a suspension of aluminum hydroxide particles having an aluminum content of 1 to 4 mg/mL.

Item 50. The pharmaceutical composition of any one of items 1 to 7 or 47 to 49, wherein the composition comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) sucrose, and a suspension of aluminum hydroxide particles having an aluminum content of 1 to 4 mg/mL.

Item 51. The pharmaceutical composition of any one of items 1 to 7 or 47 to 50, wherein the composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) sucrose, and a suspension of aluminum hydroxide particles having an aluminum content of 2 mg/mL, and wherein the composition has a pH in the range of 7.0 to 8.0.

Item 52. The pharmaceutical composition of any one of items 1 to 7 or 47 to 51, wherein the composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) sucrose, and a suspension of aluminum hydroxide particles having an aluminum content of 2 mg/mL, and wherein the composition has a pH in the range of 7.0 to 8.0.

Item 53. The pharmaceutical composition of any one of items 1 to 7 or 47 to 52, wherein the composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) sucrose, and a suspension of aluminum hydroxide particles having an aluminum content of 2 mg/mL, and wherein the composition has a pH in the range of 7.0 to 8.0.

Item 54. The pharmaceutical composition of any one of claims 1 to 8 or 39 to 53, wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, to the weight of aluminum in the suspension of aluminum-containing particles is in the range from 1:1 to 1:20.

Item 55. The pharmaceutical composition of any one of claims 1 to 8 or 39 to 53, wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, to the weight of aluminum in the suspension of aluminum-containing particles is in the range from 1:1.5 to 1:2.5.

Item 56. The pharmaceutical composition of any one of claims 1 to 8 or 39 to 53, wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, to the weight of aluminum in the suspension of aluminum-containing particles is 1:1.5.

Item 57. The pharmaceutical composition of any one of claims 1 to 8 or 39 to 53, wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, to the weight of aluminum in the suspension of aluminum-containing particles is 1:2.

Item 58. The pharmaceutical composition of any one of items 1 to 8 or 39 to 45, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) mannitol, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:20.

Item 59. The pharmaceutical composition of any one of items 1 to 8 or 39 to 45, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) mannitol, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:2 and the composition has a pH in the range of 7.0 to 8.0.

Item 60. The pharmaceutical composition of any one of items 1 to 8 or 39 to 45, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5 (w/v) mannitol, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:2 and the composition has a pH in the range of 7.0 to 8.0.

Item 61. The pharmaceutical composition of any one of items 1 to 8 or 39 to 45, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25 (w/v) mannitol, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:2 and the composition has a pH in the range of 7.0 to 8.0.

Item 62. The pharmaceutical composition of any one of items 1 to 8 or 39 to 45, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 5.5 (w/v) mannitol, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:2 and the composition has a pH in the range of 7.0 to 8.0.

Item 63. The pharmaceutical composition of any one of items 1 to 7 or 47 to 53, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) sucrose, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:20.

Item 64. The pharmaceutical composition of any one of items 1 to 7 or 47 to 53, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) sucrose, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:2 and the composition has a pH in the range of 7.0 to 8.0.

Item 65. The pharmaceutical composition of any one of items 1 to 7 or 47 to 53, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5 (w/v) sucrose, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:2 and the composition has a pH in the range of 7.0 to 8.0.

Item 66. The pharmaceutical composition of any one of items 1 to 7 or 47 to 53, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25 (w/v) sucrose, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:2 and the composition has a pH in the range of 7.0 to 8.0.

Item 67. The pharmaceutical composition of any one of items 1 to 66 further comprising an additional therapeutic agent.

Item 68. The pharmaceutical composition of item 67, wherein the additional therapeutic agents is a checkpoint inhibitor, a TLR9 agonist, a TLR8 agonist, a TLR7 agonist, a STING agonist or a chemotherapeutic agent.

Item 69. A pharmaceutical combination comprising a first pharmaceutical composition of any one of items 1 to 66, and a second pharmaceutical composition comprising a checkpoint inhibitor, a TLR9 agonist, a TLR8 agonist, a TLR7 agonist, a STING agonist or a chemotherapeutic agent.

Item 70. A pharmaceutical combination comprising a first pharmaceutical composition of any one of items 1 to 66, a second pharmaceutical composition comprising a checkpoint inhibitor, a TLR9 agonist, a TLR8 agonist, a TLR7 agonist, a STING agonist or a chemotherapeutic agent and a third pharmaceutical composition comprising a checkpoint inhibitor, a TLR9 agonist, a TLR8 agonist, a TLR7 agonist, a STING agonist or a chemotherapeutic agent Item 71. A pharmaceutical combination comprising:
a) a first pharmaceutical composition of any one of items 1 to 66, and
b) a second pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Item 72. A pharmaceutical combination comprising:
a) a first pharmaceutical composition of any one of items 1 to 66, and
b) a second pharmaceutical composition comprising a PD-1 receptor inhibitor.

Item 73. A pharmaceutical combination comprising:
a) a first pharmaceutical composition of any one of items 1 to 66, and
b) a second pharmaceutical composition comprising a PD-L1 inhibitor.

Item 74. A pharmaceutical combination comprising:
a) a first pharmaceutical composition of any one of items 1 to 66, and
b) a second pharmaceutical composition comprising an anti-PD-L1 antibody.

Item 75. A pharmaceutical combination comprising:
  a) a first pharmaceutical composition of any one of items 1 to 66, and
  b) a second pharmaceutical composition comprising an anti-PD-1 antibody.

Item 76. A pharmaceutical combination comprising:
  a) a first pharmaceutical composition of any one of items 1 to 66,
  b) a second pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, wherein the checkpoint of the third composition is different than the checkpoint inhibitor in the second composition.

Item 77. A pharmaceutical combination comprising:
  a) a first pharmaceutical composition of any one of items 1 to 66,
  b) a second pharmaceutical composition comprising a PD-L1 inhibitor, and
  c) a third pharmaceutical composition comprising a CTLA-4 receptor inhibitor.

Item 78. A pharmaceutical combination comprising:
  a) a first pharmaceutical composition of any one of items 1 to 66,
  b) a second pharmaceutical composition comprising a PD-1 inhibitor, and
  c) a third pharmaceutical composition comprising a CTLA-4 receptor inhibitor.

Item 79. A pharmaceutical combination comprising:
  a) a first pharmaceutical composition of any one of items 1 to 66,
  b) a second pharmaceutical composition comprising an anti-PD-L1 antibody, and c) a third pharmaceutical composition comprising an anti-CTLA-4 antibody.

Item 80. A pharmaceutical combination comprising:
  a) a first pharmaceutical composition of any one of items 1 to 66,
  b) a second pharmaceutical composition comprising an anti-PD-1 antibody, and
  c) a third pharmaceutical composition comprising an anti-CTLA-4 antibody.

Item 81. A method for treating a solid tumor by administering to a subject in need thereof a pharmaceutical composition of any one of items 1 to 68, or a pharmaceutical combination of any one of items 69 to 80.

Item 82. A method for treating a solid tumor by administering to a subject in need thereof a pharmaceutical combination comprising:
  a) a first pharmaceutical composition of any one of items 1 to 66,
  b) a second pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor,
  wherein the checkpoint of the third composition is different than the checkpoint inhibitor in the second composition, and
  wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion.

Item 83. A method for treating a solid tumor by administering to a subject in need thereof a pharmaceutical combination comprising:
  a) a first pharmaceutical composition of any one of items 1 to 66, and a
  b) a second pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor,
  wherein the first pharmaceutical composition is administered intratumorally, and the second pharmaceutical composition is administered intratumorally, intramuscularly, intradermally, subcutaneously, intravenously, by intraperitoneal injection, by lavage or by infusion.

Item 84. The method of any one of items 81 to 33, wherein the solid tumor is head and neck squamous cell carcinoma (HNSCC), melanoma or a visceral tumor.

Item 85. Use of a pharmaceutical composition of any one of items 1 to 68, or use a pharmaceutical combination of any one of items 69 to 80, in treating a solid tumor.

Item 86. The use of item 85, wherein the solid tumor is head and neck squamous cell carcinoma (HNSCC), melanoma or a visceral tumor.

Item 87. A pharmaceutical composition of any one of items 1 to 68, or a pharmaceutical combination of any one of items 69 to 80, for use in treating a solid tumor.

Item 88. The pharmaceutical composition of item 87, wherein the solid tumor is head and neck squamous cell carcinoma (HNSCC), melanoma or a visceral tumor.

Item 89. A lyophilisate comprising a compound having the structure of Formula (A), or a pharmaceutically acceptable salt thereof, and one or more pharmaceutically acceptable excipients:

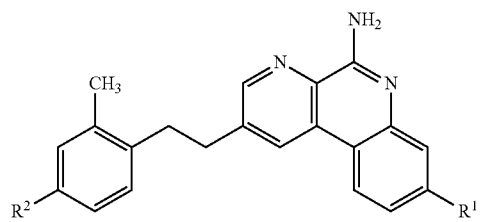

Formula (A)

wherein:
  $R^1$ is $-L_1R^4$, $-L_1R^5$, $-OL_1R^4$, $-OL_1R^5$, $CH_3$, $-C(=O)P(O)(OH)_2$ or $-C(=O)CF_2P(O)(OH)_2$;
  $R^2$ is $-L_2R^4$, $-L_2R^6$, $-L_2L_3L_2R^6$, $-L_2L_3R^4$, $-L_2L_3L_2R^4$, $-OL_2R^4$, $-OL_2R^6$, $-OL_2L_3R^6$, $-OL_2L_3L_2R^6$, $-OL_2L_{3R}{}^4\text{-}OL_2L_3L_2R^4$ or $-OCH_3$;
  each $R^3$ is independently selected from H and fluoro;

R⁴ is —P(O)(OH)₂,
R⁵ is —CF₂P(O)(OH)₂ or —C(O)OH;
R⁶ is —CF₂P(O)(OH)₂ or —C(O)OH;
L₁ is C₁-C₆alkylene, C₂-C₆alkenylene or —((CR⁴R⁴)$_p$O)$_q$(CH₂)$_p$—, wherein the C₁-C₆alkylene and C₂-C₆alkenylene of L₁ are substituted with 0 to 4 fluoro groups;
each L₂ is independently selected from C₁-C₆alkylene and —((CR³R³)$_p$O)$_q$(CH₂)$_p$—, wherein the C₁-C₆alkylene of L₂ is substituted with 0 to 4 fluoro groups;
L₃ is arylene or a 5-6 membered heteroarylene;
each p is independently selected from 1, 2, 3, 4, 5 and 6, and q is 1, 2, 3 or 4.

Item 90. The lyophilisate of item 89, wherein the compound is 3-(5-amino-2-(4-(2-(3,3-difluoro-3-phosphonopropoxy)ethoxy)-2-methylphenethyl)benzo[f][1,7]naphthyridin-8-yl)propanoic acid.

Item 91. A lyophilisate prepared from a solution having a pH between 6.5 and 9.0 and comprising a compound having the structure of Formula (A), or a pharmaceutically acceptable salt thereof, and a buffering agent:

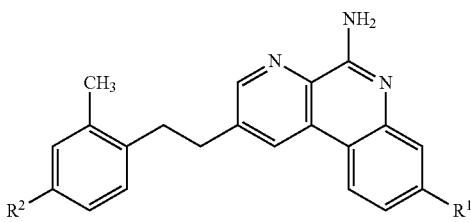

Formula (A)

wherein:
R¹ is -L₁R⁴, -L₁R⁵, —OL₁R⁴, —OL₁R⁵, CH₃, —C(=O)P(O)(OH)₂ or —C(=O)CF₂P(O)(OH)₂;
R² is -L₂R⁴, -L₂R⁶, -L₂L₃L₂R⁶, -L₂L₃R⁴, -L₂L₃L₂R⁴, —OL₂R⁴, —OL₂R⁶, —OL₂L₃R⁶, —OL₂L₃L₂R⁶, —OL₂L₃$_R$⁴-OL₂L₃L₂R⁴ or —OCH₃;
each R³ is independently selected from H and fluoro;
R⁴ is —P(O)(OH)₂,
R⁵ is —CF₂P(O)(OH)₂ or —C(O)OH;
R⁶ is —CF₂P(O)(OH)₂ or —C(O)OH;
L₁ is C₁-C₆alkylene, C₂-C₆alkenylene or —((CR⁴R⁴)$_p$O)$_q$(CH₂)$_p$—, wherein the C₁-C₆alkylene and C₂-C₆alkenylene of L₁ are substituted with 0 to 4 fluoro groups;
each L₂ is independently selected from C₁-C₆alkylene and —((CR³R³)$_p$O)$_q$(CH₂)$_p$—, wherein the C₁-C₆alkylene of L₂ is substituted with 0 to 4 fluoro groups;
L₃ is arylene or a 5-6 membered heteroarylene;
each p is independently selected from 1, 2, 3, 4, 5 and 6, and
q is 1, 2, 3 or 4.

Item 92. The lyophilisate of Item 91, wherein the compound is 3-(5-amino-2-(4-(2-(3,3-difluoro-3-phosphonopropoxy)ethoxy)-2-methylphenethyl)benzo[f][1,7]naphthyridin-8-yl)propanoic acid.

Item 93. A pharmaceutical composition prepared by reconstituting a lyophilisate of any one of items 89 to 92 with water and admixing with a suspension of aluminum-containing particles.

Item 94. The pharmaceutical composition of item 93 prepared by reconstituting a lyophilisate of any one of items 89 to 92 with water and admixing with a suspension of aluminum-containing particles having an aluminum content of 1 to 4 mg/mL.

Item 95. The pharmaceutical composition of items 93 to 94, wherein the aluminum-containing particles are aluminum hydroxide particles.

Figure 6:
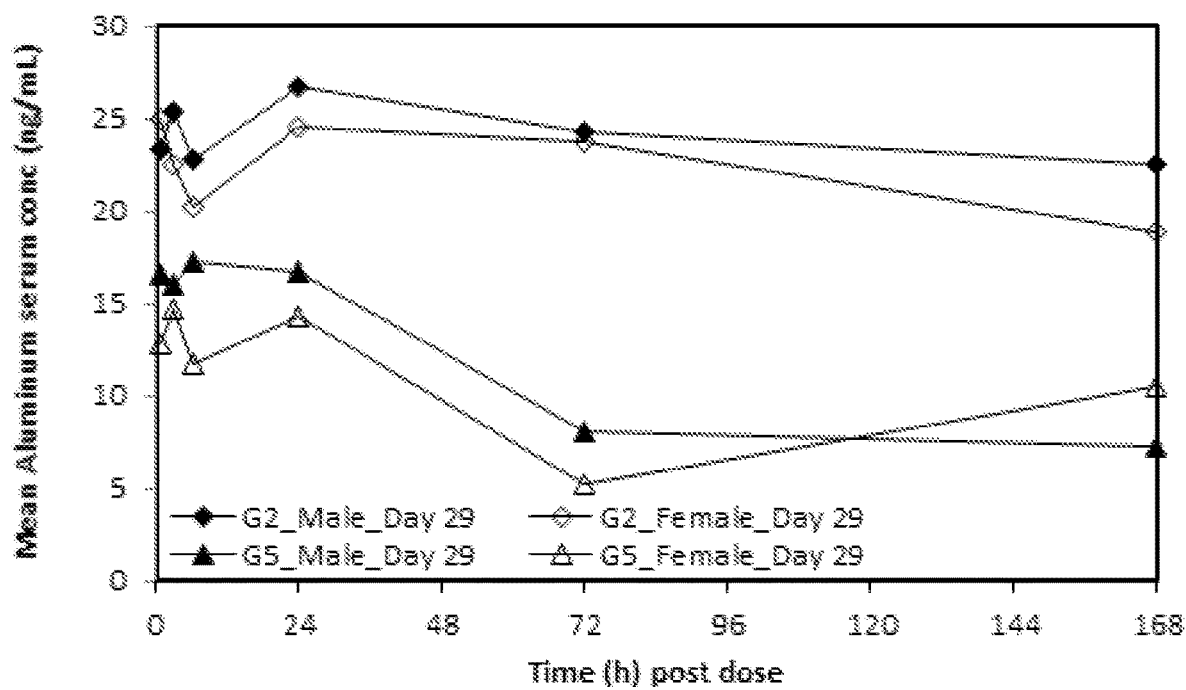

FIG. 6: Serum aluminum concentrations vs time post dose of aluminum hydroxide alone (Group 2) or post dose of Compound 15 with aluminum hydroxide (Group 5).

Figure 7:
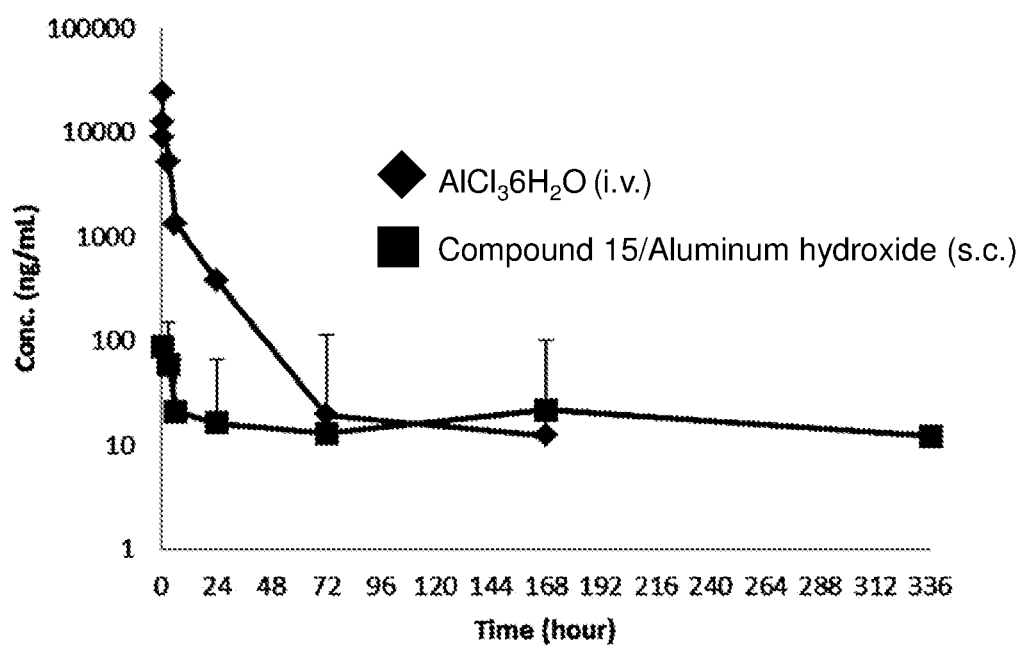

FIG. 7: Aluminum serum concentration vs. time profile after subcutaneous administration of Compound 15 adsorbed to aluminum hydroxide and intravenous administration of $AlCl_3.6H_2O$ in saline.

Figure 8:
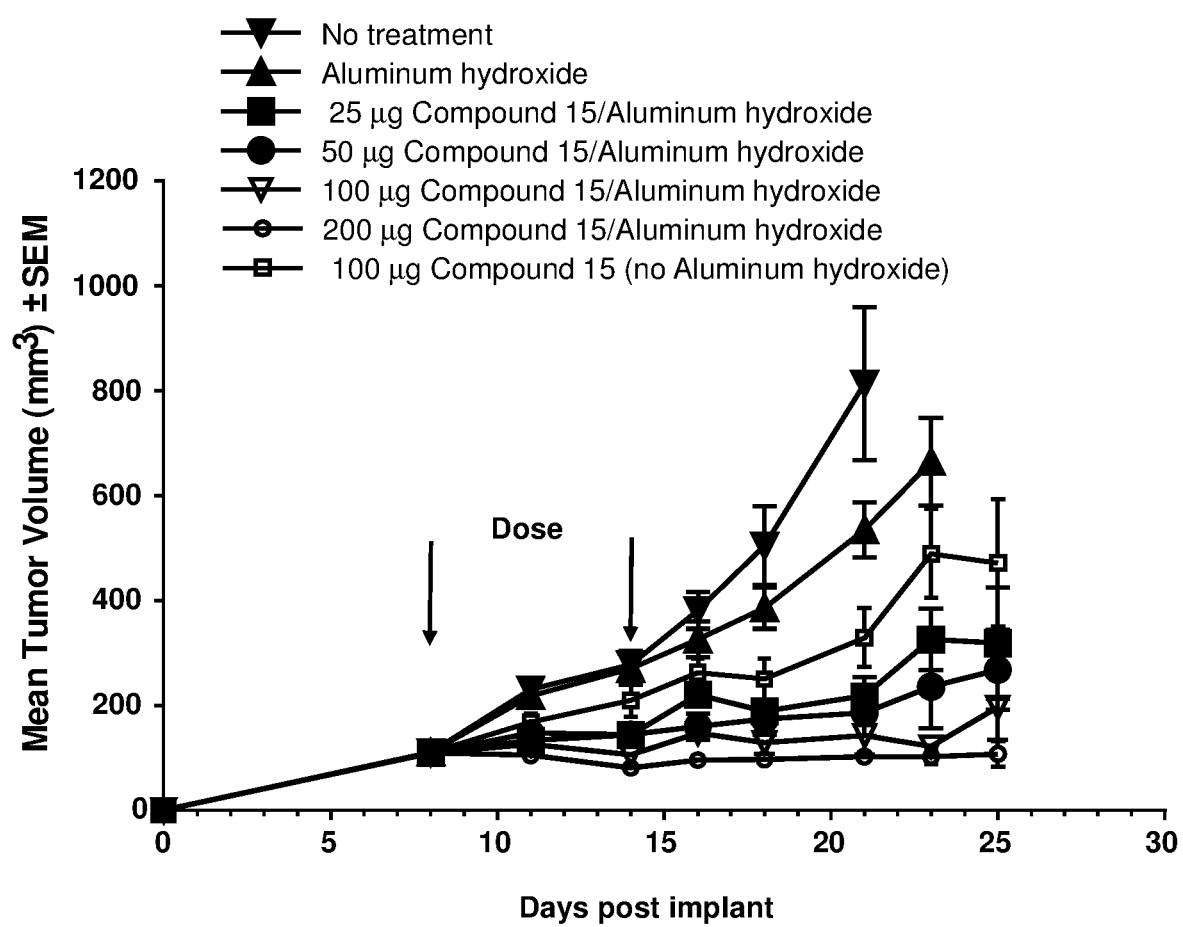

FIG. 8: Efficacy and dose response in A20 mouse lymphoma model following 2 weekly intra tumoral (i.t.) injections of different doses of Compound 15/aluminum hydroxide (at fixed ratio of 1:1.5, w/w, and 97% bound).

Figure 9:
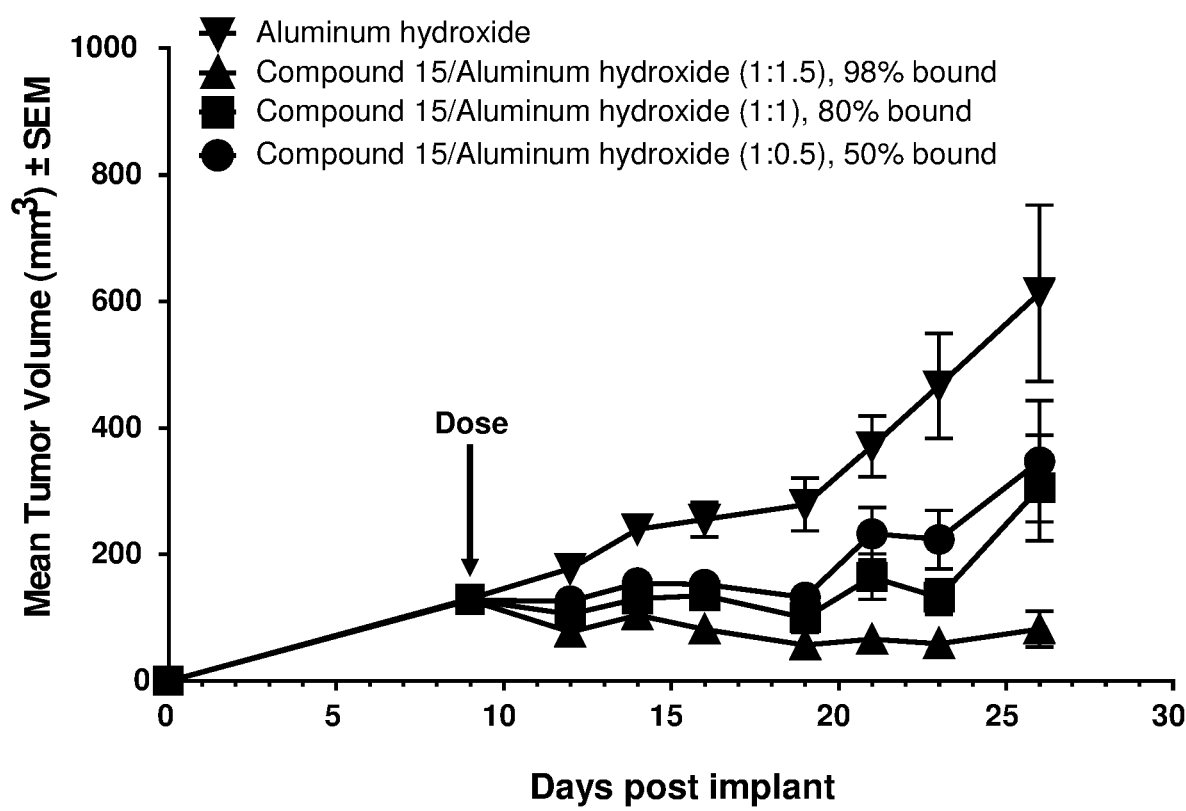

FIG. 9. Efficacy following a single 100 µg i.t. injection in A20 mouse lymphoma model of Compound 15/aluminum hydroxide at Compound 15 to aluminum hydroxide w/w ratios of 1:1.5, 1:1 and 1:0.5.

Figure 10:
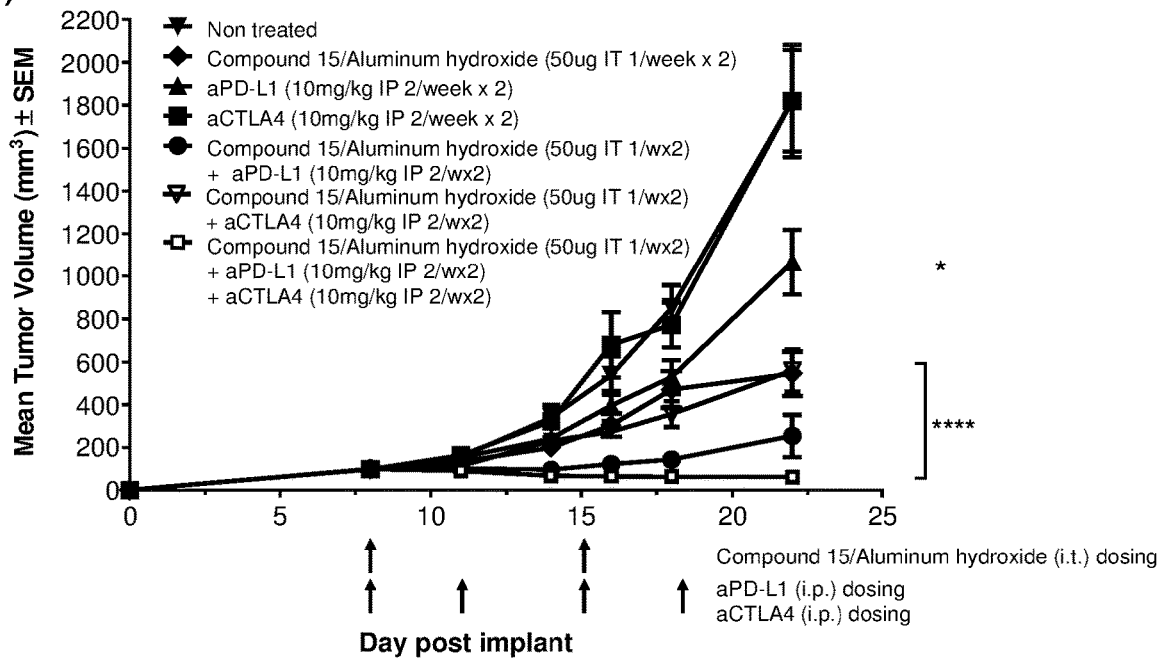
Figure 10:
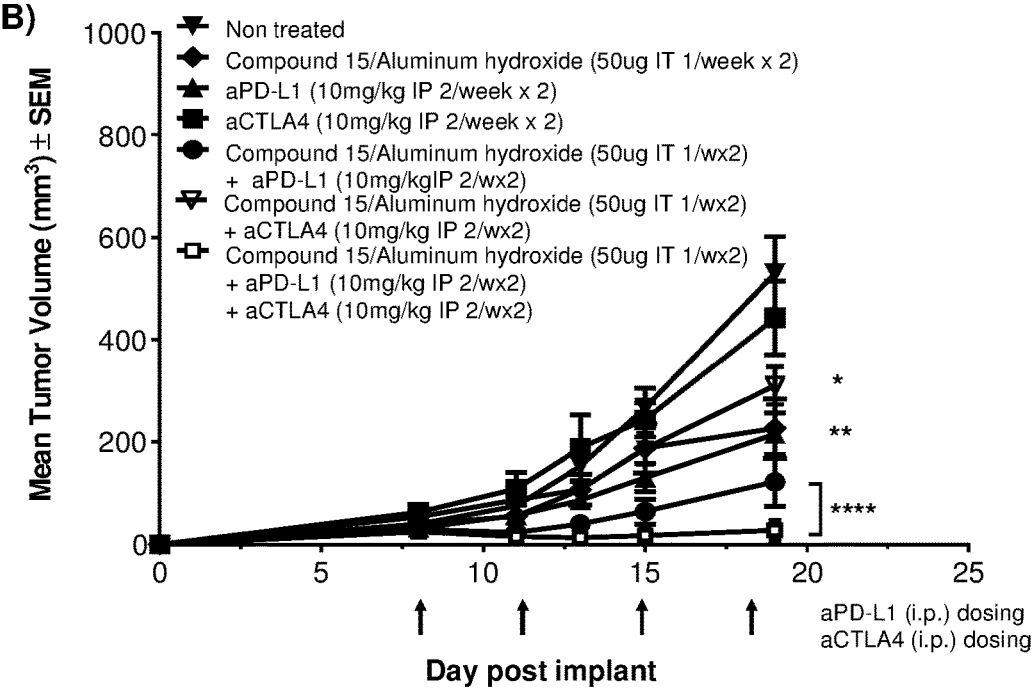
Figure 10:
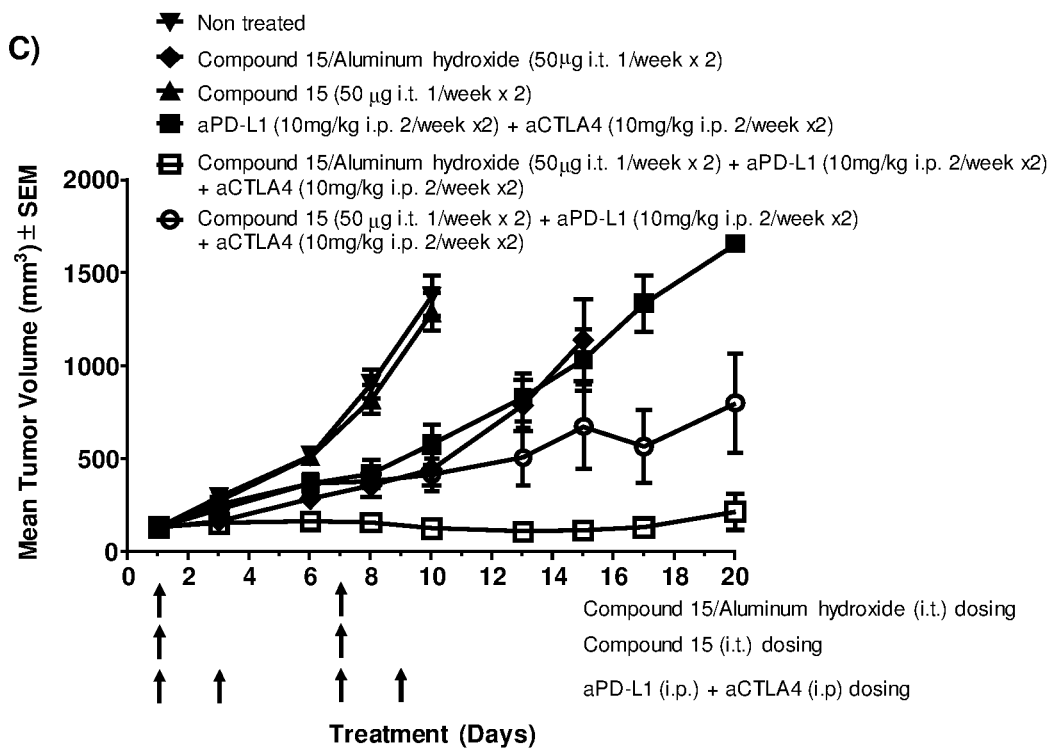
Figure 10:
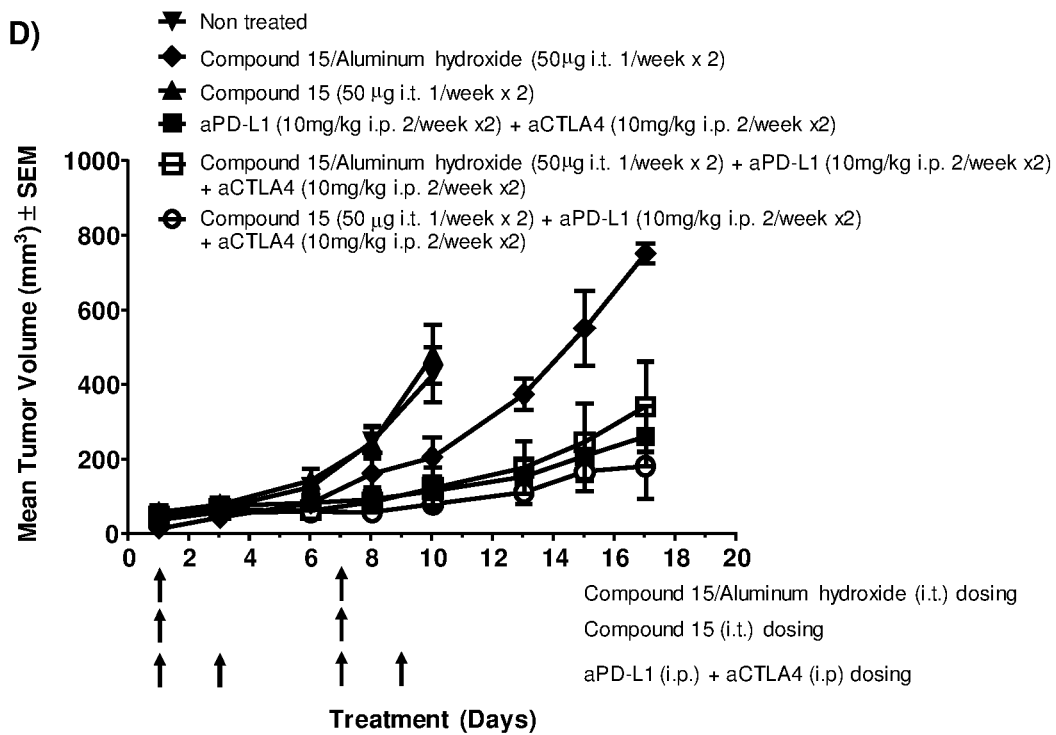

FIG. 10: A) Efficacy at the intratumor injection site following administration of Compound 15/aluminum hydroxide, an anti-PDL1 antibody or an anti-CTLA4 antibody as single agents or after the administration of combinations of Compound 15/aluminum hydroxide and an anti-PDL1 antibody and/or an anti-CTLA4 antibody. Significant differences were calculated using One-Way ANOVA post hoc Tukey multiple comparison test on post implant day 22 with N=9 per group, In treated site tumor Anti PD-L1 alone was significantly different, (*p<0.05). Compound 15/aluminum hydroxide, Compound 15/aluminum hydroxide with anti PD-L1 or antiCTLA4, Compound 15/aluminum hydroxide with anti PD-L1 and antiCTLA4 were significant different (****p<0.0001).

B) Efficacy at a site distant from the injection site following administration of Compound 15/aluminum hydroxide, an anti-PDL1 antibody or an anti-CTLA4 antibody as single agents or after the administration of combinations of Compound 15/aluminum hydroxide and an anti-PDL1 antibody and/or an anti-CTLA4 antibody. Significant differences were calculated using One-Way ANOVA post hoc Tukey multiple comparison test on post implant day 19 with N=9 per group, in distant site tumor, anti CTLA4 alone was not significantly different from no treatment, (*p>0.05). Anti PD-L1 alone was significantly different, (p<0.001). Compound 15/aluminum hydroxide alone was significantly different, (p<0.01). Compound 15/aluminum hydroxide with anti PD-L1 was significantly different, (**p<0.0001). Compound 15/aluminum hydroxide with anti CTLA4 was significantly different, (*p<0.05). Compound 15/aluminum hydroxide with anti PD-L1 and antiCTLA4 was significantly different, (****p<0.0001).

C) Efficacy at the intratumor injection site following administration of Compound 15 or Compound 15/aluminum hydroxide as single agents, or after the administration of the combination of an anti-PDL1 antibody and an anti-CTLA4 antibody or after the administration of the triple combinations of Compound 15 and an anti-PDL1 antibody and an anti-CTLA4 antibody or after administration of the triple combinations of Compound 15/aluminum hydroxide and an anti-PDL1 antibody and an anti-CTLA4 antibody.

D) Efficacy at a site distant from the injection site following administration of Compound 15 or Compound 15/aluminum hydroxide as single agents, or after the administration of the combination of an anti-PDL1 antibody and an anti-CTLA4 antibody or after the administration of the triple combinations of Compound 15 and an anti-PDL1 antibody and an anti-CTLA4 antibody or after administration of the triple combinations of Compound 15/aluminum hydroxide and an anti-PDL1 antibody and an anti-CTLA4 antibody.

DETAILED DESCRIPTION OF THE INVENTION

Definitions

The terms "alkenyl" or "alkene," as used herein, refers to a partially unsaturated branched or straight chain hydrocarbon having at least one carbon-carbon double bond. Atoms oriented about the double bond are in either the cis (Z) or trans (E) conformation. In certain embodiments, such alkenyl or alkene group are optionally substituted. The terms "$C_2$-$C_3$alkenyl", "$C_2$-$C_4$alkenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. In preferred embodiments, an alkenyl group generally is a $C_2$-$C_6$ alkenyl. Non-limiting examples of alkenyl groups include ethenyl, propenyl, butenyl, pentenyl, hexenyl, heptenyl, octenyl, nonenyl, decenyl and the like.

The term "alkenylene," as used herein, refers to a partially unsaturated branched or straight chain divalent hydrocarbon radical derived from an alkenyl group. In certain embodiments, such alkenylene group are optionally substituted. As used herein, the term "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. In preferred embodiments, an alkenylene group generally is a $C_2$-$C_6$ alkenylene. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. The terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. In preferred embodiments, an alkyl group generally is a $C_1$-$C_6$ alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. In certain embodiments such alkylene groups are optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. In preferred embodiments, an alkylene group generally is a $C_1$-$C_6$alkylene. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "aryl," as used herein, refers to phenyl or naphthalene.

The term "arylene," as used herein means a divalent radical derived from an aryl group. In preferred embodiments, an arylene group is a phenylene.

The term "5-6 membered heteroaryl," as used herein, refers to a monocyclic aromatic ring structure having 5 or 6 ring members, wherein 1 to 3 ring members are independently selected from the heteroatoms N, O and S. Non-limiting examples of 5-6 membered heteroaryls include 2- or 3-furyl; 2- or 3-thienyl; 1-, 2- or 3-pyrrolyl; 2-, 4-, or 5-oxazolyl; 2-, 4-, or 5-thiazolyl; 1-, 2-, 4-, or 5-imidazolyl; 1-, 3-, 4-, or 5-pyrazolyl; 3-, 4-, or 5-isoxazolyl; 3-, 4-, or 5-isothiazolyl; 4- or 5-1,2,3-oxadiazolyl; 4- or 5-1,2,3-triazolyl; 2- or 5-1,3,4-thiadiazolyl; 2-, 3-, or 4-pyridyl; 3-, 4-, 5- or 6-pyridazinyl; 2-, 4-, 5- or 6-pyrimidinyl, and 2- or 3-pyrazinyl.

The term "heteroatoms" as used herein, refers to nitrogen (N), oxygen (O) or sulfur (S) atoms.

The term "5-6 membered heteroarylene," as used herein, means a divalent radical derived from a 5-6 membered heteroaryl group.

The term "liquid tumor," as used herein, refers to cancers which affect bone marrow, blood cells and the lymphatic system. An example of a liquid tumor is leukemia.

The term "solid tumor," as used herein, refers to an abnormal mass of tissue that usually does not contain cysts or liquid areas. In general, the term refers to cancerous (malignant) tumors, although a solid tumor may be a non-cancerous (benign) tumor. Examples of solid tumors are sarcomas, carcinomas, and lymphomas, which include, but are not limited to, a breast cancer tumor, a bladder cancer tumor, a head and neck cancer tumor (e.g. head and neck squamous cell carcinoma (HNSCC)), a non-small cell lung cancer tumor, a small cell lung cancer tumor, a colorectal cancer tumor, a gastrointestinal stromal tumor, a gastroesophageal carcinoma, a renal cell cancer tumor, a prostate cancer tumor, a liver cancer tumor, a colon cancer tumor, a pancreatic cancer tumor, an ovarian cancer tumor, a lymphoma, a cutaneous T-cell lymphoma, visceral tumors or a melanoma.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound disclosed herein and one or more additional therapeutic agent are administered to a subject simultaneously in the form of a single entity or dosage. The term "non-fixed combination" means that the active ingredients, by way of example, a compound disclosed herein and one or more additional therapeutic agent, are administered to a subject as separate entities either simultaneously, concurrently or sequentially with no specific time limits, wherein such administration provides therapeutically effective levels of the active ingredients in the body of the subject. The latter also applies to cocktail therapy, e.g. the administration of 3 or more active ingredients.

The terms "composition" or "pharmaceutical composition," as used herein, refers to a mixture of a compound disclosed herein with at least one and optionally more than one other pharmaceutically acceptable chemical components, such as carriers, stabilizers, diluents, dispersing agents, suspending agents, thickening agents, and/or excipients.

The term "an optical isomer" or "a stereoisomer", as used herein, refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

The term "pharmaceutically acceptable salt," as used herein, refers to a salt which does not abrogate the biological activity and properties of the compounds disclosed herein, and does not cause significant irritation to a subject to which it is administered.

The term "subject", as used herein, encompasses mammals and non-mammals. Examples of mammals include, but are not limited to, humans, chimpanzees, apes, monkeys, cattle, horses, sheep, goats, swine; rabbits, dogs, cats, rats, mice, guinea pigs, and the like. Examples of non-mammals include, but are not limited to, birds, fish and the like. Frequently the subject is a human.

The term "a subject in need of such treatment", refers to a subject which would benefit biologically, medically or in quality of life from such treatment.

The term "therapeutically effective amount," as used herein, refers to an amount which may increase the immune response, ameliorate at least one symptom or clinical sign of a tumor and/or decrease the number and/or size of metastases. Ameliorating at least one symptom or clinical sign of a tumor can include a decrease in the size of a tumor, stabilization in the size or growth of a tumor, a reduction in the rate of growth of a tumor, an increase in tumor necrosis, a change in the tumor structure such as disintegration, a change in a biochemical marker associated with decrease in tumor establishment, a decrease in tumor progression or a decrease in tumor survival. An increase in immune response refers to an increase in at least one cell-mediated immune response of a cell population that includes cells of a tumor refers to an increase in at least one biochemical, histological, or immunological marker associated with improvement of the immunological profile of the tumor microenvironment. Markers in which an increase in the amount of the marker is associated with an improvement of the immunological profile of the tumor microenvironment include, but are not limited to, interferon-alpha; interferon-gamma; interferon inducible proteins; Interferon gamma-induced protein 10 (IP-10); TNF-alpha; chemokines such as CCL2, CCL3, CCL4, CXCL2; activated T-cells; activated B-cells; activated NK-cells; tumor specific T-cells, activated tumor associated macrophages; chemokine receptors such as CCR6; or tumor associated lymphoid aggregates. Markers associated with a tumor microenvironment can be determined, for example, by analysis of a biopsy (for example needle biopsy) from the tumor, the localized tumor region, or a tumor draining lymph node. Analysis for the markers can be done using standard techniques such as by histology (HNE stain), flow cytometry, gene expression assays (quantitative PCR), immunochemistry techniques, as well as other techniques commonly known to those of ordinary skill in the art.

The term "TLR7 agonist", as used herein, refers to a compound which targets or activates the biological activity of Toll-like Receptor 7 (TLR7). Particularly, the "TLR7 agonist" can be a compound that activates TLR7 with an $EC_{50}$ of less than 5 µM, measured by the reporter gene assay described herein, wherein Human embryonic kidney 293 (HEK 293) cells were stably transfected with human TLR7. Preferably, the "TLR7 agonist" is a compound that activates TLR7 with an $EC_{50}$ of less than 1 µM, measured by the reporter gene assay described herein, wherein Human embryonic kidney 293 (HEK 293) cells were stably transfected with human TLR7. The TLR7 agonists can be for example any compound described in WO2011/049677 and the exemplary compounds described herein.

The term "treat", "treating", "treatment" or "therapy" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject, e.g., a mammal or human.

The term "prevent", "preventing" or "prevention" as used herein comprises the prevention of at least one symptom associated with or caused by the state, disease or disorder being prevented.

The compound names provided herein were obtained using ChemBioDraw Ultra 14.0 (CambridgeSoft®).

Unless specified otherwise, the term "compounds of the present invention", "compounds of the invention" or "compounds disclosed herein" refers to compounds of Formula (A), and pharmaceutically acceptable salts, stereoisomers (including diastereoisomers and enantiomers), tautomers and isotopically labeled compounds (including deuterium substitutions) thereof.

As used herein, the term "a," "an," "the" and similar terms used in the context of the present invention (especially in the context of the claims) are to be construed to cover both the singular and plural unless otherwise indicated herein or clearly contradicted by the context.

DESCRIPTION OF THE INVENTION AND PREFERRED EMBODIMENTS

Pharmaceutical Compositions

One aspect of the invention are pharmaceutical compositions comprising a TLR7 agonist, or a pharmaceutically acceptable salt thereof, one or more pharmaceutically acceptable excipients and aluminum-containing particles. In certain embodiments of this aspect, the pharmaceutical compositions are liquid compositions. In certain embodiments such liquid compositions are suspensions, while in other embodiments such liquid compositions are solutions. In certain embodiments of this aspect, these pharmaceutical compositions are solid compositions. In certain embodiments such solid compositions are lyophilisates, while in other embodiments such solid compositions are spray dried powders.

Another aspect of the invention are pharmaceutical composition comprising a TLR7 agonist, or a pharmaceutically acceptable salt thereof, one or more pharmaceutically acceptable excipients and a suspension of aluminum-containing particles.

Another aspect of the invention are pharmaceutical compositions comprising a TLR7 agonist and one or more pharmaceutically acceptable excipients. In certain embodiments of this aspect, these pharmaceutical compositions are solid compositions. In certain embodiments such solid compositions are lyophilisates, while in other embodiments such solid compositions are spray dried powders.

In particular, the pharmaceutical compositions of the invention (liquid compositions or solid compositions) comprise a compound having the structure of Formula (A), or a pharmaceutically acceptable salt thereof:

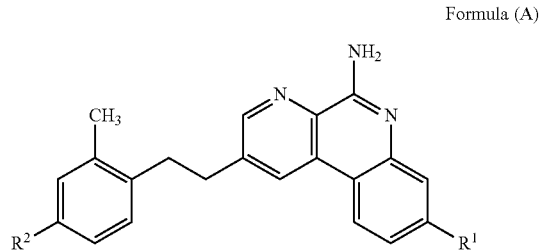

Formula (A)

wherein:
$R^1$ is $-L_1R^4$, $-L_1R^5$, $-OL_1R^4$, $-OL_1R^5$, $CH_3$, $-C(=O)P(O)(OH)_2$ or $-C(=O)CF_2P(O)(OH)_2$;
$R^2$ is $-L_2R^4$, $-L_2R^6$, $-L_2L_3L_2R^6$, $-L_2L_3R^4$, $-L_2L_3L_2R^4$, $-OL_2R^4$, $-OL_2R^6$, $-OL_2L_3R^6$, $-OL_2L_3L_2R^6$, $-OL_2L_{3R}^4$-$OL_2L_3L_2R^4$ or $-OCH_3$;
each $R^3$ is independently selected from H and fluoro;
$R^4$ is $-P(O)(OH)_2$,
$R^5$ is $-CF_2P(O)(OH)_2$ or $-C(O)OH$;
$R^6$ is $-CF_2P(O)(OH)_2$ or $-C(O)OH$;
$L_1$ is $C_1$-$C_6$alkylene, $C_2$-$C_6$alkenylene or $-((CR^4R^4)_pO)_q(CH_2)_p-$, wherein the $C_1$-$C_6$alkylene and $C_2$-$C_6$alkenylene of $L_1$ are substituted with 0 to 4 fluoro groups;
each $L_2$ is independently selected from $C_1$-$C_6$alkylene and $-((CR^3R^3)_pO)_q(CH_2)_p-$, wherein the $C_1$-$C_6$alkylene of $L_2$ is substituted with 0 to 4 fluoro groups;
$L_3$ is arylene or a 5-6 membered heteroarylene;
each p is independently selected from 1, 2, 3, 4, 5 and 6, and q is 1, 2, 3 or 4.
and wherein the compound of Formula (A) is a TLR7 agonists.

General procedures for preparing compounds of Formula (A) are described in WO2011/049677.

In certain embodiments, compounds of Formula (A) are prepared as a pharmaceutically acceptable base addition salt. Pharmaceutically acceptable base addition salts of compounds of Formula (A) include, but are not limited to, sodium, potassium, ammonium, calcium, magnesium, iron, silver, zinc, copper, isopropylamine, benzathine, cholinate, diethanolamine, diethylamine, lysine, arginine, meglumine, piperazine or tromethamine salt forms. Lists of additional suitable base addition salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002.

The pharmaceutical compositions of the invention are injectable compositions which comprise a compound of Formula (A), or a pharmaceutically acceptable salt thereof, aluminum-containing particles and one or more pharmaceutically acceptable excipients. The compound of Formula (A), or a pharmaceutically acceptable salt thereof, included in the pharmaceutical compositions of the invention are present in a therapeutically effective amount. The pharmaceutically acceptable excipients included in the pharmaceutical compositions of the invention include, but are not limited to, bulking agents, lyoprotectants, buffering agent, tonicity modifier, isotonic agents, antioxidants, antimicrobial agents, antibacterial agents, antifungal agents, solubilizing agents, surfactants and wetting agents. Such excipients for use in an injectable formulation are known to those skilled in the art (see, for example, Remington's Pharmaceutical Sciences, 18th Ed. Mack Printing Company, 1990 and Pharma Times, Vol. 45, No. 3, 2013 pp. 65-77). The parenteral pharmaceutical compositions of the invention also comprise water as the pharmaceutically and physiologically acceptable injectable fluid vehicle.

In general bulking agents are included in a lyophilized product to provide bulk and structure to the lyophilzed powder, which aids in dissolution of the active agent. Lyoprotectants help to stabilize and prevent the degradation of the active agent during freeze-drying and storage. The bulking agents and lyoprotectants which may be included in the pharmaceutical compositions of the invention include, but are no limited to, sucrose, lactose, trehalose, mannitol, sorbitol, raffinose, glycine, histidine, polyethylene glycol and low molecular weight polyvinyl pyrrrollidones (i.e. Povidone K12 and Povidone K17).

Buffering agents are included into pharmaceutical compositions to adjust and stabilize pH and optimize active agent solubility and stability. Buffering agents are also used in the pharmaceutical compositions of the invention to ensure that the phosponic acid groups of the compounds of Formula (A) are ionized (e.g. in the pH range of 7-9). The buffering agents which may be included in the pharmaceutical compositions of the invention include, but are no limited to, Tris, glycine, meglumine, histidine and citrate/citric acid.

Tonicity modifiers and isotonic agents are included into pharmaceutical compositions to maintain ensure the formulation is isotonic with human plasma. The tonicity modifiers and isotonic agents which may be included in the pharmaceutical compositions of the invention include, but are no limited to, dextrose, glycerol, sodium chloride, glycerin and mannitol.

Antioxidants are used to prevent/minimize the any oxidation of active agent or excipients during storage, whereas antimicrobial agents are used to prevent the growth of micro-organisms. The antioxidants which may be included in the pharmaceutical compositions of the invention include, but are no limited to, ascorbic acid, acetylcysteine, sulfurous acid salts (bisulfite, metabisulfite), monothioglyercol, butylated hydroxy toluene (BHT), butylated hydroxyanisole (BHA) and thiourea. The antimicrobial agents which may be included in the pharmaceutical compositions of the invention include, but are no limited to, phenol, meta-cresol, benzyl alcohol, parabens methyl, propyl, butyl), benzalkonium chloride, chlorobutanol, thimerosal, and phenylmercuric salts (acetate, borate, nitrate).

Solubilizing agents, which can be broadly classified into surfactants and co-solvents, help in dissolving or increasing the active agent solubility into the formulation. The surfactants which may be included in the pharmaceutical compositions of the invention include, but are no limited to, polyoxyethylene sorbitan monooleate (Tween 80), sorbitan monooleate polyoxyethylene sorbitan monolaurate (Tween 20), lecithin, polyoxyethylene-polyoxypropylene copolymers (Pluronics). Surfactants may also act as wetting agents and the surfactant/wetting agents which may be included in the pharmaceutical compositions of the invention include, but are no limited to, lecithin, Polysorbate 20, Polysorbate 80, Pluronic F-68 and Sorbitan trioleate (span 85).

The pharmaceutical compositions of the invention can be prepared using processes which include admixing a compound of Formula (A), or a pharmaceutically acceptable salts thereof, with one or more pharmaceutically acceptable excipients and water. Alternatively, the pharmaceutical compositions of the invention can be prepared by admixing a reconstituted lyophilisate (reconstituted with water) with a solution comprising an aluminum-containing particles, wherein the lyophilisate comprises a compound of Formula (A), or a pharmaceutically acceptable salts thereof, a buffering agent (pH 7.0 to 8.0), a bulking agent and a lyoprotectant.

In another aspect, the pharmaceutical compositions of the invention can be prepared by admixing a reconstituted lyophilisate (reconstituted with water) with a solution comprising an aluminum-containing particles, wherein the lyophilisate comprises a compound of Formula (A), or a pharmaceutically acceptable salts thereof, a buffering agent (pH 7.0 to 8.0), a bulking agent, a lyoprotectant, a surfactant and a wetting agent.

The particles that comprise aluminum included in the pharmaceutical composition or lyophilisate of the invention include, but are not limited to, aluminum hydroxide, aluminum oxyhydroxide and aluminum hydroxyphosphate. Compounds of Formula (A) can bind to such particles, such as, by way of example only, aluminum hydroxide, aluminum oxyhydroxide and aluminum hydroxyphosphate. Aluminum-containing particles have been used in vaccines to bind an antigen. A discussion of aluminum-containing particles and their uses in vaccines is given in *Expert Rev. Vaccines*, 46(5), 2007, 685-698 and Vaccines, 25, 2007, 6618-6624.

Certain aspects and examples of the pharmaceutical compositions of the invention are provided in the following listing of enumerated embodiments. It will be recognized that features specified in each embodiment may be combined with other specified features to provide further embodiments of the present invention.

Embodiment 1. A pharmaceutical composition comprising a TLR7 agonist having the structure of Formula (A), or a pharmaceutically acceptable salt thereof, and one or more pharmaceutically acceptable excipients, wherein the compound of Formula (A) is selected from any one of the compounds of Table 1:

TABLE 1

| Compound Number | Structure | Compound Name |
|---|---|---|
| 1 | 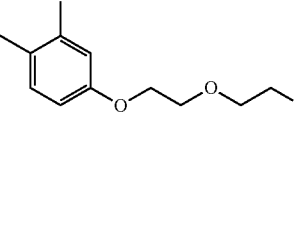 | (3-(2-(2-(4-(2-(5-amino-8-methylbenzo[f][1,7]naphthyridin-2-yl)ethyl)-3-methylphenoxy)ethoxy)ethoxy)-1,1-difluoropropyl)phosphonic acid |
| 2 | 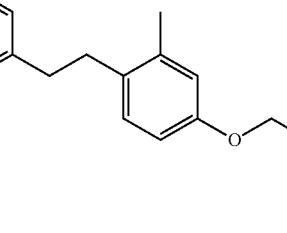 | (3-(4-(2-(5-amino-8-methylbenzo[f][1,7]naphthyridin-2-yl)ethyl)-3-methylphenoxy)propyl)phosphonic acid |
| 3 | 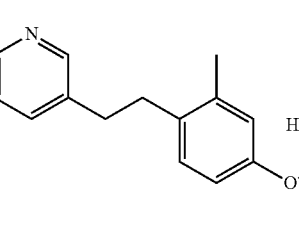 | 4-(2-(5-amino-8-methylbenzo[f][1,7]naphthyridin-2-yl)ethyl)-3-methylphenyl dihydrogen phosphate |
| 4 | 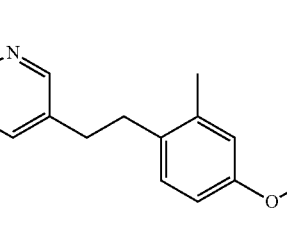 | ((4-(2-(5-amino-8-methylbenzo[f][1,7]naphthyridin-2-yl)ethyl)-3-methylphenoxy)methyl)phosphonic acid |
| 5 | 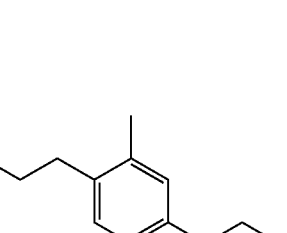 | 5-(4-(2-(5-amino-8-methylbenzo[f][1,7]naphthyridin-2-yl)ethyl)-3-methylphenoxy)-1,1-difluoropentylphosphonic acid |
| 6 | 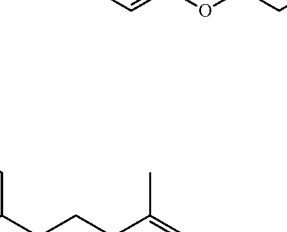 | (4-(4-(2-(5-amino-8-methylbenzo[f][1,7]naphthyridin-2-yl)ethyl)-3-methylphenoxy)-1,1-difluorobutyl)phosphonic acid |

TABLE 1-continued

| Compound Number | Structure | Compound Name |
|---|---|---|
| 7 | 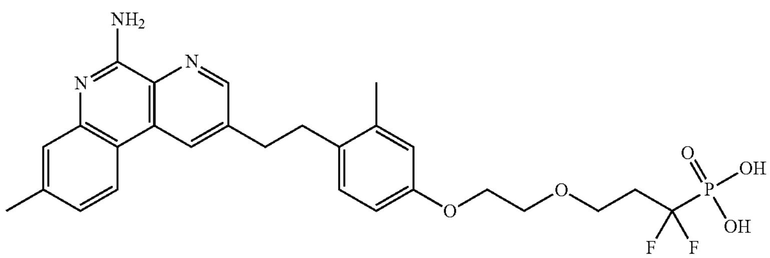 [SMILES: Cc1ccc2c(c1)nc(N)c1ncc(CCc3ccc(OCCOCCC(F)(F)P(=O)(O)O)cc3C)cc12] | 3-(2-(4-(2-(5-amino-8-methylbenzo[f][1,7]naphthyridin-2-yl)ethyl)-3-methylphenoxy)ethoxy)-1,1-difluoropropylphosphonic acid |
| 8 | 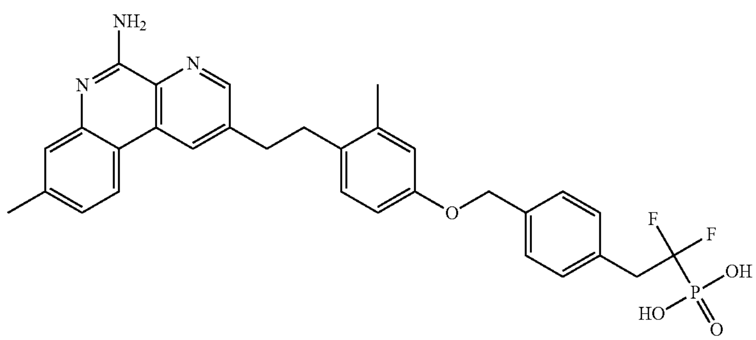 [SMILES: Cc1ccc2c(c1)nc(N)c1ncc(CCc3ccc(OCc4ccc(CC(F)(F)P(=O)(O)O)cc4)cc3C)cc12] | 2-(4-((4-(2-(5-amino-8-methylbenzo[f][1,7]naphthyridin-2-yl)ethyl)-3-methylphenoxy)methyl)phenyl)-1,1-difluoroethylphosphonic acid |
| 9 | 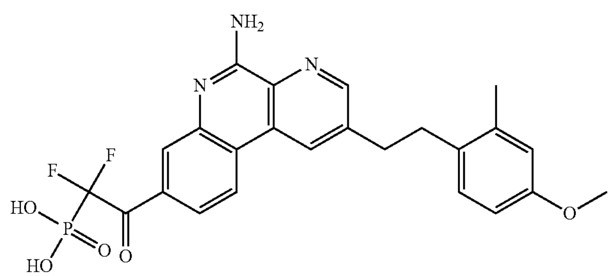 [SMILES: COc1ccc(CCc2cnc3c(N)nc4cc(C(=O)C(F)(F)P(=O)(O)O)ccc4c3c2)c(C)c1] | 2-(5-amino-2-(4-methoxy-2-methylphenethyl)benzo[f][1,7]naphthyridin-8-yl)-1,1-difluoro-2-oxoethylphosphonic acid |
| 10 | 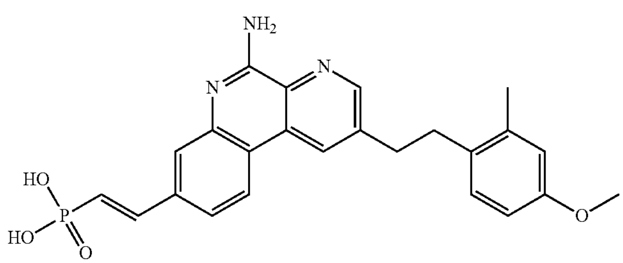 [SMILES: COc1ccc(CCc2cnc3c(N)nc4cc(/C=C/P(=O)(O)O)ccc4c3c2)c(C)c1] | (E)-(2-(5-Amino-2-(4-methoxy-2-methylphenethyl)benzo[f][1,7]naphthyridin-8-yl)vinyl)phosphonic acid |
| 11 | 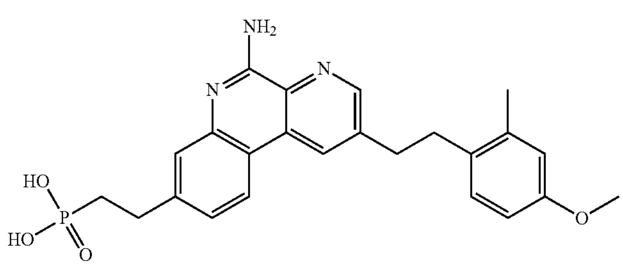 [SMILES: COc1ccc(CCc2cnc3c(N)nc4cc(CCP(=O)(O)O)ccc4c3c2)c(C)c1] | 2-(5-amino-2-(4-methoxy-2-methylphenethyl)benzo[f][1,7]naphthyridin-8-yl)ethylphosphonic acid |

TABLE 1-continued

| Compound Number | Structure | Compound Name |
|---|---|---|
| 12 | 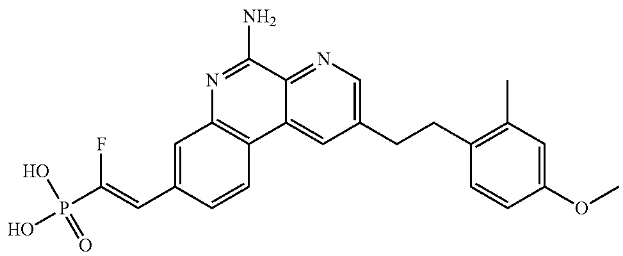 [SMILES: COc1ccc(CCc2cnc3c(N)nc4cc(/C=C(\F)P(=O)(O)O)ccc4c3c2)c(C)c1] | (E)-(2-(5-Amino-2-(4-methoxy-2-methylphenethyl)benzo[f][1,7]naphthyridin-8-yl)-1-fluorovinyl)phosphonic acid |
| 13 | 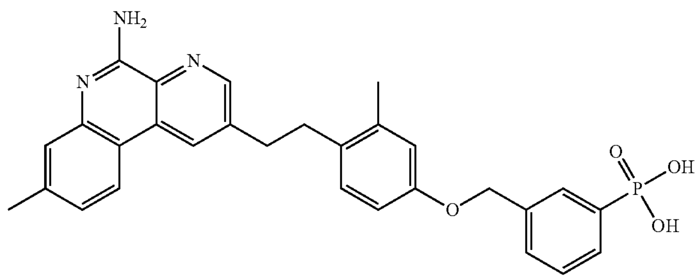 [SMILES: Cc1ccc2c(c1)nc(N)c1ncc(CCc3ccc(OCc4cccc(P(=O)(O)O)c4)cc3C)cc12] | (3-((4-(2-(5-amino-8-methylbenzo[f][1,7]naphthyridin-2-yl)ethyl)-3-methylphenoxy)methyl)phenyl)phosphonic acid |
| 14 | 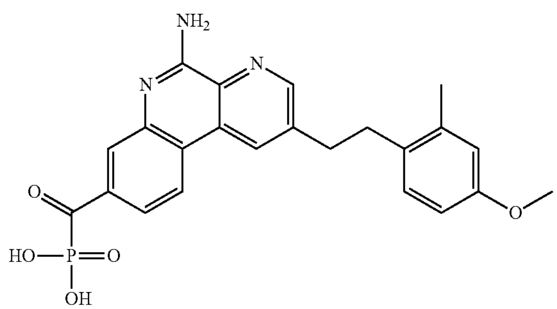 [SMILES: COc1ccc(CCc2cnc3c(N)nc4cc(C(=O)P(=O)(O)O)ccc4c3c2)c(C)c1] | (5-amino-2-(4-methoxy-2-methylphenethyl)benzo[f][1,7]naphthyridine-8-carbonyl)phosphonic acid |
| 15 | 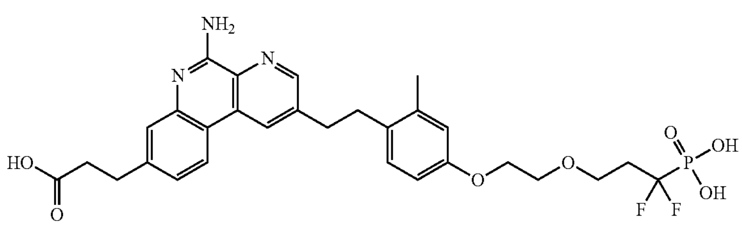 [SMILES: Cc1cc(OCCOCCC(F)(F)P(=O)(O)O)ccc1CCc1cnc2c(N)nc3cc(CCC(=O)O)ccc3c2c1] | 3-(5-amino-2-(4-(2-(3,3-difluoro-3-phosphonopropoxy)ethoxy)-2-methylphenethyl)benzo[f][1,7]naphthyridin-8-yl)propanoic acid |
| 16 | 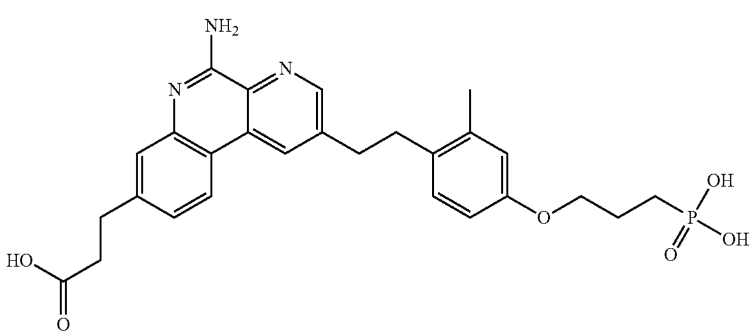 [SMILES: Cc1cc(OCCCP(=O)(O)O)ccc1CCc1cnc2c(N)nc3cc(CCC(=O)O)ccc3c2c1] | 3-(5-amino-2-(2-methyl-4-(3-phosphonopropoxy)phenethyl)benzo[f][1,7]naphthyridin-8-yl)propanoic acid |

TABLE 1-continued

| Compound Number | Structure | Compound Name |
|---|---|---|
| 17 | 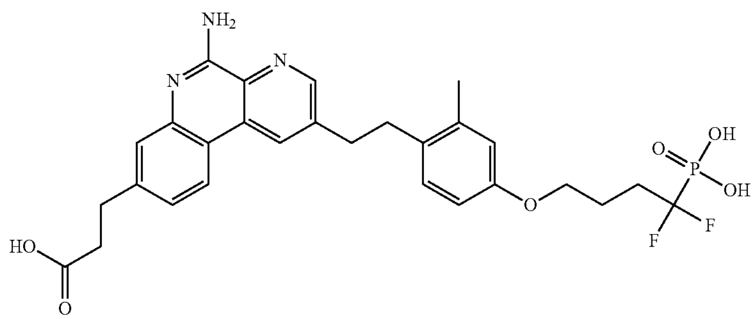 [SMILES: Cc1cc(OCCCC(F)(F)P(=O)(O)O)ccc1CCc1cnc2c(N)nc3cc(CCC(=O)O)ccc3c2c1] | 3-(5-amino-2-(4-(4,4-difluoro-4-phosphonobutoxy)-2-methylphenethyl)benzo[f][1,7]naphthyridin-8-yl)propanoic acid |
| 18 | 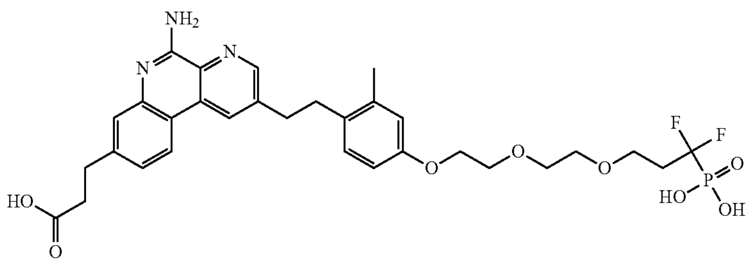 [SMILES: Cc1cc(OCCOCCOCCC(F)(F)P(=O)(O)O)ccc1CCc1cnc2c(N)nc3cc(CCC(=O)O)ccc3c2c1] | 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid |
| 19 | 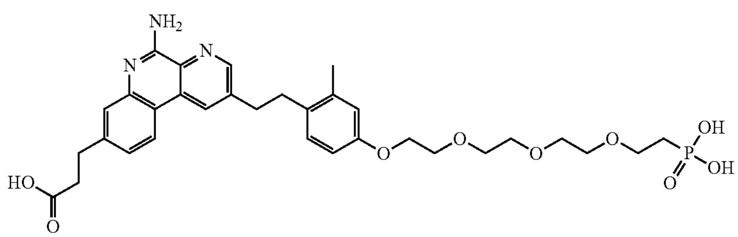 [SMILES: Cc1cc(OCCOCCOCCOCCP(=O)(O)O)ccc1CCc1cnc2c(N)nc3cc(CCC(=O)O)ccc3c2c1] | 3-(5-amino-2-(2-methyl-4-(2-(2-(2-(2-phosphonoethoxy)ethoxy)ethoxy)ethoxy)phenethyl)benzo[f][1,7]naphthyridin-8-yl)propanoic acid |
| 20 | 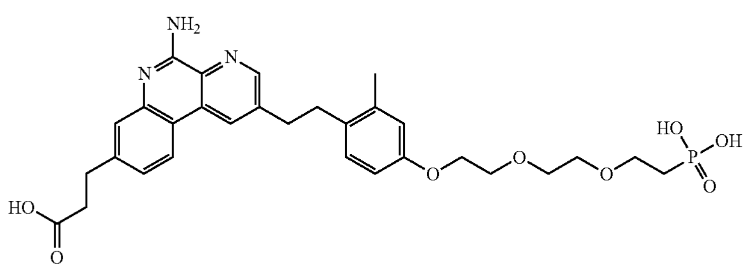 [SMILES: Cc1cc(OCCOCCOCCP(=O)(O)O)ccc1CCc1cnc2c(N)nc3cc(CCC(=O)O)ccc3c2c1] | 3-(5-amino-2-(2-methyl-4-(2-(2-(2-phosphonoethoxy)ethoxy)ethoxy)phenethyl)benzo[f][1,7]naphthyridin-8-yl)propanoic acid |
| 21 | 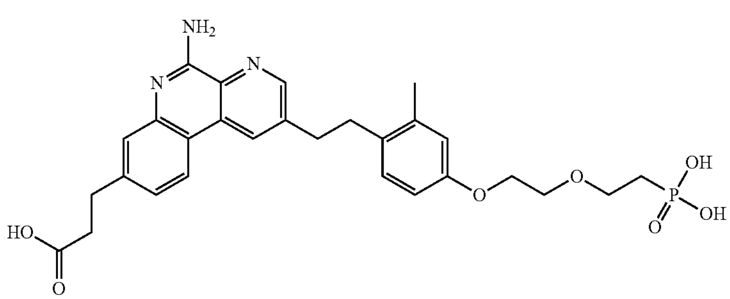 [SMILES: Cc1cc(OCCOCCP(=O)(O)O)ccc1CCc1cnc2c(N)nc3cc(CCC(=O)O)ccc3c2c1] | 3-(5-amino-2-(2-methyl-4-(2-(2-phosphonoethoxy)ethoxy)phenethyl)benzo[f][1,7]naphthyridin-8-yl)propanoic acid |

TABLE 1-continued

| Compound Number | Structure | Compound Name |
|---|---|---|
| 22 | 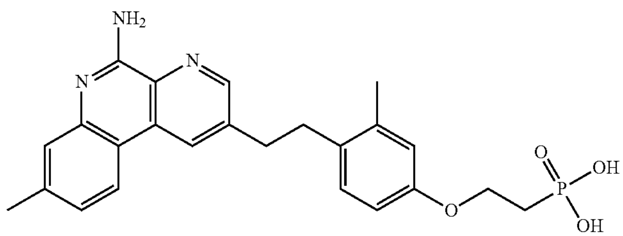 [SMILES: Cc1ccc2c(c1)nc(N)c1ncc(CCc3ccc(OCCP(=O)(O)O)cc3C)cc12] | (2-(4-(2-(5-amino-8-methylbenzo[f][1,7]naphthyridin-2-yl)ethyl)-3-methylphenoxy)ethyl)phosphonic acid |
| 23 | 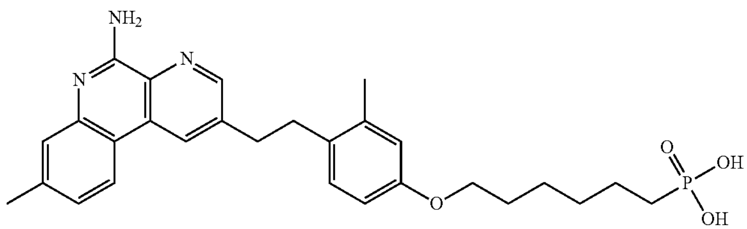 [SMILES: Cc1ccc2c(c1)nc(N)c1ncc(CCc3ccc(OCCCCCCP(=O)(O)O)cc3C)cc12] | (6-(4-(2-(5-amino-8-methylbenzo[f][1,7]naphthyridin-2-yl)ethyl)-3-methylphenoxy)hexyl)phosphonic acid |
| 24 | 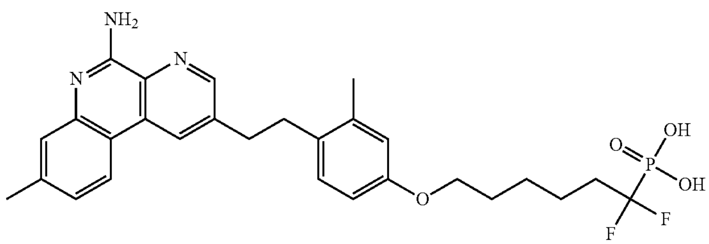 [SMILES: Cc1ccc2c(c1)nc(N)c1ncc(CCc3ccc(OCCCCCC(F)(F)P(=O)(O)O)cc3C)cc12] | (6-(4-(2-(5-amino-8-methylbenzo[f][1,7]naphthyridin-2-yl)ethyl)-3-methylphenoxy)-1,1-difluorohexyl)phosphonic acid |
| 25 | 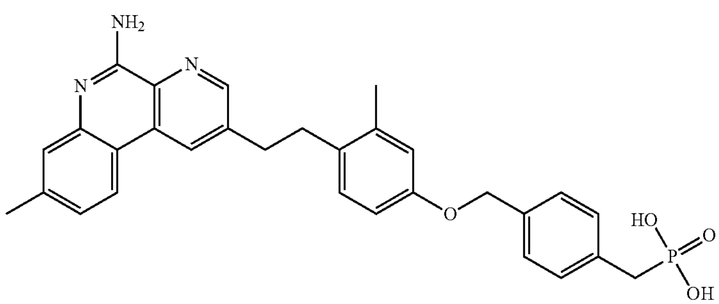 [SMILES: Cc1ccc2c(c1)nc(N)c1ncc(CCc3ccc(OCc4ccc(CP(=O)(O)O)cc4)cc3C)cc12] | (4-((4-(2-(5-amino-8-methylbenzo[f][1,7]naphthyridin-2-yl)ethyl)-3-methylphenoxy)methyl)benzyl)phosphonic acid |
| 26 | 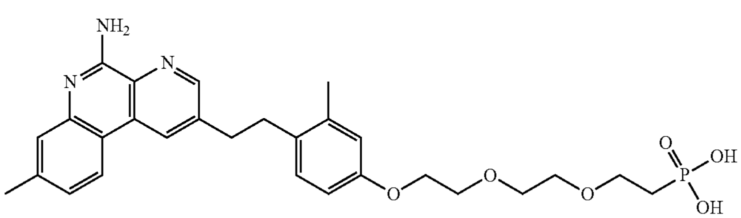 [SMILES: Cc1ccc2c(c1)nc(N)c1ncc(CCc3ccc(OCCOCCOCCP(=O)(O)O)cc3C)cc12] | (2-(2-(2-(4-(2-(5-amino-8-methylbenzo[f][1,7]naphthyridin-2-yl)ethyl)-3-methylphenoxy)ethoxy)ethoxy)ethyl)phosphonic acid |
| 27 | 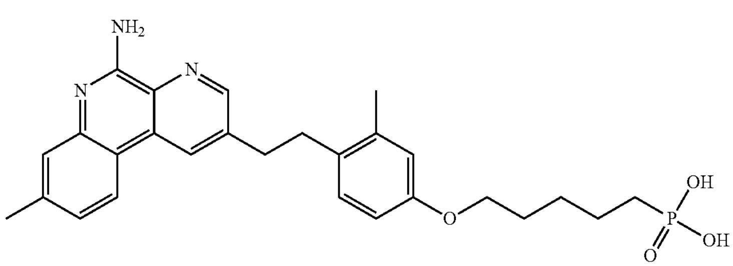 [SMILES: Cc1ccc2c(c1)nc(N)c1ncc(CCc3ccc(OCCCCCP(=O)(O)O)cc3C)cc12] | (5-(4-(2-(5-amino-8-methylbenzo[f][1,7]naphthyridin-2-yl)ethyl)-3-methylphenoxy)pentyl)phosphonic acid |

TABLE 1-continued

| Compound Number | Structure | Compound Name |
|---|---|---|
| 28 | 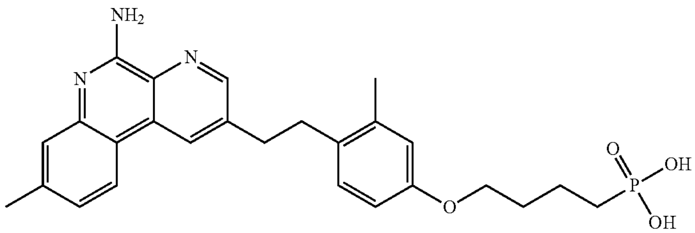 [SMILES: Cc1ccc2c(c1)nc(N)c1ncc(CCc3ccc(OCCCCP(=O)(O)O)cc3C)cc12] | (4-(4-(2-(5-amino-8-methylbenzo[f][1,7]naphthyridin-2-yl)ethyl)-3-methylphenoxy)butyl) phosphonic acid |

Embodiment 2. A pharmaceutical composition comprising a TLR7 agonist having the structure of Formula (A), or a pharmaceutically acceptable salt thereof, aluminum-containing particles, and one or more pharmaceutically acceptable excipients, wherein the TLR7 agonist is a compound selected from any one of the compounds of Table 1.

Embodiment 3. A pharmaceutical composition comprising a TLR7 agonist having the structure of Formula (A), or a pharmaceutically acceptable salt thereof, aluminum-containing particles, and one or more pharmaceutically acceptable excipients, wherein the TLR7 agonist is 3-(5-amino-2-(4-(2-(3,3-difluoro-3-phosphonopropoxy)ethoxy)-2-methylphenethyl)benzo[f][1,7]naphthyridin-8-yl)propanoic acid.

Embodiment 4. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and one or more pharmaceutically acceptable excipients.

Embodiment 5. A lyophilisate comprising a TLR7 agonist having the structure of Formula (A), or a pharmaceutically acceptable salt thereof, aluminum-containing particles, and one or more pharmaceutically acceptable excipients, wherein the TLR7 agonist is a compound selected from any one of the compounds of Table 1.

Embodiment 6. A lyophilisate comprising a TLR7 agonist having the structure of Formula (A), or a pharmaceutically acceptable salt thereof, aluminum-containing particles, and one or more pharmaceutically acceptable excipients, wherein the TLR7 agonist is 3-(5-amino-2-(4-(2-(3,3-difluoro-3-phosphonopropoxy)ethoxy)-2-methylphenethyl)benzo[f][1,7]naphthyridin-8-yl)propanoic acid.

Embodiment 7. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, and one or more pharmaceutically acceptable excipients.

Embodiment 8. A lyophilisate comprising a TLR7 agonist having the structure of Formula (A), or a pharmaceutically acceptable salt thereof and one or more pharmaceutically acceptable excipients, wherein the TLR7 agonist is 3-(5-amino-2-(4-(2-(3,3-difluoro-3-phosphonopropoxy)ethoxy)-2-methylphenethyl)benzo[f][1,7]naphthyridin-8-yl)propanoic acid.

Embodiment 9. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof and one or more pharmaceutically acceptable excipients.

Embodiment 10. A pharmaceutical composition comprising a compound having the structure of Formula (A), or a pharmaceutically acceptable salt thereof, a suspension of aluminum-containing particles, and one or more pharmaceutically acceptable excipients.

Embodiment 11. A pharmaceutical composition comprising a compound having the structure of Formula (A), or a pharmaceutically acceptable salt thereof, a suspension of aluminum-containing particles, and a buffering agent.

Embodiment 12. A pharmaceutical composition comprising a compound having the structure of Formula (A), or a pharmaceutically acceptable salt thereof, a suspension of aluminum-containing particles, a buffering agent, and one or more pharmaceutically acceptable excipients.

Embodiment 13. A pharmaceutical composition comprising a compound of Formula (A), or a pharmaceutically acceptable salt thereof, a suspension of aluminum-containing particles, and a buffering agent, wherein the composition has a pH in the range of 6.5 to 9.0.

Embodiment 14. A pharmaceutical composition comprising a compound of Formula (A), or a pharmaceutically acceptable salt thereof, a suspension of aluminum-containing particles, a buffering agent, and one or more pharmaceutically acceptable excipients, wherein the composition has a pH in the range of 6.5 to 9.0.

Embodiment 15. A pharmaceutical composition comprising a compound of Formula (A), or a pharmaceutically acceptable salt thereof, a suspension of aluminum-containing particles, and a buffering agent, wherein the composition has a pH in the range of 7.0 to 8.0.

Embodiment 16. A pharmaceutical composition comprising a compound of Formula (A), or a pharmaceutically acceptable salt thereof, a suspension of aluminum-containing particles, a buffering agent, and one or more pharmaceutically acceptable excipients, wherein the composition has a pH in the range of 7.0 to 8.0.

Embodiment 17. A pharmaceutical composition comprising a compound of Formula (A), or a pharmaceutically acceptable salt thereof, a suspension of aluminum-containing particles, a buffering agent, and sucrose, wherein the composition has a pH in the range of 7.0 to 8.0.

Embodiment 18. A pharmaceutical composition comprising a compound of Formula (A), or a pharmaceutically acceptable salt thereof, a suspension of aluminum-containing particles, a buffering agent, and mannitol, wherein the composition has a pH in the range of 7.0 to 8.0.

Embodiment 19. A pharmaceutical composition comprising a compound of Formula (A), or a pharmaceutically acceptable salt thereof, a suspension of aluminum hydroxide particles, and Tris buffer, wherein the composition has a pH in the range of 7.0 to 8.0.

Embodiment 20. A pharmaceutical composition comprising a compound of Formula (A), or a pharmaceutically acceptable salt thereof, a suspension of aluminum hydroxide particles, Tris buffer, and sucrose, wherein the composition has a pH in the range of 7.0 to 8.0.

Embodiment 21. A pharmaceutical composition comprising 0.5 to 2 mg/mL of a compound of Formula (A), or a pharmaceutically acceptable salt thereof, 5-100 mM Tris buffer, 5-10% (w/v) sucrose, and a suspension of aluminum hydroxide particles having an aluminum content of 1 to 4 mg/mL, wherein the composition has a pH in the range of 7.0 to 8.0

Embodiment 22. A pharmaceutical composition comprising 0.5 to 2 mg/mL of a compound of Formula (A), or a pharmaceutically acceptable salt thereof, 5-50 mM Tris buffer, 5-10% (w/v) sucrose, and a suspension of aluminum hydroxide particles having an aluminum content of 1 to 4 mg/mL, wherein the composition has a pH in the range of 7.0 to 8.0.

Embodiment 23. A pharmaceutical composition comprising 0.5 to 2 mg/mL of a compound of Formula (A), or a pharmaceutically acceptable salt thereof, 5-20 mM Tris buffer, 5-10% (w/v) sucrose, and a suspension of aluminum hydroxide particles having an aluminum content of 1 to 4 mg/mL, wherein the composition has a pH in the range of 7.0 to 8.0.

Embodiment 24. A pharmaceutical composition comprising 1 mg/mL of a compound of Formula (A), or a pharmaceutically acceptable salt thereof, 5-20 mM Tris buffer, 5-10% (w/v) sucrose, and a suspension of aluminum hydroxide particles having an aluminum content of 2 mg/mL, wherein the composition has a pH in the range of 7.0 to 8.0.

Embodiment 25. A pharmaceutical composition comprising 1 mg/mL of a compound of Formula (A), or a pharmaceutically acceptable salt thereof, 16 mM Tris buffer, 7.5% (w/v) sucrose, and a suspension of aluminum hydroxide particles having an aluminum content of 2 mg/mL, wherein the composition has a pH in the range of 7.0 to 8.0.

Embodiment 26. A pharmaceutical composition comprising 1 mg/mL of a compound of Formula (A), or a pharmaceutically acceptable salt thereof, 5 mM Tris buffer, 8.25% (w/v) sucrose, and a suspension of aluminum hydroxide particles having an aluminum content of 2 mg/mL, wherein the composition has a pH in the range of 7.0 to 8.0.

Embodiment 27. A pharmaceutical composition comprising 1 mg/mL of a compound of Formula (A), or a pharmaceutically acceptable salt thereof, 16 mM Tris buffer, 7.5% (w/v) sucrose, and a suspension of aluminum hydroxide particles having an aluminum content of 2 mg/mL, wherein the composition has a pH of 7.5+/−0.5.

Embodiment 28. A pharmaceutical composition comprising 1 mg/mL of a compound of Formula (A), or a pharmaceutically acceptable salt thereof, 5 mM Tris buffer, 8.25% (w/v) sucrose, and a suspension of aluminum hydroxide particles having an aluminum content of 2 mg/mL, wherein the composition has a pH of 7.5+/−0.5.

Embodiment 29. A pharmaceutical composition comprising 1 mg/mL of a compound of Formula (A), or a pharmaceutically acceptable salt thereof, 16 mM Tris buffer, 7.5% (w/v) sucrose, and a suspension of aluminum hydroxide particles having an aluminum content of 2 mg/mL, wherein the composition has a pH of 7.5+/−0.3.

Embodiment 30. A pharmaceutical composition comprising 1 mg/mL of a compound of Formula (A), or a pharmaceutically acceptable salt thereof, 5 mM Tris buffer, 8.25% (w/v) sucrose, and a suspension of aluminum hydroxide particles having an aluminum content of 2 mg/mL, wherein the composition has a pH of 7.5+/−0.3.

Embodiment 31. A pharmaceutical composition comprising a compound of Formula (A), or a pharmaceutically acceptable salt thereof, a suspension of aluminum hydroxide particles, Tris buffer, and mannitol, wherein the composition has a pH in the range of 7.0 to 8.0.

Embodiment 32. A pharmaceutical composition comprising 0.5 to 2 mg/mL of a compound of Formula (A), or a pharmaceutically acceptable salt thereof, 5-100 mM Tris buffer, 5-10% (w/v) mannitol, and a suspension of aluminum hydroxide particles having an aluminum content of 1 to 4 mg/mL, wherein the composition has a pH in the range of 7.0 to 8.0

Embodiment 33. A pharmaceutical composition comprising 0.5 to 2 mg/mL of a compound of Formula (A), or a pharmaceutically acceptable salt thereof, 5-50 mM Tris buffer, 5-10% (w/v) mannitol, and a suspension of aluminum hydroxide particles having an aluminum content of 1 to 4 mg/mL, wherein the composition has a pH in the range of 7.0 to 8.0.

Embodiment 34. A pharmaceutical composition comprising 0.5 to 2 mg/mL of a compound of Formula (A), or a pharmaceutically acceptable salt thereof, 5-20 mM Tris buffer, 5-10% (w/v) mannitol, and a suspension of aluminum hydroxide particles having an aluminum content of 1 to 4 mg/mL, wherein the composition has a pH in the range of 7.0 to 8.0.

Embodiment 35. A pharmaceutical composition comprising 1 mg/mL of a compound of Formula (A), or a pharmaceutically acceptable salt thereof, 5-20 mM Tris buffer, 5-10% (w/v) mannitol, and a suspension of aluminum hydroxide particles having an aluminum content of 2 mg/mL, wherein the composition has a pH in the range of 7.0 to 8.0.

Embodiment 36. A pharmaceutical composition comprising 1 mg/mL of a compound of Formula (A), or a pharmaceutically acceptable salt thereof, 16 mM Tris buffer, 7.5% (w/v) mannitol, and a suspension of aluminum hydroxide particles having an aluminum content of 2 mg/mL, wherein the composition has a pH in the range of 7.0 to 8.0.

Embodiment 37. A pharmaceutical composition comprising 1 mg/mL of a compound of Formula (A), or a pharmaceutically acceptable salt thereof, 5 mM Tris buffer, 8.25% (w/v) mannitol, and a suspension of aluminum hydroxide particles having an aluminum content of 2 mg/mL, wherein the composition has a pH in the range of 7.0 to 8.0.

Embodiment 38. A pharmaceutical composition comprising 1 mg/mL of a compound of Formula (A), or a pharmaceutically acceptable salt thereof, 16 mM Tris buffer, 7.5% (w/v) mannitol, and a suspension of aluminum hydroxide particles having an aluminum content of 2 mg/mL, wherein the composition has a pH of 7.5+/−0.5.

Embodiment 39. A pharmaceutical composition comprising 1 mg/mL of a compound of Formula (A), or a pharmaceutically acceptable salt thereof, 5 mM Tris buffer, 8.25% (w/v) mannitol, and a suspension of aluminum hydroxide particles having an aluminum content of 2 mg/mL, wherein the composition has a pH of 7.5+/−0.5.

Embodiment 40. A pharmaceutical composition comprising 1 mg/mL of a compound of Formula (A), or a pharmaceutically acceptable salt thereof, 16 mM Tris buffer, 7.5% (w/v) mannitol, and a suspension of aluminum hydroxide particles having an aluminum content of 2 mg/mL, wherein the composition has a pH of 7.5+/−0.3.

Embodiment 41. A pharmaceutical composition comprising 1 mg/mL of a compound of Formula (A), or a pharmaceutically acceptable salt thereof, 5 mM Tris buffer, 8.25% (w/v) mannitol, and a suspension of aluminum hydroxide particles having an aluminum content of 2 mg/mL, wherein the composition has a pH of 7.5+/−0.3.

Embodiment 42. The pharmaceutical composition of any one of Embodiments 10 to 41, wherein the compound of Formula (A) is a compound selected from any one of the compounds of Table 1, or a pharmaceutically acceptable salt thereof.

Embodiment 43. The pharmaceutical composition of any one of Embodiments 10 to 42, wherein the compound of Formula (A) is 3-(5-amino-2-(4-(2-(3,3-difluoro-3-phosphonopropoxy)ethoxy)-2-methylphenethyl)benzo[f][1,7]naphthyridin-8-yl)propanoic acid or 3-(5-amino-2-(2-methyl-4-(2-(2-(2-phosphonoethoxy)ethoxy)ethoxy)phenethyl)benzo[f][1,7]naphthyridin-8-yl)propanoic acid, or a pharmaceutically acceptable salt thereof.

Embodiment 44. The pharmaceutical composition of any one of Embodiments 10 to 42, wherein the compound of Formula (A) is 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof.

Embodiment 45. The pharmaceutical composition of any one of Embodiments 10 to 42, wherein the compound of Formula (A) is 3-(5-amino-2-(2-methyl-4-(2-(2-(2-phosphonoethoxy)ethoxy)ethoxy)phenethyl)benzo[f][1,7]naphthyridin-8-yl)propanoic acid, or a pharmaceutically acceptable salt thereof.

Embodiment 46. The pharmaceutical composition of any one of Embodiments 10 to 45, wherein the compound of Formula (A) is present in a therapeutically effective amount.

Embodiment 47. The pharmaceutical composition of any one of Embodiments 10 to 46, wherein the composition further comprises polyethylene glycol, polyoxyethylene sorbitan monooleate (Tween 80) or Pluronic F-68.

Embodiment 48. The pharmaceutical composition of any one of Embodiments 10 to 46, wherein the composition further comprises 1-2% of polyethylene glycol, polyoxyethylene sorbitan monooleate (Tween 80) or Pluronic F-68.

Embodiment 49. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, one or more pharmaceutically acceptable excipients and a suspension of aluminum-containing particles.

Embodiment 50. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and a suspension of aluminum-containing particles.

Embodiment 51. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent, one or more pharmaceutically acceptable excipients and a suspension of aluminum-containing particles.

Embodiment 52. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and a suspension of aluminum-containing particles, wherein the composition has a pH in the range of 6.5 to 9.0.

Embodiment 53. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent, one or more pharmaceutically acceptable excipients and a suspension of aluminum-containing particles, wherein the composition has a pH in the range of 6.5 to 9.0.

Embodiment 54. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and a suspension of aluminum-containing particles, wherein the composition has a pH in the range of 7.0 to 8.0.

Embodiment 55. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent, one or more pharmaceutically acceptable excipients and a suspension of aluminum-containing particles, wherein the composition has a pH in the range of 7.0 to 8.0.

Embodiment 56. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent, sucrose and a suspension of aluminum-containing particles, wherein the composition has a pH in the range of 7.0 to 8.0.

Embodiment 57. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent, mannitol and a suspension of aluminum-containing particles, wherein the composition has a pH in the range of 7.0 to 8.0.

Embodiment 58. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, Tris buffer, and a suspension of aluminum hydroxide particles.

Embodiment 59. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, Tris buffer, sucrose and a suspension of aluminum hydroxide particles, wherein the composition has a pH in the range of 7.0 to 8.0.

Embodiment 60. A pharmaceutical composition comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) sucrose, and a suspension of aluminum hydroxide particles having an aluminum content of 1 to 4 mg/mL, wherein the composition has a pH in the range of 7.0 to 8.0

Embodiment 61. A pharmaceutical composition comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-50 mM Tris buffer, 5-10% (w/v) sucrose, and a suspension of aluminum hydroxide particles having an aluminum content of 1 to 4 mg/mL, wherein the composition has a pH in the range of 7.0 to 8.0.

Embodiment 62. A pharmaceutical composition comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) sucrose, and a suspension of aluminum hydroxide particles having an aluminum content of 1 to 4 mg/mL, wherein the composition has a pH in the range of 7.0 to 8.0.

Embodiment 63. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) sucrose, and a suspension of aluminum hydroxide particles having an aluminum content of 2 mg/mL, wherein the composition has a pH in the range of 7.0 to 8.0.

Embodiment 64. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) sucrose, and a suspension of aluminum hydroxide particles having an aluminum content of 2 mg/mL, wherein the composition has a pH in the range of 7.0 to 8.0.

Embodiment 65. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) sucrose, and a suspension of aluminum hydroxide particles having an aluminum content of 2 mg/mL, wherein the composition has a pH in the range of 7.0 to 8.0.

Embodiment 66. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) sucrose, and a suspension of aluminum hydroxide particles having an aluminum content of 2 mg/mL, wherein the composition has a pH of 7.5+/−0.5.

Embodiment 67. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) sucrose, and a suspension of aluminum hydroxide particles having an aluminum content of 2 mg/mL, wherein the composition has a pH of 7.5+/−0.5.

Embodiment 68. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) sucrose, and a suspension of aluminum hydroxide particles having an aluminum content of 2 mg/mL, wherein the composition has a pH of 7.5+/−0.3.

Embodiment 69. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) sucrose, and a suspension of aluminum hydroxide particles having an aluminum content of 2 mg/mL, wherein the composition has a pH of 7.5+/−0.3.

Embodiment 70. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, Tris buffer, mannitol and a suspension of aluminum hydroxide particles, wherein the composition has a pH in the range of 7.0 to 8.0.

Embodiment 71. A pharmaceutical composition comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) mannitol, and a suspension of aluminum hydroxide particles having an aluminum content of 1 to 4 mg/mL, wherein the composition has a pH in the range of 7.0 to 8.0

Embodiment 72. A pharmaceutical composition comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-50 mM Tris buffer, 5-10% (w/v) mannitol, and a suspension of aluminum hydroxide particles having an aluminum content of 1 to 4 mg/mL, wherein the composition has a pH in the range of 7.0 to 8.0.

Embodiment 73. A pharmaceutical composition comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) mannitol, and a suspension of aluminum hydroxide particles having an aluminum content of 1 to 4 mg/mL, wherein the composition has a pH in the range of 7.0 to 8.0.

Embodiment 74. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) mannitol, and a suspension of aluminum hydroxide particles having an aluminum content of 2 mg/mL, wherein the composition has a pH in the range of 7.0 to 8.0.

Embodiment 75. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) mannitol, and a suspension of aluminum hydroxide particles having an aluminum content of 2 mg/mL, wherein the composition has a pH in the range of 7.0 to 8.0.

Embodiment 76. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) mannitol, and a suspension of aluminum hydroxide particles having an aluminum content of 2 mg/mL, wherein the composition has a pH in the range of 7.0 to 8.0.

Embodiment 77. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) mannitol, and a suspension of aluminum hydroxide particles having an aluminum content of 2 mg/mL, wherein the composition has a pH of 7.5+/−0.5.

Embodiment 78. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) mannitol, and a suspension of aluminum hydroxide particles having an aluminum content of 2 mg/mL, wherein the composition has a pH of 7.5+/−0.5.

Embodiment 79. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) mannitol, and a suspension of aluminum hydroxide particles having an aluminum content of 2 mg/mL, wherein the composition has a pH of 7.5+/−0.3.

Embodiment 80. A pharmaceutical composition comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) mannitol, and a suspension of aluminum hydroxide particles having an aluminum content of 2 mg/mL, wherein the composition has a pH of 7.5+/−0.3.

Embodiment 81. The pharmaceutical composition of any one of Embodiments 49 to 80, wherein the 3-(5-amino-2-(4-(2-(3,3-difluoro-3-phosphonopropoxy)ethoxy)-2-methylphenethyl)benzo[f][1,7]naphthyridin-8-yl)propanoic acid is present in a therapeutically effective amount.

Embodiment 82. The pharmaceutical composition of any one of Embodiments 49 to 81, wherein the composition further compises polyethylene glycol, polyoxyethylene sorbitan monooleate (Tween 80) or Pluronic F-68.

Embodiment 83. The pharmaceutical composition of any one of Embodiments 49 to 81, wherein the composition further compises 1-2% of polyethylene glycol, polyoxyethylene sorbitan monooleate (Tween 80) or Pluronic F-68.

Embodiment 84. A lyophilisate comprising a compound of Formula (A), or a pharmaceutically acceptable salt thereof, and one or more pharmaceutically acceptable excipients.

Embodiment 85. A lyophilisate comprising a compound of Formula (A), or a pharmaceutically acceptable salt thereof, and a buffering agent.

Embodiment 86. A lyophilisate comprising a compound of Formula (A), or a pharmaceutically acceptable salt thereof, a buffering agent and one or more pharmaceutically acceptable excipients.

Embodiment 87. A lyophilisate comprising a compound of Formula (A), or a pharmaceutically acceptable salt thereof and Tris buffer.

Embodiment 88. A lyophilisate comprising a compound of Formula (A), or a pharmaceutically acceptable salt thereof, Tris buffer and sucrose.

Embodiment 89. A lyophilisate comprising a compound of Formula (A), or a pharmaceutically acceptable salt thereof, Tris buffer and mannitol.

Embodiment 90. A lyophilisate prepared from a solution having a pH between 6.5 and 9.0 and comprising a compound of Formula (A), or a pharmaceutically acceptable salt thereof, and a buffering agent.

Embodiment 91. A lyophilisate prepared from a solution having a pH between 6.5 and 9.0 and comprising a compound of Formula (A), or a pharmaceutically acceptable salt thereof, a buffering agent and one or more pharmaceutically acceptable excipients.

Embodiment 92. A lyophilisate prepared from a solution having a pH between 7.0 and 8.0 and comprising a compound of Formula (A), or a pharmaceutically acceptable salt thereof, and a buffering agent.

Embodiment 93. A lyophilisate prepared from a solution having a pH between 7.0 and 8.0 and comprising a compound of Formula (A), or a pharmaceutically acceptable salt thereof, a buffering agent and one or more pharmaceutically acceptable excipients.

Embodiment 94. A lyophilisate prepared from a solution having a pH between 7.0 and 8.0 and comprising a compound of Formula (A), or a pharmaceutically acceptable salt thereof, a buffering agent and sucrose.

Embodiment 95. A lyophilisate prepared from a solution having a pH between 7.0 and 8.0 and comprising a compound of Formula (A), or a pharmaceutically acceptable salt thereof, a buffering agent and mannitol.

Embodiment 96. A lyophilisate prepared from a solution having a pH between 7.0 and 8.0 and comprising a compound of Formula (A), or a pharmaceutically acceptable salt thereof, and Tris buffer.

Embodiment 97. A lyophilisate prepared from a solution having a pH between 7.0 and 8.0 and comprising a compound of Formula (A), or a pharmaceutically acceptable salt thereof, Tris buffer and sucrose.

Embodiment 98. A lyophilisate prepared from a solution having a pH between 7.0 and 8.0 and comprising 0.5 to 2 mg/mL of a compound of Formula (A), or a pharmaceutically acceptable salt thereof, 5-100 mM Tris buffer and 5-10% (w/v) sucrose.

Embodiment 99. A lyophilisate prepared from a solution having a pH between 7.0 and 8.0 and comprising 0.5 to 2 mg/mL of a compound of Formula (A), or a pharmaceutically acceptable salt thereof, 5-50 mM Tris buffer and 5-10% (w/v) sucrose.

Embodiment 100. A lyophilisate prepared from a solution having a pH between 7.0 and 8.0 and comprising 0.5 to 2 mg/mL of a compound of Formula (A), or a pharmaceutically acceptable salt thereof, 5-20 mM Tris buffer and 5-10% (w/v) sucrose.

Embodiment 101. A lyophilisate prepared from a solution having a pH between 7.0 and 8.0 and comprising 1 mg/mL of a compound of Formula (A), or a pharmaceutically acceptable salt thereof, 5-20 mM Tris buffer and 5-10% (w/v) sucrose.

Embodiment 102. A lyophilisate prepared from a solution having a pH between 7.0 and 8.0 and comprising 1 mg/mL of a compound of Formula (A), or a pharmaceutically acceptable salt thereof, 16 mM Tris buffer and 7.5% (w/v) sucrose.

Embodiment 103. A lyophilisate prepared from a solution having a pH between 7.0 and 8.0 and comprising 1 mg/mL of a compound of Formula (A), or a pharmaceutically acceptable salt thereof, 5 mM Tris buffer and 8.25% (w/v) sucrose.

Embodiment 104. A lyophilisate prepared from a solution having a pH of 7.5+/−0.5 and comprising 1 mg/mL of a compound of Formula (A), or a pharmaceutically acceptable salt thereof, 16 mM Tris buffer and 7.5% (w/v) sucrose.

Embodiment 105. A lyophilisate prepared from a solution having a pH of 7.5+/−0.5 and comprising 1 mg/mL of a compound of Formula (A), or a pharmaceutically acceptable salt thereof, 5 mM Tris buffer and 8.25% (w/v) sucrose.

Embodiment 106. A lyophilisate prepared from a solution having a pH of 7.5+/−0.3 and comprising 1 mg/mL of a compound of Formula (A), or a pharmaceutically acceptable salt thereof, 16 mM Tris buffer and 7.5% (w/v) sucrose.

Embodiment 107. A lyophilisate prepared from a solution having a pH of 7.5+/−0.3 and comprising 1 mg/mL of a compound of Formula (A), or a pharmaceutically acceptable salt thereof, 5 mM Tris buffer and 8.25% (w/v) sucrose.

Embodiment 108. A lyophilisate prepared from a solution having a pH between 7.0 and 8.0 and comprising a compound of Formula (A), or a pharmaceutically acceptable salt thereof, Tris buffer and mannitol.

Embodiment 109. A lyophilisate prepared from a solution having a pH between 7.0 and 8.0 and comprising 0.5 to 2 mg/mL of a compound of Formula (A), or a pharmaceutically acceptable salt thereof, 5-100 mM Tris buffer and 5-10% (w/v) mannitol.

Embodiment 110. A lyophilisate prepared from a solution having a pH between 7.0 and 8.0 and comprising 0.5 to 2 mg/mL of a compound of Formula (A), or a pharmaceutically acceptable salt thereof, 5-50 mM Tris buffer and 5-10% (w/v) mannitol.

Embodiment 111. A lyophilisate prepared from a solution having a pH between 7.0 and 8.0 and comprising 0.5 to 2 mg/mL of a compound of Formula (A), or a pharmaceutically acceptable salt thereof, 5-20 mM Tris buffer and 5-10% (w/v) mannitol.

Embodiment 112. A lyophilisate prepared from a solution having a pH between 7.0 and 8.0 and comprising 1 mg/mL of a compound of Formula (A), or a pharmaceutically acceptable salt thereof, 5-20 mM Tris buffer and 5-10% (w/v) mannitol.

Embodiment 113. A lyophilisate prepared from a solution having a pH between 7.0 and 8.0 and comprising 1 mg/mL of a compound of Formula (A), or a pharmaceutically acceptable salt thereof, 16 mM Tris buffer and 7.5% (w/v) mannitol.

Embodiment 114. A lyophilisate prepared from a solution having a pH between 7.0 and 8.0 and comprising 1 mg/mL of a compound of Formula (A), or a pharmaceutically acceptable salt thereof, 5 mM Tris buffer and 8.25% (w/v) mannitol.

Embodiment 115. A lyophilisate prepared from a solution having a pH of 7.5+/−0.5 and comprising 1 mg/mL of a compound of Formula (A), or a pharmaceutically acceptable salt thereof, 16 mM Tris buffer and 7.5% (w/v) mannitol.

Embodiment 116. A lyophilisate prepared from a solution having a pH of 7.5+/−0.5 and comprising 1 mg/mL of a compound of Formula (A), or a pharmaceutically acceptable salt thereof, 5 mM Tris buffer and 8.25% (w/v) mannitol.

Embodiment 117. A lyophilisate prepared from a solution having a pH of 7.5+/−0.3 and comprising 1 mg/mL of a compound of Formula (A), or a pharmaceutically acceptable salt thereof, 16 mM Tris buffer and 7.5% (w/v) mannitol.

Embodiment 118. A lyophilisate prepared from a solution having a pH of 7.5+/−0.3 and comprising 1 mg/mL of a compound of Formula (A), or a pharmaceutically acceptable salt thereof, 5 mM Tris buffer and 8.25% (w/v) mannitol.

Embodiment 119. The lyophilisate of any one of Embodiments 84 to 118, wherein the compound of Formula (A) is a compound selected from any one of the compounds of Table 1, or a pharmaceutically acceptable salt thereof.

Embodiment 120. The lyophilisate of any one of Embodiments 84 to 118, wherein the compound of Formula (A) is 3-(5-amino-2-(4-(2-(3,3-difluoro-3-phosphonopropoxy) ethoxy)-2-methylphenethyl)benzo[f][1,7]naphthyridin-8-yl) propanoic acid or 3-(5-amino-2-(2-methyl-4-(2-(2-(2-phosphonoethoxy)ethoxy)ethoxy)phenethyl)benzo[f][1,7] naphthyridin-8-yl)propanoic acid, or a pharmaceutically acceptable salt thereof.

Embodiment 121. The lyophilisate of any one of Embodiments 84 to 118, wherein the compound of Formula (A) is 3-(5-amino-2-(4-(2-(3,3-difluoro-3-phosphonopropoxy) ethoxy)-2-methylphenethyl)benzo[f][1,7]naphthyridin-8-yl) propanoic acid, or a pharmaceutically acceptable salt thereof.

Embodiment 122. The lyophilisate of any one of Embodiments 84 to 118, wherein the compound of Formula (A) is 3-(5-amino-2-(2-methyl-4-(2-(2-(2-phosphonoethoxy) ethoxy)ethoxy)phenethyl)benzo[f][1,7]naphthyridin-8-yl) propanoic acid, or a pharmaceutically acceptable salt thereof.

Embodiment 123. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, and one or more pharmaceutically acceptable excipients.

Embodiment 124. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, and a buffering agent.

Embodiment 125. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and one or more pharmaceutically acceptable excipients.

Embodiment 126. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, and Tris buffer.

Embodiment 127. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, Tris buffer and sucrose.

Embodiment 128. A lyophilisate comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, Tris buffer and mannitol.

Embodiment 129. A lyophilisate prepared from a solution having a pH between 6.5 and 9.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, and a buffering agent.

Embodiment 130. A lyophilisate prepared from a solution having a pH between 6.5 and 9.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and one or more pharmaceutically acceptable excipients.

Embodiment 131. A lyophilisate prepared from a solution having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, and a buffering agent.

Embodiment 132. A lyophilisate prepared from a solution having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and one or more pharmaceutically acceptable excipients.

Embodiment 133. A lyophilisate prepared from a solution having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and sucrose.

Embodiment 134. A lyophilisate prepared from a solution having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a buffering agent and mannitol.

Embodiment 135. A lyophilisate prepared from a solution having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, and Tris buffer.

Embodiment 136. A lyophilisate prepared from a solution having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, Tris buffer and sucrose.

Embodiment 137. A lyophilisate prepared from a solution having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer and 5-10% (w/v) sucrose.

Embodiment 138. A lyophilisate prepared from a solution having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-50 mM Tris buffer and 5-10% (w/v) sucrose.

Embodiment 139. A lyophilisate prepared from a solution having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer and 5-10% (w/v) sucrose.

Embodiment 140. A lyophilisate prepared from a solution having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer and 5-10% (w/v) sucrose.

Embodiment 141. A lyophilisate prepared from a solution having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer and 7.5% (w/v) sucrose.

Embodiment 142. A lyophilisate prepared from a solution having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer and 8.25% (w/v) sucrose.

Embodiment 143. A lyophilisate prepared from a solution having a pH of 7.5+/−0.5 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer and 7.5% (w/v) sucrose.

Embodiment 144. A lyophilisate prepared from a solution having a pH of 7.5+/−0.5 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer and 8.25% (w/v) sucrose.

Embodiment 145. A lyophilisate prepared from a solution having a pH of 7.5+/−0.3 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer and 7.5% (w/v) sucrose.

Embodiment 146. A lyophilisate prepared from a solution having a pH of 7.5+/−0.3 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer and 8.25% (w/v) sucrose.

Embodiment 147. A lyophilisate prepared from a solution having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, Tris buffer and mannitol.

Embodiment 148. A lyophilisate prepared from a solution having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer and 5-10% (w/v) mannitol.

Embodiment 149. A lyophilisate prepared from a solution having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-50 mM Tris buffer and 5-10% (w/v) mannitol.

Embodiment 150. A lyophilisate prepared from a solution having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer and 5-10% (w/v) mannitol.

Embodiment 151. A lyophilisate prepared from a solution having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer and 5-10% (w/v) mannitol.

Embodiment 152. A lyophilisate prepared from a solution having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer and 7.5% (w/v) mannitol.

Embodiment 153. A lyophilisate prepared from a solution having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer and 8.25% (w/v) mannitol.

Embodiment 154. A lyophilisate prepared from a solution having a pH of 7.5+/−0.5 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer and 7.5% (w/v) mannitol.

Embodiment 155. A lyophilisate prepared from a solution having a pH of 7.5+/−0.5 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer and 8.25% (w/v) mannitol.

Embodiment 156. A lyophilisate prepared from a solution having a pH of 7.5+/−0.3 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer and 7.5% (w/v) mannitol.

Embodiment 157. A lyophilisate prepared from a solution having a pH of 7.5+/−0.3 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer and 8.25% (w/v) mannitol.

Embodiment 158. The lyophilisate of any one of Embodiments 84 to 157, further comprising aluminum-containing particles.

Embodiment 159. The lyophilisate of any one of Embodiments 84 to 157, further comprising aluminum hydroxide particles.

Embodiment 160. The lyophilisate of any one of Embodiments 84 to 159, further compising polyethylene glycol, polyoxyethylene sorbitan monooleate (Tween 80) or Pluronic F-68.

Embodiment 161. A pharmaceutical composition prepared by reconstituting a lyophilisate of any one of Embodiments 84 to 157, with water and admixing with a suspension of aluminum-containing particles having an aluminum content of 1 to 4 mg/mL.

Embodiment 162. A pharmaceutical composition prepared by reconstituting a lyophilisate of any one of Embodiments 84 to 157, with water and admixing with a suspension of aluminum hydroxide particles having an aluminum content of 1 to 4 mg/mL.

Embodiment 163. A pharmaceutical composition prepared by reconstituting a lyophilisate of any one of Embodiments 84 to 157, with water and admixing with a suspension of aluminum-containing particles having an aluminum content of 2 mg/mL.

Embodiment 164. A pharmaceutical composition prepared by reconstituting a lyophilisate of any one of Embodiments 84 to 157, with water and admixing with a suspension of aluminum hydroxide particles having an aluminum content of 2 mg/mL.

The aluminum-containing particles in the pharmaceutical compositions and certain lyophilisates of the invention may be present as a suspension. In general, the aluminum-containing particles are present as a 0.1-5% suspension. In certain embodiments, the aluminum-containing particles may be present as a 0.1-2% suspension. The size distribution of the aluminum-containing particles may be 0.1-20 micrometers. In certain embodiments the size distribution of the aluminum-containing particles may be 1-20 micrometers. In certain embodiments the size distribution of the aluminum-containing particles may be 2-10 micrometers. In other embodiments the aluminum-containing particles are a 0.3-0.4% suspension with a size distribution of 2-10 micrometers. Another embodiment is a 0.4% suspension of aluminum-containing particles with a size distribution of 2-10 micrometers. By way of example, the aluminum-containing particles in the pharmaceutical compositions and certain lyophilisates of the invention are aluminum hydroxide particles. In general the aluminum hydroxide particles are present as a 0.1-5% suspension, but preferably as a 0.1-2% suspension. The size distribution of the aluminum hydroxide articles is generally 1-20 micrometers, but preferably, the size distribution of the aluminum hydroxide particles is 2-10 micrometers. A certain embodiment the aluminum hydroxide particles are present as a 0.3-0.4% suspension with a size distribution of 2-10 micrometers. Another embodiment is a 0.4% suspension of aluminum hydroxide particles with a size distribution of 2-10 micrometers.

In certain embodiments, the aluminum-containing particleas are aluminum hydroxide particleas and compounds of Formula (A) are bound/adsorbed to aluminum hydroxide particles. In still other embodiments the aluminum-containing particles are aluminum hydroxide particles and the compound is 3-(5-amino-2-(4-(2-(3,3-difluoro-3-phosphonopropoxy)ethoxy)-2-methylphenethyl)benzo[f][1,7]naphthyridin-8-yl)propanoic acid, wherein 3-(5-amino-2-(4-(2-(3,3-difluoro-3-phosphonopropoxy)ethoxy)-2-methylphenethyl)benzo[f][1,7]naphthyridin-8-yl)propanoic acid is bound/adsorbed to the aluminum hydroxide particles.

Binding Efficiency of Compounds of Formula (A) to Aluminum-Containing Particles

The compounds of Formula (A) in the pharmaceutical compositions and lyophilisates of the invention can bind to aluminum-containing particles, such as, by way of example only, aluminum hydroxide particles, aluminum oxyhydroxide particles and aluminum hydroxyphosphate particles. Compounds of Formula (A) have either a phosphate or a phosphonate (ionized phosphonic acid), with certain compounds of Formula (A) having an additional ionizable groups, such as a carboxylic acid. The compounds of Formula (A) may bind/adsorb to aluminum-containing particles via ionic interactions between the aluminium ions of the aluminum-containing particle and the phosphate or phosphonate group of the compound of Formula (A).

The efficiency of binding of compounds of Formula (A) to an aluminum-containing particle, as reflected in the percentage (%) bound to an aluminum-containing particle, is a function of the (weight/weight) ratio of weight of compound to weight of aluminum of the aluminum-containing particles. In addition, depending on the (w/w) ratio, the binding efficiency has an apparent pH dependence. Binding/Adsorption of compounds of Formula (A) to aluminum-containing particles is mediated via ionic charge interactions between aluminium ions and the phosphate or phosphonate group of the compound of Formula (A). Binding/Adsorption is best accomplished in the pH interval between the point of zero charge (PZC) of the compound of Formula (A) and the PZC of the aluminum-containing particle. The adsorption of compounds of Formula (A) to aluminum-containing particles is demonstrated in Example 3 and Example 4. Example 4 illustrates the dependence of binding efficiency on the (w/w) ratio of the weight of aluminum of the aluminum-containing particles to the weight of compound, and the pH dependence. Furthermore, at a fixed aluminum to compound ratio, the binding efficiency may depend on the final concentration of the compound of Formula (A) at values below 0.5 mg/mL.

In certain embodiments the efficiency of binding of a compound of Formula (A) to aluminum-containing particles is 75-100%. In other embodiments the efficiency of binding of a compound of Formula (A) to aluminum-containing particles is 80-100%. In further embodiments the efficiency of binding of a compound of Formula (A) to aluminum-containing particles is 95-100%. In further embodiments the efficiency of binding of a compound of Formula (A) to aluminum-containing particles is 97-100%. In further embodiments the efficiency of binding of a compound of Formula (A) to aluminum-containing particles is 98-100%.

In certain embodiments the aluminum-containing particles are aluminum hydroxide particles and the efficiency of binding of a compound of Formula (A) to aluminum hydroxide particles is 75-100%. In other embodiments the aluminum-containing particles are aluminum hydroxide particles and the efficiency of binding of the compound of Formula (A) to aluminum hydroxide particles is 80-100%. In further embodiments the aluminum-containing particles are aluminum hydroxide particles and the efficiency of binding of the compound of Formula (A) to aluminum hydroxide particles is 95-100%. In further embodiments the aluminum-containing particles are aluminum hydroxide particles and the efficiency of binding of the compound of Formula (A) to aluminum hydroxide particles is 97-100%. In further embodiments the aluminum-containing particles are aluminum hydroxide particles and the efficiency of binding of the compound of Formula (A) to aluminum hydroxide particles is 98-100%.

In another embodiment the aluminum-containing particles are aluminum hydroxide particles and the compound is 3-(5-amino-2-(4-(2-(3,3-difluoro-3-phosphonopropoxy)ethoxy)-2-methylphenethyl)benzo[f][1,7]naphthyridin-8-yl)propanoic acid, wherein the efficiency of binding of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide particles is 95-100%. In a further embodiment the aluminum-containing particles are aluminum hydroxide particles and the compound is 3-(5-amino-2-(4-(2-(3,3-difluoro-3-phosphonopropoxy)ethoxy)-2-methylphenethyl)benzo[f][1,7]naphthyridin-8-yl)propanoic acid, wherein the efficiency of binding of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide particles is 97-100%. In the embodiment the aluminum-containing particles are aluminum hydroxide and the compound is 3-(5-amino-2-(4-(2-(3,3-difluoro-3-phosphonopropoxy)ethoxy)-2-methylphenethyl)benzo[f][1,7]naphthyridin-8-yl)propanoic acid, wherein the efficiency of binding of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide particles is 98-100%.

In general, a binding efficiency of about 75%-100% for binding of a compound of Formula (A) to an aluminum-containing particles, may be obtained with a (w/w) ratio of the weight of aluminum in the aluminum-containing particles to the weight of compound of Formula (A) in the range from about 0.8:1 to about 2.5:1. In certain embodiments binding efficiencies in the range of 80%-100% may be obtained with a (w/w) ratio of aluminum in the aluminum-containing particles to a compound of Formula (A) in the range from 1:1 to 2.5:1. In other embodiments binding efficiencies in the range of 90%-100% may be obtained with a (w/w) ratio of aluminum in the aluminum-containing particles to a compound of Formula (A) in the range from 1.25:1 to 2.5:1. In other embodiments binding efficiencies in the range of 97%-100% may be obtained with a (w/w) ratio of aluminum in the aluminum-containing particles to a compound of Formula (A) in the range from 1.5:1 to 2.5:1. In other embodiments binding efficiencies in the range of 97%-100% may be obtained with a (w/w) ratio of aluminum in the aluminum-containing particles to a compound of Formula (A) in the range from 1.5:1 to 2:1. In other embodiments binding efficiencies in the range of 98%-100% may be obtained with a (w/w) ratio of aluminum in the aluminum-containing particles to a compound of Formula (A) in the range from 1.5:1 to 2:1.

In general, a binding efficiency of about 75%-100% for binding of 3-(5-amino-2-(4-(2-(3,3-difluoro-3-phosphonopropoxy)ethoxy)-2-methylphenethyl)benzo[f][1,7]naphthyridin-8-yl)propanoic to aluminum-containing particles, may be obtained with a (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from about 0.8:1 to about 2.5:1. In certain embodiments binding efficiencies in the range of 80%-100% may be obtained with a (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1:1 to 2.5:1. In other embodiments binding efficiencies in the range of 90%-100% may be obtained with a (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1.25:1 to 2.5:1. In other embodiments binding efficiencies in the range of 97%-100% may be obtained with a (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1.5:1 to 2.5:1. In other embodiments binding efficiencies in the range of 97%-100% may be obtained with a (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1.5:1 to 2:1. In other embodiments binding efficiencies in the range of 98%-100% may be obtained with a (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1.5:1 to 2:1.

In general, a binding efficiency of about 75%-100% for binding of 3-(5-amino-2-(4-(2-(3,3-difluoro-3-phosphonopropoxy)ethoxy)-2-methylphenethyl)benzo[f][1,7]naphthyridin-8-yl)propanoic to aluminum hydroxide particles, may be obtained with a (w/w) ratio of the weight of aluminum in the aluminum hydroxide particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from about 0.8:1 to about 2.5:1. In certain embodiments binding efficiencies in the range of 80%-100% may be obtained with a (w/w) ratio of the weight of aluminum in the aluminum hydroxide particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1:1 to 2.5:1. In other embodiments binding efficiencies in the range of 90%-100% may be obtained with a (w/w) ratio of the weight of aluminum in the aluminum hydroxide particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1.25:1 to 2.5:1. In other embodiments binding efficiencies in the range of 97%-100% may be obtained with a (w/w) ratio of the weight of aluminum in the aluminum hydroxide particles to the weight of 3-(5-amino-2-(4-(2-(3,3-difluoro-3-phosphonopropoxy)

ethoxy)-2-methylphenethyl)benzo[f][1,7]naphthyridin-8-yl)propanoic in the range from 1.5:1 to 2.5:1. In other embodiments binding efficiencies in the range of 97%-100% may be obtained with a (w/w) ratio of the weight of aluminum in the aluminum hydroxide particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1.5:1 to 2:1. In other embodiments binding efficiencies in the range of 98%-100% may be obtained with a (w/w) ratio of the weight of aluminum in the aluminum hydroxide particles to the weight of 3-(5-amino-2-(4-(2-(3,3-difluoro-3-phosphonopropoxy)ethoxy)-2-methylphenethyl)benzo[f][1,7]naphthyridin-8-yl)propanoic in the range from 1.5:1 to 2:1.

A preferred (w/w) ratio of the weight of aluminum in the aluminum-containing particles to the weight of a compound of Formula (A) is 1.5:1, while the most preferred (w/w) ratio of the weight of aluminum in the aluminum-containing particles to the weight of a compound of Formula (A) is 2:1.

A preferred (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic acid is 1.5:1, while the most preferred (w/w) ratio of the weight of aluminum in the aluminum-containing particles to the weight of 3-(5-amino-2-(4-(2-(3,3-difluoro-3-phosphonopropoxy)ethoxy)-2-methylphenethyl)benzo[f][1,7]naphthyridin-8-yl)propanoic acid is 2:1.

A preferred (w/w) ratio of the weight of aluminum in the aluminum hydroxide particles to the weight of a compound of Formula (A) is 1.5:1, while the most preferred (w/w) ratio of the weight of aluminum in the aluminum hydroxide particles to the weight of a compound of Formula (A) is 2:1.

A preferred (w/w) ratio of the weight of aluminum in the aluminum hydroxide particles to the weight of 3-(5-amino-2-(4-(2-(3,3-difluoro-3-phosphonopropoxy)ethoxy)-2-methylphenethyl)benzo[f][1,7]naphthyridin-8-yl)propanoic acid is 1.5:1, while the most preferred (w/w) ratio of the weight of aluminum in the aluminum hydroxide particles to the weight of 3-(5-amino-2-(4-(2-(3,3-difluoro-3-phosphonopropoxy)ethoxy)-2-methylphenethyl)benzo[f][1,7]naphthyridin-8-yl)propanoic acid is 2:1.

In certain embodiments the pH used for binding/adsorbing compounds of Formula (A) to aluminum-containing particles is in the range of pH 6.5 to pH 9.0. In certain embodiments the pH used for binding/adsorbing compounds of Formula (A) to aluminum-containing particles is in the range of pH 7 to pH 8. In preferred embodiments the pH used for binding/adsorbing compounds of Formula (A) to aluminum-containing particles is in the range of pH 7.2 to pH 7.8. In preferred embodiments the pH used for binding/adsorbing compounds of Formula (A) to aluminum-containing particles is pH 7.5+/−0.5. In the most preferred embodiment the pH used for binding/adsorbing compounds of Formula (A) to aluminum-containing particles is pH 7.5+/−0.3.

Accordingly, the binding/adsorption of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum-containing particles is mediated via ionic charge interactions between aluminium ions and the phosphonate group (ionized phosphonic acid) of 3-(5-amino-2-(4-(2-(3,3-difluoro-3-phosphonopropoxy)ethoxy)-2-methylphenethyl)benzo[f][1,7]naphthyridin-8-yl)propanoic acid. Thus, the binding/adsorption of 3-(5-amino-2-(4-(2-(3,3-difluoro-3-phosphonopropoxy)ethoxy)-2-methylphenethyl)benzo[f][1,7]naphthyridin-8-yl)propanoic acid is more efficient in the pH interval between the point of zero charge (PZC) of 3-(5-amino-2-(4-(2-(3,3-difluoro-3-phosphonopropoxy)ethoxy)-2-methylphenethyl)benzo[f][1,7]naphthyridin-8-yl)propanoic acid and the PZC of the aluminum-containing particle. In certain embodiments the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to an aluminum-containing particles is in the range of pH 6.5 to pH 9. In certain embodiments the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to an aluminum-containing particles is in the range of pH 7 to pH 8. In a more preferred embodiment the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to an aluminum-containing particles is in the range of pH 7.2 to pH 7.8. In preferred embodiment the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to an aluminum-containing particles is pH 7.5+/−0.5. In preferred embodiment the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to an aluminum-containing particles is pH 7.5+/−0.3.

In preferred embodiments the aluminum-containing particles are aluminum hydroxide particles and accordingly the binding/adsorption of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide particles is mediated via ionic charge interactions between aluminium ions and the phosphonate group (ionized phosphonic acid) of 3-(5-amino-2-(4-(2-(3,3-difluoro-3-phosphonopropoxy)ethoxy)-2-methylphenethyl)benzo[f][1,7]naphthyridin-8-yl)propanoic acid. Thus, the binding/adsorption is more efficient in the pH interval between the point of zero charge (PZC) of 3-(5-amino-2-(4-(2-(3,3-difluoro-3-phosphonopropoxy)ethoxy)-2-methylphenethyl)benzo[f][1,7]naphthyridin-8-yl)propanoic acid and the PZC of the aluminum hydroxide particles. In certain embodiments the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide particles is in the range of pH 6.5 to pH 9. In certain embodiments the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide particles is in the range of pH 7 to pH 8. In a more preferred embodiment the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide particles is in the range of pH 7.2 to pH 7.8. In preferred embodiment the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide is pH 7.5+/−0.5. In preferred embodiment the pH used for the binding/adsorbtion of 3-(5-amino-2-(4-(2-(3,3-difluoro-3-phosphonopropoxy)ethoxy)-2-methylphenethyl)benzo[f][1,7]naphthyridin-8-yl)propanoic acid to aluminum hydroxide is pH 7.5+/−0.3.

Administration-Injection Site Retention

The pharmaceutical compositions of the invention comprising a compound of Formula (A), or a pharmaceutically acceptable salt thereof, may be administered by injection, specifically intratumorally (intratumoral injection), intramuscularly (intramuscular injection), intradermally (intradermal injection) or subcutaneously (subcutaneous injection). In certain embodiments pharmaceutical compositions of the invention comprising a compound of Formula (A), or a pharmaceutically acceptable salt thereof, is administered intratumorally, while in other embodiments, pharmaceutical compositions of the invention comprising a compound of Formula (A), or a pharmaceutically acceptable salt thereof is administered subcutaneously. In certain embodiments of intratumoral administration the pharmaceutical compositions of the invention comprising a compound of Formula (A), or a pharmaceutically acceptable salt thereof, may be administered/injected into the peritumoral region surrounding a tumor. The peritumoral region may contain antitumor immune cells.

The binding of compounds of Formula (A) to aluminum-containing particles increases the retention of the compound of Formula (A) at the site of injection site, which decreases clearance of the compound and increases the half-life of the compound and thereby decreasing systemic exposure. In addition, retention at the tumor site may lead to improved immune priming and reduced systemic inflammation when compared to the systemic administration of unbound (free) compounds of Formula (A), or a pharmaceutically acceptable salt thereof. Thus, the slow release of a compound of Formula (A) is considered beneficial for both efficacy and safety because it minimizes potential systemic adverse effects by a TLR7 agonist and increases drug retention in local tumor environment. The plasma concentration-time profiles obtained after intratumoral injection of Compound 15, either free or bound to aluminum hydroxide, are shown in Example 5 to illustrate this depot effect.

Unexpectedly it was found that systemic exposure to aluminum after administration of Compound 15 bound to aluminum hydroxide was significantly lower than systemic exposure after administration of aluminum hydroxide alone (see Example 11).

Pharmacology and Utility

The pharmaceutical compositions of the invention may produce an immune response to a tumor in a subject. Accordingly, the invention provides methods for treating a solid tumor by producing an immune response to the solid tumor in a subject. Additionally, the invention provides methods for treating a liquid tumor by producing an immune response to the tumor in a subject.

One aspect of the invention is a method for treating a solid tumor by administering to a subject in need thereof a pharmaceutical composition of any one of Embodiments 1 to 83 or 161 to 164.

One aspect of the invention is a method for treating a solid tumor by intratumorally administering to a subject in need thereof a pharmaceutical composition of any one of Embodiments 1 to 83 or 161 to 164.

One aspect of the invention is a method for treating a solid tumor by administering to a subject in need thereof a pharmaceutical composition comprising a TLR7 agonist compound having the structure of Formula (A), or a pharmaceutically acceptable salt thereof, aluminum-containing particles and one or more pharmaceutically acceptable excipients.

One aspect of the invention is a method for treating a solid tumor by administering to a subject in need thereof a pharmaceutical composition comprising a TLR7 agonist compound of Table 1, or a pharmaceutically acceptable salt thereof, aluminum-containing particles and one or more pharmaceutically acceptable excipients.

Another aspect of the invention is the use of a pharmaceutical composition of any one of Embodiments 1 to 83 or 161 to 164 for treating a solid tumor.

Another aspect of the invention is the use of a pharmaceutical composition comprising a TLR7 agonist compound having the structure of Formula (A), or a pharmaceutically acceptable salt thereof, aluminum-containing particles and one or more pharmaceutically acceptable excipients for treating a solid tumor.

Another aspect of the invention is the use of a pharmaceutical composition comprising a TLR7 agonist compound of Table 1, or a pharmaceutically acceptable salt thereof, aluminum-containing particles and one or more pharmaceutically acceptable excipients for treating a solid tumor.

Another aspect of the invention is a pharmaceutical composition of any one of Embodiments 1 to 83 or 161 to 164 for use in the treatment of a solid tumor.

Another aspect of the invention is a pharmaceutical composition comprising a TLR7 agonist compound having the structure of Formula (A), or a pharmaceutically acceptable salt thereof, aluminum-containing particles and one or more pharmaceutically acceptable excipients for use in treating a solid tumor.

Another aspect of the invention is a pharmaceutical composition comprising a TLR7 agonist compound of Table 1, or a pharmaceutically acceptable salt thereof, aluminum-containing particles and one or more pharmaceutically acceptable excipients for use in treating a solid tumor.

The invention provides methods for treating a solid tumor by administering, either intratumorally, intramuscularly, intradermally or subcutaneously, a pharmaceutical composition of any one of Embodiments 1 to 83 or 161 to 164.

The invention further provides methods for treating a solid tumor by administering, either intratumorally, intramuscularly, intradermally or subcutaneously, a pharmaceutical composition disclosed herein comprising a compound of Formula (A), or a pharmaceutically acceptable salt thereof, aluminum-containing particles and one or more pharmaceutically acceptable excipients.

Another aspect of the invention is a method for treating a solid tumor by intratumorally administering to a subject in need thereof a pharmaceutical composition comprising a TLR7 agonist compound having the structure of Formula (A), or a pharmaceutically acceptable salt thereof, aluminum-containing particles and one or more pharmaceutically acceptable excipients.

Another aspect of the invention is a method for treating a solid tumor by intratumorally administering to a subject in need thereof a pharmaceutical composition comprising a TLR7 agonist compound of Table 1, or a pharmaceutically acceptable salt thereof, aluminum-containing particles and one or more pharmaceutically acceptable excipients.

The solid tumors which may be treatable by such methods and uses include, but are not limited to, a breast cancer tumor, a bladder cancer tumor, a head and neck cancer tumor, a non-small cell lung cancer tumor, a small cell lung cancer tumor, a colorectal cancer tumor, a gastrointestinal stromal tumor, a gastroesophageal carcinoma, a renal cell cancer tumor, a prostate cancer tumor, a liver cancer tumor, a colon cancer tumor, a pancreatic cancer tumor, an ovarian cancer tumor, a lymphoma, a cutaneous T-cell lymphoma, or a melanoma.

Large solid tumors become infiltrated by a subpopulation of myeloid derived suppressor cells (mMDSC) that suppress anti-tumor immunity. In some embodiments, the invention provides a method for treating an immune suppressed tumor. An immune suppressed tumor is a tumor that contains immune suppressive associated cells such as for example T Reg cells, myeloid derived suppressor cells (MDSC), M2 macrophages, and the like or immune suppressive factors such as inducible nitric oxide synthase (iNOS), PD-L1, and the like.

The amount of a compound of Formula (A), or a pharmaceutically acceptable salt thereof, incorporated in a pharmaceutical composition of the invention, which is the used in a method or use of the invention, may vary according to factors known in art such as for example, the physical and clinical status of the subject, the method of administration, the content of the formulation, the intended dosing regimen or sequence. In consideration of such factors the appropriate amount incorporated can be readily determined by one of ordinary skill in the art. By way of example, the pharmaceutical composition of the invention may include an amount of a compound of Formula (A), or a pharmaceutically acceptable salt thereof, to provide a dose of a compound of Formula (A), or a pharmaceutically acceptable salt thereof, to a subject from about 0.05 mg to about 5 mg. Preferably the pharmaceutical composition of the invention includes an amount of a compound of Formula (A), or a pharmaceutically acceptable salt thereof, which provides a dose of a compound of Formula (A), or a pharmaceutically acceptable salt thereof, to a subject from about 0.1 mg to about 1 mg.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen.

Examples of dosing schedules for the administration of a compound of Formula (A), or a pharmaceutically acceptable salt thereof, adsorbed to aluminum hydroxide, either alone as a single agent or in combination with one or more additional therapeutic agents, are administration once a week, twice a week, three times a week or once a month during a cycle period, with such administration occurring over 1, 2, 3, 4, 5, 6, 7, 8, 9 or 10 cycle periods.

A cycle period is the number and timing or recommended repetitions of therapy and are usually expressed as number of days. Examples of a cycle period include every 15 days, 16 days, 17 days, 18 days, 19 days, 20 days, 21 days, 22 days, 23 days, 24 days, 25 days, 26 days, 27 days, 28 days, 29 days, 30 days or 31 days.

A dosing schedule can include a dose delay (pause), wherein a compound of Formula (A), or a pharmaceutically acceptable salt thereof, adsorbed to aluminum hydroxide is administered during cycle 1 and wherein a compound of Formula (A), or a pharmaceutically acceptable salt thereof, adsorbed to aluminum hydroxide is not administered during one or more subsequent cycle periods.

By way of example, during a nine cycle dosing schedule a compound of Formula (A), or a pharmaceutically acceptable salt thereof, adsorbed to aluminum hydroxide is administered during cycles 1, 3, 5, 7 and 9, with a dose delay (pause) during cycles 2, 4, 6, and 8 wherein a compound of Formula (A), or a pharmaceutically acceptable salt thereof, adsorbed to aluminum hydroxide is not administered.

By way of another example, during an eight cycle dosing schedule a compound of Formula (A), or a pharmaceutically acceptable salt thereof, adsorbed to aluminum hydroxide is administered during cycles 1, 2, 4, 5, 7 and 8, with a dose delay (pause) during cycles 3 and 6 wherein a compound of Formula (A), or a pharmaceutically acceptable salt thereof, adsorbed to aluminum hydroxide is not administered.

By way of a further example, during a six cycle dosing schedule a compound of Formula (A), or a pharmaceutically acceptable salt thereof, adsorbed to aluminum hydroxide is administered during cycles 1, 2, 5 and 6, with a dose delay (pause) during cycles 3 and 4 wherein a compound of Formula (A), or a pharmaceutically acceptable salt thereof, adsorbed to aluminum hydroxide is not administered. By way of example a six cycle dosing schedule for the administration of a compound of Formula (A), or a pharmaceutically acceptable salt thereof, adsorbed to aluminum hydroxide, either alone as a single agent or in combination with one or more additional therapeutic agents, a compound of Formula (A), or a pharmaceutically acceptable salt thereof, adsorbed to aluminum hydroxide can be administered by intratumoral injection on Days 1 and 15 (biweekly schedule) or Day 1 only (monthly schedule) during a 28-day cycle. Intratumoral administration occurs in Cycles 1 and 2, followed by a two cycle dosing delay (Cycles 3 and 4), and then repeat injections on Days 1 and 15 (biweekly schedule) or Day 1 only (monthly schedule) for Cycles 5 and 6. The dose of a compound of Formula (A), or a pharmaceutically acceptable salt thereof, administered during the six cycle schedule can be from about 0.1 mg to about 1 mg, or from about 0.1 mg to about 0.6 mg.

While the disclosed methods and uses of such compositions will typically be used to treat human subjects they may also be used to treat similar or identical diseases in other vertebrates, such as other primates, dogs, cats, horses, and cows.

Certain aspects and examples of the pharmaceutical composition uses, uses of the pharmaceutical compositions, and the methods of the invention are provided in the following listing of additional, enumerated embodiments. It will be recognized that features specified in each embodiment may be combined with other specified features to provide further embodiments of the present invention.

Embodiment 165. A method for treating a solid tumor by administering to a subject in need thereof a pharmaceutical composition of any one of Embodiments 1 to 83 or 161 to 164.

Embodiment 166. A method for treating a solid tumor by intratumorally administering to a subject in need thereof a pharmaceutical composition of any one of Embodiments 1 to 83 or 161 to 164.

Embodiment 167. A method for treating a solid tumor by administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and one or more pharmaceutically acceptable excipients.

Embodiment 168. A method for treating a solid tumor by administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles and one or more pharmaceutically acceptable excipients.

Embodiment 169. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles and one or more pharmaceutically acceptable excipients.

Embodiment 170. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and a buffering agent.

Embodiment 171. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles a buffering agent and one or more pharmaceutically acceptable excipients.

Embodiment 172. A method for treating a solid tumor by intratumorally administering to a subject in need thereof a pharmaceutical composition having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and a buffering agent.

Embodiment 173. A method for treating a solid tumor by intratumorally administering to a subject in need thereof a pharmaceutical composition having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic, or a pharmaceutically acceptable salt thereof, aluminum-containing particles, a buffering agent and sucrose.

Embodiment 174. A method for treating a solid tumor by intratumorally administering to a subject in need thereof a pharmaceutical composition having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic, or a pharmaceutically acceptable salt thereof, aluminum-containing particles, a buffering agent and mannitol.

Embodiment 175. A method for treating a solid tumor by intratumorally administering to a subject in need thereof a pharmaceutical composition having a pH between 7.0 and 8.0 comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles and Tris buffer.

Embodiment 176. A method for treating a solid tumor by intratumorally administering to a subject in need thereof a pharmaceutical composition having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and sucrose.

Embodiment 177. A method for treating a solid tumor by intratumorally administering to a subject in need thereof a pharmaceutical composition having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose.

Embodiment 178. A method for treating a solid tumor by intratumorally administering to a subject in need thereof a pharmaceutical composition having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose.

Embodiment 179. A method for treating a solid tumor by intratumorally administering to a subject in need thereof a pharmaceutical composition having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose.

Embodiment 180. A method for treating a solid tumor by intratumorally administering to a subject in need thereof a pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5-20 mM Tris buffer and 5-10% (w/v) sucrose.

Embodiment 181. A method for treating a solid tumor by intratumorally administering to a subject in need thereof a pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL of aluminum hydroxide, 16 mM Tris buffer and 7.5% (w/v) sucrose.

Embodiment 182. A method for treating a solid tumor by intratumorally administering to a subject in need thereof a pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL of aluminum hydroxide, 5 mM Tris buffer and 8.25% (w/v) sucrose.

Embodiment 183. A method for treating a solid tumor by intratumorally administering to a subject in need thereof a pharmaceutical composition having a pH between 7.0 and 8.0 and comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and mannitol.

Embodiment 184. A method for treating a solid tumor by intratumorally administering to a subject in need thereof a pharmaceutical composition having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol.

Embodiment 185. A method for treating a solid tumor by intratumorally administering to a subject in need thereof a pharmaceutical composition having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol.

Embodiment 186. A method for treating a solid tumor by intratumorally administering to a subject in need thereof a pharmaceutical composition having a pH between 7.0 and 8.0 and comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol.

Embodiment 187. A method for treating a solid tumor by intratumorally administering to a subject in need thereof a pharmaceutical composition having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5-20 mM Tris buffer and 5-10% (w/v) mannitol.

Embodiment 188. A method for treating a solid tumor by intratumorally administering to a subject in need thereof a pharmaceutical composition having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL of aluminum hydroxide, 16 mM Tris buffer and 7.5% (w/v) mannitol.

Embodiment 189. A method for treating a solid tumor by intratumorally administering to a subject in need thereof a pharmaceutical composition having a pH between 7.0 and 8.0 and comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL of aluminum hydroxide, 5 mM Tris buffer and 8.25% (w/v) mannitol.

Embodiment 190. Use of a pharmaceutical composition for treating a solid tumor wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and one or more pharmaceutically acceptable excipients.

Embodiment 191. Use of a pharmaceutical composition for treating a solid tumor wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles and one or more pharmaceutically acceptable excipients.

Embodiment 192. Use of a pharmaceutical composition for treating a solid tumor wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and a buffering agent.

Embodiment 193. Use of a pharmaceutical composition for treating a solid tumor wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles a buffering agent and one or more pharmaceutically acceptable excipients.

Embodiment 194. Use of a pharmaceutical composition for treating a solid tumor wherein the composition has a pH between 7.0 and 8.0 and comprises a 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and a buffering agent.

Embodiment 195. Use of a pharmaceutical composition for treating a solid tumor wherein the composition has a pH between 7.0 and 8.0 and comprises 3-(5-amino-2-(4-(2-(3,3-difluoro-3-phosphonopropoxy)ethoxy)-2-methylphenethyl)benzo[f][1,7]naphthyridin-8-yl)propanoic, or a pharmaceutically acceptable salt thereof, aluminum-containing particles, a buffering agent and sucrose.

Embodiment 196. Use of a pharmaceutical composition for treating a solid tumor wherein the composition has a pH between 7.0 and 8.0 and comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent and mannitol.

Embodiment 197. Use of a pharmaceutical composition for treating a solid tumor wherein the composition has a pH between 7.0 and 8.0 and comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles and Tris buffer.

Embodiment 198. Use of a pharmaceutical composition for treating a solid tumor wherein the composition has a pH between 7.0 and 8.0 and comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and sucrose.

Embodiment 199. Use of a pharmaceutical composition for treating a solid tumor wherein the composition has a pH between 7.0 and 8.0 and comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose.

Embodiment 200. Use of a pharmaceutical composition for treating a solid tumor wherein the composition has a pH between 7.0 and 8.0 and comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose.

Embodiment 201. Use of a pharmaceutical composition for treating a solid tumor wherein the composition has a pH between 7.0 and 8.0 and comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose.

Embodiment 202. Use of a pharmaceutical composition for treating a solid tumor wherein the composition has a pH between 7.0 and 8.0 and comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5-20 mM Tris buffer and 5-10% (w/v) sucrose.

Embodiment 203. Use of a pharmaceutical composition for treating a solid tumor wherein the composition has a pH between 7.0 and 8.0 and comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose.

Embodiment 204. Use of a pharmaceutical composition for treating a solid tumor wherein the composition has a pH between 7.0 and 8.0 and comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose.

Embodiment 205. Use of a pharmaceutical composition for treating a solid tumor wherein the composition has a pH between 7.0 and 8.0 and comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and mannitol.

Embodiment 206. Use of a pharmaceutical composition for treating a solid tumor wherein the composition has a pH between 7.0 and 8.0 and comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol.

Embodiment 207. Use of a pharmaceutical composition for treating a solid tumor wherein the composition has a pH between 7.0 and 8.0 and comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol.

Embodiment 208. Use of a pharmaceutical composition for treating a solid tumor wherein the composition has a pH between 7.0 and 8.0 and comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol.

Embodiment 209. Use of a pharmaceutical composition for treating a solid tumor wherein the composition has a pH between 7.0 and 8.0 and comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5-20 mM Tris buffer and 5-10% (w/v) mannitol.

Embodiment 210. Use of a pharmaceutical composition for treating a solid tumor wherein the composition has a pH between 7.0 and 8.0 and comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol.

Embodiment 211. Use of a pharmaceutical composition for treating a solid tumor wherein the composition has a pH between 7.0 and 8.0 and comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol.

Embodiment 212. A pharmaceutical composition for use in treating a solid tumor, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and one or more pharmaceutically acceptable excipients.

Embodiment 213. A pharmaceutical composition for use in treating a solid tumor, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles and one or more pharmaceutically acceptable excipients.

Embodiment 214. A pharmaceutical composition for use in treating a solid tumor, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and a buffering agent.

Embodiment 215. A pharmaceutical composition for use in treating a solid tumor, wherein the composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients.

Embodiment 216. A pharmaceutical composition for use in treating a solid tumor, wherein the composition has a pH between 7.0 and 8.0 and comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and a buffering agent.

Embodiment 217. A pharmaceutical composition for use in treating a solid tumor, wherein the composition has a pH between 7.0 and 8.0 and comprises 3-(5-amino-2-(4-(2-(3, 3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent and one or more pharmaceutically acceptable excipients.

Embodiment 218. A pharmaceutical composition for use in treating a solid tumor, wherein the composition has a pH between 7.0 and 8.0 and comprises 3-(5-amino-2-(4-(2-(3, 3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles and a buffering agent.

Embodiment 219. A pharmaceutical composition for use in treating a solid tumor, wherein the composition has a pH between 7.0 and 8.0 and comprises 3-(5-amino-2-(4-(2-(3, 3-difluoro-3-phosphonopropoxy)ethoxy)-2-methylphenethyl)benzo[f][1,7]naphthyridin-8-yl)propanoic, or a pharmaceutically acceptable salt thereof, aluminum-containing particles, a buffering agent and sucrose.

Embodiment 220. A pharmaceutical composition for use in treating a solid tumor, wherein the composition has a pH between 7.0 and 8.0 and comprises 3-(5-amino-2-(4-(2-(3, 3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent and mannitol.

Embodiment 221. A pharmaceutical composition for use in treating a solid tumor, wherein the composition has a pH between 7.0 and 8.0 and comprises of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles and Tris buffer.

Embodiment 222. A pharmaceutical composition for use in treating a solid tumor, wherein the composition has a pH between 7.0 and 8.0 and comprises 3-(5-amino-2-(4-(2-(3, 3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and sucrose.

Embodiment 223. A pharmaceutical composition for use in treating a solid tumor, wherein the composition has a pH between 7.0 and 8.0 and comprises 0.5 to 2 mg/mL of 3-(5-amino-2-(4-(2-(3,3-difluoro-3-phosphonopropoxy) ethoxy)-2-methylphenethyl)benzo[f][1,7]naphthyridin-8-yl) propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose.

Embodiment 224. A pharmaceutical composition for use in treating a solid tumor, wherein the composition has a pH between 7.0 and 8.0 and comprises 0.5 to 2 mg/mL of 3-(5-amino-2-(4-(2-(3,3-difluoro-3-phosphonopropoxy) ethoxy)-2-methylphenethyl)benzo[f][1,7]naphthyridin-8-yl) propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose.

Embodiment 225. A pharmaceutical composition for use in treating a solid tumor, wherein the composition has a pH between 7.0 and 8.0 and comprises 0.5 to 2 mg/mL of 3-(5-amino-2-(4-(2-(3,3-difluoro-3-phosphonopropoxy) ethoxy)-2-methylphenethyl)benzo[f][1,7]naphthyridin-8-yl) propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose.

Embodiment 226. A pharmaceutical composition for use in treating a solid tumor, wherein the composition has a pH between 7.0 and 8.0 and comprises 1.0 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5-20 mM Tris buffer and 5-10% (w/v) sucrose.

Embodiment 227. A pharmaceutical composition for use in treating a solid tumor, wherein the composition has a pH between 7.0 and 8.0 and comprises 1.0 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose.

Embodiment 228. A pharmaceutical composition for use in treating a solid tumor, wherein the composition has a pH between 7.0 and 8.0 and comprises 1.0 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose.

Embodiment 229. A pharmaceutical composition for use in treating a solid tumor, wherein the composition has a pH between 7.0 and 8.0 and comprises 0.5 to 2 mg/mL of 3-(5-amino-2-(4-(2-(3,3-difluoro-3-phosphonopropoxy) ethoxy)-2-methylphenethyl)benzo[f][1,7]naphthyridin-8-yl) propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol.

Embodiment 230. A pharmaceutical composition for use in treating a solid tumor, wherein the composition has a pH between 7.0 and 8.0 and comprises 0.5 to 2 mg/mL of 3-(5-amino-2-(4-(2-(3,3-difluoro-3-phosphonopropoxy) ethoxy)-2-methylphenethyl)benzo[f][1,7]naphthyridin-8-yl) propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol.

Embodiment 231. A pharmaceutical composition for use in treating a solid tumor, wherein the composition has a pH between 7.0 and 8.0 and comprises 0.5 to 2 mg/mL of 3-(5-amino-2-(4-(2-(3,3-difluoro-3-phosphonopropoxy) ethoxy)-2-methylphenethyl)benzo[f][1,7]naphthyridin-8-yl) propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol.

Embodiment 232. A pharmaceutical composition for use in treating a solid tumor, wherein the composition has a pH between 7.0 and 8.0 and comprises 1.0 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5-20 mM Tris buffer and 5-10% (w/v) mannitol.

Embodiment 233. A pharmaceutical composition for use in treating a solid tumor, wherein the composition has a pH between 7.0 and 8.0 and comprises 1.0 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol.

Embodiment 234. A pharmaceutical composition for use in treating a solid tumor, wherein the composition has a pH between 7.0 and 8.0 and comprises 1.0 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol.

Example 7 illustrates the effect on tumor volume by administration of a pharmaceutical composition comprising a compound of Formula (A) with or without aluminum-containing particles. Specifically, Example 7 illustrates the effect on tumor volume by administration of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid with or without aluminum-containing particles.

Combinations

The invention also provides methods for treating a solid tumor by administering, either intratumorally, intramuscularly, intradermally or subcutaneously, a pharmaceutically composition of any one of Embodiments 1 to 83 or 161 to 164 in combination with one or more pharmaceutical compositions comprising another therapeutic agent. Such additional therapeutic agents can be a checkpoint inhibitor, a TLR9 agonist, a TLR8 agonist, a TLR7 agonist, a STING agonist or a chemotherapeutic agent.

The invention further provides methods for treating a solid tumor by administering, either intratumorally, intramuscularly, intradermally or subcutaneously, a pharmaceutically composition disclosed herein comprising a compound of Formula (A), or a pharmaceutically acceptable salt thereof, aluminum-containing particles and one or more pharmaceutically acceptable excipients in combination with one or more pharmaceutical compositions comprising another therapeutic agent. Such additional therapeutic agents can be a checkpoint inhibitor, a TLR9 agonist, a TLR8 agonist, a TLR7 agonist, a STING agonist or a chemotherapeutic agent.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), epirubicin (Ellence®), oxaliplatin (Eloxatin®), exemestane (Aromasin®), letrozole (Ferrara®), and fulvestrant (Faslodex®)

Combinations with Checkpoint Inhibitors

Toll-like receptors (TLRs) are a class of proteins which play an essential role in pathogen recognition and activation of the innate immune system. To protect against autoimmunity the immune system utilizes a family of receptors, known as checkpoint receptors, to downregulate activated immune cells, such as T-cells. A number of tumors are able to expressing agonistic surface proteins to checkpoint receptors and thereby evade anti-tumor immune response in the tumor environment. In order to enable an effective anti-tumor immune response in the tumor environment, this cloaking behavior may be overcome by blocking the checkpoint pathway by the administration of checkpoint pathway inhibitors, and in conjunction activate the immune system with the administration of a Toll-like 7 receptor agonist.

Compounds of Formula (A), or a pharmaceutically acceptable salt thereof, are TLR7 agonists and thereby activate multiple cell-mediated anti-tumor immune responses (such as for example T-cell activation). Therefore, a combination of immune activation with a compound of Formula (A), or a pharmaceutically acceptable salt thereof, and blockade of immune checkpoint pathways with immune one or more checkpoint inhibitor(s) may enhance and maintain an anti-tumor immune response initiated by the compound of Formula (A), or a pharmaceutically acceptable salt thereof. Thus, the invention provides combinations of a pharmaceutical composition comprising a compound of Formula (A), or a pharmaceutically acceptable salt thereof in combination with one or more immune checkpoint inhibitors. Accordingly, the invention further provides methods and uses that may be useful for treating solid tumors by the administration of such combinations.

In particular, the invention provides combinations of a pharmaceutical composition of any one of Embodiments 1 to 83 or 161 to 164 in combination with one or more pharmaceutical compositions comprising one or more immune checkpoint inhibitors. In cetain embodiments, the invention provides a pharmaceutical composition of any one of Embodiments 1 to 83 or 161 to 164 further comprising one or more immune checkpoint inhibitors.

The invention provides combinations of a pharmaceutical composition comprising a compound of Formula (A), or a pharmaceutically acceptable salt thereof, aluminum-containing particles, one or more pharmaceutically acceptable excipients in combination with one or more pharmaceutical compositions comprising one or more immune checkpoint inhibitors.

The immune checkpoint inhibitor can be an inhibitor of the receptor or an inhibitor of the ligand. Immune checkpoint receptor which may be targeted by inhibitors, include but are not limited to, Cytotoxic T-lymphocyte associated antigen 4 (CTLA-4), Programmed death 1 (PD-1), Lymphocyte activation gene 3 (LAG-3), T cell membrane protein 3 (TIM-3), B- and T-lymphocyte attenuator receptor (BTLA) and Killer cell immunoglobulin-like receptors (KIR), and immune checkpoint receptor ligands which may be targeted by inhibitors, include but are not limited to, Programmed Death ligand 1 (PD-L1) and Programmed Death ligand 2 (PD-L2).

The immune checkpoint inhibitor used in the combinations of the invention can be an inhibitor of the receptor or an inhibitor of the ligand. By way of example, the immune checkpoint inhibitor used in the combinations of the invention is a CTLA-4 receptor inhibitor, a PD-1 receptor inhibitor, a LAG-3 receptor inhibitor, a TIM-3 receptor inhibitor, a BTLA receptor inhibitor, or a KIR receptor inhibitor. In addition, by way of example, the immune checkpoint inhibitor used in the combinations of the invention is an inhibitor of Programmed death ligand 1 (PD-L1) and/or Programmed death ligand 2 (PD-L2).

The immune checkpoint inhibitors used in the combinations of the invention can be a low molecular weight organic molecule (molecular weight less than 1000 daltons), a peptide, a polypeptide, a protein, an antibody, an antibody fragment, or an antibody derivative. In certain embodiments, the immune checkpoint inhibitor used in the combinations of the invention is an antibody. In certain embodiments, the immune checkpoint inhibitor used in the combinations of the invention the antibody is a monoclonal antibody. In certain embodiments, the immune checkpoint inhibitor used in the combinations of the invention the antibody is a human antibody or a humanized monoclonal antibody.

In certain embodiments the immune checkpoint inhibitor used in the combinations of the invention is an anti-CTLA-4 receptor antibody, an anti-PD-1 receptor antibody, an anti-LAG-3 receptor antibody, an anti-TIM-3 receptor antibody, an anti-BTLA receptor antibody, an anti-KIR receptor antibody, an anti-PD-L1 antibody, or an anti-PD-L2 antibody.

In certain embodiments the immune checkpoint inhibitor used in the combinations of the invention is an inhibitor of the PD-L1/PD-1 pathway or the PD-L2/PD-1 pathway.

In one embodiment, the anti-PD-L1 antibody molecule for use in combinations of the invention is one of those disclosed in U.S. Patent Application No. 20160108123, filed Oct. 13, 2015, entitled "Antibody Molecules to PD-L1 and Uses Thereof," incorporated by reference in its entirety.

In one embodiment, the anti-PD-L1 antibody includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of U.S. Patent Application No. 20160108123, or encoded by the nucleotide sequence in Table 1 of U.S. Patent Application No. 20160108123; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0; or as described in Table 1 of U.S. Patent Application No. 20160108123, or encoded by the nucleotide sequence in Table 1 of U.S. Patent Application No. 20160108123; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of U.S. Patent Application No. 20160108123, or encoded by a nucleotide sequence shown in Table 1 of U.S. Patent Application No. 20160108123. In one embodiment, one or more of the CDRs (or collectively all of the CDRs) have one, two, three, four, five, six or more changes, e.g., amino acid substitutions or deletions, relative to the amino acid sequence shown in Table 1 of U.S. Patent Application No. 20160108123, or encoded by a nucleotide sequence shown in Table 1 of U.S. Patent Application No. 20160108123.

In yet another embodiment, the anti-PD-L1 antibody molecule includes at least one, two, or three CDRs (or collectively all of the CDRs) from a light chain variable region comprising an amino acid sequence shown in Table 1 of U.S. Patent Application No. 20160108123, or encoded by a nucleotide sequence shown in Table 1 of U.S. Patent Application No. 20160108123. In one embodiment, one or more of the CDRs (or collectively all of the CDRs) have one, two, three, four, five, six or more changes, e.g., amino acid substitutions or deletions, relative to the amino acid sequence shown in Table 1 of U.S. Patent Application No. 20160108123, or encoded by a nucleotide sequence shown in Table 1 of U.S. Patent Application No. 20160108123. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1 of U.S. Patent Application No. 20160108123, or encoded by a nucleotide sequence shown in Table 1 of U.S. Patent Application No. 20160108123. In one embodiment, one or more of the CDRs (or collectively all of the CDRs) have one, two, three, four, five, six or more changes, e.g., amino acid substitutions or deletions, relative to the amino acid sequence shown in Table 1 of U.S. Patent Application No. 20160108123, or encoded by a nucleotide sequence shown in Table 1 of U.S. Patent Application No. 20160108123.

In one embodiment, the anti-PD-L1 antibody molecule includes at least one, two or three CDRs or hypervariable loops from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0, according to the Kabat and Chothia definition (e.g., at least one, two, or three CDRs or hypervariable loops according to the Kabat and Chothia definition as set out in Table 1 of U.S. Patent Application No. 20160108123); or encoded by the nucleotide sequence in Table 1 of U.S. Patent Application No. 20160108123; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1 of U.S. Patent Application No. 20160108123.

In one embodiment, the anti-PD-L1 antibody molecule can include VH CDR1 according to Kabat et al. ((1991), "Sequences of Proteins of Immunological Interest," 5th Ed. Public Health Service, National Institutes of Health, Bethesda, Md.) or VH hypervariable loop 1 according to Chothia et al. (1992) J. Mol. Biol. 227:799-817, or a combination thereof, e.g., as shown in Table 1 of U.S. Patent Application No. 20160108123. In one embodiment, the combination of Kabat and Chothia CDR of VHCDR1 comprises the amino acid sequence GYTFTSYWMY (SEQ ID NO:1, or an amino acid sequence substantially identical thereto (e.g., having at least one amino acid alteration, but not more than two, three or four alterations (e.g., substitutions, deletions, or insertions, e.g., conservative substitutions)). The anti-PD-L1 antibody molecule can further include, e.g., VH CDRs 2-3 according to Kabat et al. and VL CDRs 1-3 according to Kabat et al., e.g., as shown in Table 1 of U.S. Patent Application No. 20160108123.

In a preferred embodiment, the anti PD-L1 antibody molecule for use in the combinations, methods and compositions of the invention comprises (see Table 2):
  (a) a heavy chain variable region (VH) comprising a VHCDR1 amino acid sequence of SEQ ID NO:5, a VHCDR2 amino acid sequence of SEQ ID NO:6, and a VHCDR3 amino acid sequence of SEQ ID NO:4; and a light chain variable region (VL) comprising a VLCDR1 amino acid sequence of SEQ ID NO:14, a VLCDR2 amino acid sequence of SEQ ID NO:15, and a VLCDR3 amino acid sequence of SEQ ID NO:16;
  (b) a VH comprising a VHCDR1 amino acid sequence of SEQ ID NO:2; a VHCDR2 amino acid sequence of SEQ ID NO:3; and a VHCDR3 amino acid sequence of SEQ ID NO:4; and a VL comprising a VLCDR1 amino acid sequence of SEQ ID NO:11, a VLCDR2 amino acid sequence of SEQ ID NO:12, and a VLCDR3 amino acid sequence of SEQ ID NO:13;
  (c) a VH comprising a VHCDR1 amino acid sequence of SEQ ID NO:1, a VHCDR2 amino acid sequence of SEQ ID NO:6, and a VHCDR3 amino acid sequence of SEQ ID NO:4; and a VL comprising a VLCDR1 amino acid sequence of SEQ ID NO:14, a VLCDR2 amino acid sequence of SEQ ID NO:15, and a VLCDR3 amino acid sequence of SEQ ID NO:16; or
  (d) a VH comprising a VHCDR1 amino acid sequence of SEQ ID NO:1; a VHCDR2 amino acid sequence of SEQ ID NO:3; and a VHCDR3 amino acid sequence of SEQ ID NO:4; and a VL comprising a VLCDR1 amino acid sequence of SEQ ID NO:11, a VLCDR2 amino acid sequence of SEQ ID NO:12, and a VLCDR3 amino acid sequence of SEQ ID NO:13.

In one aspect the anti-PD-L1 antibody molecule used in the combinations of the invention comprises:
  (a) a heavy chain variable domain comprising the amino acid sequence of SEQ ID NO:7 and a light chain variable domain comprising the amino acid sequence of SEQ ID NO:17.

TABLE 2

Amino acid and nucleotide sequences for humanized mAbs BAP058-hum013. The amino acid and nucleotide sequences of the heavy and light chain CDRs, the heavy and light chain variable regions, and the heavy and light chains are shown.

BAP058-hum13-HC

| | | |
|---|---|---|
| SEQ ID NO: 2 (Kabat) | HCDR1 | SYWMY |
| SEQ ID NO: 3 (Kabat) | HCDR2 | RIDPNSGSTKYNEKFKN |
| SEQ ID NO: 4 (Kabat) | HCDR3 | DYRKGLYAMDY |
| SEQ ID NO: 5 (Chothia) | HCDR1 | GYTFTSY |
| SEQ ID NO: 6 (Chothia) | HCDR2 | DPNSGS |
| SEQ ID NO: 4 (Chothia) | HCDR3 | DYRKGLYAMDY |
| SEQ ID NO: 7 | VH | EVQLVQSGAEVKKPGATVKISCKVSGYTFT SYWMYWVRQARGQRLEWIGRIDPNSGSTK YNEKFKNRFTISRDNSKNTLYLQMNSLRAE DTAVYYCARDYRKGLYAMDYWGQGTTVTV SS |
| SEQ ID NO: 8 | DNA VH | GAGGTCCAGCTGGTACAGTCTGGGGCTG AGGTGAAGAAGCCTGGGGCTACAGTGAA AATCTCCTGCAAGGTTTCTGGCTACACCTT CACCAGTTACTGGATGTACTGGGTGCGAC AGGCTCGTGGACAACGCCTTGAGTGGATA GGTAGGATTGATCCTAATAGTGGGAGTAC TAAGTACAATGAGAAGTTCAAGAACAGATT CACCATCTCCAGAGACAATTCAAGAACA CGCTGTATCTTCAAATGAACAGCCTGAGA GCCGAGGACACGGCCGTGTATTACTGTG CAAGGGACTATAGAAAGGGGCTCTATGCT |

TABLE 2-continued

Amino acid and nucleotide sequences for humanized mAbs BAP058-hum013. The amino acid and nucleotide sequences of the heavy and light chain CDRs, the heavy and light chain variable regions, and the heavy and light chains are shown.

|  |  |  |
|---|---|---|
|  |  | ATGGACTACTGGGGCCAGGGCACCACCG TGACCGTGTCCTCC |
| SEQ ID NO: 9 | Heavy Chain | EVQLVQSGAEVKKPGATVKISCKVSGYTFT SYWMYWVRQARGQRLEWIGRIDPNSGSTK YNEKFKNRFTISRDNSKNTLYLQMNSLRAE DTAVYYCARDYRKGLYAMDYWGQGTTVTV SSASTKGPSVFPLAPCSRSTSESTAALGCLV KDYFPEPVTVSWNSGALTSGVHTFPAVLQS SGLYSLSSVVTVPSSSLGTKTYTCNVDHKP SNTKVDKRVESKYGPPCPPCPAPEFLGGPS VFLFPPKPKDTLMISRTPEVTCVVVDVSQED PEVQFNWYVDGVEVHNAKTKPREEQFNST YRVVSVLTVLHQDWLNGKEYKCKVSNKGLP SSIEKTISKAKGQPREPQVYTLPPSQEEMTK NQVSLTCLVKGFYPSDIAVEWESNGQPENN YKTTPPVLDSDGSFFLYSRLTVDKSRWQEG NVFSCSVMHEALHNHYTQKSLSLSLGK |
| SEQ ID NO: 10 | DNA Heavy Chain | GAGGTCCAGCTGGTACAGTCTGGGGCTG AGGTGAAGAAGCCTGGGGCTACAGTGAA AATCTCCTGCAAGGTTTCTGGCTACACCTT CACCAGTTACTGGATGTACTGGGTGCGAC AGGCTCGTGGACAACGCCTTGAGTGGATA GGTAGGATTGATCCTAATAGTGGGAGTAC TAAGTACAATGAGAAGTTCAAGAACAGATT CACCATCTCCAGAGACAATTCCAAGAACA CGCTGTATCTTCAAATGAACAGCCTGAGA GCCGAGGACACGGCCGTGTATTACTGTG CAAGGGACTATAGAAAGGGGCTCTATGCT ATGGACTACTGGGGCCAGGGCACCACCG TGACCGTGTCCTCCGCTTCCACCAAGGGC CCATCCGTCTTCCCCCTGGCGCCCTGCTC CAGGAGCACCTCCGAGAGCACAGCCGCC CTGGGCTGCCTGGTCAAGGACTACTTCCC CGAACCGGTGACGGTGTCGTGGAACTCA GGCGCCCTGACCAGCGGCGTGCACACCT TCCCGGCTGTCCTACAGTCCTCAGGACTC TACTCCCTCAGCAGCGTGGTGACCGTGCC CTCCAGCAGCTTGGGCACGAAGACCTACA CCTGCAACGTAGATCACAAGCCCAGCAAC ACCAAGGTGGACAAGAGAGTTGAGTCCAA ATATGGTCCCCCATGCCCACCGTGCCCAG CACCTGAGTTCCTGGGGGGACCATCAGTC TTCCTGTTCCCCCCAAAACCCAAGGACAC TCTCATGATCTCCCGGACCCCTGAGGTCA CGTGCGTGGTGGTGGACGTGAGCCAGGA AGACCCCGAGGTCCAGTTCAACTGGTACG TGGATGGCGTGGAGGTGCATAATGCCAA GACAAAGCCGCGGGAGGAGCAGTTCAAC AGCACGTACCGTGTGGTCAGCGTCCTCAC CGTCCTGCACCAGGACTGGCTGAACGGC AAGGAGTACAAGTGCAAGGTGTCCAACAA AGGCCTCCCGTCCTCCATCGAGAAAACCA TCTCCAAAGCCAAAGGGCAGCCCCGAGA GCCACAGGTGTACACCCTGCCCCCCATCC AGGAGGAGATGACCAAGAACCAGGTCAG CCTGACCTGCCTGGTCAAAGGCTTCTACC CCAGCGACATCGCCGTGGAGTGGGAGAG CAATGGGCAGCCGGAGAACAACTACAAGA CCACGCCTCCCGTGCTGGACTCCGACGG CTCCTTCTTCCTCTACAGCAGGCTAACCG TGGACAAGAGCAGGTGGCAGGAGGGGAA TGTCTTCTCATGCTCCGTGATGCATGAGG CTCTGCACAACCACTACACACAGAAGAGC CTCTCCCTGTCTCTGGGTAAA |

BAP058-hum13-LC

| | | |
|---|---|---|
| SEQ ID NO: 11 (Kabat) | LCDR1 | KASQDVGTAVA |
| SEQ ID NO: 12 (Kabat) | LCDR2 | WASTRHT |
| SEQ ID NO: 13 (Kabat) | LCDR3 | QQYNSYPLT |

TABLE 2-continued

Amino acid and nucleotide sequences for humanized mAbs BAP058-hum013. The amino acid and nucleotide sequences of the heavy and light chain CDRs, the heavy and light chain variable regions, and the heavy and light chains are shown.

| | | | |
|---|---|---|---|
| SEQ ID NO: 14 | (Chothia) | LCDR1 | SQDVGTA |
| SEQ ID NO: 15 | (Chothia) | LCDR2 | WAS |
| SEQ ID NO: 16 | (Chothia) | LCDR3 | YNSYPL |
| SEQ ID NO: 17 | | VL | AIQLTQSPSSLSASVGDRVTITCKASQDVGT AVAWYLQKPGQSPQLLIYWASTRHTGVPSR FSGSGSGTDFTFTISSLEAEDAATYYCQQY NSYPLTFGQGTKVEIK |
| SEQ ID NO: 18 | | DNA VL | GCCATCCAGTTGACCCAGTCTCCATCCTC CCTGTCTGCATCTGTAGGAGACAGAGTCA CCATCACTTGCAAGGCCAGTCAGGATGTG GGTACTGCTGTAGCCTGGTACCTGCAGAA GCCAGGGCAGTCTCCACAGCTCCTGATCT ATTGGGCATCCACCCGGCACACTGGGGT CCCCTCGAGGTTCAGTGGCAGTGGATCTG GGACAGATTTCACCTTTACCATCAGTAGC CTGGAAGCTGAAGATGCTGCAACATATTA CTGTCAGCAGTATAACAGCTATCCTCTCA CGTTCGGCCAAGGGACCAAGGTGGAAAT CAAA |
| SEQ ID NO: 19 | | Light Chain | AIQLTQSPSSLSASVGDRVTITCKASQDVGT AVAWYLQKPGQSPQLLIYWASTRHTGVPSR FSGSGSGTDFTFTISSLEAEDAATYYCQQY NSYPLTFGQGTKVEIKRTVAAPSVFIFPPSD EQLKSGTASVVCLLNNFYPREAKVQWKVDN ALQSGNSQESVTEQDSKDSTYSLSSTLTLS KADYEKHKVYACEVTHQGLSSPVTKSFNRG EC |
| SEQ ID NO: 20 | | DNA Light Chain | GCCATCCAGTTGACCCAGTCTCCATCCTC CCTGTCTGCATCTGTAGGAGACAGAGTCA CCATCACTTGCAAGGCCAGTCAGGATGTG GGTACTGCTGTAGCCTGGTACCTGCAGAA GCCAGGGCAGTCTCCACAGCTCCTGATCT ATTGGGCATCCACCCGGCACACTGGGGT CCCCTCGAGGTTCAGTGGCAGTGGATCTG GGACAGATTTCACCTTTACCATCAGTAGC CTGGAAGCTGAAGATGCTGCAACATATTA CTGTCAGCAGTATAACAGCTATCCTCTCA CGTTCGGCCAAGGGACCAAGGTGGAAAT CAAACGTACGGTGGCTGCACCATCTGTCT TCATCTTCCCGCCATCTGATGAGCAGTTG AAATCTGGAACTGCCTCTGTTGTGTGCCT GCTGAATAACTTCTATCCCAGAGAGGCCA AAGTACAGTGGAAGGTGGATAACGCCCTC CAATCGGGTAACTCCCAGGAGAGTGTCAC AGAGCAGGACAGCAAGGACAGCACCTAC AGCCTCAGCAGCACCCTGACGCTGAGCA AAGCAGACTACGAGAAACACAAAGTCTAC GCCTGCGAAGTCACCCATCAGGGCCTGA GCTCGCCCGTCACAAAGAGCTTCAACAGG GGAGAGTGT |

In one embodiment, the PD-1 inhibitor partner of a combination of the invention is an anti-PD-1 antibody molecule. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety.

In one embodiment, the anti-PD-1 antibody molecule comprises at least one, two, three, four, five or six complementarity determining regions (CDRs) (or collectively all of the CDRs) from a heavy and light chain variable region comprising an amino acid sequence shown in Table 3 (e.g., from the heavy and light chain variable region sequences of BAP049-Clone-E or BAP049-Clone-B disclosed in Table 3), or encoded by a nucleotide sequence shown in Table 3. In some embodiments, the CDRs are according to the Kabat definition (e.g., as set out in Table 3). In some embodiments, the CDRs are according to the Chothia definition (e.g., as set out in Table 3). In some embodiments, the CDRs are according to the combined CDR definitions of both Kabat and Chothia (e.g., as set out in Table 3). In one embodiment, the combination of Kabat and Chothia CDR of VHCDR1 comprises the amino acid sequence GYTFTTYWMH (SEQ ID NO: 21). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 1, or encoded by a nucleotide sequence shown in Table 3.

In one embodiment, the anti-PD-1 antibody molecule comprises a heavy chain variable region (VH) comprising a VHCDR1 amino acid sequence of SEQ ID NO: 22, a VHCDR2 amino acid sequence of SEQ ID NO: 23, and a VHCDR3 amino acid sequence of SEQ ID NO: 24; and a light chain variable region (VL) comprising a VLCDR1 amino acid sequence of SEQ ID NO: 31, a VLCDR2 amino acid sequence of SEQ ID NO: 32, and a VLCDR3 amino acid sequence of SEQ ID NO: 33, each disclosed in Table 3.

In one embodiment, the antibody molecule comprises a VH comprising a VHCDR1 encoded by the nucleotide sequence of SEQ ID NO: 45, a VHCDR2 encoded by the nucleotide sequence of SEQ ID NO: 46, and a VHCDR3 encoded by the nucleotide sequence of SEQ ID NO: 47; and a VL comprising a VLCDR1 encoded by the nucleotide sequence of SEQ ID NO: 50, a VLCDR2 encoded by the nucleotide sequence of SEQ ID NO: 51, and a VLCDR3 encoded by the nucleotide sequence of SEQ ID NO: 52, each disclosed in Table 3.

In one embodiment, the anti-PD-1 antibody molecule comprises a VH comprising the amino acid sequence of SEQ ID NO: 27, or an amino acid sequence at least 85%, 90%, 95%, or 99% identical or higher to SEQ ID NO: 27. In one embodiment, the anti-PD-1 antibody molecule comprises a VL comprising the amino acid sequence of SEQ ID NO: 41, or an amino acid sequence at least 85%, 90%, 95%, or 99% identical or higher to SEQ ID NO: 41. In one embodiment, the anti-PD-1 antibody molecule comprises a VL comprising the amino acid sequence of SEQ ID NO: 37, or an amino acid sequence at least 85%, 90%, 95%, or 99% identical or higher to SEQ ID NO: 37. In one embodiment, the anti-PD-1 antibody molecule comprises a VH comprising the amino acid sequence of SEQ ID NO: 27 and a VL comprising the amino acid sequence of SEQ ID NO: 41. In one embodiment, the anti-PD-1 antibody molecule comprises a VH comprising the amino acid sequence of SEQ ID NO: 27 and a VL comprising the amino acid sequence of SEQ ID NO: 37.

In one embodiment, the antibody molecule comprises a VH encoded by the nucleotide sequence of SEQ ID NO: 28, or a nucleotide sequence at least 85%, 90%, 95%, or 99% identical or higher to SEQ ID NO: 28. In one embodiment, the antibody molecule comprises a VL encoded by the nucleotide sequence of SEQ ID NO: 42 or 38, or a nucleotide sequence at least 85%, 90%, 95%, or 99% identical or higher to SEQ ID NO: 42 or 38. In one embodiment, the antibody molecule comprises a VH encoded by the nucleotide sequence of SEQ ID NO: 28 and a VL encoded by the nucleotide sequence of SEQ ID NO: 42 or 38.

In one embodiment, the anti-PD-1 antibody molecule comprises a heavy chain comprising the amino acid sequence of SEQ ID NO: 29, or an amino acid sequence at least 85%, 90%, 95%, or 99% identical or higher to SEQ ID NO: 29. In one embodiment, the anti-PD-1 antibody molecule comprises a light chain comprising the amino acid sequence of SEQ ID NO: 43, or an amino acid sequence at least 85%, 90%, 95%, or 99% identical or higher to SEQ ID NO: 43. In one embodiment, the anti-PD-1 antibody molecule comprises a light chain comprising the amino acid sequence of SEQ ID NO: 39, or an amino acid sequence at least 85%, 90%, 95%, or 99% identical or higher to SEQ ID NO: 39. In one embodiment, the anti-PD-1 antibody molecule comprises a heavy chain comprising the amino acid sequence of SEQ ID NO: 29 and a light chain comprising the amino acid sequence of SEQ ID NO: 43. In one embodiment, the anti-PD-1 antibody molecule comprises a heavy chain comprising the amino acid sequence of SEQ ID NO: 29 and a light chain comprising the amino acid sequence of SEQ ID NO: 39.

In one embodiment, the antibody molecule comprises a heavy chain encoded by the nucleotide sequence of SEQ ID NO: 30, or a nucleotide sequence at least 85%, 90%, 95%, or 99% identical or higher to SEQ ID NO: 30. In one embodiment, the antibody molecule comprises a light chain encoded by the nucleotide sequence of SEQ ID NO: 44 or 40, or a nucleotide sequence at least 85%, 90%, 95%, or 99% identical or higher to SEQ ID NO: 44 or 40. In one embodiment, the antibody molecule comprises a heavy chain encoded by the nucleotide sequence of SEQ ID NO: 30 and a light chain encoded by the nucleotide sequence of SEQ ID NO: 44 or 40.

The antibody molecules described herein can be made by vectors, host cells, and methods described in US 2015/0210769, incorporated by reference in its entirety.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102

(HCDR3) in human VH and amino acid residues 24-34 (LCDR1), 50-56 (LCDR2), and 89-97 (LCDR3) in human VL.

Generally, unless specifically indicated, the anti-PD-1 antibody molecules can include any combination of one or more Kabat CDRs and/or Chothia CDRs, e.g., described in Table 3. In one embodiment, the following definitions are used for the anti-PD-1 antibody molecules described in Table 3: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CAB/OS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See www.ncbi.nlm.nih.gov.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

TABLE 3

Amino acid and nucleotide sequences of exemplary anti-PD-1 antibody molecules

BAP049-Clone-B HC

SEQ ID NO: 22 (Kabat)   HCDR1   TYWMH

SEQ ID NO: 23 (Kabat)   HCDR2   NIYPGTGGSNFDEKFKN

SEQ ID NO: 24 (Kabat)   HCDR3   WTTGTGAY

SEQ ID NO: 25 (Chothia) HCDR1   GYTFTTY

SEQ ID NO: 26 (Chothia) HCDR2   YPGTGG

SEQ ID NO: 24 (Chothia) HCDR3   WTTGTGAY

TABLE 3-continued

Amino acid and nucleotide sequences of exemplary anti-PD-1 antibody molecules

| SEQ ID NO: 27 | VH | EVQLVQSGAEVKKPGESLRISCKGSGY TFTTYWMHWVRQATGQGLEWMGNIYP GTGGSNFDEKFKNRVTITADKSTSTAY MELSSLRSEDTAVYYCTRWTTGTGAY WGQGTTVTVSS |
|---|---|---|
| SEQ ID NO: 28 | DNA VH | GAGGTGCAGCTGGTGCAGTCAGGCG CCGAAGTGAAGAAGCCCGGCGAGTC ACTGAGAATTAGCTGTAAAGGTTCAG GCTACACCTTCACTACCTACTGGATG CACTGGGTCCGCCAGGCTACCGGTC AAGGCCTCGAGTGGATGGGTAATATC TACCCCGGCACCGGCGGCTCTAACTT CGACGAGAAGTTTAAGAATAGAGTGA CTATCACCGCCGATAAGTCTACTAGC ACCGCCTATATGGAACTGTCTAGCCT GAGATCAGAGGACACCGCCGTCTACT ACTGCACTAGGTGGACTACCGGCACA GGCGCCTACTGGGGTCAAGGCACTA CCGTGACCGTGTCTAGC |
| SEQ ID NO: 29 | HC | EVQLVQSGAEVKKPGESLRISCKGSGY TFTTYWMHWVRQATGQGLEWMGNIYP GTGGSNFDEKFKNRVTITADKSTSTAY MELSSLRSEDTAVYYCTRWTTGTGAY WGQGTTVTVSSASTKGPSVFPLAPCSR STSESTAALGCLVKDYFPEPVTVSWNS GALTSGVHTFPAVLQSSGLYSLSSVVT VPSSSLGTKTYTCNVDHKPSNTKVDKR VESKYGPPCPPCPAPEFLGGPSVFLFP PKPKDTLMISRTPEVTCVVVDVSQEDP EVQFNWYVDGVEVHNAKTKPREEQFN STYRVVSVLTVLHQDWLNGKEYKCKVS NKGLPSSIEKTISKAKGQPREPQVYTLP PSQEEMTKNQVSLTCLVKGFYPSDIAV EWESNGQPENNYKTTPPVLDSDGSFFL YSRLTVDKSRWQEGNVFSCSVMHEAL HNHYTQKSLSLSLG |
| SEQ ID NO: 30 | DNA HC | GAGGTGCAGCTGGTGCAGTCAGGCG CCGAAGTGAAGAAGCCCGGCGAGTC ACTGAGAATTAGCTGTAAAGGTTCAG GCTACACCTTCACTACCTACTGGATG CACTGGGTCCGCCAGGCTACCGGTC AAGGCCTCGAGTGGATGGGTAATATC TACCCCGGCACCGGCGGCTCTAACTT CGACGAGAAGTTTAAGAATAGAGTGA CTATCACCGCCGATAAGTCTACTAGC ACCGCCTATATGGAACTGTCTAGCCT GAGATCAGAGGACACCGCCGTCTACT ACTGCACTAGGTGGACTACCGGCACA GGCGCCTACTGGGGTCAAGGCACTA CCGTGACCGTGTCTAGCGCTAGCACT AAGGGCCCGTCCGTGTTCCCCCTGG CACCTTGTAGCCGGAGCACTAGCGAA TCCACCGCTGCCCTCGGCTGCCTGGT CAAGGATTACTTCCCGGAGCCCGTGA CCGTGTCCTGGAACAGCGGAGCCCT GACCTCCGGAGTGCACACCTTCCCCG CTGTGCTGCAGAGCTCCGGGCTGTAC TCGCTGTCGTCGGTGGTCACGGTGCC TTCATCTAGCCTGGGTACCAAGACCT ACACTTGCAACGTGGACCACAAGCCT TCCAACACTAAGGTGGACAAGCGCGT CGAATCGAAGTACGGCCCACCGTGCC CGCCTTGTCCCGCGCCGGAGTTCCTC GGCGGTCCCTCGGTCTTTCTGTTCCC ACCGAAGCCCAAGGACACTTTGATGA TTTCCCGCACCCCTGAAGTGACATGC GTGGTCGTGGACGTGTCACAGGAAGA TCCGGAGGTGCAGTTCAATTGGTACG TGGATGGCGTCGAGGTGCACAACGC CAAAACCAAGCCGAGGGAGGAGCAG TTCAACTCCACTTACCGTGTCGTGTC CGTGCTGACGGTGCTGCATCAGGACT GGCTGAACGGGAAGGAGTACAAGTG CAAAGTGTCCAACAAGGGGACTTCCTA |

TABLE 3-continued

Amino acid and nucleotide sequences of exemplary anti-PD-1 antibody molecules

|  |  |  |
|---|---|---|
|  |  | GCTCAATCGAAAAGACCATCTCGAAA<br>GCCAAGGGACAGCCCCGGGAACCCC<br>AAGTGTATACCCTGCCACCGAGCCAG<br>GAAGAAATGACTAAGAACCAAGTCTC<br>ATTGACTTGCCTTGTGAAGGGCTTCTA<br>CCCATCGGATATCGCCGTGGAATGGG<br>AGTCCAACGGCCAGCCGGAAAACAAC<br>TACAAGACCACCCCTCCGGTGCTGGA<br>CTCAGACGGATCCTTCTTCCTCTACTC<br>GCGGCTGACCGTGGATAAGAGCAGAT<br>GGCAGGAGGGAAATGTGTTCAGCTGT<br>TCTGTGATGCATGAAGCCCTGCACAA<br>CCACTACACTCAGAAGTCCCTGTCCC<br>TCTCCCTGGGA |

BAP049-Clone-B LC

| SEQ ID NO: 31 (Kabat) | LCDR1 | KSSQSLLDSGNQKNFLT |
|---|---|---|
| SEQ ID NO: 32 (Kabat) | LCDR2 | WASTRES |
| SEQ ID NO: 33 (Kabat) | LCDR3 | QNDYSYPYT |
| SEQ ID NO: 34 (Chothia) | LCDR1 | SQSLLDSGNQKNF |
| SEQ ID NO: 35 (Chothia) | LCDR2 | WAS |
| SEQ ID NO: 36 (Chothia) | LCDR3 | DYSYPY |
| SEQ ID NO: 37 | VL | EIVLTQSPATLSLSPGERATLSCKSSQS<br>LLDSGNQKNFLTWYQQKPGKAPKLLIY<br>WASTRESGVPSRFSGSGSGTDFTFTIS<br>SLQPEDIATYYCQNDYSYPYTFGQGTK<br>VEIK |
| SEQ ID NO: 38 | DNA VL | GAGATCGTCCTGACTCAGTCACCCGC<br>TACCCTGAGCCTGAGCCCTGGCGAG<br>CGGGCTACACTGAGCTGTAAATCTAG<br>TCAGTCACTGCTGGATAGCGGTAATC<br>AGAAGAACTTCCTGACCTGGTATCAG<br>CAGAAGCCCGGTAAAGCCCCTAAGCT<br>GCTGATCTACTGGGCCTCTACTAGAG<br>AATCAGGCGTGCCCTCTAGGTTTAGC<br>GGTAGCGGTAGTGGCACCGACTTCAC<br>CTTCACTATCTCTAGCCTGCAGCCCG<br>AGGATATCGCTACCTACTACTGTCAG<br>AACGACTATAGCTACCCCTACACCTTC<br>GGTCAAGGCACTAAGGTCGAGATTAA<br>G |
| SEQ ID NO: 39 | LC | EIVLTQSPATLSLSPGERATLSCKSSQS<br>LLDSGNQKNFLTWYQQKPGKAPKLLIY<br>WASTRESGVPSRFSGSGSGTDFTFTIS<br>SLQPEDIATYYCQNDYSYPYTFGQGTK<br>VEIKRTVAAPSVFIFPPSDEQLKSGTAS<br>VVCLLNNFYPREAKVQWKVDNALQSG<br>NSQESVTEQDSKDSTYSLSSTLTLSKA<br>DYEKHKVYACEVTHQGLSSPVTKSFNR<br>GEC |
| SEQ ID NO: 40 | DNA LC | GAGATCGTCCTGACTCAGTCACCCGC<br>TACCCTGAGCCTGAGCCCTGGCGAG<br>CGGGCTACACTGAGCTGTAAATCTAG<br>TCAGTCACTGCTGGATAGCGGTAATC<br>AGAAGAACTTCCTGACCTGGTATCAG<br>CAGAAGCCCGGTAAAGCCCCTAAGCT<br>GCTGATCTACTGGGCCTCTACTAGAG<br>AATCAGGCGTGCCCTCTAGGTTTAGC<br>GGTAGCGGTAGTGGCACCGACTTCAC<br>CTTCACTATCTCTAGCCTGCAGCCCG<br>AGGATATCGCTACCTACTACTGTCAG<br>AACGACTATAGCTACCCCTACACCTTC<br>GGTCAAGGCACTAAGGTCGAGATTAA<br>GCGTACGGTGGCCGCTCCCAGCGTG<br>TTCATCTTCCCCCCCAGCGACGAGCA<br>GCTGAAGAGCGGCACCGCCAGCGTG<br>GTGTGCCTGCTGAACAACTTCTACCC |

TABLE 3-continued

Amino acid and nucleotide sequences of exemplary anti-PD-1 antibody molecules

|  |  |  | CCGGGAGGCCAAGGTGCAGTGGAAG<br>GTGGACAACGCCCTGCAGAGCGGCA<br>ACAGCCAGGAGAGCGTCACCGAGCA<br>GGACAGCAAGGACTCCACCTACAGCC<br>TGAGCAGCACCCTGACCCTGAGCAAG<br>GCCGACTACGAGAAGCATAAGGTGTA<br>CGCCTGCGAGGTGACCCACCAGGGC<br>CTGTCCAGCCCCGTGACCAAGAGCTT<br>CAACAGGGGCGAGTGC |
|---|---|---|---|
| BAP049-Clone-E HC | | | |
| SEQ ID NO: 22 | (Kabat) | HCDR1 | TYWMH |
| SEQ ID NO: 23 | (Kabat) | HCDR2 | NIYPGTGGSNFDEKFKN |
| SEQ ID NO: 24 | (Kabat) | HCDR3 | WTTGTGAY |
| SEQ ID NO: 25 | (Chothia) | HCDR1 | GYTFTTY |
| SEQ ID NO: 26 | (Chothia) | HCDR2 | YPGTGG |
| SEQ ID NO: 24 | (Chothia) | HCDR3 | WTTGTGAY |
| SEQ ID NO: 27 | | VH | EVQLVQSGAEVKKPGESLRISCKGSGY<br>TFTTYWMHWVRQATGQGLEWMGNIYP<br>GTGGSNFDEKFKNRVTITADKSTSTAY<br>MELSSLRSEDTAVYYCTRWTTGTGAY<br>WGQGTTVTVSS |
| SEQ ID NO: 28 | | DNA VH | GAGGTGCAGCTGGTGCAGTCAGGCG<br>CCGAAGTGAAGAAGCCCGGCGAGTC<br>ACTGAGAATTAGCTGTAAAGGTTCAG<br>GCTACACCTTCACTACCTACTGGATG<br>CACTGGGTCCGCCAGGCTACCGGTC<br>AAGGCCTCGAGTGGATGGGTAATATC<br>TACCCCGGCACCGGCGGCTCTAACTT<br>CGACGAGAAGTTTAAGAATAGAGTGA<br>CTATCACCGCCGATAAGTCTACTAGC<br>ACCGCCTATATGGAACTGTCTAGCCT<br>GAGATCAGAGGACACCGCCGTCTACT<br>ACTGCACTAGGTGGACTACCGGCACA<br>GGCGCCTACTGGGGTCAAGGCACTA<br>CCGTGACCGTGTCTAGC |
| SEQ ID NO: 29 | | HC | EVQLVQSGAEVKKPGESLRISCKGSGY<br>TFTTYWMHWVRQATGQGLEWMGNIYP<br>GTGGSNFDEKFKNRVTITADKSTSTAY<br>MELSSLRSEDTAVYYCTRWTTGTGAY<br>WGQGTTVTVSSASTKGPSVFPLAPCSR<br>STSESTAALGCLVKDYFPEPVTVSWNS<br>GALTSGVHTFPAVLQSSGLYSLSSVVT<br>VPSSSLGTKTYTCNVDHKPSNTKVDKR<br>VESKYGPPCPPCPAPEFLGGPSVFLFP<br>PKPKDTLMISRTPEVTCVVVDVSQEDP<br>EVQFNWYVDGVEVHNAKTKPREEQFN<br>STYRVVSVLTVLHQDWLNGKEYKCKVS<br>NKGLPSSIEKTISKAKGQPREPQVYTLP<br>PSQEEMTKNQVSLTCLVKGFYPSDIAV<br>EWESNGQPENNYKTTPPVLDSDGSFFL<br>YSRLTVDKSRWQEGNVFSCSVMHEAL<br>HNHYTQKSLSLSLG |
| SEQ ID NO: 30 | | DNA HC | GAGGTGCAGCTGGTGCAGTCAGGCG<br>CCGAAGTGAAGAAGCCCGGCGAGTC<br>ACTGAGAATTAGCTGTAAAGGTTCAG<br>GCTACACCTTCACTACCTACTGGATG<br>CACTGGGTCCGCCAGGCTACCGGTC<br>AAGGCCTCGAGTGGATGGGTAATATC<br>TACCCCGGCACCGGCGGCTCTAACTT<br>CGACGAGAAGTTTAAGAATAGAGTGA<br>CTATCACCGCCGATAAGTCTACTAGC<br>ACCGCCTATATGGAACTGTCTAGCCT<br>GAGATCAGAGGACACCGCCGTCTACT<br>ACTGCACTAGGTGGACTACCGGCACA<br>GGCGCCTACTGGGGTCAAGGCACTA<br>CCGTGACCGTGTCTAGCGCTAGCACT |

TABLE 3-continued

Amino acid and nucleotide sequences of exemplary anti-PD-1 antibody molecules

```
AAGGGCCCGTCCGTGTTCCCCCTGG
CACCTTGTAGCCGGAGCACTAGCGAA
TCCACCGCTGCCCTCGGCTGCCTGGT
CAAGGATTACTTCCCGGAGCCCGTGA
CCGTGTCCTGGAACAGCGGAGCCCT
GACCTCCGGAGTGCACACCTTCCCCG
CTGTGCTGCAGAGCTCCGGGCTGTAC
TCGCTGTCGTCGGTGGTCACGGTGCC
TTCATCTAGCCTGGGTACCAAGACCT
ACACTTGCAACGTGGACCACAAGCCT
TCCAACACTAAGGTGGACAAGCGCGT
CGAATCGAAGTACGGCCCACCGTGCC
CGCCTTGTCCCGCGCCGGAGTTCCTC
GGCGGTCCCTCGGTCTTTCTGTTCCC
ACCGAAGCCCAAGGACACTTTGATGA
TTTCCCGCACCCCTGAAGTGACATGC
GTGGTCGTGGACGTGTCACAGGAAGA
TCCGGAGGTGCAGTTCAATTGGTACG
TGGATGGCGTCGAGGTGCACAACGC
CAAAACCAAGCCGAGGGAGGAGCAG
TTCAACTCCACTTACCGCGTCGTGTC
CGTGCTGACGGTGCTGCATCAGGACT
GGCTGAACGGGAAGGAGTACAAGTG
CAAAGTGTCCAACAAGGGACTTCCTA
GCTCAATCGAAAAGACCATCTCGAAA
GCCAAGGGACAGCCCCGGGAACCCC
AAGTGTATACCCTGCCACCGAGCCAG
GAAGAAATGACTAAGAACCAAGTCTC
ATTGACTTGCCTTGTGAAGGGCTTCTA
CCCATCGGATATCGCCGTGGAATGGG
AGTCCAACGGCCAGCCGGAAAACAAC
TACAAGACCACCCCTCCGGTGCTGGA
CTCAGACGGATCCTTCTTCCTCTACTC
GCGGCTGACCGTGGATAAGAGCAGAT
GGCAGGAGGGAAATGTGTTCAGCTGT
TCTGTGATGCATGAAGCCCTGCACAA
CCACTACACTCAGAAGTCCCTGTCCC
TCTCCCTGGGA
```

BAP049-Clone-E LC

| SEQ ID NO: 31 (Kabat) | LCDR1 | KSSQSLLDSGNQKNFLT |
| --- | --- | --- |
| SEQ ID NO: 32 (Kabat) | LCDR2 | WASTRES |
| SEQ ID NO: 33 (Kabat) | LCDR3 | QNDYSYPYT |
| SEQ ID NO: 34 (Chothia) | LCDR1 | SQSLLDSGNQKNF |
| SEQ ID NO: 35 (Chothia) | LCDR2 | WAS |
| SEQ ID NO: 36 (Chothia) | LCDR3 | DYSYPY |
| SEQ ID NO: 41 | VL | EIVLTQSPATLSLSPGERATLSCKSSQS LLDSGNQKNFLTWYQQKPGQAPRLLIY WASTRESGVPSRFSGSGSGTDFTFTIS SLEAEDAATYYCQNDYSYPYTFGQGTK VEIK |
| SEQ ID NO: 42 | DNA VL | GAGATCGTCCTGACTCAGTCACCCGC TACCCTGAGCCTGAGCCCTGGCGAG CGGGCTACACTGAGCTGTAAATCTAG TCAGTCACTGCTGGATAGCGGTAATC AGAAGAACTTCCTGACCTGGTATCAG CAGAAGCCCGGTCAAGCCCCTAGACT GCTGATCTACTGGGCCTCTACTAGAG AATCAGGCGTGCCCTCTAGGTTTAGC GGTAGCGGTAGTGGCACCGACTTCAC CTTCACTATCTCTAGCCTGGAAGCCG AGGACGCCGCTACCTACTACTGTCAG AACGACTATAGCTACCCCTACACCTTC GGTCAAGGCACTAAGGTCGAGATTAA G |
| SEQ ID NO: 43 | LC | EIVLTQSPATLSLSPGERATLSCKSSQS LLDSGNQKNFLTWYQQKPGQAPRLLIY WASTRESGVPSRFSGSGSGTDFTFTIS |

TABLE 3-continued

Amino acid and nucleotide sequences of exemplary anti-PD-1 antibody molecules

| | | | |
|---|---|---|---|
| | | | SLEAEDAATYYCQNDYSYPYTFGQGTK VEIKRTVAAPSVFlFPPSDEQLKSGTAS VVCLLNNFYPREAKVQWKVDNALQSG NSQESVTEQDSKDSTYSLSSTLTLSKA DYEKHKVYACEVTHQGLSSPVTKSFNR GEC |
| SEQ ID NO: 44 | | DNA LC | GAGATCGTCCTGACTCAGTCACCCGC TACCCTGAGCCTGAGCCCTGGCGAG CGGGCTACACTGAGCTGTAAATCTAG TCAGTCACTGCTGGATAGCGGTAATC AGAAGAACTTCCTGACCTGGTATCAG CAGAAGCCCGGTCAAGCCCCTAGACT GCTGATCTACTGGGCCTCTACTAGAG AATCAGGCGTGCCCTCTAGGTTTAGC GGTAGCGGTAGTGGCACCGACTTCAC CTTCACTATCTCTAGCCTGGAAGCCG AGGACGCCGCTACCTACTACTGTCAG AACGACTATAGCTACCCCTACACCTTC GGTCAAGGCACTAAGGTCGAGATTAA GCGTACGGTGGCCGCTCCCAGCGTG TTCATCTTCCCCCCCAGCGACGAGCA GCTGAAGAGCGGCACCGCCAGCGTG GTGTGCCTGCTGAACAACTTCTACCC CCGGGAGGCCAAGGTGCAGTGGAAG GTGGACAACGCCCTGCAGAGCGGCA ACAGCCAGGAGAGCGTCACCGAGCA GGACAGCAAGGACTCCACCTACAGCC TGAGCAGCACCCTGACCCTGAGCAAG GCCGACTACGAGAAGCATAAGGTGTA CGCCTGCGAGGTGACCCACCAGGGC CTGTCCAGCCCCGTGACCAAGAGCTT CAACAGGGGCGAGTGC |

BAP049-Clone-B HC

| | | | |
|---|---|---|---|
| SEQ ID NO: 45 | (Kabat) | HCDR1 | ACCTACTGGATGCAC |
| SEQ ID NO: 46 | (Kabat) | HCDR2 | AATATCTACCCCGGCACCGGCGGCTC TAACTTCGACGAGAAGTTTAAGAAT |
| SEQ ID NO: 47 | (Kabat) | HCDR3 | TGGACTACCGGCACAGGCGCCTAC |
| SEQ ID NO: 48 | (Chothia) | HCDR1 | GGCTACACCTTCACTACCTAC |
| SEQ ID NO: 49 | (Chothia) | HCDR2 | TACCCCGGCACCGGCGGC |
| SEQ ID NO: 47 | (Chothia) | HCDR3 | TGGACTACCGGCACAGGCGCCTAC |

BAP049-Clone-B LC

| | | | |
|---|---|---|---|
| SEQ ID NO: 50 | (Kabat) | LCDR1 | AAATCTAGTCAGTCACTGCTGGATAG CGGTAATCAGAAGAACTTCCTGACC |
| SEQ ID NO: 51 | (Kabat) | LCDR2 | TGGGCCTCTACTAGAGAATCA |
| SEQ ID NO: 52 | (Kabat) | LCDR3 | CAGAACGACTATAGCTACCCCTACAC C |
| SEQ ID NO: 53 | (Chothia) | LCDR1 | AGTCAGTCACTGCTGGATAGCGGTAA TCAGAAGAACTTC |
| SEQ ID NO: 54 | (Chothia) | LCDR2 | TGGGCCTCT |
| SEQ ID NO: 55 | (Chothia) | LCDR3 | GACTATAGCTACCCCTAC |

BAP049-Clone-E HC

| | | | |
|---|---|---|---|
| SEQ ID NO: 45 | (Kabat) | HCDR1 | ACCTACTGGATGCAC |
| SEQ ID NO: 46 | (Kabat) | HCDR2 | AATATCTACCCCGGCACCGGCGGCTC TAACTTCGACGAGAAGTTTAAGAAT |
| SEQ ID NO: 47 | (Kabat) | HCDR3 | TGGACTACCGGCACAGGCGCCTAC |
| SEQ ID NO: 48 | (Chothia) | HCDR1 | GGCTACACCTTCACTACCTAC |

TABLE 3-continued

Amino acid and nucleotide sequences of exemplary anti-PD-1 antibody molecules

| SEQ ID NO: 49 (Chothia) HCDR2 | TACCCCGGCACCGGCGGC |
| --- | --- |
| SEQ ID NO: 47 (Chothia) HCDR3 | TGGACTACCGGCACAGGCGCCTAC |

BAP049-Clone-E LC

| SEQ ID NO: 50 (Kabat) LCDR1 | AAATCTAGTCAGTCACTGCTGGATAGCGGTAATCAGAAGAACTTCCTGACC |
| --- | --- |
| SEQ ID NO: 51 (Kabat) LCDR2 | TGGGCCTCTACTAGAGAATCA |
| SEQ ID NO: 52 (Kabat) LCDR3 | CAGAACGACTATAGCTACCCCTACACC |
| SEQ ID NO: 53 (Chothia) LCDR1 | AGTCAGTCACTGCTGGATAGCGGTAATCAGAAGAACTTC |
| SEQ ID NO: 54 (Chothia) LCDR2 | TGGGCCTCT |
| SEQ ID NO: 55 (Chothia) LCDR3 | GACTATAGCTACCCCTAC |

In a preferred embodiment, the anti PD-1 antibody for use in the combinations, methods and compositions of the invention comprises:
  (a) a heavy chain variable region (VH) comprising a VHCDR1 amino acid sequence of SEQ ID NO: 25, a VHCDR2 amino acid sequence of SEQ ID NO: 26, and a VHCDR3 amino acid sequence of SEQ ID NO: 24; and a light chain variable region (VL) comprising a VLCDR1 amino acid sequence of SEQ ID NO: 34, a VLCDR2 amino acid sequence of SEQ ID NO: 35, and a VLCDR3 amino acid sequence of SEQ ID NO: 36;
  (b) a heavy chain variable region (VH) comprising a VHCDR1 amino acid sequence of SEQ ID NO: 22; a VHCDR2 amino acid sequence of SEQ ID NO: 23; and a VHCDR3 amino acid sequence of SEQ ID NO: 24; and a light chain variable region (VL) comprising a VLCDR1 amino acid sequence of SEQ ID NO: 31, a VLCDR2 amino acid sequence of SEQ ID NO: 32, and a VLCDR3 amino acid sequence of SEQ ID NO: 33;
  (c) a heavy chain variable region (VH) comprising a VHCDR1 amino acid sequence of SEQ ID NO: 21, a VHCDR2 amino acid sequence of SEQ ID NO: 26, and a VHCDR3 amino acid sequence of SEQ ID NO: 24; and a a light chain variable region (VL) comprising a VLCDR1 amino acid sequence of SEQ ID NO: 34, a VLCDR2 amino acid sequence of SEQ ID NO: 35, and a VLCDR3 amino acid sequence of SEQ ID NO: 36; or
  (d) a heavy chain variable region (VH) comprising a VHCDR1 amino acid sequence of SEQ ID NO: 21; a VHCDR2 amino acid sequence of SEQ ID NO: 23; and a VHCDR3 amino acid sequence of SEQ ID NO: 24; and a a light chain variable region (VL) comprising a VLCDR1 amino acid sequence of SEQ ID NO: 31, a VLCDR2 amino acid sequence of SEQ ID NO: 32, and a VLCDR3 amino acid sequence of SEQ ID NO: 33, In another preferred embodiment, the anti PD-1 antibody for use in the combinations, methods and compositions of the invention comprises a VH comprising the amino acid sequence of SEQ ID NO: 27 and a VL comprising the amino acid sequence of SEQ ID NO: 41.

In another preferred embodiment, the anti PD-1 antibody for use in the combinations, methods and compositions of the invention comprises a VH comprising the amino acid sequence of SEQ ID NO: 27 and a VL comprising the amino acid sequence of SEQ ID NO: 37.

In another preferred embodiment, the anti PD-1 antibody for use in the combinations, methods and compositions of the invention comprises a heavy chain comprising the amino acid sequence of SEQ ID NO: 29 and a light chain comprising the amino acid sequence of SEQ ID NO: 43.

In another preferred embodiment, the anti PD-1 antibody for use in the combinations, methods and compositions of the invention comprises a heavy chain comprising the amino acid sequence of SEQ ID NO: 29 and a light chain comprising the amino acid sequence of SEQ ID NO: 39.

Other Exemplary PD-1 Inhibitors for Use in the Combinations Described Herein

In one embodiment, the anti-PD-1 antibody molecule is Nivolumab (Bristol-Myers Squibb), also known as MDX-1106, MDX-1106-04, ONO-4538, BMS-936558, or OPDIVO®. Nivolumab (clone 5C4) and other anti-PD-1 antibodies are disclosed in U.S. Pat. No. 8,008,449 and WO 2006/121168, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Nivolumab, e.g., as disclosed in Table 4.

In one embodiment, the anti-PD-1 antibody molecule is Pembrolizumab (Merck & Co), also known as Lambrolizumab, MK-3475, MK03475, SCH-900475, or KEYTRUDA®. Pembrolizumab and other anti-PD-1 antibodies are disclosed in Hamid, O. et al. (2013) *New England Journal of Medicine* 369 (2): 134-44, U.S. Pat. No. 8,354,509, and WO 2009/114335, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pembrolizumab, e.g., as disclosed in Table 4.

In one embodiment, the anti-PD-1 antibody molecule is Pidilizumab (CureTech), also known as CT-011. Pidilizumab and other anti-PD-1 antibodies are disclosed in Rosenblatt, J. et al. (2011) *J Immunotherapy* 34(5): 409-18, U.S. Pat. Nos. 7,695,715, 7,332,582, and 8,686,119, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pidilizumab, e.g., as disclosed in Table 4.

In one embodiment, the anti-PD-1 antibody molecule is MEDI0680 (Medimmune), also known as AMP-514. MEDI0680 and other anti-PD-1 antibodies are disclosed in U.S. Pat. No. 9,205,148 and WO 2012/145493, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of MEDI0680.

In one embodiment, the anti-PD-1 antibody molecule is REGN2810 (Regeneron). In one embodiment, the anti-PD-1 antibody molecule comprises one or more of the CDR sequences (or collectively all of the CDR sequences), the heavy chain or light chain variable region sequence, or the heavy chain or light chain sequence of REGN2810.

In one embodiment, the anti-PD-1 antibody molecule is PF-06801591 (Pfizer). In one embodiment, the anti-PD-1 antibody molecule comprises one or more of the CDR sequences (or collectively all of the CDR sequences), the heavy chain or light chain variable region sequence, or the heavy chain or light chain sequence of PF-06801591.

In one embodiment, the anti-PD-1 antibody molecule is BGB-A317 or BGB-108 (Beigene). In one embodiment, the anti-PD-1 antibody molecule comprises one or more of the CDR sequences (or collectively all of the CDR sequences), the heavy chain or light chain variable region sequence, or the heavy chain or light chain sequence of BGB-A317 or BGB-108.

In one embodiment, the anti-PD-1 antibody molecule is INCSHR1210 (Incyte), also known as INCSHR01210 or SHR-1210. In one embodiment, the anti-PD-1 antibody molecule comprises one or more of the CDR sequences (or collectively all of the CDR sequences), the heavy chain or light chain variable region sequence, or the heavy chain or light chain sequence of INCSHR1210.

In one embodiment, the anti-PD-1 antibody molecule is TSR-042 (Tesaro), also known as ANB011. In one embodiment, the anti-PD-1 antibody molecule comprises one or more of the CDR sequences (or collectively all of the CDR sequences), the heavy chain or light chain variable region sequence, or the heavy chain or light chain sequence of TSR-042.

Further known anti-PD-1 antibodies include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the anti-PD-1 antibody is an antibody that competes for binding with, and/or binds to the same epitope on PD-1 as, one of the anti-PD-1 antibodies described herein.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

TABLE 4

Amino acid sequences of other exemplary anti-PD-1 antibody molecules

Nivolumab

| SEQ ID NO: 56 | HC | QVQLVESGGGVVQPGRSLRLDCKASGI TFSNSGMHWVRQAPGKGLEWVAVIWY DGSKRYYADSVKGRFTISRDNSKNTLFL QMNSLRAEDTAVYYCATNDDYWGQGT LVTVSSASTKGPSVFPLAPCSRSTSEST AALGCLVKDYFPEPVTVSWNSGALTSG VHTFPAVLQSSGLYSLSSVVTVPSSSLG TKTYTCNVDHKPSNTKVDKRVESKYGP PCPPCPAPEFLGGPSVFLFPPKPKDTL MISRTPEVTCVVVDVSQEDPEVQFNWY VDGVEVHNAKTKPREEQFNSTYRVVSV LTVLHQDWLNGKEYKCKVSNKGLPSSI EKTISKAKGQPREPQVYTLPPSQEEMT KNQVSLTCLVKGFYPSDIAVEWESNGQ PENNYKTTPPVLDSDGSFFLYSRLTVDK SRWQEGNVFSCSVMHEALHNHYTQKS LSLSLGK |
| --- | --- | --- |
| SEQ ID NO: 57 | LC | EIVLTQSPATLSLSPGERATLSCRASQS VSSYLAWYQQKPGQAPRLLIYDASNRA TGIPARFSGSGSGTDFTLTISSLEPEDF AVYYCQQSSNWPRTFGQGTKVEIKRTV AAPSVFIFPPSDEQLKSGTASVVCLLNN FYPREAKVQWKVDNALQSGNSQESVT EQDSKDSTYSLSSTLTLSKADYEKHKV YACEVTHQGLSSPVTKSFNRGEC |

Pembrolizumab

| SEQ ID NO: 58 | HC | QVQLVQSGVEVKKPGASVKVSCKASG YTFTNYYMYWVRQAPGQGLEWMGGIN PSNGGTNFNEKFKNRVTLTTDSSTTTA YMELKSLQFDDTAVYYCARRDYRFDM GFDYWGQGTTVTVSSASTKGPSVFPLA PCSRSTSESTAALGCLVKDYFPEPVTV SWNSGALTSGVHTFPAVLQSSGLYSLS SVVTVPSSSLGTKTYTCNVDHKPSNTK VDKRVESKYGPPCPPCPAPEFLGGPSV FLFPPKPKDTLMISRTPEVTCVVVDVSQ EDPEVQFNWYVDGVEVHNAKTKPREE QFNSTYRVVSVLTVLHQDWLNGKEYKC KVSNKGLPSSIEKTISKAKGQPREPQVY TLPPSQEEMTKNQVSLTCLVKGFYPSDI AVEWESNGQPENNYKTTPPVLDSDGS FFLYSRLTVDKSRWQEGNVFSCSVMH EALHNHYTQKSLSLSLGK |
| --- | --- | --- |
| SEQ ID NO: 59 | LC | EIVLTQSPATLSLSPGERATLSCRASKG VSTSGYSYLHWYQQKPGQAPRLLIYLA SYLESGVPARFSGSGSGTDFTLTISSLE PEDFAVYYCQHSRDLPLTFGGGTKVEI KRTVAAPSVFIFPPSDEQLKSGTASVVC LLNNFYPREAKVQWKVDNALQSGNSQ ESVTEQDSKDSTYSLSSTLTLSKADYEK HKVYACEVTHQGLSSPVTKSFNRGEC |

Pidilizumab

| SEQ ID NO: 60 | HC | QVQLVQSGSELKKPGASVKISCKASGY TFTNYGMNWVRQAPGQGLQWMGWIN TDSGESTYAEEFKGRFVFSLDTSVNTA YLQITSLTAEDTGMYFCVRVGYDALDY WGQGTLVTVSSASTKGPSVFPLAPSSK STSGGTAALGCLVKDYFPEPVTVSWNS GALTSGVHTFPAVLQSSGLYSLSSVVT VPSSSLGTQTYICNVNHKPSNTKVDKR VEPKSCDKTHTCPPCPAPELLGGPSVF LFPPKPKDTLMISRTPEVTCVVVDVSHE DPEVKFNWYVDGVEVHNAKTKPREEQ YNSTYRVVSVLTVLHQDWLNGKEYKCK |
| --- | --- | --- |

TABLE 4-continued

Amino acid sequences of other exemplary
anti-PD-1 antibody molecules

|  |  |  |
|---|---|---|
|  |  | VSNKALPAPIEKTISKAKGQPREPQVYT<br>LPPSREEMTKNQVSLTCLVKGFYPSDIA<br>VEWESNGQPENNYKTTPPVLDSDGSF<br>FLYSKLTVDKSRWQQGNVFSCSVMHE<br>ALHNHYTQKSLSLSPGK |
| SEQ ID NO: 61 | LC | EIVLTQSPSSLSASVGDRVTITCSARSS<br>VSYMHWFQQKPGKAPKLWIYRTSNLAS<br>GVPSRFSGSGSGTSYCLTINSLQPEDF<br>ATYYCQQRSSFPLTFGGGTKLEIKRTVA<br>APSVFIFPPSDEQLKSGTASVVCLLNNF<br>YPREAKVQWKVDNALQSGNSQESVTE<br>QDSKDSTYSLSSTLTLSKADYEKHKVY<br>ACEVTHQGLSSPVTKSFNRGEC |

Certain aspects and examples of combinations of the invention are provided in the following listing of enumerated embodiments. It will be recognized that features specified in each embodiment may be combined with other specified features to provide further embodiments of the present invention.

Embodiment 235. A pharmaceutical combination comprising:
  a) a first pharmaceutical composition selected from any one of Embodiments 1 to 83 or 161 to 164, and
  b) a second pharmaceutical composition comprising an immune checkpoint inhibitor and one or more pharmaceutically acceptable excipients.

Embodiment 236. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an immune checkpoint inhibitor and one or more pharmaceutically acceptable excipients.

Embodiment 237. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 238. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an anti-PD-1 antibody and one or more pharmaceutically acceptable excipients.

Embodiment 239. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an anti-PD-L1 antibody and one or more pharmaceutically acceptable excipients.

Embodiment 240. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an anti-PD-L1 antibody selected from Table 2, and one or more pharmaceutically acceptable excipients.

Embodiment 241. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients.

Embodiment 242. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an anti-PD-1 antibody selected from Table 3, and one or more pharmaceutically acceptable excipients.

Embodiment 243. A pharmaceutical combination comprising:
  a) a first pharmaceutical composition comprising a compound of Formula (A), or a pharmaceutically acceptable salt thereof, aluminum-containing particles, a buffering agent and one or more pharmaceutically acceptable excipients, and
  b) a second pharmaceutical composition comprising an anti-PD-1 antibody comprising a heavy chain variable domain comprising the amino acid sequence of SEQ ID NO:27 and a light chain variable domain comprising the amino acid sequence of SEQ ID NO: 37, and one or more pharmaceutically acceptable excipients.

Embodiment 244. A pharmaceutical combination comprising:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
  b) a second pharmaceutical composition comprising an immune checkpoint inhibitor and one or more pharmaceutically acceptable excipients.

Embodiment 245. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 246. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising an immune checkpoint inhibitor and one or more pharmaceutically acceptable excipients, wherein the checkpoint inhibitor is an anti-PD-1 antibody.

Embodiment 247. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising an immune checkpoint inhibitor and one or more pharmaceutically acceptable excipients, wherein the checkpoint inhibitor is an anti-PD-1 antibody of Table 3.

Embodiment 248. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising an immune checkpoint inhibitor and one or more pharmaceutically acceptable excipients, wherein the checkpoint inhibitor is an anti-PD-L1 antibody comprising a heavy chain variable domain comprising the amino acid sequence of SEQ ID NO:27 and a light chain variable domain comprising the amino acid sequence of SEQ ID NO:37.

Embodiment 249. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising an immune checkpoint inhibitor and one or more pharmaceutically acceptable excipients, wherein the checkpoint inhibitor is an anti-PD-L1 antibody.

Embodiment 250. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising an immune checkpoint inhibitor and one or more pharmaceutically acceptable excipients, wherein the checkpoint inhibitor is an anti-PD-L1 antibody of Table 2.

Embodiment 251. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising an immune checkpoint inhibitor and one or more pharmaceutically acceptable excipients, wherein the checkpoint inhibitor is an anti-PD-L1 antibody comprising a heavy chain variable domain comprising the amino acid sequence of SEQ ID NO:7 and a light chain variable domain comprising the amino acid sequence of SEQ ID NO:17.

Embodiment 252. A pharmaceutical combination comprising:
- a) a first pharmaceutical composition having a pH between 7.0 and 8.0 comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and mannitol, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 253. A pharmaceutical combination comprising:
- a) a first pharmaceutical composition having a pH between 7.0 and 8.0 comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and sucrose, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 254. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 255. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 256. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 257. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 258. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 259. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 260. A pharmaceutical combination comprising:
  a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 261. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 262. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 263. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 264. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-L1 antibody.

Embodiment 265. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-L1 antibody.

Embodiment 266. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-L1 antibody.

Embodiment 267. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-L1 antibody.

Embodiment 268. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-L1 antibody.

Embodiment 269. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-L1 antibody.

Embodiment 270. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
- b) a second pharmaceutical composition comprising an immune checkpoint inhibitor and one or more pharmaceutically acceptable excipients, wherein the checkpoint inhibitor is an anti-PD-L1 antibody.

Embodiment 271. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
- b) a second pharmaceutical composition comprising an immune checkpoint inhibitor and one or more pharmaceutically acceptable excipients, wherein the checkpoint inhibitor is an anti-PD-L1 antibody.

Embodiment 272. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
- b) a second pharmaceutical composition comprising an immune checkpoint inhibitor and one or more pharmaceutically acceptable excipients, wherein the checkpoint inhibitor is an anti-PD-L1 antibody.

Embodiment 273. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
- b) a second pharmaceutical composition comprising an immune checkpoint inhibitor and one or more pharmaceutically acceptable excipients, wherein the checkpoint inhibitor is an anti-PD-L1 antibody.

Embodiment 274. The pharmaceutical combination of any one of Embodiments 264 to 273, wherein the anti-PD-L1 antibody is an anti-PD-L1 antibody of Table 2.

Embodiment 275. The pharmaceutical combination of any one of Embodiments 264 to 274, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 276. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-1 antibody.

Embodiment 277. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-1 antibody.

Embodiment 278. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-1 antibody.

Embodiment 279. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 280. A pharmaceutical combination comprising:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-1 antibody.

Embodiment 281. A pharmaceutical combination comprising:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-1 antibody.

Embodiment 282. A pharmaceutical combination comprising:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
b) a second pharmaceutical composition comprising an immune checkpoint inhibitor and one or more pharmaceutically acceptable excipients, wherein the checkpoint inhibitor is an anti-PD-1 antibody.

Embodiment 283. A pharmaceutical combination comprising:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
b) a second pharmaceutical composition comprising an immune checkpoint inhibitor and one or more pharmaceutically acceptable excipients, wherein the checkpoint inhibitor is an anti-PD-1 antibody.

Embodiment 284. A pharmaceutical combination comprising:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
b) a second pharmaceutical composition comprising an immune checkpoint inhibitor and one or more pharmaceutically acceptable excipients, wherein the checkpoint inhibitor is an anti-PD-1 antibody.

Embodiment 285. A pharmaceutical combination comprising:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
b) a second pharmaceutical composition comprising an immune checkpoint inhibitor and one or more pharmaceutically acceptable excipients, wherein the checkpoint inhibitor is an anti-PD-1 antibody.

Embodiment 286. The pharmaceutical combination of any one of Embodiments 276 to 285, wherein the anti-PD-1 antibody is an anti-PD-1 antibody of Table 3.

Embodiment 287. The pharmaceutical combination of any one of Embodiments 276 to 286, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 288. The pharmaceutical combination of any one of Embodiments 236 to 287, wherein the first pharmaceutical composition comprises a therapeutically effective amount of the compound of Formula A and the second pharmaceutical composition comprises a therapeutically effective amount of the immune checkpoint inhibitor, the anti-PD-L1 antibody or the anti-PD-1 antibody.

Embodiment 289. The pharmaceutical combination of any one of Embodiments 244 to 287, wherein the first pharmaceutical composition comprises a therapeutically effective amount of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, and the second pharmaceutical composition comprises a therapeutically effective amount of the immune checkpoint inhibitor, the anti-PD-L1 antibody or the anti-PD-1 antibody.

Embodiment 290. A pharmaceutical combination comprising:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
b) a second pharmaceutical composition comprising tremelimumab and one or more pharmaceutically acceptable excipients.

Embodiment 291. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising lambrolizumab and one or more pharmaceutically acceptable excipients.

Embodiment 292. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising pidilizumab and one or more pharmaceutically acceptable excipients.

Embodiment 293. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising nivolumab and one or more pharmaceutically acceptable excipients.

Embodiment 294. A combination of a pharmaceutical composition comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, and
- b) a second pharmaceutical composition comprising lirilumab and one or more pharmaceutically acceptable excipients.

Embodiment 295. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an immune checkpoint inhibitor and one or more pharmaceutically acceptable excipients, and
- c) a third pharmaceutical composition comprising an immune checkpoint inhibitor, which is different from the immune checkpoint inhibitor in the second pharmaceutical composition, and one or more pharmaceutically acceptable excipients.

Embodiment 296. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 297. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-L1 antibody and one or more pharmaceutically acceptable excipients, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 298. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-L1 antibody and one or more pharmaceutically acceptable excipients, and
- c) a third pharmaceutical composition comprising an anti-CTLA-4 antibody and one or more pharmaceutically acceptable excipients.

Embodiment 299. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-L1 antibody of Table 2, and one or more pharmaceutically acceptable excipients, and
- c) a third pharmaceutical composition comprising an anti-CTLA-4 antibody and one or more pharmaceutically acceptable excipients.

Embodiment 300. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients, and
- c) a third pharmaceutical composition comprising an anti-CTLA-4 antibody and one or more pharmaceutically acceptable excipients.

Embodiment 301. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-1 antibody and one or more pharmaceutically acceptable excipients, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 302. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-1 antibody and one or more pharmaceutically acceptable excipients, and
- c) a third pharmaceutical composition comprising an anti-CTLA-4 antibody and one or more pharmaceutically acceptable excipients.

Embodiment 303. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-1 antibody of Table 3, and one or more pharmaceutically acceptable excipients, and
- c) a third pharmaceutical composition comprising an anti-CTLA-4 antibody and one or more pharmaceutically acceptable excipients.

Embodiment 304. A pharmaceutical combination comprising:
- a) a first pharmaceutical composition comprising a compound of Formula (A), or a pharmaceutically acceptable salt thereof, aluminum-containing particles, a buffering agent and one or more pharmaceutically acceptable excipients,
- b) a second pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients, and
- c) a third pharmaceutical composition comprising an anti-CTLA-4 antibody and one or more pharmaceutically acceptable excipients.

Embodiment 305. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients,
- b) a second pharmaceutical composition comprising an immune checkpoint inhibitor and one or more pharmaceutically acceptable excipients, and
- c) a third pharmaceutical composition comprising an immune checkpoint inhibitor, which is different from the immune checkpoint inhibitor in the second pharmaceutical composition, and one or more pharmaceutically acceptable excipients.

Embodiment 306. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients,
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 307. A pharmaceutical combination comprising:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising an anti-PD-L1 antibody and one or more pharmaceutically acceptable excipients, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 308. A pharmaceutical combination comprising:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising an anti-PD-L1 antibody of Table 2, and one or more pharmaceutically acceptable excipients, and c) a third pharmaceutical composition comprising an anti-CTLA-4 antibody and one or more pharmaceutically acceptable excipients.

Embodiment 309. A pharmaceutical combination comprising:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients, and c) a third pharmaceutical composition comprising an anti-CTLA-4 antibody and one or more pharmaceutically acceptable excipients.

Embodiment 310. A pharmaceutical combination comprising:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising an anti-PD-1 antibody and one or more pharmaceutically acceptable excipients, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 311. A pharmaceutical combination comprising:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising an anti-PD-1 antibody of Table 3 and one or more pharmaceutically acceptable excipients, and c) a third pharmaceutical composition comprising an anti-CTLA-4 antibody and one or more pharmaceutically acceptable excipients.

Embodiment 312. A pharmaceutical combination comprising:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients, and c) a third pharmaceutical composition comprising an anti-CTLA-4 antibody and one or more pharmaceutically acceptable excipients.

Embodiment 313. A pharmaceutical combination comprising:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising ipilimumab and one or more pharmaceutically acceptable excipients, c) and a third pharmaceutical composition comprising nivolumab and one or more pharmaceutically acceptable excipients.

Embodiment 314. A pharmaceutical combination comprising:

a) first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent and one or more pharmaceutically acceptable excipients, b) a second pharmaceutical composition comprising ipilimumab and one or more pharmaceutically acceptable excipients, and c) a third pharmaceutical composition comprising lambrolizumab and one or more pharmaceutically acceptable excipients.

Embodiment 315. A pharmaceutical combination comprising:
  a) a first pharmaceutical composition having a pH between 7.0 and 8.0 comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 316. A pharmaceutical combination comprising:
  a) a first pharmaceutical composition having a pH between 7.0 and 8.0 comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, Tris buffer and sucrose, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 317. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 318. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 319. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 320. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 321. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 322. A pharmaceutical combination comprising:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 323. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 324. A pharmaceutical combination comprising:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 325. A pharmaceutical combination comprising:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 326. A pharmaceutical combination comprising:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 327. A pharmaceutical combination comprising:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 328. A pharmaceutical combination comprising:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 329. A pharmaceutical combination comprising:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 330. A pharmaceutical combination comprising:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 331. A pharmaceutical combination comprising:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 332. A pharmaceutical combination comprising:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 333. A pharmaceutical combination comprising:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 334. A pharmaceutical combination comprising:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 335. A pharmaceutical combination comprising:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 336. A pharmaceutical combination comprising:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 337. The pharmaceutical combination of any one of Embodiments 355 to 364, wherein the anti-PD-L1 antibody is an anti-PD-L1 antibody of Table 2.

Embodiment 338. The pharmaceutical combination of any one of Embodiments 355 to 364, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 339. A pharmaceutical combination comprising:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 340. A pharmaceutical combination comprising:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 341. A pharmaceutical combination comprising:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 342. A pharmaceutical combination comprising:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 343. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 344. A pharmaceutical combination comprising:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 345. A pharmaceutical combination comprising:
  a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, and one or more pharmaceutically acceptable excipients, wherein the checkpoint inhibitor is an anti-CTLA-4 antibody.

Embodiment 346. A pharmaceutical combination comprising:
  a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, and one or more pharmaceutically acceptable excipients, wherein the checkpoint inhibitor is an anti-CTLA-4 antibody.

Embodiment 347. A pharmaceutical combination comprising:
  a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, and one or more pharmaceutically acceptable excipients, wherein the checkpoint inhibitor is an anti-CTLA-4 antibody.

Embodiment 348. A pharmaceutical combination comprising:
  a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, and one or more pharmaceutically acceptable excipients, wherein the checkpoint inhibitor is an anti-CTLA-4 antibody.

Embodiment 349. The pharmaceutical combination of any one of Embodiments 367 to 376, wherein the anti-PD-1 antibody is an anti-PD-1 antibody of Table 3.

Embodiment 350. The pharmaceutical combination of any one of Embodiments 367 to 376, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 351. The pharmaceutical combination of any one of Embodiments 295 to 304, wherein the first pharmaceutical composition comprises a therapeutically effective amount of the compound of Formula A, the second pharmaceutical composition comprise a therapeutically effective amount of the immune checkpoint inhibitor, the anti-PD-L1 antibody, the anti-CTLA-4 antibody or the anti-PD-1 antibody, and the third pharmaceutical composition comprise a therapeutically effective amount of the immune checkpoint inhibitor, the anti-PD-L1 antibody, the anti-CTLA-4 antibody or the anti-PD-1 antibody.

Embodiment 352. The pharmaceutical combination of any one of Embodiments 305 to 350, wherein the first pharmaceutical composition comprises a therapeutically effective amount of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, the second pharmaceutical composition comprise a therapeutically effective amount of the immune checkpoint inhibitor, the anti-PD-L1 antibody, the anti-CTLA-4 antibody or the anti-PD-1 antibody, and the third pharmaceutical composition comprise a therapeutically effective amount of the immune checkpoint inhibitor, the anti-PD-L1 antibody, the anti-CTLA-4 antibody or the anti-PD-1 antibody.

The invention further provides a method for treating a solid tumor by administering to a subject a pharmaceutical composition which comprises a compound of Formula (A), or a pharmaceutically acceptable salt thereof, aluminum-containing particles, one or more pharmaceutically acceptable excipients and an immune checkpoint inhibitor.

The invention further provides a method for treating a solid tumor by administering to a subject, either intratumorally, intramuscularly, intradermally or subcutaneously, a pharmaceutical composition which comprises a compound of Formula (A), or a pharmaceutically acceptable salt thereof, aluminum-containing particles, one or more pharmaceutically acceptable excipients and an immune checkpoint inhibitor.

The invention further provides a method for treating a solid tumor by intratumorally administering to a subject a pharmaceutical composition which comprises a compound of Formula (A), or a pharmaceutically acceptable salt thereof, aluminum-containing particles, one or more pharmaceutically acceptable excipients and an immune checkpoint inhibitor.

The invention further provides a method for treating a solid tumor by administering a pharmaceutical combination comprising:
  a) a pharmaceutical composition comprising a compound of Formula (A), or a pharmaceutically acceptable salt thereof, aluminum-containing particles and one or more pharmaceutically acceptable excipients, and
  b) a pharmaceutical composition comprises an immune checkpoint inhibitors and one or more pharmaceutically acceptable excipients,
wherein the pharmaceutical compositions are administered separately by the same or different routes of administration, either concurrently or at different times. The pharmaceutical composition comprising a compound of Formula (A), or a pharmaceutically acceptable salt thereof, aluminum-containing particles and one or more pharmaceutically acceptable excipients may be adminstered either intratumorally, intramuscularly, intradermally or subcutaneously, whereas the pharmaceutical composition comprising the immune checkpoint inhibitors and one or more pharmaceutically acceptable excipients may be administered either intratumorally, intramuscularly, intradermally, subcutaneously, intravenously, by intraperitoneal injection, by lavage or by infusion.

In one embodiment is a method for treating a solid tumor by intratumorally administering a pharmaceutical combination comprising:
  a) a first pharmaceutical composition comprising a compound of Formula (A), or a pharmaceutically acceptable salt thereof, aluminum-containing particles and one or more pharmaceutically acceptable excipients and
  b) a second pharmaceutical composition comprising one or more immune checkpoint inhibitors and one or more pharmaceutically acceptable excipients,
wherein both pharmaceutical compositions are intratumorally administered into the same tumor or into the area immediately surrounding the outer edge of the same tumor. In certain embodiments these pharmaceutical compositions are administered at different times, while in other embodiments these pharmaceutical compositions are administered concurrently.

The invention further provide a method for treating a solid tumor by administering a pharmaceutical combination comprising:
  a) a first pharmaceutical composition comprises a compound of Formula (A), or a pharmaceutically acceptable salt thereof, aluminum-containing particles and one or more pharmaceutically acceptable excipients,
  b) a second pharmaceutical composition comprises an immune checkpoint inhibitor and one or more pharmaceutically acceptable excipients, and
  c) a third pharmaceutical composition comprises an immune checkpoint inhibitor, which is different from the immune checkpoint inhibitor in the second pharmaceutical composition, and one or more pharmaceutically acceptable excipients,
wherein the pharmaceutical compositions are administered separately by the same or different routes of administration, either concurrently or at different times. The pharmaceutical composition comprising a compound of Formula (A), or a pharmaceutically acceptable salt thereof, aluminum-containing particles and one or more pharmaceutically acceptable excipients may be adminstered either intratumorally, intramuscularly, intradermally or subcutaneously, whereas the pharmaceutical compositions comprising an immune checkpoint inhibitor and one or more pharmaceutically acceptable excipients may be administered either intratumorally, intramuscularly, intradermally, subcutaneously, intravenously, by intraperitoneal injection, by lavage or by infusion.

In one embodiment is a method for treating a solid tumor by administering a pharmaceutical combination:
  a) a first pharmaceutical composition comprises a compound of Formula (A), or a pharmaceutically acceptable salt thereof, aluminum-containing particles and one or more pharmaceutically acceptable excipients,
  b) a second pharmaceutical composition comprises an immune checkpoint inhibitor and one or more pharmaceutically acceptable excipients, and
  c) a third pharmaceutical composition comprises an immune checkpoint inhibitor, which is different from the immune checkpoint inhibitor in the second pharmaceutical composition, and one or more pharmaceutically acceptable excipients, wherein the pharmaceutically compositions are intratumorally administered into the same tumor or into the area immediately surrounding the outer edge of the same tumor. In certain embodiments, these three pharmaceutical compositions are administered at different times, while in other embodiments these three pharmaceutical compositions are administered concurrently.

The invention further provides the use of a pharmaceutical composition for treating a solid tumor, wherein the pharmaceutical composition comprises a compound of Formula (A), or a pharmaceutically acceptable salt thereof, aluminum-containing particles, one or more pharmaceutically acceptable excipients and an immune checkpoint inhibitor.

The invention further provides the use of a pharmaceutical combination for treating a solid tumor, wherein the pharmaceutical combination comprises
  a) a first pharmaceutical composition comprising a compound of Formula (A), or a pharmaceutically acceptable salt thereof, aluminum-containing particles and one or more pharmaceutically acceptable excipients, and
  b) a second pharmaceutical composition comprises an immune checkpoint inhibitors and one or more pharmaceutically acceptable excipients.

The invention further provides the use of a pharmaceutical combination for treating a solid tumor, wherein the pharmaceutical combination comprises
  a) a first pharmaceutical composition comprises a compound of Formula (A), or a pharmaceutically acceptable salt thereof, aluminum-containing particles and one or more pharmaceutically acceptable excipients,
  b) a second pharmaceutical composition comprises an immune checkpoint inhibitor and one or more pharmaceutically acceptable excipients, and
  c) a third pharmaceutical composition comprises an immune checkpoint inhibitor, which is different from the immune checkpoint inhibitor in the second pharmaceutical composition, and one or more pharmaceutically acceptable excipients.

The invention further provides a pharmaceutical composition for use in treating a solid tumor, wherein the pharmaceutical composition comprises a compound of Formula (A), or a pharmaceutically acceptable salt thereof, aluminum-containing particles, one or more pharmaceutically acceptable excipients and an immune checkpoint inhibitor.

The invention further provides a pharmaceutical combination for use in treating a solid tumor, wherein the pharmaceutical combination comprises:
  a) a first pharmaceutical composition comprising a compound of Formula (A), or a pharmaceutically acceptable salt thereof, aluminum-containing particles and one or more pharmaceutically acceptable excipients, and
  b) a second pharmaceutical composition comprises an immune checkpoint inhibitors and one or more pharmaceutically acceptable excipients.

The invention further provides a pharmaceutical combination for use in treating a solid tumor, wherein the pharmaceutical combination comprises
  a) a first pharmaceutical composition comprises a compound of Formula (A), or a pharmaceutically acceptable salt thereof, aluminum-containing particles and one or more pharmaceutically acceptable excipients,
  b) a second pharmaceutical composition comprises an immune checkpoint inhibitor and one or more pharmaceutically acceptable excipients, and
  c) a third pharmaceutical composition comprises an immune checkpoint inhibitor, which is different from the immune checkpoint inhibitor in the second pharmaceutical composition, and one or more pharmaceutically acceptable excipients.

The solid tumors which may be treatable by such methods and uses include, but are not limited to, a breast cancer tumor, a bladder cancer tumor, a head and neck cancer tumor, a non-small cell lung cancer tumor, a small cell lung cancer tumor, a colorectal cancer tumor, a gastrointestinal stromal tumor, a gastroesophageal carcinoma, a renal cell cancer tumor, a prostate cancer tumor, a liver cancer tumor, a colon cancer tumor, a pancreatic cancer tumor, an ovarian cancer tumor, a lymphoma, a cutaneous T-cell lymphoma, or a melanoma.

Large solid tumors become infiltrated by a subpopulation of myeloid derived suppressor cells (mMDSC) that suppress anti-tumor immunity. In some embodiments, the invention provides a method for treating an immune suppressed tumor. An immune suppressed tumor is a tumor that contains immune suppressive associated cells such as for example T Reg cells, myeloid derived suppressor cells (MDSC), M2 macrophages, and the like or immune suppressive factors such as inducible nitric oxide synthase (iNOS), PD-L1, and the like.

The amount of a compound of Formula (A), or a pharmaceutically acceptable salt thereof, incorporated in a pharmaceutical composition of the invention, which is the used in a method or use of the invention, may vary according to factors known in art such as for example, the physical and clinical status of the subject, the method of administration, the content of the formulation, the intended dosing regimen or sequence. In consideration of such factors the appropriate amount incorporated can be readily determined by one of ordinary skill in the art. By way of example, the pharmaceutical composition of the invention may include an amount of a compound of Formula (A), or a pharmaceutically acceptable salt thereof, to provide a dose of a compound of Formula (A), or a pharmaceutically acceptable salt thereof, to a subject from about 0.05 mg to about 5 mg. Preferably the pharmaceutical composition of the invention includes an amount of a compound of Formula (A), or a pharmaceutically acceptable salt thereof, which provides a dose of a compound of Formula (A), or a pharmaceutically acceptable salt thereof, to a subject from about 0.1 mg to about 1 mg.

While the disclosed methods and uses of such compositions and combinations will typically be used to treat human subjects they may also be used to treat similar or identical diseases in other vertebrates, such as other primates, dogs, cats, horses, and cows.

Certain aspects and examples of the methods of the invention are provided in the following listing of additional, enumerated embodiments. It will be recognized that features specified in each embodiment may be combined with other specified features to provide further embodiments of the present invention.

Embodiment 353. A method for treating a solid tumor by administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, one or more pharmaceutically acceptable excipients and an immune checkpoint inhibitor.

Embodiment 354. A method for treating a solid tumor by administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an immune checkpoint inhibitor.

Embodiment 355. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an immune checkpoint inhibitor.

Embodiment 356. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an immune checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 357. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and a PD-L1 inhibitor.

Embodiment 358. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and a PD-1 receptor inhibitor.

Embodiment 359. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an anti-PD-L1 antibody.

Embodiment 360. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an anti-PD-L1 antibody of Table 2.

Embodiment 361. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an anti-PD-L1 antibody comprising a heavy chain variable domain comprising the amino acid sequence of SEQ ID NO:7 and a light chain variable domain comprising the amino acid sequence of SEQ ID NO:17.

Embodiment 362. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an anti-PD-1 antibody of Table 3.

Embodiment 363. A method for treating a solid tumor by intratumorally administering to a subject in need thereof a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients and an anti-PD-1 antibody comprising a heavy chain variable domain comprising the amino acid sequence of SEQ ID NO:27 and a light chain variable domain comprising the amino acid sequence of SEQ ID NO:37.

Embodiment 364. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, one or more pharmaceutically acceptable excipients excipient and an immune checkpoint inhibitor for treating a solid tumor.

Embodiment 365. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an immune checkpoint inhibitor for treating a solid tumor.

Embodiment 366. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an immune checkpoint inhibitor for treating a solid tumor, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 367. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and a PD-1 receptor inhibitor for treating a solid tumor.

Embodiment 368. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and a PD-L1 inhibitor for treating a solid tumor.

Embodiment 369. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-L1 antibody for treating a solid tumor.

Embodiment 370. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-L1 antibody of Table 2 for treating a solid tumor.

Embodiment 371. Use of a pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-L1 antibody comprising a heavy chain variable domain comprising the amino acid sequence of SEQ ID NO:7 and a light chain variable domain comprising the amino acid sequence of SEQ ID NO:17 for treating a solid tumor.

Embodiment 372. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, one or more pharmaceutically acceptable excipients excipient and an immune checkpoint inhibitor for use in treating a solid tumor.

Embodiment 373. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an immune checkpoint inhibitor for use in treating a solid tumor.

Embodiment 374. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an immune checkpoint inhibitor for use in treating a solid tumor, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 375. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and a PD-1 receptor inhibitor for use in treating a solid tumor.

Embodiment 376. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and a PD-L1 inhibitor for use in treating a solid tumor.

Embodiment 377. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-L1 antibody for use in treating a solid tumor.

Embodiment 378. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-L1 antibody of Table 2 for use in treating a solid tumor.

Embodiment 379. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-L1 antibody comprising a heavy chain variable domain comprising the amino acid sequence of SEQ ID NO:7 and a light chain variable domain comprising the amino acid sequence of SEQ ID NO:17 for use in treating a solid tumor.

Embodiment 380. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-1 antibody of Table 3 for use in treating a solid tumor.

Embodiment 381. A pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, one or more pharmaceutically acceptable excipients excipient and an anti-PD-L1 antibody comprising a heavy chain variable domain comprising the amino acid sequence of SEQ ID NO:27 and a light chain variable domain comprising the amino acid sequence of SEQ ID NO:37 for use in treating a solid tumor.

Embodiment 382. A method for treating a solid tumor in a subject by administering a pharmaceutical combination of any one of Embodiments 235 to 294.

Embodiment 383. A method for treating a solid tumor in a subject by administering a pharmaceutical combination of any one of Embodiments 235 to 294, wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 384. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients, and
- b) a second pharmaceutical composition comprises an immune checkpoint inhibitors and one or more pharmaceutically acceptable excipients.

Embodiment 385. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprises an immune checkpoint inhibitors and one or more pharmaceutically acceptable excipients.

Embodiment 386. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprises an immune checkpoint inhibitors and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 387. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprises an immune checkpoint inhibitors and one or more pharmaceutically acceptable excipients, and wherein the first pharmaceutical composition is administered intratumorally and the second pharmaceutical composition is administered by intraperitoneal injection.

Embodiment 388. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an immune checkpoint inhibitors and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 389. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising a PD-1 receptor inhibitor and one or more pharmaceutically acceptable excipients.

Embodiment 390. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprises a PD-L1 inhibitor and one or more pharmaceutically acceptable excipients.

Embodiment 391. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an immune checkpoint inhibitors and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 392. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising an immune checkpoint inhibitors and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally and the second pharmaceutical composition is administered by intraperitoneal injection.

Embodiment 393. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising a PD-1 receptor inhibitor and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 394. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising a PD-1 receptor inhibitor and one or more pharmaceutically acceptable excipients, and wherein the first pharmaceutical composition is administered intratumorally and the second pharmaceutical composition is administered by intraperitoneal injection.

Embodiment 395. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising a PD-L1 inhibitor and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 396. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising a PD-L1 inhibitor and one or more pharmaceutically acceptable excipients, and wherein the first pharmaceutical composition is administered intratumorally and the second pharmaceutical composition is administered by intraperitoneal injection.

Embodiment 397. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising an anti-PD-L1 antibody and one or more pharmaceutically acceptable excipients, and wherein the first pharmaceutical composition is administered intratumorally and the second pharmaceutical composition is administered by intraperitoneal injection.

Embodiment 398. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising an anti-PD-L1 antibody of Table 2 and one or more pharmaceutically acceptable excipients, and wherein the first pharmaceutical composition is administered intratumorally and the second pharmaceutical composition is administered by intraperitoneal injection.

Embodiment 399. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17 and one or more pharmaceutically acceptable excipients, and wherein the first pharmaceutical composition is administered intratumorally and the second pharmaceutical composition is administered by intraperitoneal injection.

Embodiment 400. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an anti-PD-1 antibody and one or more pharmaceutically acceptable excipients, and wherein the first pharmaceutical composition is administered intratumorally and the second pharmaceutical composition is administered by intraperitoneal injection.

Embodiment 401. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an anti-PD-1 antibody of Table 3 and one or more pharmaceutically acceptable excipients, and wherein the first pharmaceutical composition is administered intratumorally and the second pharmaceutical composition is administered by intraperitoneal injection.

Embodiment 402. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37 and one or more pharmaceutically acceptable excipients, and wherein the first pharmaceutical composition is administered intratumorally and the second pharmaceutical composition is administered by intraperitoneal injection.

Embodiment 403. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising ipilimumab and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 404. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising tremelimumab and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 405. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising lambrolizumab and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 406. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising pidilizumab and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 407. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising nivolumab and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 408. A method for treating a solid tumor in a subject by administering a pharmaceutical combination, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising lirilumab and one or more pharmaceutically acceptable excipients, and wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 409. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 410. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 411. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 412. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 413. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 414. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 415. A method for treating a solid tumor in a subject by administering a pharmaceutical combination, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-L1 antibody.

Embodiment 416. A method for treating a solid tumor in a subject by administering a pharmaceutical combination, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 417. A method for treating a solid tumor in a subject by administering a pharmaceutical combination, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 418. A method for treating a solid tumor in a subject by administering a pharmaceutical combination, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 419. The method of any one of Embodiments 409 to 418, wherein the anti-PD-L1 antibody is an anti-PD-L1 antibody of Table 2.

Embodiment 420. The method of any one of Embodiments 409 to 418, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 421. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-1 antibody.

Embodiment 422. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-1 antibody.

Embodiment 423. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-1 antibody.

Embodiment 424. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-1 antibody.

Embodiment 425. A method for treating a solid tumor in a subject by administering a pharmaceutical combination, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody.

Embodiment 426. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 427. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-1 antibody.

Embodiment 428. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 429. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is an anti-PD-1 antibody.

Embodiment 430. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 431. The method of any one of Embodiments 421 to 430, wherein the anti-PD-1 antibody is an anti-PD-1 antibody of Table 3.

Embodiment 432. The method of any one of Embodiments 421 to 430, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 433. The method of any one of Embodiments 409 to 432, wherein the first pharmaceutical composition is administered intratumorally and the second pharmaceutical composition is administered intratumorally, intramuscularly, intradermally, subcutaneously, intravenously, by intraperitoneal injection, by lavage or by infusion.

Embodiment 434. The method of any one of Embodiments 409 to 433, the first pharmaceutical composition is administered intratumorally and the second pharmaceutical composition is administered by intraperitoneal injection.

Embodiment 435. Use of a pharmaceutical combination of any one of Embodiments 235 to 294 for treating a solid tumor.

Embodiment 436. Use of a pharmaceutical combination for treating a solid tumor, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients, and b) a second pharmaceutical composition comprises an immune checkpoint inhibitors and one or more pharmaceutically acceptable excipients.

Embodiment 437. Use of a pharmaceutical combination for treating a solid tumor, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprises an immune checkpoint inhibitors and one or more pharmaceutically acceptable excipients.

Embodiment 438. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising an immune checkpoint inhibitors and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 439. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising a PD-1 receptor inhibitor and one or more pharmaceutically acceptable excipients.

Embodiment 440. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprises a PD-L1 inhibitor and one or more pharmaceutically acceptable excipients.

Embodiment 441. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising an anti-PD-L1 antibody and one or more pharmaceutically acceptable excipients.

Embodiment 442. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising an anti-PD-L1 antibody of Table 2 and one or more pharmaceutically acceptable excipients.

Embodiment 443. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17.

Embodiment 444. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising an anti-PD-1 antibody and one or more pharmaceutically acceptable excipients.

Embodiment 445. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising an anti-PD-1 antibody of Table 3 and one or more pharmaceutically acceptable excipients.

Embodiment 446. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
  b) a second pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37.

Embodiment 447. Use of a pharmaceutical combination for treating a solid tumor, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising ipilimumab and one or more pharmaceutically acceptable excipients.

Embodiment 448. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising tremelimumab and one or more pharmaceutically acceptable excipients.

Embodiment 449. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising lambrolizumab and one or more pharmaceutically acceptable excipients.

Embodiment 450. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising pidilizumab and one or more pharmaceutically acceptable excipients.

Embodiment 451. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising nivolumab and one or more pharmaceutically acceptable excipients.

Embodiment 452. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising lirilumab and one or more pharmaceutically acceptable excipients.

Embodiment 453. Use of a pharmaceutical combination for treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7] naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-L1 antibody.

Embodiment 454. Use of a pharmaceutical combination for treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7] naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-L1 antibody.

Embodiment 455. Use of a pharmaceutical combination for treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7] naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-L1 antibody.

Embodiment 456. Use of a pharmaceutical combination for treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7] naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody.

Embodiment 457. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 458. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 459. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 460. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 461. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 462. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
b) a second pharmaceutical composition comprising an immune checkpoint inhibitor and one or more pharmaceutically acceptable excipients, wherein the checkpoint inhibitor is an anti-PD-L1 antibody.

Embodiment 463. The use of any one of Embodiments 453 to 462, wherein the anti-PD-L1 antibody is an anti-PD-L1 antibody of Table 2.

Embodiment 464. The use of any one of Embodiments 453 to 462, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 465. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-1 antibody.

Embodiment 466. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 467. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody.

Embodiment 468. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 469. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody.

Embodiment 470. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 471. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-1 antibody.

Embodiment 472. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 473. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is an anti-PD-1 antibody.

Embodiment 474. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 475. The use of any one of Embodiments 464 to 476, wherein the anti-PD-1 antibody is an anti-PD-1 antibody of Table 3.

Embodiment 476. The use of any one of Embodiments 464 to 476, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 477. A pharmaceutical combination of any one of Embodiments for

Embodiments 235 to 294 for use in treating a solid tumor.

Embodiment 478. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients, and
- b) a second pharmaceutical composition comprises an immune checkpoint inhibitors and one or more pharmaceutically acceptable excipients.

Embodiment 479. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprises an immune checkpoint inhibitors and one or more pharmaceutically acceptable excipients.

Embodiment 480. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an immune checkpoint inhibitors and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 481. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising a PD-1 receptor inhibitor and one or more pharmaceutically acceptable excipients.

Embodiment 482. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprises a PD-L1 inhibitor and one or more pharmaceutically acceptable excipients.

Embodiment 483. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an anti-PD-L1 antibody and one or more pharmaceutically acceptable excipients.

Embodiment 484. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an anti-PD-L1 antibody of Table 2 and one or more pharmaceutically acceptable excipients.

Embodiment 485. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
- b) a second pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17.

Embodiment 486. A pharmaceutical combination for use in treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and b) a second pharmaceutical composition comprising an anti-PD-1 antibody and one or more pharmaceutically acceptable excipients.

Embodiment 487. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising an anti-PD-1 antibody of Table 3 and one or more pharmaceutically acceptable excipients.

Embodiment 488. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37.

Embodiment 489. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising ipilimumab and one or more pharmaceutically acceptable excipients.

Embodiment 490. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising tremelimumab and one or more pharmaceutically acceptable excipients.

Embodiment 491. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising lambrolizumab and one or more pharmaceutically acceptable excipients.

Embodiment 492. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising pidilizumab and one or more pharmaceutically acceptable excipients.

Embodiment 493. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising nivolumab and one or more pharmaceutically acceptable excipients.

Embodiment 494. A method for treating a solid tumor in a subject by administering a pharmaceutical combination, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, and
b) a second pharmaceutical composition comprising lirilumab and one or more pharmaceutically acceptable excipients.

Embodiment 495. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody.

Embodiment 496. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody.

Embodiment 497. A pharmaceutical combination for use in treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody.

Embodiment 498. A pharmaceutical combination for use in treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody.

Embodiment 499. A pharmaceutical combination for use in treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody.

Embodiment 500. A pharmaceutical combination for use in treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody.

Embodiment 501. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-L1 antibody.

Embodiment 502. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-L1 antibody.

Embodiment 503. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is an anti-PD-L1 antibody.

Embodiment 504. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is an anti-PD-L1 antibody.

Embodiment 505. The pharmaceutical combination of any one of Embodiments 495 to 504, wherein the anti-PD-L1 antibody is an anti-PD-L1 antibody of Table 2.

Embodiment 506. The pharmaceutical combination of any one of Embodiments 495 to 504, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 507. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-1 antibody.

Embodiment 508. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-1 antibody.

Embodiment 509. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-1 antibody.

Embodiment 510. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-1 antibody.

Embodiment 511. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-1 antibody.

Embodiment 512. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-1 antibody.

Embodiment 513. A pharmaceutical combination for use in treating a solid tumor, wherein the pharmaceutical combination comprises:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
- b) a second pharmaceutical composition comprising an immune checkpoint inhibitor and one or more pharmaceutically acceptable excipients, wherein the checkpoint inhibitor is an anti-PD-1 antibody.

Embodiment 514. A pharmaceutical combination for use in treating a solid tumor, wherein the pharmaceutical combination comprises:
- a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-1 antibody.

Embodiment 515. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
b) a second pharmaceutical composition comprising an immune checkpoint inhibitor and one or more pharmaceutically acceptable excipients, wherein the checkpoint inhibitor is an anti-PD-1 antibody.

Embodiment 516. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
b) a second pharmaceutical composition comprising an immune checkpoint inhibitor and one or more pharmaceutically acceptable excipients, wherein the checkpoint inhibitor is an anti-PD-1 antibody.

Embodiment 517. The pharmaceutical combination of any one of Embodiments 506 to 518, wherein the anti-PD-1 antibody is an anti-PD-1 antibody of Table 3.

Embodiment 518. The pharmaceutical combination of any one of Embodiments 506 to 518, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 519. A method for treating a solid tumor in a subject by administering a pharmaceutical combination of any one of Embodiments 295 to 352.

Embodiment 520. A method for treating a solid tumor in a subject by administering a pharmaceutical combination of any one of Embodiments 295 to 352, wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion.

Embodiment 521. A method for treating a solid tumor in a subject by administering a pharmaceutical combination, wherein the pharmaceutical combination comprises:
a) a first pharmaceutical composition comprising a compound of Formula (A), or a pharmaceutically acceptable salt thereof, aluminum-containing particles, a buffering agent, and one or more pharmaceutically acceptable excipients,
b) a second pharmaceutical composition comprising an immune checkpoint inhibitor and one or more pharmaceutically acceptable excipients, and
c) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition, the second pharmaceutical composition and the third pharmaceutical composition are administered separately and sequentially in any order.

Embodiment 522. A method for treating a solid tumor in a subject by administering a pharmaceutical combination, wherein the pharmaceutical combination comprises:
a) a first pharmaceutical composition comprising a compound of Formula (A), or a pharmaceutically acceptable salt thereof, aluminum-containing particles, a buffering agent, and one or more pharmaceutically acceptable excipients,
b) a second pharmaceutical composition comprising an immune checkpoint inhibitor and one or more pharmaceutically acceptable excipients, and
c) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition is administered first and the second pharmaceutical composition the third pharmaceutical are then administered separately and sequentially in any order.

Embodiment 523. A method for treating a solid tumor in a subject by administering a pharmaceutical combination, wherein the pharmaceutical combination comprises:
a) a first pharmaceutical composition comprising a compound of Formula (A), or a pharmaceutically acceptable salt thereof, aluminum-containing particles, a buffering agent, and one or more pharmaceutically acceptable excipients,
b) a second pharmaceutical composition comprising an immune checkpoint inhibitor and one or more pharmaceutically acceptable excipients, and
c) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition, the second pharmaceutical composition and the third pharmaceutical composition comprising are administered simultaneously.

Embodiment 524. A method for treating a solid tumor in a subject by administering a pharmaceutical combination, wherein the pharmaceutical combination comprises:
a) a first pharmaceutical composition comprising a compound of Formula (A), or a pharmaceutically acceptable salt thereof, aluminum hydroxide particles, a buffering agent, and one or more pharmaceutically acceptable excipients,
b) a second pharmaceutical composition comprising an immune checkpoint inhibitor and one or more pharmaceutically acceptable excipients, and
c) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition, the second pharmaceutical composition and the third pharmaceutical composition are administered separately and sequentially in any order.

Embodiment 525. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients, and
- c) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition is administered first and the second pharmaceutical composition and the third pharmaceutical composition are then administered separately and sequentially in any order.

Embodiment 526. A method for treating a solid tumor in a subject by administering a pharmaceutical combination, wherein the pharmaceutical combination comprises: d) a first pharmaceutical composition comprising a compound of Formula (A), or a pharmaceutically acceptable salt thereof, aluminum hydroxide particles, a buffering agent, and one or more pharmaceutically acceptable excipients,
- e) a second pharmaceutical composition comprising an immune checkpoint inhibitor and one or more pharmaceutically acceptable excipients, and
- f) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition, the second pharmaceutical composition and the third pharmaceutical composition are administered simultaneously.

Embodiment 527. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical, the second pharmaceutical composition and the third pharmaceutical composition are administered separately and sequentially in any order.

Embodiment 528. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered first and the second pharmaceutical composition and the third pharmaceutical composition are then administered separately and sequentially in any order.

Embodiment 529. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition, the second pharmaceutical composition and the third pharmaceutical composition comprising a different checkpoint inhibitor are administered simultaneously.

Embodiment 530. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 531. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally first, and the second pharmaceutical composition and the third pharmaceutical composition are then administered by intraperitoneal injection separately and sequentially in any order.

Embodiment 532. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally, and the second pharmaceutical composition and the third pharmaceutical composition are administered by intraperitoneal injection, and the first pharmaceutical composition, the second pharmaceutical composition and the third pharmaceutical composition are administered simultaneously.

Embodiment 533. A method for treating a solid tumor in a subject by administering a pharmaceutical combination, wherein the pharmaceutical combination comprises: a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising a CTLA-4 receptor inhibitor and one or more pharmaceutically acceptable excipients, and
- c) a third pharmaceutical composition comprising a PD-L1 inhibitor and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 534. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising a CTLA-4 receptor inhibitor and one or more pharmaceutically acceptable excipients, and c) a third pharmaceutical composition comprising a PD-L1 inhibitor and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 535. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising a CTLA-4 receptor inhibitor and one or more pharmaceutically acceptable excipients, and
- c) a third pharmaceutical composition comprising a PD-L1 inhibitor and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 536. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 537. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 538. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 539. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody of Table 2, and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 540. A method for treating a solid tumor in a subject by administering a pharmaceutical combination, wherein the pharmaceutical combination comprises:
- a) a first pharmaceutical composition comprising a compound of Formula (A), or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody of Table 2, and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 541. A method for treating a solid tumor in a subject by administering a pharmaceutical combination, wherein the pharmaceutical combination comprises:
 a) a first pharmaceutical composition comprising a compound of Formula (A), or a pharmaceutically acceptable salt thereof, aluminum hydroxide particles, a buffering agent, and one or more pharmaceutically acceptable excipients,
 b) a second pharmaceutical composition comprising an anti-CTLA-4 antibody and one or more pharmaceutically acceptable excipients, and
 c) a third pharmaceutical composition comprising an anti-PD-L1 antibody of Table 2, and one or more pharmaceutically acceptable excipients,
and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 542. A method for treating a solid tumor in a subject by administering a pharmaceutical combination, wherein the pharmaceutical combination comprises:
 a) a first pharmaceutical composition comprising a compound of Formula (A), or a pharmaceutically acceptable salt thereof, aluminum hydroxide particles, a buffering agent, and one or more pharmaceutically acceptable excipients,
 b) a second pharmaceutical composition comprising an anti-CTLA-4 antibody and one or more pharmaceutically acceptable excipients, and
 c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients,
and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 543. A method for treating a solid tumor in a subject by administering a pharmaceutical combination, wherein the pharmaceutical combination comprises:
 a) a first pharmaceutical composition comprising a compound of Formula (A), or a pharmaceutically acceptable salt thereof, aluminum hydroxide particles, a buffering agent, and one or more pharmaceutically acceptable excipients,
 b) a second pharmaceutical composition comprising an anti-CTLA-4 antibody and one or more pharmaceutically acceptable excipients, and
 c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients,
and wherein the first pharmaceutical composition is administered intratumorally first, and the second pharmaceutical composition and the third pharmaceutical composition are then administered by intraperitoneal injection separately and sequentially in any order.

Embodiment 544. A method for treating a solid tumor in a subject by administering a pharmaceutical combination, wherein the pharmaceutical combination comprises:
 a) a first pharmaceutical composition comprising a compound of Formula (A), or a pharmaceutically acceptable salt thereof, aluminum hydroxide particles, a buffering agent, and one or more pharmaceutically acceptable excipients,
 b) a second pharmaceutical composition comprising an anti-CTLA-4 antibody and one or more pharmaceutically acceptable excipients, and
 c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients,
and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 545. A method for treating a solid tumor in a subject by administering a pharmaceutical combination, wherein the pharmaceutical combination comprises:
 a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients,
 b) a second pharmaceutical composition comprising an immune checkpoint inhibitor and one or more pharmaceutically acceptable excipients, and
 c) a third pharmaceutical composition comprising an immune checkpoint inhibitor, which is different from the immune checkpoint inhibitor in the second pharmaceutical composition, and one or more pharmaceutically acceptable excipients,
and wherein the first pharmaceutical composition, the second pharmaceutical composition and the third pharmaceutical composition are administered separately and sequentially in any order.

Embodiment 546. A method for treating a solid tumor in a subject by administering a pharmaceutical combination, wherein the pharmaceutical combination comprises:
 a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients,
 b) a second pharmaceutical composition comprising an immune checkpoint inhibitor and one or more pharmaceutically acceptable excipients, and
 c) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition is administered first and the second pharmaceutical composition the third pharmaceutical are then administered separately and sequentially in any order.

Embodiment 547. A method for treating a solid tumor in a subject by administering a pharmaceutical combination, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients,
  b) a second pharmaceutical composition comprising an immune checkpoint inhibitor and one or more pharmaceutically acceptable excipients, and
  c) a third pharmaceutical composition comprising an immune checkpoint inhibitor, which is different from the immune checkpoint inhibitor in the second pharmaceutical composition, and one or more pharmaceutically acceptable excipients,
and wherein the first pharmaceutical composition, the second pharmaceutical composition and the third pharmaceutical composition comprising are administered simultaneously.

Embodiment 548. A method for treating a solid tumor in a subject by administering a pharmaceutical combination, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, and
  c) a third pharmaceutical composition comprising an immune checkpoint inhibitor, which is different from the immune checkpoint inhibitor in the second pharmaceutical composition, and one or more pharmaceutically acceptable excipients,
and wherein the first pharmaceutical composition, the second pharmaceutical composition and the third pharmaceutical composition are administered separately and sequentially in any order.

Embodiment 549. A method for treating a solid tumor in a subject by administering a pharmaceutical combination, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, and
  c) a third pharmaceutical composition comprising an immune checkpoint inhibitor, which is different from the immune checkpoint inhibitor in the second pharmaceutical composition, and one or more pharmaceutically acceptable excipients, and wherein the first pharmaceutical composition is administered first and the second pharmaceutical composition and the third pharmaceutical composition are then administered separately and sequentially in any order.

Embodiment 550. A method for treating a solid tumor in a subject by administering a pharmaceutical combination, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, and
  c) a third pharmaceutical composition comprising an immune checkpoint inhibitor, which is different from the immune checkpoint inhibitor in the second pharmaceutical composition, and one or more pharmaceutically acceptable excipients,
and wherein the first pharmaceutical composition, the second pharmaceutical composition and the third pharmaceutical composition are administered simultaneously.

Embodiment 551. A method for treating a solid tumor in a subject by administering a pharmaceutical combination, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a
PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor,
and wherein the first pharmaceutical, the second pharmaceutical composition and the third pharmaceutical composition are administered separately and sequentially in any order.

Embodiment 552. A method for treating a solid tumor in a subject by administering a pharmaceutical combination, wherein the pharmaceutical combination comprises:
  a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered first and the second pharmaceutical composition and the third pharmaceutical composition are then administered separately and sequentially in any order.

Embodiment 553. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition, the second pharmaceutical composition and the third pharmaceutical composition comprising a different checkpoint inhibitor are administered simultaneously.

Embodiment 554. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 555. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally first, and the second pharmaceutical composition and the third pharmaceutical composition are then administered by intraperitoneal injection separately and sequentially in any order.

Embodiment 556. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an immune checkpoint inhibitor and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and wherein the first pharmaceutical composition is administered intratumorally, and the second pharmaceutical composition and the third pharmaceutical composition are administered by intraperitoneal injection, and the first pharmaceutical composition, the second pharmaceutical composition and the third pharmaceutical composition are administered simultaneously.

Embodiment 557. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising a CTLA-4 receptor inhibitor and one or more pharmaceutically acceptable excipients, and c) a third pharmaceutical composition comprising a PD-L1 inhibitor and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 558. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising a CTLA-4 receptor inhibitor and one or more pharmaceutically acceptable excipients, and c) a third pharmaceutical composition comprising a PD-L1 inhibitor and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 559. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising a CTLA-4 receptor inhibitor and one or more pharmaceutically acceptable excipients, and c) a third pharmaceutical composition comprising a PD-L1 inhibitor and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 560. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 561. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 562. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 563. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-L1 antibody of Table 2, and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 564. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-L1 antibody of Table 2, and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 565. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-L1 antibody of Table 2, and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 566. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 567. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 568. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 569. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising a CTLA-4 receptor inhibitor and one or more pharmaceutically acceptable excipients, and
- c) a third pharmaceutical composition comprising a PD-1 inhibitor and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 570. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising a CTLA-4 receptor inhibitor and one or more pharmaceutically acceptable excipients, and
- c) a third pharmaceutical composition comprising a PD-1 inhibitor and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 571. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising a CTLA-4 receptor inhibitor and one or more pharmaceutically acceptable excipients, and
- c) a third pharmaceutical composition comprising a PD-1 inhibitor and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 572. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-1 antibody and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 573. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-1 antibody and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 574. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-1 antibody and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 575. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-1 antibody of Table 3, and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 576. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-1 antibody of Table 3, and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 577. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-1 antibody of Table 3, and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 578. A method for treating a solid tumor in a subject by administering a pharmaceutical combination, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 579. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 580. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising an anti-CTLA-4 antibody and one or more pharmaceutically acceptable excipients, and c) a third pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 581. A method for treating a solid tumor in a subject by administering a pharmaceutical combination, wherein the pharmaceutical combination comprises:

a) a first pharmaceutical composition comprising a compound of Formula (A), or a pharmaceutically acceptable salt thereof, aluminum hydroxide particles, a buffering agent, and one or more pharmaceutically acceptable excipients, b) a second pharmaceutical composition comprising ipilimumab and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 582. A method for treating a solid tumor in a subject by administering a pharmaceutical combination, wherein the pharmaceutical combination comprises:

a) a first pharmaceutical composition comprising a compound of Formula (A), or a pharmaceutically acceptable salt thereof, aluminum hydroxide particles, a buffering agent, and one or more pharmaceutically acceptable excipients, b) a second pharmaceutical composition comprising ipilimumab and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 583. A method for treating a solid tumor in a subject by administering a pharmaceutical combination, wherein the pharmaceutical combination comprises:

a) a first pharmaceutical composition comprising a compound of Formula (A), or a pharmaceutically acceptable salt thereof, aluminum hydroxide particles, a buffering agent, and one or more pharmaceutically acceptable excipients, b) a second pharmaceutical composition comprising ipilimumab and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 584. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising ipilimumab and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion, and wherein the first pharmaceutical composition, the second pharmaceutical composition and the third pharmaceutical composition are administered separately and sequentially in any order.

Embodiment 585. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising ipilimumab and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally first, and the second pharmaceutical composition and the third pharmaceutical composition are then administered by intraperitoneal injection separately and sequentially in any order.

Embodiment 586. A method for treating a solid tumor in a subject by administering a pharmaceutical combination, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients, b) a second pharmaceutical composition comprising ipilimumab and one or more pharmaceutically acceptable excipients, and c) a third pharmaceutical composition comprising an anti-PD-L1 antibody and one or more pharmaceutically acceptable excipients, and wherein the first pharmaceutical composition is administered intratumorally, and the second pharmaceutical composition and the third pharmaceutical composition are administered by intraperitoneal injection, and wherein the first pharmaceutical composition, the second pharmaceutical composition and the third pharmaceutical composition are administered simultaneously.

Embodiment 587. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 588. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 589. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]

naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 590. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 591. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 592. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 593. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 594. A method for treating a solid tumor in a subject by administering a pharmaceutical combination, wherein the pharmaceutical combination comprises:
 a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
 b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
 c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 595. A method for treating a solid tumor in a subject by administering a pharmaceutical combination, wherein the pharmaceutical combination comprises:
 a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
 b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
 c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 596. A method for treating a solid tumor in a subject by administering a pharmaceutical combination, wherein the pharmaceutical combination comprises: a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
 b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
 c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 597. A method for treating a solid tumor in a subject by administering a pharmaceutical combination, wherein the pharmaceutical combination comprises:
 a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
 b) a second pharmaceutical composition comprising an immune checkpoint inhibitor and one or more pharmaceutically acceptable excipients, wherein the checkpoint inhibitor is an anti-PD-L1 antibody, and
 c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 598. A method for treating a solid tumor in a subject by administering a pharmaceutical combination, wherein the pharmaceutical combination comprises:
 a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 599. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 600. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 601. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 602. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 603. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 604. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 605. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 606. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 607. The method of any one of Embodiments 587 to 606, wherein the anti-PD-L1 antibody is an anti-PD-L1 antibody of Table 2.

Embodiment 608. The method of any one of Embodiments 587 to 606, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 609. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 610. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 611. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 612. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7] naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 613. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7] naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 614. A method for treating a solid tumor in a subject by administering a pharmaceutical combination, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7] naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 615. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 616. A method for treating a solid tumor in a subject by administering a pharmaceutical combination, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy) ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 617. A method for treating a solid tumor in a subject by administering a pharmaceutical combination, wherein the pharmaceutical combination comprises: a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, and one or more pharmaceutically acceptable excipients, wherein the checkpoint inhibitor is an anti-CTLA-4 antibody.

Embodiment 618. A method for treating a solid tumor in a subject by administering a pharmaceutical combination, wherein the pharmaceutical combination comprises:
  a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
  b) a second pharmaceutical composition comprising an immune checkpoint inhibitor and one or more pharmaceutically acceptable excipients, wherein the checkpoint inhibitor is an anti-PD-1 antibody, and
  c) a third pharmaceutical composition comprising an immune checkpoint inhibitor, and one or more pharmaceutically acceptable excipients, wherein the checkpoint inhibitor is an anti-CTLA-4 antibody.

Embodiment 619. The method of any one of Embodiments 609 to 618, wherein the anti-PD-1 antibody is an anti-PD-1 antibody of Table 3.

Embodiment 620. The method of any one of Embodiments 609 to 618, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 621. The method of any one of Embodiments 587 to 620, wherein the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion.

Embodiment 622. The method of any one of Embodiments 587 to 620, the first pharmaceutical composition is administered intratumorally and the second pharmaceutical composition and third pharmaceutical composition are administered by intraperitoneal injection.

Embodiment 623. Use of a pharmaceutical combination of any one of Embodiments 295 to 352 for treating a solid tumor.

Embodiment 624. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum-containing particles, a buffering agent, and one or more pharmaceutically acceptable excipients,
  b) a second pharmaceutical composition comprising an immune checkpoint inhibitor and one or more pharmaceutically acceptable excipients, and
  c) a third pharmaceutical composition comprising an immune checkpoint inhibitor, which is different from the immune checkpoint inhibitor in the second pharmaceutical composition, and one or more pharmaceutically acceptable excipients.

Embodiment 625. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, and
  c) a third pharmaceutical composition comprising an immune checkpoint inhibitor, which is different from the immune checkpoint inhibitor in the second pharmaceutical composition, and one or more pharmaceutically acceptable excipients.

Embodiment 626. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 627. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 628. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising a CTLA-4 receptor inhibitor and one or more pharmaceutically acceptable excipients, and
  c) a third pharmaceutical composition comprising a PD-L1 inhibitor and one or more pharmaceutically acceptable excipients.

Embodiment 629. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-L1 antibody and one or more pharmaceutically acceptable excipients.

Embodiment 630. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-L1 antibody of Table 2, and one or more pharmaceutically acceptable excipients.

Embodiment 631. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients.

Embodiment 632. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising a CTLA-4 receptor inhibitor and one or more pharmaceutically acceptable excipients, and
  c) a third pharmaceutical composition comprising a PD-1 inhibitor and one or more pharmaceutically acceptable excipients.

Embodiment 633. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-1 antibody and one or more pharmaceutically acceptable excipients.

Embodiment 634. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-1 antibody of Table 3, and one or more pharmaceutically acceptable excipients.

Embodiment 635. Use of a pharmaceutical combination for treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients.

Embodiment 636. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients,
- b) a second pharmaceutical composition comprising an immune checkpoint inhibitor and one or more pharmaceutically acceptable excipients, and
- c) a third pharmaceutical composition comprising an immune checkpoint inhibitor, which is different from the immune checkpoint inhibitor in the second pharmaceutical composition, and one or more pharmaceutically acceptable excipients.

Embodiment 637. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients, and
- c) a third pharmaceutical composition comprising an immune checkpoint inhibitor, which is different from the immune checkpoint inhibitor in the second pharmaceutical composition, and one or more pharmaceutically acceptable excipients.

Embodiment 638. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
- c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 639. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising a CTLA-4 receptor inhibitor and one or more pharmaceutically acceptable excipients, and
- c) a third pharmaceutical composition comprising a PD-L1 inhibitor and one or more pharmaceutically acceptable excipients.

Embodiment 640. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody and one or more pharmaceutically acceptable excipients.

Embodiment 641. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody of Table 2, and one or more pharmaceutically acceptable excipients.

Embodiment 642. Use of a pharmaceutical combination for treating a solid tumor, wherein the pharmaceutical combination comprises:
- a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
- b) a second pharmaceutical composition comprising an anti-CTLA-4 antibody and one or more pharmaceutically acceptable excipients, and
- c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients.

Embodiment 643. Use of a pharmaceutical combination for treating a solid tumor, wherein the pharmaceutical combination comprises:

a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising a CTLA-4 receptor inhibitor and one or more pharmaceutically acceptable excipients, and
c) a third pharmaceutical composition comprising a PD-1 inhibitor and one or more pharmaceutically acceptable excipients.

Embodiment 644. Use of a pharmaceutical combination for treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising an anti-CTLA-4 antibody and one or more pharmaceutically acceptable excipients, and
c) a third pharmaceutical composition comprising an anti-PD-1 antibody and one or more pharmaceutically acceptable excipients.

Embodiment 645. Use of a pharmaceutical combination for treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising an anti-CTLA-4 antibody and one or more pharmaceutically acceptable excipients, and
c) a third pharmaceutical composition comprising an anti-PD-1 antibody of Table 3, and one or more pharmaceutically acceptable excipients.

Embodiment 646. Use of a pharmaceutical combination for treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising an anti-CTLA-4 antibody and one or more pharmaceutically acceptable excipients, and
c) a third pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients.

Embodiment 647. Use of a pharmaceutical combination for treating a solid tumor, wherein the pharmaceutical combination comprises:
a) a first pharmaceutical composition comprising a compound of Formula (A), or a pharmaceutically acceptable salt thereof, aluminum hydroxide particles, a buffering agent, and one or more pharmaceutically acceptable excipients,
b) a second pharmaceutical composition comprising ipilimumab and one or more pharmaceutically acceptable excipients, and
c) a third pharmaceutical composition comprising an anti-PD-L1 antibody and one or more pharmaceutically acceptable excipients.

Embodiment 648. Use of a pharmaceutical combination for treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising ipilimumab and one or more pharmaceutically acceptable excipients, and
c) a third pharmaceutical composition comprising an anti-PD-L1 antibody and one or more pharmaceutically acceptable excipients.

Embodiment 649. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 650. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 651. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 652. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 653. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 654. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 655. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 656. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 657. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 658. Use of a pharmaceutical combination for treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 659. Use of a pharmaceutical combination for treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 660. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 661. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 662. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 663. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 664. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 665. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 666. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 667. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 668. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is an anti-PD-L1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 669. The use of any one of Embodiments 649 to 668, wherein the anti-PD-L1 antibody is an anti-PD-L1 antibody of Table 2.

Embodiment 670. The use of any one of Embodiments 649 to 668, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 671. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 672. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 673. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 674. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 675. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 676. Use of a pharmaceutical combination for treating a solid tumor, wherein the pharmaceutical combination comprises:

a) a first pharmaceutical composition having a pH between 7.0 and 8.0 comprising 0.5 to 2 mg/mL of 3-(5-amino-2-(4-(2-(3,3-difluoro-3-phosphono-propoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 677. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 678. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 679. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 680. Use of a pharmaceutical combination for treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is an anti-CTLA-4 antibody.

Embodiment 681. The use of any one of Embodiments 671 to 680, wherein the anti-PD-1 antibody is an anti-PD-1 antibody of Table 3.

Embodiment 682. The use of any one of Embodiments 671 to 680, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 683. A pharmaceutical combination of any one of Embodiments 295 to 352 for use in treating a solid tumor.

Embodiment 684. A pharmaceutical combination for use in treating a solid tumor, wherein the pharmaceutical combination comprises:

a) a first pharmaceutical composition comprising a compound of Formula (A), or a pharmaceutically acceptable salt thereof, aluminum-containing particles, a buffering agent, and one or more pharmaceutically acceptable excipients, b) a second pharmaceutical composition comprising an immune checkpoint inhibitor and one or more pharmaceutically acceptable excipients, and c) a third pharmaceutical composition comprising an immune checkpoint inhibitor, which is different from the immune checkpoint inhibitor in the second pharmaceutical composition, and one or more pharmaceutically acceptable excipients.

Embodiment 685. A pharmaceutical combination for use in treating a solid tumor, wherein the pharmaceutical combination comprises:

a) a first pharmaceutical composition comprising a compound of Formula (A), or a pharmaceutically acceptable salt thereof, aluminum hydroxide particles, a buffering agent, and one or more pharmaceutically acceptable excipients, b) a second pharmaceutical composition comprising an immune checkpoint inhibitor and one or more pharmaceutically acceptable excipients, and c) a third pharmaceutical composition comprising an immune checkpoint inhibitor, which is different from the immune checkpoint inhibitor in the second pharmaceutical composition, and one or more pharmaceutically acceptable excipients.

Embodiment 686. A pharmaceutical combination for use in treating a solid tumor, wherein the pharmaceutical combination comprises:

a) a first pharmaceutical composition comprising a compound of Formula (A), or a pharmaceutically acceptable salt thereof, aluminum hydroxide particles, a buffering agent, and one or more pharmaceutically acceptable excipients, b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 687. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 688. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising a CTLA-4 receptor inhibitor and one or more pharmaceutically acceptable excipients, and
  c) a third pharmaceutical composition comprising a PD-L1 inhibitor and one or more pharmaceutically acceptable excipients.

Embodiment 689. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-L1 antibody and one or more pharmaceutically acceptable excipients.

Embodiment 690. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-L1 antibody of Table 2, and one or more pharmaceutically acceptable excipients.

Embodiment 691. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients.

Embodiment 692. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising a CTLA-4 receptor inhibitor and one or more pharmaceutically acceptable excipients, and
  c) a third pharmaceutical composition comprising a PD-1 inhibitor and one or more pharmaceutically acceptable excipients.

Embodiment 693. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-1 antibody and one or more pharmaceutically acceptable excipients.

Embodiment 694. A pharmaceutical combination for use in treating a solid tumor, wherein the pharmaceutical combination comprises:
  a) a first pharmaceutical composition comprising a compound of Formula (A), or a pharmaceutically acceptable salt thereof, aluminum hydroxide particles, a buffering agent, and one or more pharmaceutically acceptable excipients,
  b) a second pharmaceutical composition comprising an anti-CTLA-4 antibody and one or more pharmaceutically acceptable excipients, and
  c) a third pharmaceutical composition comprising an anti-PD-1 antibody of Table 3, and one or more pharmaceutically acceptable excipients.

Embodiment 695. A pharmaceutical combination for use in treating a solid tumor, wherein the pharmaceutical combination comprises:
   a) a first pharmaceutical composition comprising a compound of Formula (A), or a pharmaceutically acceptable salt thereof, aluminum hydroxide particles, a buffering agent, and one or more pharmaceutically acceptable excipients,
   b) a second pharmaceutical composition comprising an anti-CTLA-4 antibody and one or more pharmaceutically acceptable excipients, and
   c) a third pharmaceutical composition comprising an anti-PD-1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients.

Embodiment 696. A pharmaceutical combination for use in treating a solid tumor, wherein the pharmaceutical combination comprises:
   a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum-containing particles, a buffering agent, and one or more pharmaceutically acceptable excipients,
   b) a second pharmaceutical composition comprising an immune checkpoint inhibitor and one or more pharmaceutically acceptable excipients, and
   c) a third pharmaceutical composition comprising an immune checkpoint inhibitor, which is different from the immune checkpoint inhibitor in the second pharmaceutical composition, and one or more pharmaceutically acceptable excipients.

Embodiment 697. A pharmaceutical combination for use in treating a solid tumor, wherein the pharmaceutical combination comprises:
   a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
   b) a second pharmaceutical composition comprising an immune checkpoint inhibitor and one or more pharmaceutically acceptable excipients, and
   c) a third pharmaceutical composition comprising an immune checkpoint inhibitor, which is different from the immune checkpoint inhibitor in the second pharmaceutical composition, and one or more pharmaceutically acceptable excipients.

Embodiment 698. A pharmaceutical combination for use in treating a solid tumor, wherein the pharmaceutical combination comprises:
   a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
   b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
   c) a third pharmaceutical composition comprising an immune checkpoint inhibitor, which is different from the immune checkpoint inhibitor in the second pharmaceutical composition, and one or more pharmaceutically acceptable excipients wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 699. A pharmaceutical combination for use in treating a solid tumor, wherein the pharmaceutical combination comprises:
   a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
   b) a second pharmaceutical composition comprising a CTLA-4 receptor inhibitor and one or more pharmaceutically acceptable excipients, and
   c) a third pharmaceutical composition comprising a PD-L1 inhibitor and one or more pharmaceutically acceptable excipients.

Embodiment 700. A pharmaceutical combination for use in treating a solid tumor, wherein the pharmaceutical combination comprises:
   a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
   b) a second pharmaceutical composition comprising an anti-CTLA-4 antibody and one or more pharmaceutically acceptable excipients, and
   c) a third pharmaceutical composition comprising an anti-PD-L1 antibody and one or more pharmaceutically acceptable excipients.

Embodiment 701. A pharmaceutical combination for use in treating a solid tumor, wherein the pharmaceutical combination comprises:
   a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
   b) a second pharmaceutical composition comprising an anti-CTLA-4 antibody and one or more pharmaceutically acceptable excipients, and
   c) a third pharmaceutical composition comprising an anti-PD-L1 antibody of Table 2, and one or more pharmaceutically acceptable excipients.

Embodiment 702. A pharmaceutical combination for use in treating a solid tumor, wherein the pharmaceutical combination comprises:
   a) a first pharmaceutical composition comprising 3-(5-amino-2-(4-(2-(3,3-difluoro-3-phosphonopropoxy)

ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising an anti-CTLA-4 antibody and one or more pharmaceutically acceptable excipients, and
c) a third pharmaceutical composition comprising an anti-PD-L1 antibody comprising a heavy chain variable domain comprising the amino acid sequence of SEQ ID NO:7 and a light chain variable domain comprising the amino acid sequence of SEQ ID NO:17, and one or more pharmaceutically acceptable excipients.

Embodiment 703. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising a CTLA-4 receptor inhibitor and one or more pharmaceutically acceptable excipients, and
c) a third pharmaceutical composition comprising a PD-1 inhibitor and one or more pharmaceutically acceptable excipients.

Embodiment 704. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising an anti-CTLA-4 antibody and one or more pharmaceutically acceptable excipients, and
c) a third pharmaceutical composition comprising an anti-PD-1 antibody and one or more pharmaceutically acceptable excipients.

Embodiment 705. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising an anti-CTLA-4 antibody and one or more pharmaceutically acceptable excipients, and
c) a third pharmaceutical composition comprising an anti-PD-1 antibody of Table 3, and one or more pharmaceutically acceptable excipients.

Embodiment 706. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising an anti-CTLA-4 antibody and one or more pharmaceutically acceptable excipients, and
c) a third pharmaceutical composition comprising an anti-PD-L1 antibody comprising a heavy chain variable domain comprising the amino acid sequence of SEQ ID NO:27 and a light chain variable domain comprising the amino acid sequence of SEQ ID NO:37, and one or more pharmaceutically acceptable excipients.

Embodiment 707. A pharmaceutical combination for use in treating a solid tumor, wherein the pharmaceutical combination comprises:
a) a first pharmaceutical composition comprising a compound of Formula (A), or a pharmaceutically acceptable salt thereof, aluminum hydroxide particles, a buffering agent, and one or more pharmaceutically acceptable excipients,
b) a second pharmaceutical composition comprising ipilimumab and one or more pharmaceutically acceptable excipients, and
c) a third pharmaceutical composition comprising an anti-PD-L1 antibody and one or more pharmaceutically acceptable excipients.

Embodiment 708. A pharmaceutical combination for use in treating a solid tumor, wherein the pharmaceutical combination comprises:
a) a first pharmaceutical composition comprising 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, aluminum hydroxide particles, a buffering agent, and one or more pharmaceutically acceptable excipients,
b) a second pharmaceutical composition comprising ipilimumab and one or more pharmaceutically acceptable excipients, and
c) a third pharmaceutical composition comprising an anti-PD-L1 antibody and one or more pharmaceutically acceptable excipients.

Embodiment 709. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 710. A pharmaceutical combination for use in treating a solid tumor, wherein the pharmaceutical combination comprises:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 711. A pharmaceutical combination for use in treating a solid tumor, wherein the pharmaceutical combination comprises:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 712. A pharmaceutical combination for use in treating a solid tumor, wherein the pharmaceutical combination comprises:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 713. A pharmaceutical combination for use in treating a solid tumor, wherein the pharmaceutical combination comprises:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
  b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and
  c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 714. A pharmaceutical combination for use in treating a solid tumor, wherein the pharmaceutical combination comprises:
  a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]

naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 715. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 716. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 717. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 718. A pharmaceutical combination for use in treating a solid tumor, wherein the pharmaceutical combination comprises:

a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and b) a second pharmaceutical composition comprising an immune checkpoint inhibitor and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 719. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 720. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 721. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 722. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 723. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 724. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 725. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 726. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 727. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 728. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
b) a second pharmaceutical composition comprising an immune checkpoint inhibitor and one or more pharmaceutically acceptable excipients, wherein the checkpoint inhibitor is an anti-PD-L1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 729. The pharmaceutical combination of any one of Embodiments 709 to 728, wherein the anti-PD-L1 antibody is an anti-PD-L1 antibody of Table 2.

Embodiment 730. The pharmaceutical combination of any one of Embodiments 709 to 728, wherein the anti-PD-L1 antibody is an anti-PD-L1 antibody comprising a heavy chain variable domain comprising the amino acid sequence of SEQ ID NO:7 and a light chain variable domain comprising the amino acid sequence of SEQ ID NO:17.

Embodiment 731. A pharmaceutical combination for use in treating a solid tumor, wherein the pharmaceutical combination comprises:
a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) mannitol, and
b) a second pharmaceutical composition comprising an immune checkpoint inhibitor and one or more pharmaceutically acceptable excipients, wherein the checkpoint inhibitor is an anti-PD-1 antibody, and c) a third pharmaceutical composition comprising an immune checkpoint inhibitor, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 732. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-100 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-1 antibody, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 733. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-1 antibody, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 734. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-50 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-1 antibody, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 735. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) mannitol, and
- b) a second pharmaceutical composition comprising an immune checkpoint inhibitor and one or more pharmaceutically acceptable excipients, wherein the checkpoint inhibitor is an anti-PD-1 antibody, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 736. A pharmaceutical combination for use in treating a solid tumor, wherein the pharmaceutical combination comprises:
- a) a first pharmaceutical composition having a pH between 7.0 and 8.0 comprising 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 1 to 4 mg/mL, 5-20 mM Tris buffer and 5-10% (w/v) sucrose, and
- b) a second pharmaceutical composition comprising an immune checkpoint inhibitor and one or more pharmaceutically acceptable excipients, wherein the checkpoint inhibitor is an anti-PD-1 antibody, and
- c) a third pharmaceutical composition comprising an immune checkpoint inhibitor, which is different from the immune checkpoint inhibitor in the second pharmaceutical composition, and one or more pharmaceutically acceptable excipients, wherein the checkpoint inhibitor is selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor.

Embodiment 737. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) mannitol, and
b) a second pharmaceutical composition comprising an immune checkpoint inhibitor and one or more pharmaceutically acceptable excipients, wherein the checkpoint inhibitor is an anti-PD-1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 738. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 16 mM Tris buffer and 7.5% (w/v) sucrose, and
b) a second pharmaceutical composition comprising an immune checkpoint inhibitor and one or more pharmaceutically acceptable excipients, wherein the checkpoint inhibitor is an anti-PD-1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 739. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) mannitol, and
b) a second pharmaceutical composition comprising an immune checkpoint inhibitor and one or more pharmaceutically acceptable excipients, wherein the checkpoint inhibitor is an anti-PD-1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 740. A pharmaceutical combination for use in treating a solid tumor, wherein the pharmaceutical combination comprises:
a) a first pharmaceutical composition having a pH between 7.0 and 8.0 comprising 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles having an aluminum content of 2 mg/mL, 5 mM Tris buffer and 8.25% (w/v) sucrose, and
b) a second pharmaceutical composition comprising an immune checkpoint inhibitor and one or more pharmaceutically acceptable excipients, wherein the checkpoint inhibitor is an anti-PD-1 antibody, and
c) a third pharmaceutical composition comprising an immune checkpoint inhibitor, and one or more pharmaceutically acceptable excipients, wherein the checkpoint inhibitor is an anti-CTLA-4 antibody.

Embodiment 741. The pharmaceutical combination of any one of Embodiments 731 to 740, wherein the anti-PD-1 antibody is an anti-PD-1 antibody of Table 3.

Embodiment 742. The pharmaceutical combination of any one of Embodiments 731 to 740, wherein the anti-PD1 antibody is an anti-PD-1 antibody comprising a heavy chain variable domain comprising the amino acid sequence of SEQ ID NO:27 and a light chain variable domain comprising the amino acid sequence of SEQ ID NO:37.

Embodiment 743. The method of any one of Embodiments 165 to 189 or Embodiments 353 to 363 or Embodiments 382 to 434 or Embodiments 519 to 622, wherein the solid tumor is head and neck squamous cell carcinoma (HNSCC), melanoma or a visceral tumor.

Embodiment 744. The use of any one of Embodiments 190 to 211 or Embodiments 364 to 371 or Embodiments 435 to 476 or of Embodiments 623 to 682, wherein the solid tumor is head and neck squamous cell carcinoma (HNSCC), melanoma or a visceral tumor.

Embodiment 745. The pharmaceutical composition of any one of Embodiments 212 to 234 or Embodiments 372 to 381, wherein the solid tumor is head and neck squamous cell carcinoma (HNSCC), melanoma or a visceral tumor.

Embodiment 746. The pharmaceutical combination of any one of Embodiments 478 to 518 or Embodiments 683 to 742, wherein the solid tumor is head and neck squamous cell carcinoma (HNSCC), melanoma or a visceral tumor.

Embodiment 747. Use of a pharmaceutical composition of any one of Embodiments 1 to 4, Embodiments 10 to 83 or Embodiments 161 to 164, in the manufacture of a medicament for treating a solid tumor.

Embodiment 748. The use of Embodiment 747, wherein the solid tumor is head and neck squamous cell carcinoma (HNSCC), melanoma or a visceral tumor.

Embodiment 749. Use of a pharmaceutical combination of any one of Embodiments 235 to 352, in the manufacture of a medicament for treating a solid tumor.

Embodiment 750. The use of Embodiment 749, wherein the solid tumor is head and neck squamous cell carcinoma (HNSCC), melanoma or a visceral tumor.

The effect on tumor volume by administration of a compound of Formula (A), in the presence of aluminum-containing particles, with and without the administration of one or more checkpoint inhibitors is shown in Example 14. It was found that the administration of a pharmaceutical composition comprising a compound of Formula (A), or a pharmaceutically acceptable salt thereof, and aluminum-containing particlesin was found to be as effective in enhancing the immune response to a tumor when administered alone (not in combination), as that obtained with the administration of a pharmaceutical composition comprising a compound of Formula (A), or a pharmaceutically acceptable salt thereof, and aluminum-containing particlesin in combination with the administration of an immune checkpoint inhibitor. FIG. 9A shows the efficacy obtained in the MC38 syngeneic colon cancer tumor model for a pharmaceutical composition comprising Compound 15 and aluminum hydroxide administered alone (not in combination), or administered in combination with the administration of a pharmaceutical composition comprising either a CTLA4 receptor inhibitor (anti-CTLA4 antibody) or an inhibitor of the PD-L1 ligand (anti-PD-L1 antibody). It is also evident from FIG. 9A that the administration of a pharmaceutical composition comprising Compound 15 and aluminum hydroxide alone is more effective than the administration of either the CTLA4 receptor inhibitor alone (not in combination) or administration of the inhibitor of the PD-L1 ligand alone (not in combination).

In addition it was found that the immune response to a tumor was even further enhanced by the administration of a pharmaceutical composition comprising a compound of Formula (A), or a pharmaceutically acceptable salt thereof, and aluminum-containing particles in combination with the administration of two different checkpoint inhibitors. FIG. 9 further shows the enhanced efficacy obtained using a triple combination of two different checkpoint inhibitors and a pharmaceutical composition comprising a compound of Formula (A), or a pharmaceutically acceptable salt thereof, and aluminum-containing particles. Specifically, FIG. 9A shows efficacy obtained with the intratumor administration of a pharmaceutical composition comprising Compound 15 and aluminum hydroxide in combination with the systemic administration (intraperitoneal) of a CTLA4 receptor inhibitor and the separate systemic administration (intraperitoneal) of a PD-L1 ligand inhibitor.

FIG. 9A is data obtained at the site of injection, whereas FIG. 9B shows the data obtained at a distant location from the injection site. FIG. 9B the same behavior described above for FIG. 9A and demonstrates that systemic antitumor efficacy of a compound of Formula (A) adsorbed to aluminum hydroxide.

EXAMPLES

The compounds, pharmaceutical compositions comprising such compounds, pharmaceutical combinations comprising such compounds, methods of using such pharmaceutical compositions and pharmaceutical combinations and use of such pharmaceutical compositions and pharmaceutical combinations of the present invention are shown in the following examples which are intended to illustrate the invention and are not to be construed as being limitations thereon.

Materials and Methods

Compound 15/Alhydrogel® Suspensions

TABLE 5

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Water Volume (mL) |
| --- | --- | --- | --- | --- | --- |
| 0.25 | 0.013 | 0.05:1 | 0.125 | 0.013 | 9.86 |
| 0.25 | 0.025 | 0.1:1 | 0.125 | 0.025 | 9.85 |
| 0.25 | 0.063 | 0.25:1 | 0.125 | 0.063 | 9.81 |
| 0.25 | 0.125 | 0.5:1 | 0.125 | 0.125 | 9.75 |
| 0.25 | 0.250 | 1:1 | 0.125 | 0.250 | 9.63 |
| 0.25 | 0.375 | 1.5:1 | 0.125 | 0.375 | 9.50 |

TABLE 5-continued

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Water Volume (mL) |
| --- | --- | --- | --- | --- | --- |
| 0.25 | 0.500 | 2:1 | 0.125 | 0.500 | 9.38 |
| 0.30 | 0.015 | 0.05:1 | 0.150 | 0.015 | 9.84 |
| 0.30 | 0.030 | 0.1:1 | 0.150 | 0.030 | 9.82 |
| 0.30 | 0.075 | 0.25:1 | 0.150 | 0.075 | 9.78 |
| 0.30 | 0.150 | 0.5:1 | 0.150 | 0.150 | 9.70 |
| 0.30 | 0.300 | 1:1 | 0.150 | 0.300 | 9.55 |
| 0.30 | 0.450 | 1.5:1 | 0.150 | 0.450 | 9.40 |
| 0.30 | 0.600 | 2:1 | 0.150 | 0.600 | 9.25 |
| 0.50 | 0.025 | 0.05:1 | 0.250 | 0.025 | 9.73 |
| 0.50 | 0.050 | 0.1:1 | 0.250 | 0.050 | 9.70 |
| 0.50 | 0.125 | 0.25:1 | 0.250 | 0.125 | 9.63 |
| 0.50 | 0.250 | 0.5:1 | 0.250 | 0.250 | 9.50 |
| 0.50 | 0.500 | 1:1 | 0.250 | 0.500 | 9.25 |
| 0.50 | 0.750 | 1.5:1 | 0.250 | 0.750 | 9.00 |
| 0.50 | 1.000 | 2:1 | 0.250 | 1.000 | 8.75 |
| 1.00 | 0.050 | 0.05:1 | 0.500 | 0.050 | 9.45 |
| 1.00 | 0.100 | 0.1:1 | 0.500 | 0.100 | 9.40 |
| 1.00 | 0.250 | 0.25:1 | 0.500 | 0.250 | 9.25 |
| 1.00 | 0.500 | 0.5:1 | 0.500 | 0.500 | 9.00 |
| 1.00 | 1.000 | 1:1 | 0.500 | 1.000 | 8.50 |
| 1.00 | 1.500 | 1.5:1 | 0.500 | 1.500 | 8.00 |
| 1.00 | 2.000 | 2:1 | 0.500 | 2.000 | 7.50 |
| 2.00 | 0.100 | 0.05:1 | 1.000 | 0.100 | 8.90 |
| 2.00 | 0.200 | 0.1:1 | 1.000 | 0.200 | 8.80 |
| 2.00 | 0.500 | 0.25:1 | 1.000 | 0.500 | 8.50 |
| 2.00 | 1.000 | 0.5:1 | 1.000 | 1.000 | 8.00 |
| 2.00 | 2.000 | 1:1 | 1.000 | 2.000 | 7.00 |
| 2.00 | 3.000 | 1.5:1 | 1.000 | 3.000 | 6.00 |
| 2.00 | 4.000 | 2:1 | 1.000 | 4.000 | 5.00 |
| 3.00 | 0.150 | 0.05:1 | 1.500 | 0.150 | 8.35 |
| 3.00 | 0.300 | 0.1:1 | 1.500 | 0.300 | 8.20 |
| 3.00 | 0.750 | 0.25:1 | 1.500 | 0.750 | 7.75 |
| 3.00 | 1.500 | 0.5:1 | 1.500 | 1.500 | 7.00 |
| 3.00 | 3.000 | 1:1 | 1.500 | 3.000 | 5.50 |
| 3.00 | 4.500 | 1.5:1 | 1.500 | 4.500 | 4.00 |
| 3.00 | 6.000 | 2:1 | 1.500 | 6.000 | 2.50 |
| 5.00 | 0.250 | 0.05:1 | 2.500 | 0.250 | 7.25 |
| 5.00 | 0.500 | 0.1:1 | 2.500 | 0.500 | 7.00 |
| 5.00 | 1.250 | 0.25:1 | 2.500 | 1.250 | 6.25 |
| 5.00 | 2.500 | 0.5:1 | 2.500 | 2.500 | 5.00 |
| 5.00 | 5.000 | 1:1 | 2.500 | 5.000 | 2.50 |
| 5.00 | 7.500 | 1.5:1 | 2.500 | 7.500 | 0.00 |

In the preparation of the Compound 15/Alhydrogel® suspension used in the Examples herein, the stock suspension of Alhydrogel® was filtered by gravity filtration through a 100 μm cell strainer before mixing with stock solution comprising Compound 15. The resulting mixture/suspension was stirred for 5 minutes to allow Compound 15 to adsorb/bind to the aluminum of Alhydrogel®.

To determine the extent of Compound 15 binding to Alhydrogel® (i.e. % bound) in the Compound 15/Alhydrogel® suspension used in the Examples herein, aliquots of the suspension were centrifuged to pellet the bound Compound 15/Alhydrogel® (e.g. 21,000×g for 10 min), and the amount of free Compound 15 in the supernatant was analyzed by HPLC/UV or LC/MS/MS.

Animals.

All animal related procedures were conducted in compliance with Animal Welfare Act regulations and the Guide for the Care and Use of Laboratory Animals.

C57/Bl6 mice were purchased from Jackson Laboratory, Bar Harbor, Me., USA.

Male Wistar rats (weight range of 250300 g) were purchased from Envigo, Indianapolis, Ind. USA.

Charles River Laboratories Balb/c female mice (age 6-8 weeks) were purchased from Jackson Laboratory, Bar Harbor, Me., USA Cell Lines MC38 and A20 cell line was purchased from ATCC (American Type Culture Collection, Manassas, Va.).

Pharmacokinetic Regression Analysis

Pharmacokinetic parameters were calculated by non-compartmental regression analysis using an in house fitting program. The highest plasma concentration of Compound 15 (Cmax) and the corresponding times ($T_{max}$) were recorded. The area under each concentration-time curve, AUC0-t or AUC0-∞ was calculated using the linear trapezoidal rule. Clearance (CL), the steady-state volume of distribution (Vss) and mean residence time (MRT) of Compound 15 were calculated using the data from the intravenous dose and the following equations:

$$CL = Dose/AUC_{0-\infty}$$

$$Vss = (Dose * AUMC_{0-\infty})/(AUC_{0-\infty})$$

$$MRT = (AUMC_{0-\infty})/(AUMC_{0-\infty}) = Vss/CL$$

where $AUC_{0-\infty}$ and $AUMC_{0-\infty}$ are the area under the concentration-time curve and area under the first moment concentration-time curve from time 0 to infinity, respectively.

Bioavailability following subcutaneous injection of free or Alhydrogel adsorbed LHC165 was estimated as follows:

$$F = (AUMC_{0-\infty,s.c.})/(AUMC_{0-\infty,i.v.}) * (Dose_{i.v.}/Dose_{s.c.})$$

Percent Treatment/Control (T/C)

Percent treatment/control (T/C) values for tumor were calculated using the following formula:

$$\% \ T/C = 100 \times \Delta T/\Delta C \text{ if } \Delta T > 0\%$$

$$\% \ Regression = 100 \times \Delta T/T_{initial} \text{ if } \Delta T < 0$$

where:
T=mean tumor volume of the drug-treated group on the final day of the study;
ΔT=mean tumor volume of the drug-treated group on the final day of the study minus mean tumor volume of the drug-treated group on initial day of dosing;
$T_{initial}$=mean tumor volume of the drug-treated group on initial day of dosing;
C=mean tumor volume of the control group on the final day of the study;
ΔC=mean tumor volume of the control group on the final day of the study minus mean tumor volume of the control group on initial day of dosing.

All data were expressed as mean±standard error of the mean (SEM). Delta tumor volume
and body weight were used for statistical analysis. Between groups comparisons were carried
out using a one-way ANOVA followed by a post hoc Tukey or Dunn's. For all statistical
evaluations the level of significance was set at p<0.05. Significance compared to the vehicle
control group is reported unless otherwise stated.

Example 1: Synthesis of Exemplary Compounds

Compound Nos. 1-28 of Table 1 were synthesized using the methods described in WO2011/049677.

Example 2: TLR7 Activation Assay

The $EC_{50}$ for TLR-7 stimulation by the exemplary compounds of Formula (A) are given in Table 6. Such $EC_{50}$ values were obtained using a reporter gene assay wherein Human embryonic kidney 293 (HEK 293) cells were stably transfected with human TLR7 and an NF-kB-driven luciferase reporter vector (pNifty-Luciferase). As a control assay, normal Hek293 transfected with pNifty-Luc were used. Cells were cultured in DMEM supplemented with 2 mM L-glutamine, 10% heart inactivated FBS, 1% penicillin and streptomycin, 2 µg/ml puromycin (InvivoGen #ant-pr-5) and 5 µg/ml of blasticidin (Invitrogen #46-1120). Bright-Glo™ Luciferase assay buffer and substrate were supplied by Promega #E263B and #E264B (assay substrate and buffer respectively). 384 well clear-bottom plates were supplied by Greiner bio-one (#789163-G) and were custom bar-coded plates. Cells were plated at 25,000 cells/well in 384-well plates in a final volume of 50 µl of media. Cells were allowed to adhere to the plates after overnight (18 hours) culture at 37° C. and 5% $CO_2$. Serially diluted experimental and positive control compounds were then dispensed to each well and incubated for 7 hours at 37° C. and 5% $CO_2$. Cells stimulated with DMSO alone also serve as negative controls. After the incubation, 30 µl of the pre-mix assay buffer and substrate buffer were added to each well according to manufacturer's instructions. The luminescence signal was read on a CLIPR machine with an integration time of 20 seconds per plate. Dose response curves are generated for each compound and $EC_{50}$ values were determined as the concentration that gives 50% of the maximal signal. Such $EC_{50}$ values were obtained relative to the activity of resiquimod set to 100%.

TABLE 6

| Compound Number | Human TLR7 $EC_{50}$ (nM) HEK293 |
|---|---|
| 1 | 1640 |
| 2 | 226 |
| 3 | 315 |
| 4 | 3170 |
| 5 | 559 |
| 6 | 308 |
| 7 | 1010 |
| 8 | 375 |
| 9 | 390 |
| 10 | 153 |
| 11 | 90 |
| 12 | 201 |
| 13 | 1051 |
| 14 | 885 |
| 15 | 96 |
| 16 | 65 |
| 17 | 137 |
| 18 | 5 |
| 19 | 964 |
| 20 | 384 |
| 21 | 204 |
| 22 | 1160 |
| 23 | 791 |
| 24 | 4260 |
| 25 | 975 |
| 26 | 2592 |
| 27 | 921 |
| 28 | 524 |

Example 3: Adsorption of Compounds of Formula (A) to Aluminum-Containing Particles By way of example, the percentage (%) of a compounds 6, 15, 17, 18 and 20 to aluminum hydroxide in histidine buffer (pH 6.8) is given in Table 7. The percentage (%) bound for compounds 6, 15, 17, 18 and 20 was obtained as follows: to three volume equivalents of aqueous aluminum hydroxide (2 mg/mL) was added one volume equivalent of compound in 10 mM histidine buffer (4 mg/mL) at pH 6.8. The resulting solution was diluted 10-fold with blank histidine buffer to a final compound concentration of 0.1 mg/mL. Diluted solutions were incubated at 37° C. for 5 hours. The samples were centrifuged at 14,000 rpm for 10 minutes to pellet the insoluble. The supernatant (along with an internal standard) was then evaluated by LC-MS/MS using a ballistic gradient (from 5% $CH_3CN$-0.5% formic acid to 95% $CH_3CN$-1.0% formic acid in 3.5 minutes) on a Waters Atlantis dC18 (50 mm×2.1 mm) column at room temperature against a calibration curve prepared at known compound concentrations ranging from 0.005 to 50 µM. The concentration in the supernatant was calculated as % unbound to aluminum hydroxide compared to control; the % bound to aluminum hydroxide was calculated as 100% minus % unbound.

TABLE 7

| Compound | % Bound |
|---|---|
| 1 | 98.2 |
| 15 | 96.0 |
| 17 | 94.5 |
| 18 | 96.2 |
| 20 | 97.0 |

Example 4: Binding Efficiency of Compounds of Formula (A) to Aluminum-Containing Particles The efficiency of binding of compounds of Formula (A) to aluminum-containing particles, as reflected in the percentage (%) bound to aluminum-containing particles, is a function of the (weight/weight) ratio of aluminum-containing particles to compound and to the final concentration (mg/mL) of compound in suspension with aluminum hydroxide. By way of example, the dependence of binding efficiency on the aluminum-containing particles to compound (w/w) ratio is shown in Table 8, where the final concentration of Compound 15 is fixed at 2 mg/mL and the amount of aluminum hydroxide is varied to obtain the desired ratio. The percentage of Compound 15 bound were obtained as described above in the "Materials and Method", and the suspensions of Compound 15/Alhydrogel® were prepared in 20 mM Tris buffer (pH 7.4) as described above in "Compound 15/Alhydrogel® Suspensions".

TABLE 8

| Compound 15 Final Conc (mg/mL) | Aluminum Final Conc (mg/mL) | Aluminum to Compound 15 ratio | Compound 15 % Bound | Compound 15 % Free |
|---|---|---|---|---|
| 2 | 0.1 | 0.05:1 | 9.6 | 90.4 |
| 2 | 0.2 | 0.1:1 | 12.5 | 87.5 |
| 2 | 0.5 | 0.25:1 | 25.7 | 74.3 |
| 2 | 1 | 0.5:1 | 43.5 | 56.5 |
| 2 | 2 | 1:1 | 80.8 | 19.2 |
| 2 | 3 | 1.5:1 | 97.6 | 2.4 |
| 2 | 4 | 2:1 | 99.7 | 0.3 |

However, at a fixed aluminum hydroxide to Compound 15 ratio it was observed that the binding efficiency was also dependent on the final concentration of Compound 15 (see Table 9).

TABLE 9

| Compound 15 Final Conc (mg/mL) | Aluminum Final Conc (mg/mL) | Aluminum to Compound 15 ratio | Compound 15 % Bound | Compound 15 % Free |
|---|---|---|---|---|
| 0.25 | 0.625 | 2.5:1 | 90.7 | 9.3 |
| 0.25 | 5 | 20:1 | 97.6 | 1.4 |
| 1 | 2.5 | 2.5:1 | 93.5 | 6.5 |
| 3 | 7.5 | 2.5:1 | 97.1 | 2.9 |
| 3 | 5 | 1.7:1 | 99.6 | 0.4 |

Although, as seen in Table 10, % Bound levels >97% were obtained for low final concentrations of Compound 15 by increasing the final concentration of aluminum. Sustained release of a Compound of Formula (A) was observed for % Bound >97, which allowed for control of the systemic release of cytokines (see Example 5-9).

In addition, for (w/w) ratios of aluminum-containing particles to compound of 1.5:1 and below, the binding efficiency has an apparent pH dependence. The effect of pH on binding efficiency is seen in Table 10, where the binding efficiency of Compound 15 at either a ratio of aluminum hydroxide to Compound 15 (w/w) of 1.5:1 or 2:1 is given shown. The percentage of Compound bound was obtained as described above, although in Tris buffer at differing pH values. The suspensions of Compound 15/Alhydrogel® in Tris buffer at various were prepared as described above in "Compound 15/Alhydrogel® Suspensions".

TABLE 10

| Aluminum hydroxide: Compound 15 Ratio (w/w) | pH | Compound 15 % Bound |
|---|---|---|
| 1.5:1 | 7 | 98.5 |
| 1.5:1 | 7.5 | 85.9 |
| 1.5:1 | 8 | 91.1 |
| 2:1 | 7 | 99.3 |
| 2:1 | 7.5 | 99.7 |
| 2:1 | 8 | 99.1 |

Example 5: Injection Site Retention—MC38 Syngeneic Mouse Tumor Model One Week Study Mouse Pharmacokinetic Analysis of Free Compound 15 and Compound 15 Adsorbed to Alhydrogel®

A MC38 syngeneic mouse tumor model was used to investigate the systemic exposure of Compound 15 following:

a) a single intra-tumoral (i.t.) injection of 100 µg (~4 mg/kg) of free form Compound 15 in 20 mM Tris buffer pH 7.4, b) a single intra-tumoral (i.t.) injection of Compound 15 adsorbed to Alhydrogel® suspension at a 1:1.5 ratio (w/w) of Compound 15 to Alhydrogel®)-Suspension A described below and c) a single subcutaneous (s.c.) injection of Compound 15 adsorbed to Alhydrogel® suspension at a 1:1.5 ratio (w/w) of Compound 15 to Alhydrogel®-Suspension A described below.

Suspension A 2 mg/mL Compound 15, 3 mg/mL Aluminum Hydroxide and 7.5% (w/v) Sucrose in 16 mM Tris (pH 7.4)—Compound 15/Alhydrogel® (1:1.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 2.86 mg/mL of Compound 15, 12.5% (w/v) sucrose in 33.4 mM Tris (pH 7.4) buffer was prepared for dilution with the 2% Alhydrogel® stock. The table below gives the volumes used to make 5 mL of a suspension comprising 2 mg/mL Compound 15, 3 mg/mL Aluminum hydroxide and 7.5% (w/v) sucrose in 16 mM Tris (pH 7.4) at a 1.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogele ® (mL) |
|---|---|---|---|---|
| 2 | 3 | 1.5:1 | 3.5 | 1.5 |

MC38 Tumor Implantation in C57/BL6 Mice

MC38 cells were grown in sterile conditions in a 37° C. incubator with 5% $CO_2$ for two weeks. The cells were cultured in DMEM media supplemented with 10% FBS, cells were passed every 2-3 days. On the day of injection, cells were harvested (Passage 12) and re-suspended in HBSS at a concentration of $2.5 \times 10^6$/ml. Cells were Radil tested for *mycoplasma* and murine viruses.

For each mouse, $0.25 \times 10^6$ cells were implanted with subcutaneously injection into right flank using a 28½ g needle (100⁴ injection volume). Female C57BL/6 mice bearing the MC38 tumors were randomized into separate groups (n=3-24 mice per group) 10 days post tumor cell implantation with an average tumor volume range of 95.05-194.36 mm³.

Dosing and Sampling in MC38 Tumor Bearing C57/BL6 Mice

Approximately 10 days after MC38 tumor implant, tumor bearing mice received a single dose of vehicle, 100 µg of free Compound 15 solution (2 mg/mL) or Compound 15 adsorbed to Alhydrogel (1:1.5 w/w; 97% bound) by direct intra-tumoral (i.t.) injection or subcutaneous (s.c.) injection. The dose volume was 50 µL per animal. Plasma samples were taken up to 7 days post dose at time points indicated in Table 11 (n=3 animal per time point).

TABLE 11

| Compound 15 Dose (µg) | Formulation | Plasma Collection Times post dose (h) |
|---|---|---|
| 100 (i.t) | 20 mM Tris | 0.083, 0.5, 1, 3, 6, 24 |
| 100 (i.t) | Suspension A | 1, 6, 24, 48, 72, 96, 120, 144, 168 |
| 100 (s.c) | Suspension A | 1, 6, 24, 48, 72, 96, 120, 144, 168 |

Analysis of Mouse Plasma Samples by LC/MS/MS

Plasma concentrations of Compound 15 were quantified using a Liquid Chromatography/Mass Spectrometry (LC/MS/MS) assay. Compound 20 (100 ng/mL in water) was used as an internal standard. To 20 µL of each plasma sample or appropriately diluted plasma sample, 25 µL of internal standard solution was added, then mixed with 150 µL of extraction solvent (methanol/acetonitrile, 80/20 by volume) to precipitate plasma proteins. The samples were vortexed for 5 minutes then centrifuged with an Eppendorf Centrifuge 5810R (Eppendorf, Hamburg, Germany) at a setting of 4,000 rpm for 10 minutes at 4° C. Aliquot of supernatant (50 µL) was transferred to a clean 96-well plate and mixed with 100 µL of Milli-Q water. The mixed samples were injected (25 µL) onto a Waters XBridge C4 analytical column (2.1×50 mm, 3.5 µm), and mobile phases consisted of 0.1% formic acid in water (solvent A) and 0.1% formic acid in acetonitrile (solvent B). A gradient elution method at flow rate of 800 µL/min was used from 20% B to 95% B in 1.5 min, held at 95% B until 2 min, and return to initial condition with 20% B at 2.1 min, total run time was 3 minutes.

The HPLC system, consisting of Agilent 1200 series binary pump (Agilent Technologies Inc.), Agilent 1200 series micro vacuum degasser (Agilent Technologies Inc.), CTC PAL-HTC autosampler (LEAP Technologies, Carborro, N.C., USA) was interfaced to a AB Sciex API 4000 QTrap mass spectrometer (AB Sciex LLC., Framingham, Mass., USA). Mass spectral analyses were carried out using electrospray ionization (ESI) in the positive ion mode. Compound 15 (604.2>281.0) and internal standard (598.2>263.1) peak integration were performed using Analyst™ 1.4 software. The lower limit of quantitation (LLOQ) in plasma was 0.25 ng/mL. Known amounts of Compound 15 were spiked into plasma to create quality control samples with known concentrations of 4, 40, 200 and 1000 ng/mL.

Figure 1:
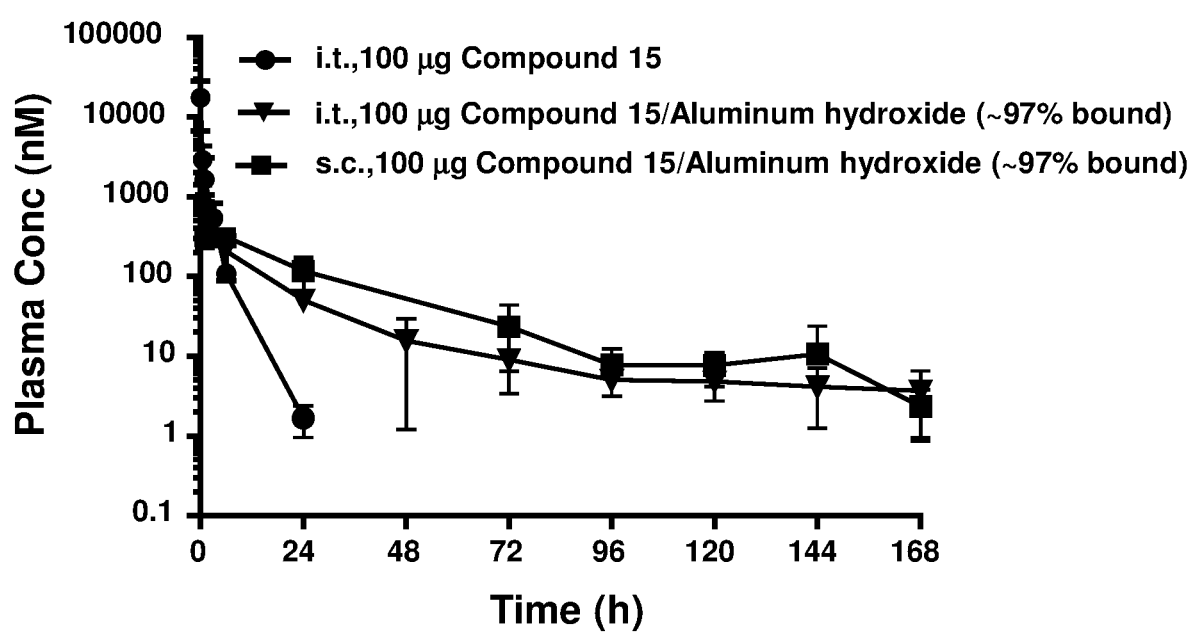
FIG. 1: Plasma concentration-time profiles of Compound 15 in a MC38 tumor bearing C57/BL6 mice following a single intratumoral (i.t.) or subcutaneous (sc) injection of 100 μg free Compound 15 solution or Compound 15 adsorbed to aluminum hydroxide at 1:1.5, w/w ratio.

Plasma PK profiles of Compound 15 are shown in FIG. 1 and systemic exposures are summarized in Table 12. Direct intra-tumoral (i.t.) injection of 100 µg soluble or Alhydrogel® adsorbed Compound 15 in MC38 tumor bearing mice gave very different PK profiles. Without the Alhydrogel®, soluble free Compound 15 was very quickly released into systemic circulation and most drug eliminated by 24 h post i.t. injection with a half-life of 2.65 h. Alhydrogel® adsorbed Compound 15 (or referred to Compound 15/Alhydrogel®) gave a controlled release PK profile of Compound 15 as compared to soluble Compound 15. $T_{max}$ was delayed, and Cmax was dramatically reduced to 2-4% of that following i.t. injection of soluble Compound 15.

The half-life of Compound 15 when adsorbed onto Alhydrogel® was significantly longer, and the slow release profile observed for Compound 15 adsorbed onto Alhydrogel® demonstrates prolonged retention of Compound 15 in the local tumor environment. In addition, subcutaneous injection of Compound 15/Alhydrogel® gave a similar systemic PK profile as that following i.t. injection (FIG. 1), with similar $C_{max}$, but higher AUC. The AUC following a single s.c. or i.t. injection of 100 µg Compound 15/Alhydrogel® was ~60% and 96% of that following i.t. injection of 100 µg soluble Compound 15, suggesting that the majority of Compound 15 was desorbed from Alhydrogel® and cleared systemically after 1 week following i.t. or s.c. injection.

TABLE 12

| Compound 15 Dose (µg) | Formulation | $T_{1/2}$ (h) | $T_{max}$ (h) | $C_{max}$ (ng/mL) | $AUC_{(0-\infty)}$ (ng*h/mL) |
|---|---|---|---|---|---|
| 100 (i.t) | 20 mM Tris | 2.65 | 0.083 | 10611 | 6219 |
| 100 (i.t) | Suspension A | 56.9 | 1-6 | 202 | 2762 |
| 100 (s.c) | Suspension A | 29.4 | 1-6 | 191 | 6061 | where: AUC(0-∞) is the area under the curve from time zero extrapolated to infinity;

$C_{max}$ is the maximum concentration observed;

$T_{max}$ is the time in which maximum concentration observed

Note: The pharmacokinetic properties of Compound 15 were examined in female C57/BL6 mice following a single 2 mg/kg intravenous bolus administration. The compound exhibited low plasma clearance of 18.1 mL/min/kg, which is ~20% of mouse liver blood flow (90 mL/min/kg, Davies and Morris 1993). The mean volume of distribution at steady-state was low (0.19 L/kg) as compared to total body water volume (0.725 L/kg, Davies and Morris 1993). Compound 15 had a short residence time (MRT) of 0.17 h and elimination half-life of 1 h in mice.

Example 6: Injection Site Retention—MC38 Syngeneic Mouse Tumor Model Two Week Study Mouse Pharmacokinetic Analysis of Compound 15 Adsorbed to Alhydrogel®

To evaluate systemic exposure of Compound 15 over an extended period of time, a MC38 syngeneic mouse tumor model as described in Example 5 was used, where the plasma concentration of Compound 15 was monitored for 2 weeks following a single 504 intra-tumoral (i.t.) or subcutaneous (s.c.) 50 µL injection of Suspension B (described below) which delivered 100 µg of Compound 15. Suspension B comprises a Compound 15/Alhydrogel® ratio of 1:2.

Suspension B 2 mg/mL Compound 15, 4 mg/mL Aluminum Hydroxide and 7.5% (w/v) Sucrose in 16 mM Tris (pH 7.4)—Compound 15/Alhydrogel® (1:2 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 3.34 mg/mL of Compound 15, 9.375% (w/v) sucrose in 20 mM Tris (pH 7.4) buffer was prepared for dilution with the 2% Alhydrogel® stock. The table below gives the volumes used to make 5 mL of a suspension comprising 1 mg/mL Compound 15, 2 mg/mL Aluminum hydroxide and 7.5% (w/v) sucrose in 16 mM Tris (pH 7.4) at a 2:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogele ® (mL) |
|---|---|---|---|---|
| 2 | 4 | 2:1 | 3 | 2 |

Plasma sample were obtained and analyzed as described in Example 5. The Compound 15 systemic PK profiles in MC38 tumor bearing mice were similar to those shown in FIG. 1, showing sustained release of Compound 15 into systemic circulation from Compound 15/Alhydrogel® retained at local injection sites. The pharmacokinetic parameters (PK) are summarized in Table 13.

TABLE 13

| Compound 15 Dose (µg) | Formulation | $T_{max}$ (h) | $C_{max}$ (ng/mL) | $AUC_{(0-\infty)}$ (ng*h/mL) |
|---|---|---|---|---|
| 100 (i.t) | Suspension B | 1 | 343 | 8526 |
| 100 (s.c) | Suspension B | 6 | 388 | 9799 | where: AUC(0-∞) is the area under the curve from time zero extrapolated to infinity;

$C_{max}$ is the maximum concentration observed;

$T_{max}$ is the time in which maximum concentration observed

The Compound 15/Alhydrogel® suspension provided a consistent, slow and sustained release of Compound 15 into systemic circulation, retaining Compound 15 at the local injection site for up to 2 week following intratumoral (i.t.) injection and thereby prolonged and maximized local activation, leading to enhanced anti-tumor efficacy. Systemic Cmax of Compound 15 was markedly reduced, and thereby minimizing cytokines produced systemically and potential cytokine related adverse effects (See Examples 7 and 8). Subcutaneous (s.c.) and intra-tumoral (i.t.) injections of Compound 15/Alhydrogel® suspension yielded similar systemic PK profiles of Compound 15.

Example 7: Cytokine Profiles—MC38 Syngeneic Mouse Tumor Model One Week Study

Mouse Pharmacodynamic Analysis of Free Compound 15 and Compound 15 Adsorbed to Alhydrogel®

A MC38 syngeneic mouse tumor model (see Example 5) was used to obtain plasma cytokine profiles, including TNFa, IL-6 and IP-10 following:
a) a single 50 µL intra-tumoral (i.t.) injection of 100 µg (~4 mg/kg) of free form Compound 15 in 20 mM Tris buffer pH 7.4,
b) a single 50 µL intra-tumoral (i.t.) injection of Compound 15 adsorbed to Alhydrogel® suspension at a 1:1.5 ratio (w/w) of Compound 15 to Alhydrogel®)—Suspension A described above and
c) a single 50 µL subcutaneous (s.c.) injection of Compound 15 adsorbed to Alhydrogel® suspension at a 1:1.5 ratio (w/w) of Compound 15 to Alhydrogel®-Suspension A described above.

The plasma samples obtained in Example 5 were analysed to obtain the plasma cytokine levels of Tumor necrosis factor alpha (TNFα), Interleukin 6 (IL-6) and Interferon gamma-induced protein 10 (IP-10).

Cytokine Measurements: IP-10 Levels Measured by ELISA

Plasma IP-10 (a proximal biomarker)_levels were measured using the Quantikine ELISA kit for mouse $C \times CL_{10}$/IP-10 (R&D Systems, Minneapolis, Minn.). Plasma samples were diluted 1:5 with calibrator diluent. 50 µL assay diluent/well was added to precoated plates followed by the addition of standard, control or diluted samples/well. The plate was incubated for 2 h at room temperature with shaking. After the 2 h incubation, the solution was decanted and wells washed 5 times with 400 µL wash buffer. 100 µL of mouse IP-10 conjugate/well was added, and the plate was incubated for 2 h at room temperature with shaking. The solution was decanted and the wash step repeated as above. 100 µL of substrate solution/well was added, and the plate was incubated for 30-45 minutes at room temperature protected from light. Finally 100 µL of stop solution/well was added followed by measurement of absorbance at 450 nm using a SpectraMax Plus microplate reader (Molecular Devices). Lower limit of detection (LLOQ) for IP-10 from this measurement was 125 µg/mL, effective LLOQ for plasma unknown samples was 625 µg/mL due to 5 fold dilution.

Plasma IP-10 levels were also measured using the Mouse IP-10 Platinum ELISA kit (eBioscience, San Diego, Calif.) according to manufacturer's protocol. Briefly, microwell strips were pre-coated with a polyclonal antibody to mouse IP-10 and washed 2 times with 400 µL wash buffer. 100 µL of diluted plasma samples (1:10 dilution), standard (1:2 dilution) and blank/well was added, followed by 50 µL of Biotin conjugate/well. The plate was incubated on a microplate shaker set to 400 rpm for 2 hours at room temperature. The supernatant was discarded and wells were washed 6 times with 400 µL wash buffer. 100 µL/well of Streptavidin-HRP was added, and plate was incubated with shaking for 1 hr at room temperature. The supernatant was discarded and washing step repeated as above. 100 µL/well of TMB substrate solution was added and incubated at room temperature for 10 minutes protected from light. The enzyme reaction was stopped by the addition of 100 µL/well of stop solution, followed by measurement of absorbance at 450 nm using a SpectraMax Plus microplate reader (Molecular Devices). Lower limit of detection (LLOQ) for IP-10 from this measurement was 7.8 µg/mL, effective LLOQ for plasma unknown samples was 78 µg/mL due to 10 fold dilution.

Cytokine Measurements: IL-6 and TNFα Levels

IL-6, TNFa and other cytokines were measured using the MultiPlex Mouse Proinflammatory Panel 1 ELISA kit (Meso Scale Discovery (MSD), Rockville, Md.) according to manufacturer's protocol. Briefly, 50 µL/well of prepared control or diluted plasma samples (1:2 with diluent 41) was added onto a pre-coated plate with capture antibodies on independent spots in each well. The plate was incubated for 2 h at room temperature with shaking, solution was decanted and the plate washed 3 times with 200 µL of PBS/0.05% Tween 20. The detection antibody conjugated with electrochemiluminescent labels (MSD SulfoTag) was then added (25 µL/well), and incubation was repeated as above. The detection antibody solution was discarded and the wash step was repeated. Finally, 150 µL of 2× Read Buffer T was added to each well, followed by measurement on a Sector Imager 6000 (Meso Scale Discovery). Effective LLOQ in plasma unknown samples was 0.3 µg/mL for TNFα, and 1.8-2.8 pg/mL for IL-6.

Cytokine Release Profiles

Plasma samples from Example 5 were measured for several cytokine protein concentrations including IP-10 by ELISA assay, TNFα, IL-6 and other cytokines by Meso scale discovery multiplex assay (MSD).

Figure 2:
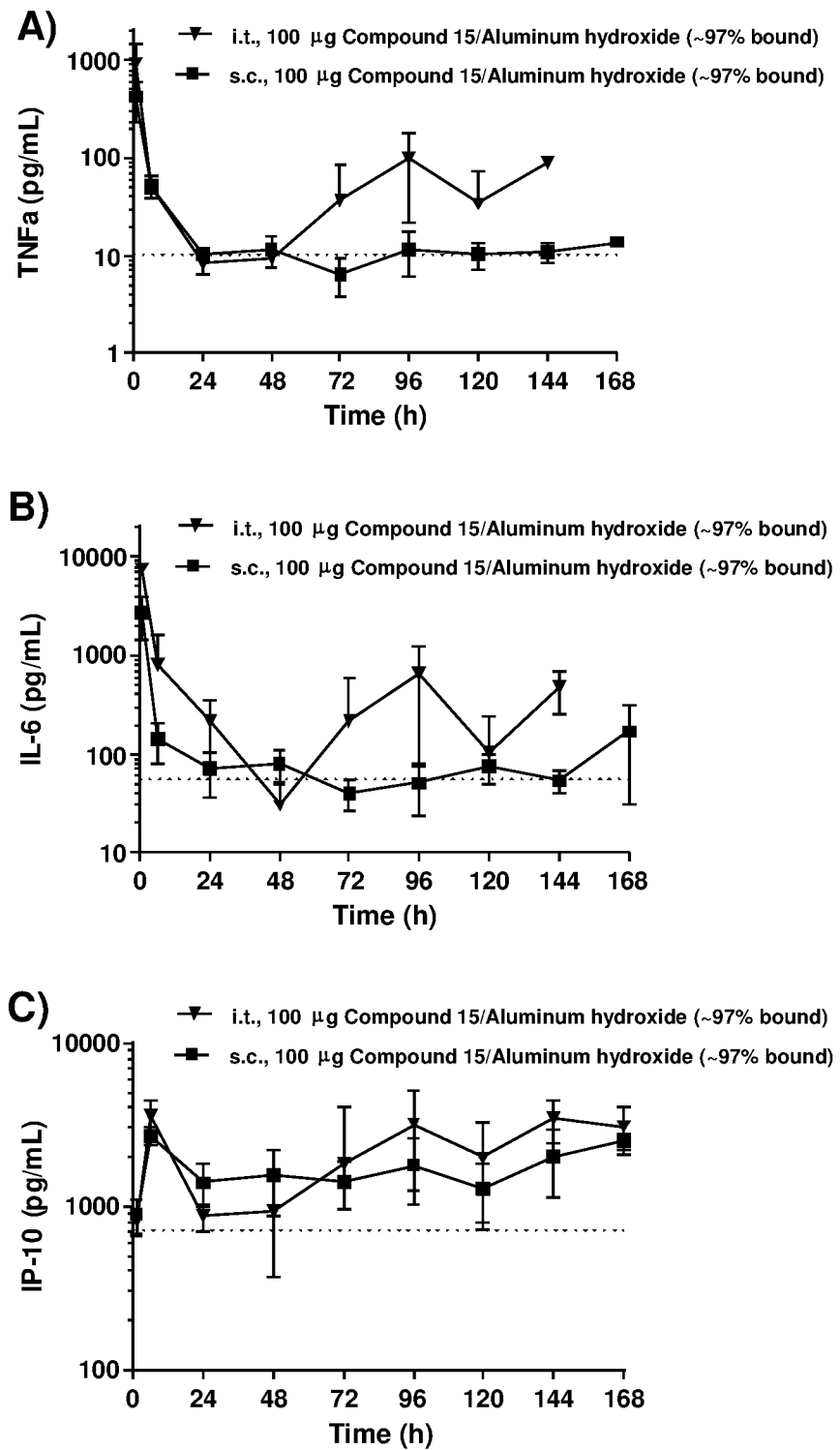
FIG. 2: A) Plasma TNFα levels in a MC38 tumor bearing C57/BL6 mice following a single intratumoral (i.t.) or subcutaneous (sc) injection of Compound 15 adsorbed to aluminum hydroxide at 1:1.5, w/w ratio.
B) Plasma IL-6 levels from a MC38 tumor bearing C57/BL6 mice following a single intratumoral (i.t.) or subcutaneous (sc) injection of Compound 15 adsorbed to aluminum hydroxide at 1:1.5, w/w ratio.
C) Plasma IP-10 levels from a MC38 tumor bearing C57/BL6 mice following a single intratumoral (i.t.) or subcutaneous (sc) injection of Compound 15 adsorbed to aluminum hydroxide at 1:1.5, w/w ratio.

Plasma samples were diluted 2 fold before cytokine measurements by MSD multiplex assay, and TNFα, IL-6 profiles are shown in FIG. 2A and FIG. 2B. Following both i.t. and s.c. injection of Compound 15/Alhydrogel® formulation in MC38 tumor bearing mice, the TNFα and IL-6 levies increased over pre-dose levels, where maximum induction occurred at ~1 h post injection, and the cytokine levels returned to baseline after 24 h post dose. However, in mice with Compound 15/Alhydrogel® injected intra-tumorally, both TNFα and IL-6 subsequently elevated above baseline from 96 h through 168 h post dose, while in s.c. injected mice, the cytokines remained at baseline.

Plasma IP-10 profiles are shown in FIG. 2C, maximum IP-10 induction occurred at 1-6 h post i.t. or s.c. injection of Compound 15/Alhydrogel®, similar to or slightly delayed with respect to $T_{max}$ of Compound 15 systemic concentration. IP-10 levels returned to baseline at 2448 h post dose, however in the i.t. dosed groups the IP-10 were elevated again from 72 h through 168 h. Overall the findings were similar to those observed for TNFα and IL-6.

Example 8: Cytokine Profiles—MC38 Syngeneic Mouse Tumor Model Two Week Study

Mouse Pharmacodynamic analysis of Compound 15 adsorbed to Alhydrogel® To evaluate plasma cytokine profiles TNFa, IL-6 and IP-10 over an extended period of time, a MC38 syngeneic mouse tumor model as described in Example 5 was used, where the TNFa, IL-6 and IP-10 levels were monitored for 2 weeks following a single 504 intra-tumoral (i.t.) or subcutaneous (s.c.) 504 injection of Suspension B (described above) which delivered 100 µg of Compound 15. Suspension B comprises a Compound 15/Alhydrogel® ratio of 1:2.

TNFa, IL-6 and IP-10 levels were obtained and analyzed as described in Example 5 and Example 7. The resulting profiles for TNFα and IL-6 are shown in FIG. 3A and FIG. 3B, where following both i.t. and s.c. injection of Compound 15/Alhydrogel® to MC38 tumor bearing mice, the levels of TNFα and IL-6 increased over pre-dose levels, and maximum induction occurred at ~1 h post injection, with the cytokine levels returning to baseline after 24 h post dose. In mice with Compound 15/Alhydrogel® injected intra-tumorally (i.t.), both TNFα and IL-6 level subsequently elevated above baseline from 96 h through 288 h post dose, while in s.c. injected mice, the cytokines remained at baseline after 24 h. Intra-tumoral (i.t.) injection of a Alhydrogel® control did not induce any cytokine level changes, suggesting the cytokine induction in Compound 15/Alhydrogel® treated groups was due to effect of Compound 15. Overall profiles were similar to those observed in the one-week study (Example 7). The plasma IP-10 levels are shown in FIG. 3C. Similar to TNFα and IL-6, plasma IP-10 levels were induced following i.t. and s.c. injection of Compound 15/Alhydrogel®.

Free soluble Compound 15 injected intra-tumorally (i.t.), was released quickly from the injection site with a $T_{max}$ min, and at 24 h post injection, essentially all of the injected Compound 15 was released and eliminated. However, when Compound 15 is adsorbed to Alhydrogel® the fast release rate of Compound 15 into the systemic circulation is minimized and a controlled release profile is observed, where Compound 15 is slowly released over a period up to 2 weeks. Specifically, Cmax was reduced, and the half-life was extended, suggesting longer local retention of Compound 15/Alhydrogel® at the injection site, which thereby minimized cytokines produced systemically and potential cytokine related adverse effects. Systemic cytokines, TNFα and IL-6, were induced as a result of TLR7 pathways activation following i.t. and s.c. injections of Compound 15/Alhydrogel® with maximum induction of these cytokines occurring at 1-6 h post injection, similar to or slightly delayed relative to Tmax of Compound 15 systemic PK. The early phase of cytokine release may be attributed mostly to the initial compound release into systemic circulation, however the second wave of cytokine induction observed from 96 h up to 2 weeks following a single i.t. injection of Compound 15/Alhydrogel® (not observed in mice dosed with Compound 15/Alhydrogel® injected subcutaneously), may reflect target recruitment, activation and changes in local tumor environment.

Example 9: Injection Site Retention—Wistar Rat Dose Study

Wistar Rat Pharmacokinetic Analysis of Free Compound 15 and Compound 15 Adsorbed to Aluminum Hydroxide The pharmacokinetic properties of Compound 15 were examined in naïve male Wistar rats following:
a) a single 200 μL subcutaneous (s.c.) injection of 600 μg of free form Compound 15 in 100 mM Tris buffer pH 7.4;
b) a single 200 μL subcutaneous (s.c.) injection of 50 μg of Compound 15 adsorbed to aluminum hydroxide at a 1:2.5 ratio (w/w) of Compound 15 to aluminum hydroxide-Suspension E described below;
c) a single 200 μL subcutaneous (s.c.) injection of 200 μg of Compound 15 adsorbed to aluminum hydroxide at a 1:2.5 ratio (w/w) of Compound 15 to aluminum hydroxide-Suspension D described below, and
d) a single 200 μL subcutaneous (s.c.) injection of 600 μg of Compound 15 adsorbed to aluminum hydroxide at a 1:2.5 ratio (w/w) of Compound 15 to aluminum hydroxide-Suspension C described below.

Suspension C 3 mg/mL Compound 15, 7.5 mg/mL Aluminum Hydroxide 100 mM Tris (pH 7.4)—Compound 15/Alhydrogel® (1:2.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 12 mg/mL of Compound 15 in 400 mM Tris-HCl (pH 7.4) buffer was prepared, and mixed with 2% Alhydrogel® stock (10 mg/mL aluminum hydroxide) to obtain Suspension C.

The table below gives the volumes used to make 10 mL of Suspension C comprising 3 mg/mL Compound 15 and 7.5 mg/mL Aluminum hydroxide in 100 mM Tris (pH 7.4) at a 2.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogele® (mL) |
|---|---|---|---|---|
| 3 | 7.5 | 2.5:1 | 2.5 | 7.5 |

Suspension D 1 mg/mL Compound 15, 2.5 mg/mL Aluminum Hydroxide 100 mM Tris (pH 7.4)—Compound 15/Alhydrogel® (1:2.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 4 mg/mL of Compound 15 in 200 mM Tris-HCl (pH 7.4) buffer was prepared, and mixed with 2% Alhydrogel® stock (10 mg/mL aluminum hydroxide) to obtain Suspension D.

The table below gives the volumes used to make 10 mL of Suspension D comprising 1 mg/mL Compound 15 and 2.5 mg/mL Aluminum hydroxide in 100 mM Tris (pH 7.4) at a 2.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel (mL) | Volume 100 mM Tris (mL) |
|---|---|---|---|---|---|
| 1 | 2.5 | 2.5:1 | 2.5 | 2.5 | 5 |

Suspension E 0.25 mg/mL Compound 15, 0.625 mg/mL Aluminum Hydroxide 100 mM Tris (pH 7.4)—Compound 15/Alhydrogel® (1:2.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 1 mg/mL of Compound 15 in 125 mM Tris-HCl (pH 7.4) buffer was prepared, and mixed with 2% Alhydrogel® stock (10 mg/mL aluminum hydroxide) to obtain Suspension E.

The table below gives the volumes used to make 10 mL of Suspension E comprising 0.25 mg/mL Compound 15 and 0.625 mg/mL Aluminum hydroxide in 100 mM Tris (pH 7.4) at a 2.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel (mL) | Volume 100 mM Tris (mL) |
|---|---|---|---|---|---|
| 0.25 | 0.625 | 2.5:1 | 2.5 | 0.625 | 6.875 |

In this study, male Wistar rats (n=3 per group) were injected subcutaneously (s.c.) with 600 μg free Compound 15 or increasing doses of 50, 200 and 600 μg of Compound 15 absorbed to aluminum hydroxide. An injection volume of 200 μL of Suspension E, Suspension D and Suspension C was used to obtain 50, 200 and 600 μg of Compound 15 absorbed to aluminum hydroxide, respectively. The injection volume of 200 μL per rat was not normalized to body weights of the rats. As described above the Compound 15/aluminum hydroxide ratio for Suspension E, Suspension D and Suspension C was fixed at 1:2.5 w/w.

Blood samples (~100 μL each) were taken serially via saphenous bleed from each rat until 96 h post dose (see Table 9 for sampling schedule). Blood samples were centrifuged to separate plasma and the plasma samples were frozen at −20° C. prior to analysis using LC/MS/MS (as described in Example 5) to obtain the systemic concentrations of Compound 15.

In addition, plasma samples were analyzed for Interferon gamma-induced protein 10 (IP-10) levels as described in Example 7.

Figure 4:
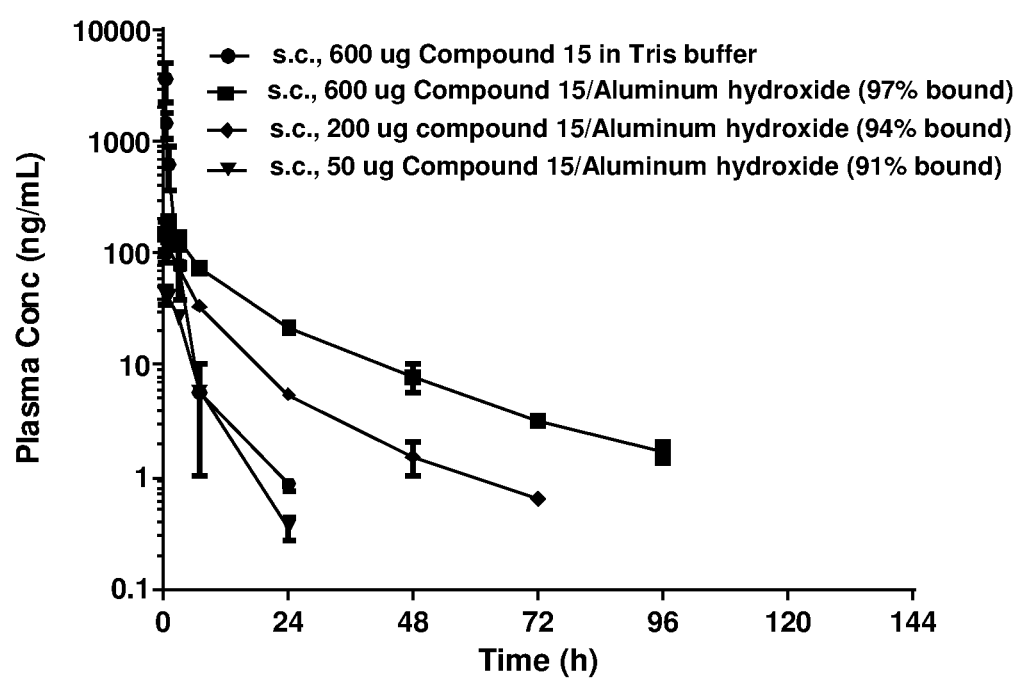
FIG. 4: Plasma concentration-time profiles of Compound 15 in male Wistar rats following a single subcutaneous (sc) injection of 600 μg free Compound 15 in 100 mM Tris buffer (pH 7.4), a single subcutaneous (sc) injection of 600 μg free Compound 15 adsorbed to aluminum hydroxide in 100 mM Tris buffer (pH 7.4) at 1:2.5, w/w ratio, (97% bound), a single subcutaneous (sc) injection of 200 μg free Compound 15 adsorbed to aluminum hydroxide in 100 mM Tris buffer (pH 7.4) at 1:2.5, w/w ratio, (94% bound) and a single subcutaneous (sc) injection of 50 μg free Compound 15 in 100 mM Tris buffer (pH 7.4) adsorbed to aluminum hydroxide at 1:2.5, w/w ratio, (91% bound).

Plasma PK profiles of Compound 15 are shown in FIG. 4 and systemic exposures are summarized in Table 14.

TABLE 14

| Compound 15 Dose (µg) | | Formulation | % Free Compound 15 | $T_{1/2}$ (h) | $T_{max}$ (h) | $C_{max}$ (ng/mL) | $AUC_{(0-\infty)}$ (ng*h/mL) |
|---|---|---|---|---|---|---|---|
| 50 | (s.c) | Suspension E | 9.3 | 2.2 | 0.38 | 45 | 188 |
| 200 | (s.c) | Suspension D | 6.5 | 10.5 | 1.00 | 114 | 937 |
| 600 | (s.c) | Suspension C | 2.9 | 21.1 | 0.83 | 185 | 2236 |
| 600 | (s.c) | 100 mM Tris | 100 | 2.1 | 0.25 | 3655 | 2560 | where: AUC(0-∞) is the area under the curve from time zero extrapolated to infinity; Cmax is the maximum concentration observed; Tmax is the time in which maximum concentration observed.

The adsorption efficiency appeared to decrease at lower concentrations of Compound 15 (at a fixed Compound 15/aluminum hydroxide ratio), resulting in a higher percent of free Compound 15 and consequently an increase in systemic IP-10 (see below).

The total AUC approximately increased proportionally with the dose of a single subcutaneous injection of 50 to 600 µg of Compound 15 adsorbed to aluminum hydroxide, whereas Cmax increased less proportionally with dose level, likely due to the higher percent of free Compound 15 at lower dose and the resulting shorter half-lives at lower doses.

FIG. 4 shows that at the 600 µg dose level, free Compound 15 in 100 mM Tris buffer exhibited rapid release of Compound 15 into systemic circulation following subcutaneous injection (plasma concentration of 3655 ng/mL at first sampling time point of 0.25 h), whereas when Compound 15 was adsorbed onto aluminum hydroxide a sustained slow release profile was obtained. Also, in comparison to free Compound 15, Cmax was reduced, and half-life extended for Compound 15 adsorbed onto aluminum hydroxide.

Note: The pharmacokinetic properties of Compound 15 in 50 mM Tris/0.9% NaCl (pH 7.4) were examined in male Wistar rats following a single 1 mg/kg intravenous bolus administration. The compound exhibited low plasma clearance of 9.2 mL/min/kg, which is ~17% of rat liver plasma flow (55 mL/min/kg, Davies and Morris 1993). The mean volume of distribution at steady-state was low (0.11 L/kg) as compared to extracellular fluid volume (0.3 L/kg, Davies and Morris 1993). As a result, the compound exhibited a short residence time (MRT) of 0.2 h and terminal half-life of 1.2 h.

Example 10: Injection Site Retention—Wistar Rat Study

Wistar Rat Pharmacokinetic Analysis of Free Compound 15 and Compound 15 Adsorbed to Aluminum Hydroxide The pharmacokinetic properties of Compound 15 were examined in naïve male Wistar rats following:
a) a single 200 µL subcutaneous (s.c.) injection of 600 µg of free form Compound 15 in 100 mM Tris buffer pH 7.4;
b) a single 200 µL subcutaneous (s.c.) injection of 50 µg of Compound 15 adsorbed to aluminum hydroxide at a 1:20 ratio (w/w) of Compound 15 to aluminum hydroxide-Suspension G described below; and
c) a single 200 µL subcutaneous (s.c.) injection of 600 µg of Compound 15 adsorbed to aluminum hydroxide at a 1:1.7 ratio (w/w) of Compound 15 to aluminum hydroxide-Suspension F described below.

Suspension F 3 mg/mL Compound 15, 5 mg/mL Aluminum Hydroxide 100 mM Tris (pH 7.4)—Compound 15/Alhydrogel® (1:1.7 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 12 mg/mL of Compound 15 in 300 mM Tris-HCl (pH 7.4) buffer was prepared, and mixed with 2% Alhydrogel® stock (10 mg/mL aluminum hydroxide) to obtain Suspension F.

The table below gives the volumes used to make 10 mL of Suspension F comprising 3 mg/mL Compound 15 and 5 mg/mL Aluminum hydroxide in 100 mM Tris (pH 7.4) at a 1.7:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel (mL) | Volume 100 mM Tris (mL) |
|---|---|---|---|---|---|
| 3 | 5 | 1.7:1 | 2.5 | 5 | 2.5 |

Suspension G 0.25 mg/mL Compound 15, 5 mg/mL Aluminum Hydroxide 100 mM Tris (pH 7.4)—Compound 15/Alhydrogel® (1:20 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 1 mg/mL of Compound 15 in 200 mM Tris-HCl (pH 7.4) buffer was prepared, and mixed with 2% Alhydrogel® stock (10 mg/mL aluminum hydroxide) to obtain Suspension G.

The table below gives the volumes used to make 10 mL of Suspension G comprising 0.25 mg/mL Compound 15 and 5 mg/mL Aluminum hydroxide in 100 mM Tris (pH 7.4) at a 20:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel (mL) | Volume 100 mM Tris (mL) |
|---|---|---|---|---|---|
| 0.25 | 5 | 20:1 | 2.5 | 5 | 2.5 |

The systemic concentration of Compound 15 was evaluated following a single 200 µL subcutaneous injection of two different dose levels of Compound 15 adsorbed to aluminum hydroxide, where the aluminum hydroxide was at a fixed dose concentration of 5 mg/mL.

In this study, two groups male Wistar rats (n=3 per group) were injected subcutaneously (s.c.) with either 50 µg or 600 µg of Compound 15 absorbed to aluminum hydroxide. An injection volume of 200 µL of Suspension G and Suspension F was used to obtain 50 and 600 µg of Compound 15 absorbed to aluminum hydroxide, respectively. The injection volume of 200 µL per rat was not normalized to body weights of the rats. As described above the Compound 15/aluminum hydroxide ratio for Suspension F was 1:1.7 w/w, while for Suspension G it was 1:20 w/w.

Blood samples (~100 µL each) were taken serially via saphenous bleed from each rat until 168 h post dose (see Table 9 for sampling schedule). Blood samples were centrifuged to separate plasma and the plasma samples were frozen at −20° C. prior to analysis using LC/MS/MS (as described in Example 5) to obtain the systemic concentrations of Compound 15.

In addition, plasma samples were analyzed for Interferon gamma-induced protein 10 (IP-10) levels as described in Example 7.

Figure 5:
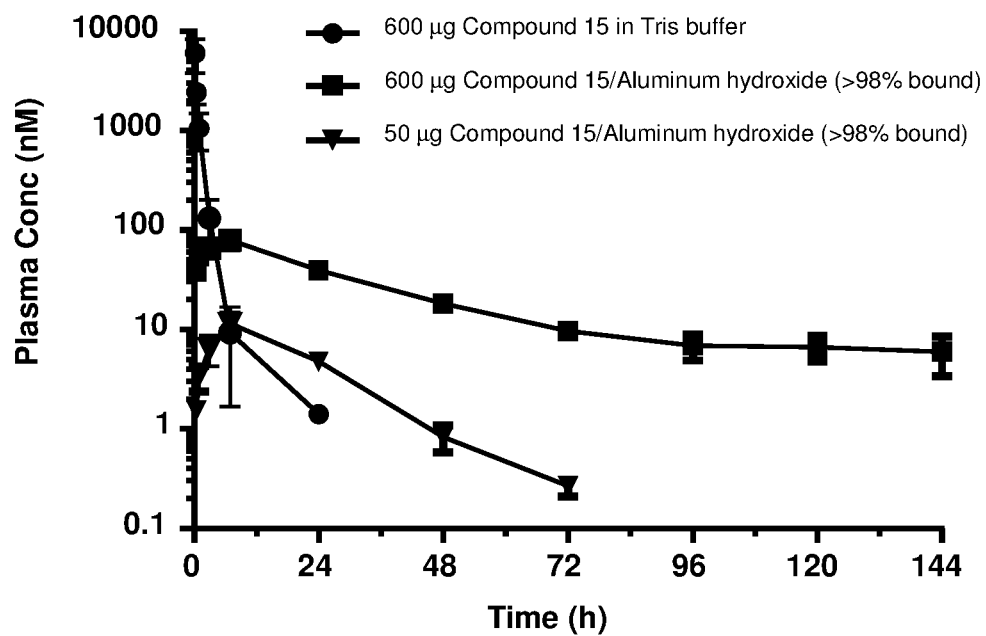
FIG. 5: A) Plasma concentration-time profiles of Compound 15 in male Wistar rats following a single subcutaneous injection for 600 μg of Compound 15 in 100 mM Tris buffer (pH 7.4), a single subcutaneous injection of 600 kg of Compound 15 adsorbed to aluminum hydroxide in 100 mM Tris buffer buffer (pH 7.4) at 1:1.7, w/w ratio, (98% bound) and a single subcutaneous injection of 50 kg of Compound 15 adsorbed to aluminum hydroxide in 100 mM Tris buffer buffer (pH 7.4) at 1:20, w/w ratio, (98% bound)
B) Plasma IP-10 levels in male Wistar rats following a single subcutaneous injection for 600 μg of Compound 15 in 100 mM Tris buffer (pH 7.4), a single subcutaneous injection of 600 kg of Compound 15 adsorbed to aluminum hydroxide in 100 mM Tris buffer buffer (pH 7.4) at 1:1.7, w/w ratio, (98% bound) and a single subcutaneous injection of 50 μg of Compound 15 adsorbed to aluminum hydroxide in 100 mM Tris buffer buffer (pH 7.4) at 1:20, w/w ratio, (98% bound).
Figure 5:
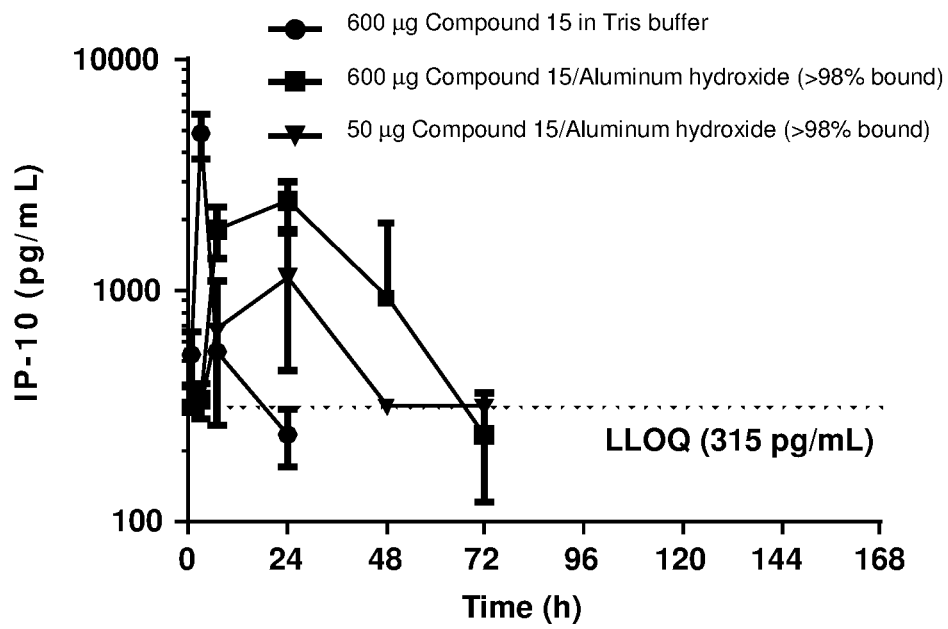

In this study, two formulations with a fixed aluminum hydroxide concentration (5 mg/mL) but differing concentrations of Compound 15 (i.e. two different Compound 15 to aluminum hydroxide ratios) were used to evaluate the binding efficiency on the systemic exposure of Compound 15. Systemic exposures of Compound 15 following a single s.c. injection of 50 and 600 µg of Compound 15/aluminum hydroxide are summarized in Table 15, and PK profiles are illustrated in FIG. 5A. The data obtained in Example 9 for free Compound 15 in 100 mM Tris buffer is also included.

TABLE 15

| Compound 15 Dose (µg) | Formulation | % Free Compound 15 | $T_{1/2}$ (h) | $T_{max}$ (h) | $C_{max}$ (ng/mL) | $AUC_{(0-\infty)}$ (ng*h/mL) |
|---|---|---|---|---|---|---|
| 50 (s.c) | Suspension G | 1.4 | 12.3 | 7 | 7 | 164 |
| 600 (s.c) | Suspension F | 0.4 | 37.3 | 7 | 48 | 2053 |
| 600 (s.c) | 100 mM Tris | 100 | 2.1 | 0.25 | 3655 | 2560 | where: AUC(0-∞) is the area under the curve from time zero extrapolated to infinity;

Cmax is the maximum concentration observed;

Tmax is the time in which maximum concentration observed.

As seen in Table 15, the two formulations resulted in high adsorption of Compound 15 to aluminum hydroxide (>98%). When the PK data obtained from Example 9 and Example 10 are compared, it is evident that the AUC for both 50 and 600 µg dose levels are similar, whereas the $T_{max}$ is delayed and the Cmax values are further reduced in Example 10.

FIG. 5A shows the systemic PK profiles of Compound 15 obtained from the different doses and shows that adsorption of Compound 15 onto aluminum hydroxide resulted in a consistent, slow and sustained release of Compound 15 into systemic circulation and retained Compound 15 at the local injection site for up to 1 week following subcutaneous injection.

FIG. 5B show the plasma IP-10 profiles in male Wistar rats following a single subcutaneous injection of free Compound 15 or Compound 15 adsorbed onto aluminum hydroxide at 50 and 600 µg dose levels. The PD response as measured by IP-10 induction was delayed relative to plasma Tmax, and maximum IP-10 levels were between 7 to 24 h post s.c. injection of 50 and 600 µg Compound 15/aluminum hydroxide. Whereas, and the maximum IP-10 response occurred around 3 h post s.c. injection of 600 µg free Compound 15. Also, in comparison to the results obtained for 600 µg Compound 15/aluminum hydroxide, the results obtained for 600 µg free Compound 15 showed higher peak IP-10 levels with a fast rate of decline, which is consistent with respective PK profiles.

Example 11: Systemic Exposure to Aluminum

ICP-MS was used to analyze of the serum aluminum levels after administration of Compound 15 with aluminum hydroxide and after administration of aluminum hydroxide alone.

Whole blood samples were collected into a serum-separator tube (Covidien Monoject™ Royal Blue Stopper trace element blood collection tube, Code 8881307006). After collection, the tube was gently inverted 5 times to mix clot activator with blood and allow clotting for at least 30 minutes in a vertical position but maximum 60 minutes at room temperature. A clot must be visually confirmed before centrifugation. All blood specimens were centrifuged at approximately 1500 to 2200×g force for approximately 10 minutes at room temperature. The resultant serum was poured/transferred (using metal free tips-Thomas Brand pipette tips/transfer tips) into uniquely labeled metal free tubes (Sorenson™ multi safeseal microcentrifuge tubes) and frozen as soon as practical over dry ice before being transferred into a freezer set to maintain at −80° C.

Metal free/trace metal grade containers/tubes/tips (<1 ng/g Al) were used for sample handling and samples were transferred by pouring or using metal free tips. The specimen handling area was kept clean and free of dust and the venipuncture site were cleaned with alcohol. No iodone containing products were used, including povidone-iodine swabs or pads. Serum samples were not reamed with a wooden stick to remove clots and specimen were not reamed with a wooden stick to assist serum transfer.

All containers, tubes and pipette tips were soaked in 10% TraceMetal Grade Nitric acid overnight and then soaked in purified water for at least 12 hours. This was followed by rinse with purified water for at least three times before use.

Study animals were divided in five groups, receiving 2 mL/animal of buffer without aluminum hydroxide (group 1) or 2 mL/animal of buffer containing aluminum hydroxide formulated with Compound 15 at 0 mg/animal (group 2), 0.3 mg/animal (group 3), 1 mg/animal (group 4) and 2 mg/animal (group 5). The buffer used was 16 mM Tris, 7.5% (w/v) sucrose, pH 7.5 and for groups 2-5 the aluminum hydroxide was present at 2 mg/mL.

Groups 1, 2, and 5 consisted of five animals/sex/group; two of which were designated for recovery. Groups 3 and 4 consisted of three animals/sex/group. Blood samples were collected from all animals on Day 1 pre-dose and at approximately 0.5, 3, 6, 24, 72, and 168 hours post dose. Blood samples were collected from all main and recovery study animals on Day 29 at approximately 0.5, 3, 6, and 24 hours post dose. Blood samples were also collected from recovery animals (Groups 1, 2, and 5) on Day 29 at 72 hours post dose, and on Days 36, 43, 50, 57, and 63.

For ICP-MS analysis, 50 µL of sample (surrogate matrix (for double blank and blank), calibration standards (10 to 1000 ng/mL), QC samples (30, 300 and 750 ng/mL), and study samples) was added into assigned 1.5-mL metal free plastic centrifuge tube pre-washed using acid as above. A 20 µL aliquot of the internal standard working solution (50 ng/mL) and a 500 µL aliquot of 0.1% HNO3 were added to all tubes. This was followed by vortex-mixing for about 3 minutes and centrifugation at 12,000 rpm for 5 min. A 500 µL volume of the supernatant from each tube was transferred into assigned plastic sample tube pre-washed using the acid as above. All tubes were placed in the auto-sampler according to the pre-arranged assay sequence.

Aluminium at m/z 27 and Rhodium at m/z 103 were measured using an Agilent 7700×ICP-MS instrument (Agilent Technologies UK Ltd) equipped with an Agilent ASX-500 autosampler. The Agilent MassHunter (version C.01.02) software was used for data collection and integration Watson LIMS Version 7.3 was used for the sample management, data management, and calculation of the sample concentrations. (Thermo Fisher Scientific, USA).

Instrument Auto Tune and Tune Check.

Tuning solution that contains 1 ng/mL of Ce, Co, Li, Mg, Tl, and Y in 2% HNO3 (Agilent part #5188-6564 or equivalent) was used for autotune and tune check. Auto tune was performed when the ICP was ignited. A Tune Check was set at the beginning of a batch analysis. If the Tune Check results failed to meet the criteria determined, the batch was stopped automatically.

Autosampler and Operation Conditions:

| Autosampler | | |
|---|---|---|
| Needle rinse | 8 sec, pump speed 0.5 rps | Purified water |
| Wash 1 | 120 sec, pump speed 0.4 rps | 2% HNO$_3$/H$_2$O (v/v) |
| Wash 2 | 60 sec, pump speed 0.3 rps | 0.1% HNO$_3$/H$_2$O (v/v) |
| Sample introduction | | |

20 sec, pump speed 0.4 rpm
Stabilize 20 sec, pump speed 0.1 rps

ICP-MS Parameters:

| ICP Mass Spectrometer | Agilent 7700x | |
|---|---|---|
| Nebulizer | Concentric MicroMist nebulizer | |
| Spray chamber temp | 2° C. | |
| Operation mode | He | |
| Tuning parameters* | | |
| Serum | RF power (W) | 1550 |
| | RF matching (V) | 1.8 |
| | Sampling depth (mm) | 8.0 |
| | Carrier gas (L/min) | 1.00 |
| | Nebulizer pump (rps) | 0.10 |
| | Make up gas (L/min) | 0.10 |
| Lenses | Extract 1 | −5.8 |
| | Extract 2 | −185 |
| | Omega bias | −90 |
| | Omega Lens | 7.4 |
| | Cell entrance | −112 |
| | Cell exit | −109 |
| | Deflect | 8.2 |
| | Plate bias | −104 |
| Cell | Gas (helium, mL/min) | 4.5 |
| | OctP bias | −18.2 |
| | OctP RF | 200 |
| | Energy discrimination | 4.0 |
| Integration peak pattern: 3 points Replicates: 3 | Aluminum | 0.099 sec |
| | Rhodium ISTD | 0.099 sec |

Results

No quantifiable aluminum concentrations were observed in the serum samples collected from the control group animals (group 1) administered without aluminum hydroxide and Compound 15.

Figure 3:
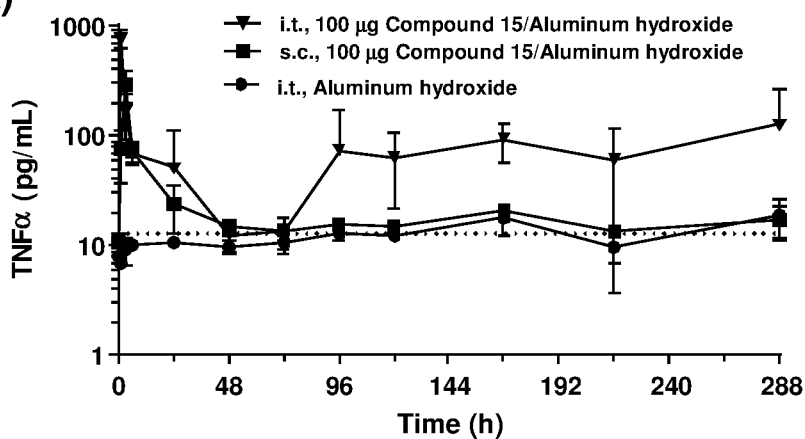
FIG. 3: A) Plasma TNFα levels in a MC38 tumor bearing C57/BL6 mice following a single intratumoral (i.t.) or subcutaneous (sc) injection of Compound 15 adsorbed to aluminum hydroxide at 1:2, w/w ratio.
B) Plasma IL-6 levels in a MC38 tumor bearing C57/BL6 mice following a single intratumoral (i.t.) or subcutaneous (sc) injection of Compound 15 adsorbed to aluminum hydroxide at 1:2, w/w ratio.
C) Plasma IP-10 levels in a MC38 tumor bearing C57/BL6 mice following a single intratumoral (i.t.) or subcutaneous (sc) injection of Compound 15 adsorbed to aluminum hydroxide at 1:2, w/w ratio.
Figure 3:
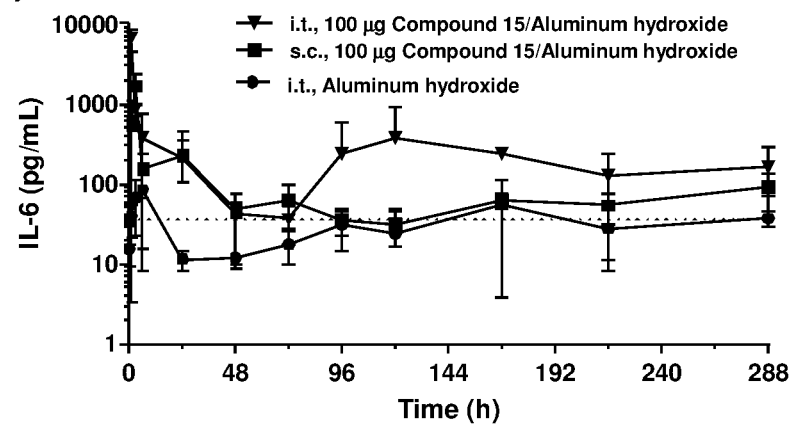
Figure 3:
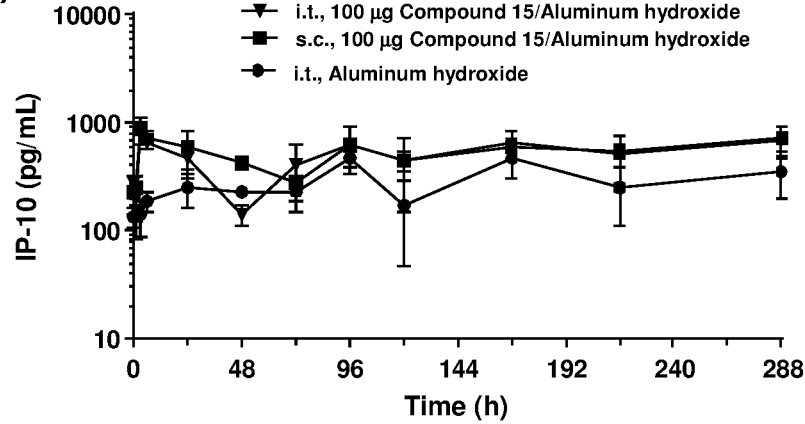

FIG. 6 shows the serum aluminum concentrations vs time post dose for Group 2 (aluminum hydroxide (2 mL/animal) Al(OH)$_3$ in 16 mM Tris, 7.5% (w/v) sucrose, pH 7.5, (0 mg/animal of Compound 15)) and Group 5 (aluminum hydroxide (2 mL/animal) Al(OH)$_3$ in 16 mM Tris, 7.5% (w/v) sucrose, pH 7.5, (2 mg/animal of Compound 15)). In FIG. 3 a difference in the serum aluminum concentration between Group 2 (no Compound 15) and Group 5 (2 mg/animal of Compound 15) is seen which indicates that systemic exposure to aluminum after administration of Compound 15 bound to aluminum hydroxide was significantly lower than systemic exposure after administration of aluminum hydroxide alone.

Example 12: Serum and Urine Exposure to Aluminum

The pharmacokinetics and mass balance of aluminum and Compound 15 were investigated following a single subcutaneous (s.c.) dose (1 mL) of Suspension H (Compound 15/Alhydrogel® at a 2:1 ratio of aluminum to Compound 15) in male Wistar rats. In addition, the pharmacokinetics of aluminum were investigated following a single intravenous (i.v.) dose (0.5 mL) of 0.4 mg/mL AlCl$_3$.6H$_2$O (equivalent to 0.2 mg of aluminum) in male Wistar rat. Additionally, a control group dosed subcutaneously with saline were evaluated for environmental background aluminum levels.

Suspension H 1 mg/mL Compound 15, 2 mg/mL Aluminum Hydroxide and 5.5% (w/v) Mannitol in 5 mM Tris (pH 7.5)—Compound 15/Alhydrogel® (1:2 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 1.25 mg/mL of Compound 15, 6.875% (w/v) mannitol in 6.25 mM Tris (pH 7.5) buffer was prepared for dilution with the 2% Alhydrogel® stock. The table below gives the volumes used to make 5 mL of a suspension comprising 1 mg/mL Compound 15, 2 mg/mL Aluminum hydroxide and 5.5% (w/v) mannitol in 5 mM Tris (pH 7.5) at a 2:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogele (mL) |
|---|---|---|---|---|
| 1 | 2 | 2:1 | 4 | 1 |

Serum and Urine Sample Collection & Handling: i.v. And s.c. Groups

Metal free/trace metal grade containers/tubes/tips (<1 ng/g Al) were used for sample handling. Aluminum content was analyzed in serum and urine (Frontage Laboratories).

Approximately 0.3 to 0.5 mL of blood samples were collected from carotid artery cannulation at 0 (pre dose), 0.083 (IV only), 0.25 (IV only), 0.5, 3, 6, 24, 72, 168, 336, 504, 672 hours post dose.

Urine was collected from each animal for the following periods: 0 (24 h before dose), 0-24, 24-48, 48-72, 72-96, 96-168 hours post dose, then weekly up to 672 h. The urine samples were stored at −20° C. until analyzed. Feces were collected from each animal and samples were pooled per subject at the end of study at 672 h.

Compound 15 and aluminum levels were analyzed in the serum and urine samples obtained from the s.c. group whereas only aluminum levels were analyzed in the i.v. group.

Serum and urine sample collection & handling: Control Groups

Approximately 0.3 to 0.5 mL of blood samples were collected by carotid artery cannulation at 0 (pre dose), 0.5, 3, 24, 168, 336, 504, 672 hours post dose. Blood samples sat at room temperature for at least 20 min before centrifuging to obtain the serum. Serum samples were transferred to another tube and stored at −70° C. until analyzed.

Urine was collected from each animal for the following periods: 0 (24 h before dose), 0-24, 48-72, 96-168 hours post dose, then weekly up to 672 h. The urine samples were stored at −20° C. until analyzed. Feces were collected from each animal and samples were pooled per subject at the end of study at 672 h. The feces samples were stored at −20° C.

FIG. 7 shows the aluminum serum concentration vs. time profile after subcutaneous administration of Suspension H and intravenous administration of $AlCl_3 \cdot 6H_2O$ in saline.

The aluminum pharmacokinetics parameters obtained after a single subcutaneous dose of Compound 15/Alhydrogel® (equivalent to 2 mg of aluminum per animal) show low systemic exposure, with a mean $C_{max}$ of aluminum in serum of 76.2 ng/mL and a mean $T_{max}$ at 3.2 hours post dose. The $AUC_{last}$ and $AUC_{inf}$ were 3950 ng·h/mL and 4490 ng/mL, respectively. The elimination half-life was 23.8 hours. The bioavailability was low (0.6%).

The aluminum pharmacokinetics parameters obtained after a single intravenous dose of $AlCl_3 \cdot 6H_2O$ (equivalent to 0.2 mg of aluminum per animal) gave a mean $C_{max}$ of aluminum in serum of 26000 ng/mL and a mean $T_{max}$ at 0.22 hours post dose. The $AUC_{last}$ and AUCinf were 67400 ng·h/mL and 67500 ng/mL, respectively. The elimination half-life was 3.40 hours. The CL was 0.71 mL/h, mainly via renal excretion based on mass balance data. The Vss was moderate at 7.66 mL, based on total body water of 7.8 mL in rat (Davies B and Morris T (1993) Physiological parameters in laboratory animals and humans, Pharmaceutical Research. Vol. 10, pp 1093-95).

Following a single intravenous dose of $AlCl_3 \cdot 6H_2O$, urine was the only excreta analyzed and the mean recovery of aluminum in urine was near complete at ~0.2 mg, suggesting renal excretion was the main clearance pathway. For the mass balance after a single subcutaneous dose of Compound 15/Alhydrogel® the majority of the aluminum was found at the site of injection (71.7% to 85.7%), with ~1% and ~2% of aluminum recovered in urine and feces, respectively. There were trace amounts of aluminum (<0.01%) found in bone, brain, kidney and liver.

Based on the control group, the background environmental exposure of aluminum in urine and serum was ~10 ng/mL.

Taken together, the aluminum pharmacokinetic parameters obtained show that the systemic levels of aluminum are low after a single subcutaneous dose of Compound 15/Alhydrogel, or after a single intravenous dose of $AlCl_3 \cdot 6H_2O$.

Finally, the pharmacokinetic parameters obtained for Compound 15 after a single subcutaneous dose of Suspension H were similar to those obtained in Example 5, specifically a mean $C_{max}$ of 75.8 ng/mL for Compound 15 was obtained, with a mean $T_{max}$ of 5 hours post dose. The $AUC_{last}$ and $AUC_{inf}$ were 3660 ng·h/mL and 3730 ng/mL, respectively. The elimination half-life was 66.2 hours, further demonstrating controlled release of Compound 15 at the injection site.

Example 13: In Vivo Efficacy as Single Agent

Suspension I 4 mg/mL Compound 15, 6 mg/mL Aluminum Hydroxide and 0.9% NaCl in 50 mM Tris (pH 7.4)—Compound 15/Alhydrogel® (1:1.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 10 mg/mL of Compound 15, 2.25% (w/v) NaCl in 125 mM Tris (pH 7.4) buffer was prepared for dilution with the 2% Alhydrogel® stock. The table below gives the volumes used to make 5 mL of a suspension comprising 4 mg/mL Compound 15, 6 mg/mL Aluminum hydroxide and 0.9% NaCl in 50 mM Tris (pH 7.4) at a 1.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Volume Water (mL) |
|---|---|---|---|---|---|
| 4 | 6 | 1.5:1 | 2.0 | 3.0 | 0.0 |

Suspension J 2 mg/mL Compound 15, 3 mg/mL Aluminum Hydroxide and 0.9% NaCl in 50 mM Tris (pH 7.4)—Compound 15/Alhydrogel® (1:1.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 5 mg/mL of Compound 15, 2.25% (w/v) NaCl in 125 mM Tris (pH 7.4) buffer was prepared for dilution with the 2% Alhydrogel® stock. The table below gives the volumes used to make 5 mL of a suspension comprising 2 mg/mL Compound 15, 3 mg/mL Aluminum hydroxide and 0.9% NaCl in 50 mM Tris (pH 7.4) at a 1.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Volume Water (mL) |
|---|---|---|---|---|---|
| 2 | 3 | 1.5:1 | 2.0 | 1.5 | 1.5 |

Suspension K 1 mg/mL Compound 15, 1.5 mg/mL Aluminum Hydroxide and 0.9% NaCl in 50 mM Tris (pH 7.4)—Compound 15/Alhydrogel® (1:1.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 2.5 mg/mL of Compound 15, 2.25% (w/v) NaCl in 125 mM Tris (pH 7.4) buffer was prepared for dilution with the 2% Alhydrogel® stock. The table below gives the volumes used to make 5 mL of a suspension comprising 1 mg/mL Compound 15, 1.5 mg/mL Aluminum hydroxide and 0.9% NaCl in 50 mM Tris (pH 7.4) at a 1.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Volume Water (mL) |
|---|---|---|---|---|---|
| 1 | 1.5 | 1.5:1 | 2.0 | 0.75 | 2.25 |

Suspension L 0.5 mg/mL Compound 15, 0.75 mg/mL Aluminum Hydroxide and 0.9% NaCl in 50 mM Tris (pH 7.4)—Compound 15/Alhydrogel® (1:1.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 1.25 mg/mL of Compound 15, 2.25% (w/v) NaCl in 125 mM Tris (pH 7.4) buffer was prepared for dilution with the 2% Alhydrogel® stock. The table below gives the volumes used to make 5 mL of a suspension comprising 0.5 mg/mL Compound 15, 0.75 mg/mL Aluminum hydroxide and 0.9% NaCl in 50 mM Tris (pH 7.4) at a 1.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Volume Water (mL) |
|---|---|---|---|---|---|
| 0.5 | 0.75 | 1.5:1 | 2.0 | 0.375 | 2.63 |

Controls:
  a) No treatment
  b) Compound 15 only: 2 mg/mL of Compound 15 and 0.9% NaCl in 50 mM Tris (pH 7.4)
  c) Alhydrogel® only: 3 mg/mL of Alhydrogel® in 50 mM Tris (pH 7.4)

The anti-tumor efficacy of Compound 15 adsorbed to Alhydrogel® was determined using the mouse syngeneic lymphoma A20 bilateral tumor model in female BALB/c mice.

A20 cells were grown in sterile conditions in a 37° C. incubator with 5% $CO_2$ for two weeks. Cells were grown in RPMI 1640 medium with 2 mM L-glutamine adjusted to contain 1.5 g/L sodium bicarbonate, 4.5 g/L glucose, 10 mM HEPES, and 1.0 mM sodium pyruvate and supplemented with 0.05 mM 2-mercaptoethanol, 10% fetal bovine serum. Cells were passaged every 2-3 days. For the day of implant cells were lifted (passage 12) and re-suspended in HBSS at a concentration of $5 \times 10^6$ cells/100 µL. Cells were Radil tested for mycoplasma and murine viruses. For each mouse, $5 \times 10^6$ cells were implanted by subcutaneous injection into the right and left flank using a 28.5 g needle (100 µl injection volume). Tumor sizes were assessed three times a week once tumors were palpable. Tumor sizes were determined by using caliper measurements, with tumor volumes calculated using the formula: (Length×Width×Width)/2.

The female Balb/c mice bearing the A20 tumors were randomized into 7 groups (n=10 mice per group) 8 days post tumor cell implantation with an average tumor volume range of $111.40 \pm 23.57$ mm$^3$. 50 µL of either Suspension I, Suspension J, Suspension K, Suspension L, Compound 15 only control or Alhydrogel® only control were intratumorally administered to different groups of animals once a week for two weeks. Table 16 gives the Compound 15 dose obtained from the 50 µL intratumoral administration of the controls and suspension.

TABLE 16

|  | Compound 15 Dose (µg) |
|---|---|
| Compound 15 control | 100 |
| Alhydrogel ® control | 0 |
| Suspension I | 25 |
| Suspension J | 50 |
| Suspension K | 100 |
| Suspension L | 200 |

Tumor volumes were measured by digital caliper 3 times a week and body weights of all animals were recorded throughout the study. The mice were sacrificed when tumor volumes were over 1500 mm3 or mouse was moribund.

FIG. 8 shows the efficacy and dose response of 0 µg, 25 µg, 50 µg, 100 µg and 200 µg of Compound 15 adsorbed to aluminum hydroxide (at fixed ratio of 1:1.5, w/w, and 97% bound) in the mouse syngeneic lymphoma A20 bilateral tumor model. After two weekly doses, 25 µg, 50 µg, 100 µg and 200 µg of Compound 15 adsorbed to aluminum hydroxide showed significant tumor growth inhibition ($p<0.05$ to 0.001) on day 21 in the treated tumor site with a dose dependent increase in anti-tumor efficacy with intratumoral delivery (i.t.) being observed. However, no significant tumor growth inhibition ($p>0.05$) on day 21 in distal tumor site tumor was seen. In addition, after two weekly doses, Compound 15 adsorbed to Alhydrogel® showed better efficacy than 100 kg of Compound 15 alone, and 100 kg of Compound 15 alone had no significant difference in both tumor sites.

Example 14: In Vivo Efficacy-Effect of Binding Efficiency

Suspension M 2 mg/mL Compound 15, 2 mg/mL Aluminum Hydroxide and 0.9% NaCl in 50 mM Tris (pH 7.4)—Compound 15/Alhydrogel® (1:1 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 5 mg/mL of Compound 15, 2.25% (w/v) NaCl in 125 mM Tris (pH 7.4) buffer was prepared for dilution with the 2% Alhydrogel® stock. The table below gives the volumes used to make 5 mL of a suspension comprising 2 mg/mL Compound 15, 32 mg/mL Aluminum hydroxide and 0.9% NaCl in 50 mM Tris (pH 7.4) at a 1:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Volume Water (mL) |
|---|---|---|---|---|---|
| 2 | 2 | 1:1 | 2.0 | 1.0 | 2.0 |

Suspension N 2 mg/mL Compound 15, 1.0 mg/mL Aluminum Hydroxide and 0.9% NaCl in 50 mM Tris (pH 7.4)—Compound 15/Alhydrogel® (1:0.5 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 5 mg/mL of Compound 15, 2.25% (w/v) NaCl in 125 mM Tris (pH 7.4) buffer was prepared for dilution with the 2% Alhydrogel® stock. The table below gives the volumes used to make 5 mL of a suspension comprising 2 mg/mL Compound 15, 0.5 mg/mL Aluminum hydroxide and 0.9% NaCl in 50 mM Tris (pH 7.4) at a 0.5:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel® (mL) | Volume Water (mL) |
|---|---|---|---|---|---|
| 2 | 1.0 | 0.5:1 | 2.0 | 0.50 | 2.50 |

Control: Alhydrogel® Only: 3 mg/mL of Alhydrogel® in 50 mM Tris (pH 7.4)

The effect of binding efficiency of Compound 15 adsorbed to Alhydrogel® on anti-tumor efficacy was determined using the mouse syngeneic lymphoma A20 bilateral tumor model in female BALB/c mice (described in Example 12). A dose response study was performed using Suspension J, Suspension M and Suspension N having a Compound 15/Alhydrogel® ratio and binding efficiency of 1:1.5 (approx. 98% bound), 1:1 (approx. 80% bound) and 1:0.5 (approx. 50% bound), respectively.

Female Balb/c mice bearing the A20 tumors were randomized into 4 groups (n=10 mice per group) 9 days post tumor cell implantation with an average tumor volume range of 128.43±23.42 mm$^3$. 50 μL of either Suspension J, Suspension M, Suspension N or Alhydrogel® only control were intratumorally administered to different groups of animals. The 50 μL dose volume intratumoral administration 100 μg of Compound 15. Tumor volumes were measured and calculated as in Example 12. The mice would be sacrificed for tumor volume over 1500 mm3 or the mouse was moribund.

FIG. 9 shows the efficacy and dose response of 100 μg of Compound 15 adsorbed to aluminum hydroxide at approx. 98% bound (Compound 15/Alhydrogel® ratio of 1:1.5, w/w), at approx. 80% bound (Compound 15/Alhydrogel® ratio of 1:1, w/w) and at approx. 50% bound (Compound 15/Alhydrogel® ratio of 1:0.5, w/w). After a single dose, Compound 15 was found to induce tumor regression only when it was approx. 98% bound to Alhydrogel®, and showed reduced efficacy with decreasing Alhydrogel® binding percentages.

Example 15: In Vivo Efficacy as Agent in Combination with One or More Checkpoint Inhibitors Suspension O 1 Mg/mL Compound 15, 2 mg/mL Aluminum Hydroxide and 7.5% (w/v) Sucrose in 16 mM Tris (pH 7.4)—Compound 15/Alhydrogel® (1:2 Ratio)

2% Alhydrogel® (aluminum hydroxide gel: 10 mg/mL aluminum) was obtained from Brenntag Biosector A/S, Elsenbakken 23, 3600 Frederikssund, Denmark and was used as stock for dilution to obtain the required concentration of aluminum. A stock solution of 1.25 mg/mL of Compound 15, 9.375% (w/v) sucrose in 20 mM Tris (pH 7.4) buffer was prepared for dilution with the 2% Alhydrogel® stock. The table below gives the volumes used to make 5 mL of a suspension comprising 1 mg/mL Compound 15, 2 mg/mL Aluminum hydroxide and 7.5% (w/v) sucrose in 16 mM Tris (pH 7.4) at a 2:1 ratio of Alhydrogel® to Compound 15.

| Compound 15 Final Conc (mg/mL) | Aluminum Final Conc (mg/mL) | Aluminum to Compound 15 ratio | Volume Compound 15 stock (mL) | Volume 2% Alhydrogel® (mL) |
|---|---|---|---|---|
| 1 | 2 | 2:1 | 4 | 1 |

Reagents.

Compound 15 was in a suspension with Alhydrogel® (Suspension N).

Anti-PD-L1 antibody (BAP058-hum13 with heavy chain variable domain of SEQ ID NO:7 and a light chain variable domain of SEQ ID NO:17).

Anti-CTLA4 was purchased from Bio X Cell. Clone 9D9, Lot No: 5311-11/1014. Cat No: 6E0146.

Establishment of Mouse Colon Cancer Syngeneic MC38 Tumor Model

MC38 cells were grown in sterile conditions in a 37° C. incubator with 5% $CO_2$ for two weeks. The cells were cultured in Dulbecco's Modified Eagle's medium (DMEM) media supplemented with 10% FBS, cells were passed every 2-3 days. On the day of injection, cells were harvested (Passage 12) and re-suspended in Hanks' Balanced Salt Solution (HBSS) at a concentration of 2.5×106/ml. Cells were Radil tested for mycoplasma and murine viruses.

For each mouse, $0.25 \times 10^6$ cells were implanted with subcutaneously injection into right flank using a 28½ g needle (100ł injection volume). After the first implantation on day 3 ($0.25 \times 10^6$) cells are implanted with a subcutaneous injection into left flank using a 28½ g needle (100 μL injection volume). Tumor sizes were assessed three times a week once tumors were palpable. Tumor sizes were determined by using caliper measurements, with tumor volumes calculated using the formula: (Length×Width×Width)/2.

Dosing and Sampling in MC38 Tumor Bearing C57/BL6 Mice

Female C57BL/6 mice bearing the MC38 tumors were randomized into 7 groups (n=9 mice per group) 9 days post tumor cell implantation with an average tumor volume range of 69.09-142.25 mm³, and the separate groups of tumor bearing mice received treatment as shown in Table 17.

TABLE 17

| Group | Treatment | Dose | Dose Volume | Route of Administration | Schedule |
|---|---|---|---|---|---|
| 1 | No treatment | — | — | — | — |
| 2 | Compound 15 | 50 (μg) | 50 (μL) of (Suspension N) | Intratumoral (i.t.) | once a week for 2 weeks |
| 3 | aPD-L1 | 10 (mg/kg) | 10 (μL/g) | Intraperitoneally (i.p.) | twice a week for 2 weeks |
| 4 | aCTLA4 | 10 (mg/kg) | 10 (μL/g) | Intraperitoneally (i.p.) | twice a week for 2 weeks |
| 5 | Compound 15 | 50 (μg) | 50 (μL) of (Suspension N) | Intratumoral (i.t.) | once a week for 2 weeks |
|   | aPD-L1 | 10 (mg/kg) | 10 (μL/g) | Intraperitoneally (i.p.) | twice a week for 2 weeks |
| 6 | Compound 15 | 50 (μg) | 50 (μL) of (Suspension N) | Intratumoral (i.t.) | once a week for 2 weeks |
|   | aCTLA4 | 10 (mg/kg) | 10 (μL/g) | Intraperitoneally (i.p.) | twice a week for 2 weeks |
| 7 | Compound 15 | 50 (μg) | 50 (μL) of (Suspension N) | Intratumoral (i.t.) | once a week for 2 weeks |
|   | aPD-L1 | 10 (mg/kg) | 10 (μL/g) | Intraperitoneally (i.p.) | twice a week for 2 weeks |
|   | aCTLA4 | 10 (mg/kg) | 10 (μL/g) | Intraperitoneally (i.p.) | twice a week for 2 weeks | where the anti-PD-L1 antibody solution was 10 (mg/mL) in phosphate buffered saline (PBS) (pH 7) at and the anti-CTLA4 antibody solution was 10 (mg/mL) in phosphate buffered saline (PBS) (pH 7).

The anti-tumor efficacy of Compound 15 adsorbed to aluminum hydroxide (Alhydrogel®) alone or in combination with checkpoint inhibitors, was determined using a contralateral MC38 colon cancer model. The tumor volume was obtained after two weekly intratumoral injections of Compound 15 adsorbed to aluminum hydroxide (50 μg each) either alone (Group 2), in a double combination with intraperitoneal injection (twice weekly) of an anti-PD-L1 antibody (10 mg/kg) (Group 5), in a double combination with intraperitoneal injection (twice weekly) of an anti-CTLA4 antibody (10 mg/kg) (Group 6), or in a triple combination with intraperitoneal injection (twice weekly) of an anti-PD-L1 antibody (10 mg/kg) and with intraperitoneal injection of an anti-CTLA4 antibody (10 mg/kg) (group 7). For comparison, data was obtained after an intraperitoneal injection (twice weekly) of the anti-PD-L1 antibody (10 mg/kg) alone (Group 3) and after an intraperitoneal injection (twice weekly) of the anti-CTLA4 antibody (10 mg/kg) alone (Group 4). The untreated control data was also obtained (Group 1). FIG. 10A shows the tumor volume at the primary intratumor injection site and FIG. 10B shows the tumor volume at the distant contralateral site.

The anti-tumor efficacy of Compound 15 alone (without aluminum hydroxide (Alhydrogel®)) or in combination with checkpoint inhibitors was determined using a contralateral MC38 colon cancer model. The tumor volume was obtained after two weekly intratumoral injections of Compound 15 alone (without aluminum hydroxide (Alhydrogel®) (50 μg each)) or in a triple combination with intraperitoneal injection (twice weekly) of an anti-PD-L1 antibody (10 mg/kg) and anti-CTLA4 antibody (10 mg/kg). For comparison data was obtained after an intraperitoneal injection (twice weekly) of the combination of anti-PD-L1 antibody (10 mg/kg) and the anti-CTLA4 antibody (10 mg/kg) alone. In addition, the anti-tumor efficacy of Compound 15 adsorbed to aluminum hydroxide (Alhydrogel®) alone or in a triple combination with checkpoint inhibitors was determined using a contralateral MC38 colon cancer model. The tumor volume was obtained after two weekly intratumoral injections of Compound 15 adsorbed to aluminum hydroxide (Alhydrogel®) (50 μg each)) alone or in a triple combination with intraperitoneal injection (twice weekly) of an anti-PD-L1 antibody (10 mg/kg) and anti-CTLA4 antibody (10 mg/kg). For comparison data was obtained after an intraperitoneal injection (twice weekly) of the combination of anti-PD-L1 antibody (10 mg/kg) and the anti-CTLA4 antibody (10 mg/kg) alone. The untreated control data was also obtained. FIG. 10C shows the tumor volume obtained at the primary intratumor injection site and FIG. 10D shows the tumor volume obtained at the distant contralateral site.

Dosing as Simile Agents:

At the primary injection site anti-CTLA4 alone and was not significantly different from the no treatment group, (p>0.05) with a % T/C of 99.98%. Similarly, Compound 15 alone (without aluminum hydroxide (Alhydrogel®) did not show a difference from the no treatment group. However, anti-PD-L1 alone was significantly different, (p<0.05) with a % T/C of 56.22% and Compound 15/Alhydrogel® alone was also significantly different, (p<0.0001) with a % T/C of 25.22%. Compound 15 adsorbed to aluminum hydroxide appeared to have improved efficacy as a single agent at the site of injection relative to either antibody administered as single agents.

At the contralateral tumor site anti-CTLA4 alone was not significantly different from the no treatment group, (p>0.05) with a % T/C of 79.72%. Similarly, Compound 15 alone (without aluminum hydroxide (Alhydrogel®) did not show a difference from the no treatment group. However, anti-PD-L1 alone was significantly different, (p<0.001) with a % T/C of 27.02%, and Compound 15/Alhydrogel® alone was also significantly different, (p<0.01) with a T/C of 29.50%. Compound 15 adsorbed to aluminum hydroxide appeared to have improved efficacy as a single agent at the distant site relative to either antibody administered as single agents.

Dosing in Combination with a Checkpoint Inhibitor:

The combination of intratumoral administration of Compound 15 adsorbed to aluminum hydroxide with intraperitoneal injection of anti-PD-L1 exhibited significant improvement in anti-tumor efficacy at both the primary intratumoral injection site and contralateral site, with (p<0.0001) with a T/C of 8.93% and (p<0.0001) with a % T/C of 5.39%, for the primary intratumoral injection site and contralateral site, respectively, being obtained.

At the primary intratumor injection site the combination of intratumoral administration of Compound 15 adsorbed to aluminum hydroxide with intraperitoneal administration of anti-CTLA4 exhibited similar behavior as that obtained for Compound 15 adsorbed to aluminum hydroxide administered alone, while at the contralateral site the combination appeared less effective than Compound 15 adsorbed to aluminum hydroxide administered alone. However a significant difference from the non-treated group was observed, with a (p<0.0001) with a % T/C of 26.74% and a (p<0.05) with a % T/C of 48.70%, for the primary intratumoral injection site and contralateral site, respectively, being obtained.

In addition, dosing anti-PD-L1 and anti-CTLA-4 in combination did not result in complete tumor regression (data not shown).

Dosing in Combination with Two Checkpoint Inhibitors:

The triple combination of intratumoral injection of Compound 15 adsorbed to aluminum hydroxide, intraperitoneal injection of the anti-PD-L1 antibody and intraperitoneal injection of the anti-CTLA4 antibody showed full tumor regression in 7 of 9 animals, with a (p<0.0001) with a T/C of −38.51% and a (p<0.0001) with a T/C of −9.60% for the primary intratumoral injection site and contralateral site, respectively, being obtained.

It is understood that the examples and embodiments described herein are for illustrative purposes only and that various modifications or changes in light thereof will be suggested to persons skilled in the art and are to be included within the spirit and purview of this application and scope of the appended claims.

---

The invention claimed is:

1. A pharmaceutical combination, wherein the pharmaceutical combination is a non-fixed combination comprising:

a) a first pharmaceutical composition comprising a compound having the structure of Formula (A), or a pharmaceutically acceptable salt thereof, aluminum-containing particles, a buffering agent and one or more pharmaceutically acceptable excipients:

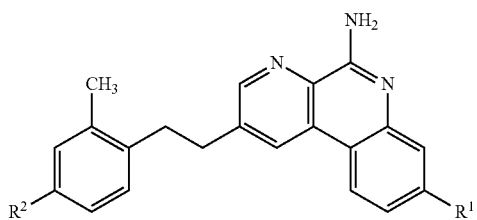

Formula (A)

wherein:
$R^1$ is -$L_1R^4$, -$L_1R^5$, —O$L_1R^4$, —O$L_1R^5$, $CH_3$, —C(=O)P(O)(OH)$_2$ or —C(=O)CF$_2$P(O)(OH)$_2$;
$R^2$ is -$L_2R^4$, -$L_2R^6$, -$L_2L_3L_2R^6$, -$L_2L_3R^4$, -$L_2L_3L_2R^4$, —O$L_2R^4$, —O$R^4$, —O$L_2R^6$, —O$L_2L_3R^6$, —O$L_2L_3L_2R^6$, —O$L_2L_3R^4$, —O$L_2L_3L_2R^4$ or —OCH$_3$;
each $R^3$ is independently selected from H and fluoro;
$R^4$ is —P(O)(OH)$_2$,
$R^5$ is —CF$_2$P(O)(OH)$_2$ or —C(O)OH;
$R^6$ is —CF$_2$P(O)(OH)$_2$ or —C(O)OH;
$L_1$ is $C_1$-$C_6$alkylene, $C_2$-$C_6$alkenylene or —((CR$^4$R$^4$)$_p$O)$_q$(CH$_2$)$_p$—, wherein the $C_1$-$C_6$alkylene and $C_2$-$C_6$alkenylene of $L_1$ are substituted with 0 to 4 fluoro groups;
each $L_2$ is independently selected from $C_1$-$C_6$alkylene and —((CR$^3$R$^3$)$_p$O)$_q$(CH$_2$)$_p$—, wherein the $C_1$-$C_6$alkylene of $L_2$ is substituted with 0 to 4 fluoro groups;
$L_3$ is arylene or a 5-6 membered heteroarylene;
each p is independently selected from 1, 2, 3, 4, 5 and 6, and
q is 1, 2, 3 or 4
and wherein
one of the one or more pharmaceutically acceptable excipients is selected from mannitol and sucrose;
the composition has a pH in the range of 6.5 to 9.0, and
the aluminum-containing particles are a suspension of aluminum hydroxide particles;

b) a second pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and c) a third pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, wherein the checkpoint inhibitor of the third composition is different than the checkpoint inhibitor in the second composition.

2. A method for treating a solid tumor by administering to a subject in need thereof:

a pharmaceutical combination comprising:

i. a first pharmaceutical composition, ii. a second pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, and iii. a third pharmaceutical composition comprising a checkpoint inhibitor selected from a CTLA-4 receptor inhibitor, a PD-1 receptor inhibitor, a LAG-3 receptor inhibitor, TIM-3 receptor inhibitor, a BTLA receptor inhibitor, a KIR receptor inhibitor, a PD-L1 inhibitor or a PD-L2 inhibitor, wherein:
the checkpoint inhibitor of the third composition is different than the checkpoint inhibitor in the second composition;
the first pharmaceutical composition is administered intratumorally, and the second pharmaceutical composition and the third pharmaceutical composition are administered intratumorally, intramuscularly, intradermally, subcutaneously, intravenously, by intraperitoneal injection, by lavage or by infusion;
the pharmaceutical combination is a non-fixed combination, and the first pharmaceutical composition comprises a compound having the structure of Formula (A), or a pharmaceutically acceptable salt thereof, aluminum-containing particles, a buffering agent and one or more pharmaceutically acceptable excipients:

Formula (A)

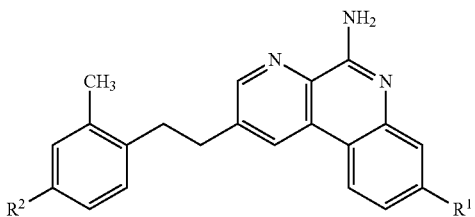

wherein:
R¹ is -L₁R⁴, -L₁R⁵, —OL₁R⁴, —OL₁R⁵, CH₃, —C(=O)P(O)(OH)₂ or —C(=O)CF₂P(O)(OH)₂;
R² is -L₂R⁴, -L₂R⁶, -L₂L₃L₂R⁶, -L₂L₃R⁴, -L₂L₃L₂R⁴, —OL₂R⁴, —OR⁴, —OL₂R⁶, —OL₂L₃R⁶, —OL₂L₃L₂R⁶, —OL₂L₃R⁴, —OL₂L₃L₂R⁴ or —OCH₃;
each R³ is independently selected from H and fluoro;
R⁴ is —P(O)(OH)₂,
R⁵ is —CF₂P(O)(OH)₂ or —C(O)OH;
R⁶ is —CF₂P(O)(OH)₂ or —C(O)OH;
L₁ is C₁-C₆alkylene, C₂-C₆alkenylene or —((CR⁴R⁴)ₚO)_q(CH₂)ₚ—, wherein the C₁-C₆alkylene and C₂-C₆alkenylene of L₁ are substituted with 0 to 4 fluoro groups;
each L₂ is independently selected from C₁-C₆alkylene and —((CR³R³)ₚO)_q(CH₂)ₚ—, wherein the C₁-C₆alkylene of L₂ is substituted with 0 to 4 fluoro groups;
L₃ is arylene or a 5-6 membered heteroarylene;
each p is independently selected from 1, 2, 3, 4, 5 and 6, and
q is 1, 2, 3 or 4
and wherein:
one of the one or more pharmaceutically acceptable excipients is selected from mannitol and sucrose;
the composition has a pH in the range of 6.5 to 9.0, and
the aluminum-containing particles are a suspension of aluminum hydroxide particles.

3. The method of claim 2, wherein the solid tumor is head and neck squamous cell carcinoma (HNSCC), melanoma or a visceral tumor.

4. The method of claim 2, wherein the compound having the structure of Formula (A) is:
3-(5-amino-2-(4-(2-(3,3-difluoro-3-phosphonopropoxy)ethoxy)-2-methylphenethyl)benzo[f][1,7]naphthyridin-8-yl)propanoic acid;
3-(5-amino-2-(2-methyl-4-(2-(2-(2-phosphonoethoxy)ethoxy)ethoxy)phenethyl)benzo[f][1,7]naphthyridin-8-yl)propanoic acid;
3-(5-amino-2-(4-(4,4-difluoro-4-phosphonobutoxy)-2-methylphenethyl)benzo[f][1,7]naphthyridin-8-yl)propanoic acid;
3-(5-amino-2-(2-methyl-4-(3-phosphonopropoxy)phenethyl)benzo[f][1,7]naphthyridin-8-yl)propanoic acid;
3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid;
3-(5-amino-2-(2-methyl-4-(2-(2-(2-phosphonoethoxy)ethoxy)ethoxy)phenethyl)benzo[f][1,7]naphthyridin-8-yl)propanoic acid;
3-(5-amino-2-(2-methyl-4-(2-(2-phosphonoethoxy)ethoxy)phenethyl)benzo[f][1,7]naphthyridin-8-yl)propanoic acid;
(3-(4-(2-(5-amino-8-methylbenzo[f][1,7]naphthyridin-2-yl)ethyl)-3-methylphenoxy)propyl)phosphonic acid;
4-(2-(5-amino-8-methylbenzo[f][1,7]naphthyridin-2-yl)ethyl)-3-methylphenyl dihydrogen phosphate;
((4-(2-(5-amino-8-methylbenzo[f][1,7]naphthyridin-2-yl)ethyl)-3-methylphenoxy)methyl)phosphonic acid;
5-(4-(2-(5-amino-8-methylbenzo[f][1,7]naphthyridin-2-yl)ethyl)-3-methylphenoxy)-1,1-difluoropentylphosphonic acid;
(4-(4-(2-(5-amino-8-methylbenzo[f][1,7]naphthyridin-2-yl)ethyl)-3-methylphenoxy)-1,1-difluorobutyl)phosphonic acid;
(3-(2-(2-(4-(2-(5-amino-8-methylbenzo[f][1,7]naphthyridin-2-yl)ethyl)-3-methylphenoxy)ethoxy)ethoxy)-1,1-difluoropropyl)phosphonic acid;
3-(2-(4-(2-(5-amino-8-methylbenzo[f][1,7]naphthyridin-2-yl)ethyl)-3-methylphenoxy)ethoxy)-1,1-difluoropropylphosphonic acid;
2-(4-((4-(2-(5-amino-8-methylbenzo[f][1,7]naphthyridin-2-yl)ethyl)-3-methylphenoxy)methyl)phenyl)-1,1-difluoroethylphosphonic acid;
(3-((4-(2-(5-amino-8-methylbenzo[f][1,7]naphthyridin-2-yl)ethyl)-3-methylphenoxy)methyl)phenyl)phosphonic acid;
(2-(4-(2-(5-amino-8-methylbenzo[f][1,7]naphthyridin-2-yl)ethyl)-3-methylphenoxy)ethyl)phosphonic acid;
(6-(4-(2-(5-amino-8-methylbenzo[f][1,7]naphthyridin-2-yl)ethyl)-3-methylphenoxy)hexyl)phosphonic acid;
(6-(4-(2-(5-amino-8-methylbenzo[f][1,7]naphthyridin-2-yl)ethyl)-3-methylphenoxy)-1,1-difluorohexyl)phosphonic acid;
(4-((4-(2-(5-amino-8-methylbenzo[f][1,7]naphthyridin-2-yl)ethyl)-3-methylphenoxy)methyl)benzyl)phosphonic acid;
(2-(2-(2-(4-(2-(5-amino-8-methylbenzo[f][1,7]naphthyridin-2-yl)ethyl)-3-methylphenoxy)ethoxy)ethoxy)ethyl)phosphonic acid;
(5-(4-(2-(5-amino-8-methylbenzo[f][1,7]naphthyridin-2-yl)ethyl)-3-methylphenoxy)pentyl)phosphonic acid;
(4-(4-(2-(5-amino-8-methylbenzo[f][1,7]naphthyridin-2-yl)ethyl)-3-methylphenoxy)butyl)phosphonic acid,
2-(5-amino-2-(4-methoxy-2-methylphenethyl)benzo[f][1,7]naphthyridin-8-yl)-1,1-difluoro-2-oxoethylphosphonic acid;
(E)-(2-(5-amino-2-(4-methoxy-2-methylphenethyl)benzo[f][1,7]naphthyridin-8-yl)vinyl)phosphonic acid;
2-(5-amino-2-(4-methoxy-2-methylphenethyl)benzo[f][1,7]naphthyridin-8-yl)ethylphosphonic acid;
(E)-(2-(5-amino-2-(4-methoxy-2-methylphenethyl)benzo[f][1,7]naphthyridin-8-yl)-1-fluorovinyl)phosphonic acid, or
(5-amino-2-(4-methoxy-2-methylphenethyl)benzo[f][1,7]naphthyridine-8-carbonyl)phosphonic acid.

5. The method of claim 2, wherein the compound having the structure of Formula (A) is 3-(5-amino-2-(4-(2-(3,3-difluoro-3-phosphonopropoxy)ethoxy)-2-methylphenethyl)benzo[f][1,7]naphthyridin-8-yl)propanoic acid.

6. The method of claim 2, wherein the first pharmaceutical composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles, Tris buffer and mannitol.

7. The method of claim 2, wherein the first pharmaceutical composition comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) mannitol, and a suspension of aluminum hydroxide particles having an aluminum content of 1 to 4 mg/mL, and wherein the composition has a pH in the range of 7.0 to 8.0.

8. The method of claim 2, wherein the first pharmaceutical composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 5.5% (w/v) mannitol, and a suspension of aluminum hydroxide particles having an aluminum content of 2 mg/mL, and wherein the composition has a pH of 7.5+/−0.3.

9. The method of claim 2, wherein the second pharmaceutical composition comprises a PD-1 receptor inhibitor.

10. The method of claim 2, wherein the second pharmaceutical composition comprises an anti-PD-1 antibody.

11. The pharmaceutical combination of claim 1, wherein the compound having the structure of Formula (A) is:
- 3-(5-amino-2-(4-(2-(3,3-difluoro-3-phosphonopropoxy)ethoxy)-2-methylphenethyl)benzo[f][1,7]naphthyridin-8-yl)propanoic acid;
- 3-(5-amino-2-(2-methyl-4-(2-(2-(2-phosphonoethoxy)ethoxy)ethoxy)phenethyl)benzo[f][1,7]naphthyridin-8-yl)propanoic acid;
- 3-(5-amino-2-(4-(4,4-difluoro-4-phosphonobutoxy)-2-methylphenethyl)benzo[f][1,7]naphthyridin-8-yl)propanoic acid;
- 3-(5-amino-2-(2-methyl-4-(3-phosphonopropoxy)phenethyl)benzo[f][1,7]naphthyridin-8-yl)propanoic acid;
- 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid;
- 3-(5-amino-2-(2-methyl-4-(2-(2-(2-phosphonoethoxy)ethoxy)ethoxy)phenethyl)benzo[f][1,7]naphthyridin-8-yl)propanoic acid;
- 3-(5-amino-2-(2-methyl-4-(2-(2-phosphonoethoxy)ethoxy)phenethyl)benzo[f][1,7]naphthyridin-8-yl)propanoic acid;
- (3-(4-(2-(5-amino-8-methylbenzo[f][1,7]naphthyridin-2-yl)ethyl)-3-methylphenoxy)propyl)phosphonic acid;
- 4-(2-(5-amino-8-methylbenzo[f][1,7]naphthyridin-2-yl)ethyl)-3-methylphenyl dihydrogen phosphate;
- ((4-(2-(5-amino-8-methylbenzo[f][1,7]naphthyridin-2-yl)ethyl)-3-methylphenoxy)methyl)phosphonic acid;
- 5-(4-(2-(5-amino-8-methylbenzo[f][1,7]naphthyridin-2-yl)ethyl)-3-methylphenoxy)-1,1-difluoropentylphosphonic acid;
- (4-(4-(2-(5-amino-8-methylbenzo[f][1,7]naphthyridin-2-yl)ethyl)-3-methylphenoxy)-1,1-difluorobutyl)phosphonic acid;
- (3-(2-(2-(4-(2-(5-amino-8-methylbenzo[f][1,7]naphthyridin-2-yl)ethyl)-3-methylphenoxy)ethoxy)ethoxy)-1,1-difluoropropyl)phosphonic acid;
- 3-(2-(4-(2-(5-amino-8-methylbenzo[f][1,7]naphthyridin-2-yl)ethyl)-3-methylphenoxy)ethoxy)-1,1-difluoropropylphosphonic acid;
- 2-(4-((4-(2-(5-amino-8-methylbenzo[f][1,7]naphthyridin-2-yl)ethyl)-3-methylphenoxy)methyl)phenyl)-1,1-difluoroethylphosphonic acid;
- (3-((4-(2-(5-amino-8-methylbenzo[f][1,7]naphthyridin-2-yl)ethyl)-3-methylphenoxy)methyl)phenyl)phosphonic acid;
- (2-(4-(2-(5-amino-8-methylbenzo[f][1,7]naphthyridin-2-yl)ethyl)-3-methylphenoxy)ethyl)phosphonic acid;
- (6-(4-(2-(5-amino-8-methylbenzo[f][1,7]naphthyridin-2-yl)ethyl)-3-methylphenoxy)hexyl)phosphonic acid;
- (6-(4-(2-(5-amino-8-methylbenzo[f][1,7]naphthyridin-2-yl)ethyl)-3-methylphenoxy)-1,1-difluorohexyl)phosphonic acid;
- (4-((4-(2-(5-amino-8-methylbenzo[f][1,7]naphthyridin-2-yl)ethyl)-3-methylphenoxy)methyl)benzyl)phosphonic acid;
- (2-(2-(2-(4-(2-(5-amino-8-methylbenzo[f][1,7]naphthyridin-2-yl)ethyl)-3-methylphenoxy)ethoxy)ethoxy)ethyl)phosphonic acid;
- (5-(4-(2-(5-amino-8-methylbenzo[f][1,7]naphthyridin-2-yl)ethyl)-3-methylphenoxy)pentyl)phosphonic acid;
- (4-(4-(2-(5-amino-8-methylbenzo[f][1,7]naphthyridin-2-yl)ethyl)-3-methylphenoxy)butyl)phosphonic acid;
- 2-(5-amino-2-(4-methoxy-2-methylphenethyl)benzo[f][1,7]naphthyridin-8-yl)-1,1-difluoro-2-oxoethylphosphonic acid;
- (E)-(2-(5-amino-2-(4-methoxy-2-methylphenethyl)benzo[f][1,7]naphthyridin-8-yl)vinyl)phosphonic acid;
- 2-(5-amino-2-(4-methoxy-2-methylphenethyl)benzo[f][1,7]naphthyridin-8-yl)ethylphosphonic acid;
- (E)-(2-(5-amino-2-(4-methoxy-2-methylphenethyl)benzo[f][1,7]naphthyridin-8-yl)-1-fluorovinyl)phosphonic acid, or
- (5-amino-2-(4-methoxy-2-methylphenethyl)benzo[f][1,7]naphthyridine-8-carbonyl)phosphonic acid.

12. The pharmaceutical combination of claim 1, wherein the compound having the structure of Formula (A) is 3-(5-amino-2-(4-(2-(3,3-difluoro-3-phosphonopropoxy)ethoxy)-2-methylphenethyl)benzo[f][1,7]naphthyridin-8-yl)propanoic acid.

13. The pharmaceutical combination of claim 1, wherein the first pharmaceutical composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, a suspension of aluminum hydroxide particles, Tris buffer and mannitol.

14. The pharmaceutical combination of claim 1, wherein the first pharmaceutical composition comprises 0.5 to 2 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) mannitol, and a suspension of aluminum hydroxide particles having an aluminum content of 1 to 4 mg/mL, and wherein the composition has a pH in the range of 7.0 to 8.0.

15. The pharmaceutical combination of claim 3, wherein the first pharmaceutical composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-20 mM Tris buffer, 5-10% (w/v) mannitol, and a suspension of aluminum hydroxide particles having an aluminum content of 2 mg/mL, and wherein the composition has a pH in the range of 7.0 to 8.0.

16. The pharmaceutical combination of claim 1, wherein the first pharmaceutical composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 16 mM Tris buffer, 7.5% (w/v) mannitol, and a suspension of aluminum hydroxide particles having an alu- 17. The pharmaceutical combination of claim 1, wherein the first pharmaceutical composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 8.25% (w/v) mannitol, and a suspension of aluminum hydroxide particles having an aluminum content of 2 mg/mL, and wherein the composition has a pH in the range of 7.0 to 8.0.

18. The pharmaceutical combination of claim 1, wherein the first pharmaceutical composition comprises 1 mg/mL of 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5 mM Tris buffer, 5.5% (w/v) mannitol, and a suspension of aluminum hydroxide particles having an aluminum content of 2 mg/mL, and wherein the composition has a pH of 7.5+/−0.3.

19. The pharmaceutical combination of claim 1, wherein the first pharmaceutical composition comprises 3-(5-amino-2-(4-(2-(3,3-difluoro-3-phosphonopropoxy)ethoxy)-2-methylphenethyl)benzo[f][1,7]naphthyridin-8-yl)propanoic acid, or a pharmaceutically acceptable salt thereof, 5-100 mM Tris buffer, 5-10% (w/v) mannitol, and a suspension of aluminum hydroxide particles, and wherein the (w/w) ratio of the weight of 3-(5-amino-2-(4-(2-(3,3-difluoro-3-phosphonopropoxy)ethoxy)-2-methylphenethyl)benzo[f][1,7]naphthyridin-8-yl)propanoic acid to the weight of aluminum in the suspension of particles is 1:20.

20. The pharmaceutical combination of claim 1, wherein the second pharmaceutical composition comprises a PD-1 receptor inhibitor.

21. The pharmaceutical combination of claim 1, wherein the second pharmaceutical composition comprises an anti-PD-1 antibody.

* * * * *

SEQUENCE LISTING

<160> NUMBER OF SEQ ID NOS: 61

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Ser Tyr Trp Met Tyr
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Trp Met Tyr
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ile Asp Pro Asn Ser Gly Ser Thr Lys Tyr Asn Glu Lys Phe Lys
1               5                   10                  15

Asn

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Arg Lys Gly Leu Tyr Ala Met Asp Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Thr Phe Thr Ser Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Pro Asn Ser Gly Ser
1               5

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 8
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gaggtccagc tggtacagtc tggggctgag gtgaagaagc ctggggctac agtgaaaatc    60

```
tcctgcaagg tttctggcta caccttcacc agttactgga tgtactgggt gcgacaggct    120
cgtggacaac gccttgagtg gataggtagg attgatccta atagtgggag tactaagtac    180
aatgagaagt tcaagaacag attcaccatc tccagagaca attccaagaa cacgctgtat    240
cttcaaatga acagcctgag agccgaggac acggccgtgt attactgtgc aagggactat    300 agaaagggc tctatgctat ggactactgg ggccagggca ccaccgtgac cgtgtcctcc    360
```

<210> SEQ ID NO 9
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 10
<211> LENGTH: 1341
<212> TYPE: PRT
<213> ORGANISM: Artificial Sequence
<220> FEATURE:
<223> OTHER INFORMATION: Description of Artificial Sequence: Synthetic
      polynucleotide

<400> SEQUENCE: 10

Gly Ala Gly Gly Thr Cys Cys Ala Gly Cys Thr Gly Gly Thr Ala Cys
1               5                   10                  15

Ala Gly Thr Cys Thr Gly Gly Gly Gly Cys Thr Gly Ala Gly Gly Thr
            20                  25                  30

Gly Ala Ala Gly Ala Ala Gly Cys Cys Thr Gly Gly Gly Gly Cys Thr
            35                  40                  45

Ala Cys Ala Gly Thr Gly Ala Ala Ala Thr Cys Thr Cys Cys Thr
50                  55                  60

Gly Cys Ala Ala Gly Gly Thr Thr Thr Cys Thr Gly Gly Cys Thr Ala
65                  70                  75                  80

Cys Ala Cys Cys Thr Thr Cys Ala Cys Cys Ala Gly Cys Thr Ala Cys
                85                  90                  95

Thr Gly Gly Ala Thr Gly Thr Ala Cys Thr Gly Gly Gly Thr Gly Cys
            100                 105                 110

Gly Ala Cys Ala Gly Gly Cys Thr Cys Gly Thr Gly Gly Ala Cys Ala
            115                 120                 125

Ala Cys Gly Cys Cys Thr Gly Ala Gly Thr Gly Gly Ala Thr Ala
            130                 135                 140

Gly Gly Thr Ala Gly Gly Ala Thr Thr Gly Ala Thr Cys Cys Thr Ala
145                 150                 155                 160

Ala Thr Ala Gly Thr Gly Gly Ala Gly Thr Ala Cys Thr Ala Ala
                165                 170                 175

Gly Thr Ala Cys Ala Ala Thr Gly Ala Gly Ala Ala Gly Thr Thr Cys
            180                 185                 190

Ala Ala Gly Ala Ala Cys Ala Gly Ala Thr Cys Ala Cys Cys Ala
            195                 200                 205

Thr Cys Thr Cys Cys Ala Gly Ala Gly Ala Cys Ala Ala Thr Thr Cys
            210                 215                 220
```

-continued

```
Cys Ala Gly Ala Ala Cys Ala Cys Gly Cys Thr Gly Thr Ala Thr
225                 230                 235                 240

Cys Thr Thr Cys Ala Ala Thr Gly Ala Ala Cys Ala Gly Cys Cys
                245                 250                 255

Thr Gly Ala Gly Ala Gly Cys Cys Gly Ala Gly Gly Ala Cys Ala Cys
            260                 265                 270

Gly Gly Cys Cys Gly Thr Gly Thr Ala Thr Ala Cys Thr Gly Thr
            275                 280                 285

Gly Cys Ala Ala Gly Gly Ala Cys Thr Ala Thr Ala Gly Ala Ala
            290                 295                 300

Ala Gly Gly Gly Gly Cys Thr Cys Thr Ala Thr Gly Cys Thr Ala Thr
305                 310                 315                 320

Gly Gly Ala Cys Thr Ala Cys Thr Gly Gly Gly Cys Cys Ala Gly
                325                 330                 335

Gly Gly Cys Ala Cys Cys Ala Cys Cys Gly Thr Gly Ala Cys Cys Gly
                340                 345                 350

Thr Gly Thr Cys Cys Thr Cys Cys Gly Cys Thr Thr Cys Ala Cys
            355                 360                 365

Cys Ala Ala Gly Gly Gly Cys Cys Cys Ala Thr Cys Cys Gly Thr Cys
370                 375                 380

Thr Thr Cys Cys Cys Cys Thr Gly Gly Cys Gly Cys Cys Cys Thr
385                 390                 395                 400

Gly Cys Thr Cys Cys Ala Gly Gly Ala Gly Cys Ala Cys Cys Thr Cys
            405                 410                 415

Cys Gly Ala Gly Ala Gly Cys Ala Cys Ala Gly Cys Cys Gly Cys Cys
            420                 425                 430

Cys Thr Gly Gly Gly Cys Thr Gly Cys Cys Thr Gly Gly Thr Cys Ala
            435                 440                 445

Ala Gly Gly Ala Cys Thr Ala Cys Thr Thr Cys Cys Cys Cys Gly Ala
450                 455                 460

Ala Cys Cys Gly Gly Thr Gly Ala Cys Gly Gly Thr Gly Thr Cys Gly
465                 470                 475                 480

Thr Gly Gly Ala Ala Cys Thr Cys Ala Gly Gly Cys Gly Cys Cys Cys
                485                 490                 495

Thr Gly Ala Cys Cys Ala Gly Cys Gly Gly Cys Gly Thr Gly Cys Ala
            500                 505                 510

Cys Ala Cys Cys Thr Thr Cys Cys Cys Gly Gly Cys Thr Gly Thr Cys
            515                 520                 525

Cys Thr Ala Cys Ala Gly Thr Cys Cys Thr Cys Ala Gly Gly Ala Cys
            530                 535                 540

Thr Cys Thr Ala Cys Thr Cys Cys Cys Thr Cys Ala Gly Cys Ala Gly
545                 550                 555                 560

Cys Gly Thr Gly Gly Thr Gly Ala Cys Cys Gly Thr Gly Cys Cys Cys
                565                 570                 575

Thr Cys Cys Ala Gly Cys Ala Gly Cys Thr Thr Gly Gly Gly Cys Ala
            580                 585                 590

Cys Gly Ala Ala Gly Ala Cys Cys Thr Ala Cys Ala Cys Cys Thr Gly
            595                 600                 605

Cys Ala Ala Cys Gly Thr Ala Gly Ala Thr Cys Ala Cys Ala Ala Gly
            610                 615                 620

Cys Cys Cys Ala Gly Cys Ala Ala Cys Ala Cys Cys Ala Ala Gly Gly
625                 630                 635                 640
```

-continued

Thr Gly Gly Ala Cys Ala Ala Gly Ala Gly Thr Thr Gly Ala
            645                 650                 655

Gly Thr Cys Cys Ala Ala Ala Thr Ala Thr Gly Gly Thr Cys Cys Cys
            660                 665                 670

Cys Cys Ala Thr Gly Cys Cys Ala Cys Cys Gly Thr Gly Cys Cys
            675                 680                 685

Cys Ala Gly Cys Ala Cys Cys Thr Gly Ala Gly Thr Thr Cys Cys Thr
690                 695                 700

Gly Gly Gly Gly Gly Ala Cys Cys Ala Thr Cys Ala Gly Thr Cys
705                 710                 715                 720

Thr Thr Cys Cys Thr Gly Thr Thr Cys Cys Cys Cys Cys Ala Ala
            725                 730                 735

Ala Ala Cys Cys Cys Ala Ala Gly Gly Ala Cys Ala Cys Thr Cys Thr
            740                 745                 750

Cys Ala Thr Gly Ala Thr Cys Thr Cys Cys Cys Gly Gly Ala Cys Cys
            755                 760                 765

Cys Cys Thr Gly Ala Gly Gly Thr Cys Ala Cys Gly Thr Gly Cys Gly
            770                 775                 780

Thr Gly Gly Thr Gly Gly Thr Gly Gly Ala Cys Gly Thr Gly Ala Gly
785                 790                 795                 800

Cys Cys Ala Gly Gly Ala Ala Gly Ala Cys Cys Cys Gly Ala Gly
            805                 810                 815

Gly Thr Cys Cys Ala Gly Thr Thr Cys Ala Ala Cys Thr Gly Gly Thr
            820                 825                 830

Ala Cys Gly Thr Gly Gly Ala Thr Gly Gly Cys Gly Thr Gly Gly Ala
            835                 840                 845

Gly Gly Thr Gly Cys Ala Thr Ala Ala Thr Gly Cys Cys Ala Ala Gly
            850                 855                 860

Ala Cys Ala Ala Ala Gly Cys Cys Gly Cys Gly Gly Gly Ala Gly Gly
865                 870                 875                 880

Ala Gly Cys Ala Gly Thr Thr Cys Ala Ala Cys Ala Gly Cys Ala Cys
            885                 890                 895

Gly Thr Ala Cys Cys Gly Thr Gly Thr Gly Gly Thr Cys Ala Gly Cys
            900                 905                 910

Gly Thr Cys Cys Thr Cys Ala Cys Cys Gly Thr Cys Thr Gly Cys
            915                 920                 925

Ala Cys Cys Ala Gly Gly Ala Cys Thr Gly Gly Cys Thr Gly Ala Ala
            930                 935                 940

Cys Gly Gly Cys Ala Ala Gly Gly Ala Gly Thr Ala Cys Ala Ala Gly
945                 950                 955                 960

Thr Gly Cys Ala Ala Gly Gly Thr Gly Thr Cys Cys Ala Ala Cys Ala
            965                 970                 975

Ala Ala Gly Gly Cys Cys Thr Cys Cys Cys Gly Thr Cys Cys Thr Cys
            980                 985                 990

Cys Ala Thr Cys Gly Ala Gly Ala Ala Ala Cys Cys Ala Thr Cys
            995                 1000                1005

Thr Cys Cys Ala Ala Ala Gly Cys Cys Ala Ala Ala Gly Gly Gly
            1010                1015                1020

Cys Ala Gly Cys Cys Cys Cys Gly Ala Gly Ala Gly Cys Cys Ala
            1025                1030                1035

Cys Ala Gly Gly Thr Gly Thr Ala Cys Ala Cys Cys Cys Thr Gly
            1040                1045                1050

Cys Cys Cys Cys Cys Ala Thr Cys Cys Cys Ala Gly Gly Ala Gly

```
                 1055                1060                1065

Gly Ala  Gly Ala Thr Gly  Ala Cys Cys Ala  Ala Gly  Ala Ala Cys
             1070                1075                1080

Cys Ala  Gly Gly Thr Cys  Ala Gly Cys Cys  Thr Gly  Ala Cys Cys
             1085                1090                1095

Thr Gly  Cys Cys Thr Gly  Gly Thr Cys Ala  Ala Ala  Gly Gly Cys
             1100                1105                1110

Thr Thr  Cys Thr Ala Cys  Cys Cys Cys Ala  Gly Cys  Gly Ala Cys
             1115                1120                1125

Ala Thr  Cys Gly Cys Cys  Gly Thr Gly Gly  Ala Gly  Thr Gly Gly
             1130                1135                1140

Gly Ala  Gly Ala Gly Cys  Ala Ala Thr Gly  Gly Gly  Cys Ala Gly
             1145                1150                1155

Cys Cys  Gly Gly Ala Gly  Ala Ala Cys Ala  Ala Cys  Thr Ala Cys
             1160                1165                1170

Ala Ala  Gly Ala Cys Cys  Ala Cys Gly Cys  Cys Thr  Cys Cys Cys
             1175                1180                1185

Gly Thr  Gly Cys Thr Gly  Gly Ala Cys Thr  Cys Cys  Gly Ala Cys
             1190                1195                1200

Gly Gly  Cys Thr Cys Cys  Thr Thr Cys Thr  Thr Cys  Cys Thr Cys
             1205                1210                1215

Thr Ala  Cys Ala Gly Cys  Ala Gly Gly Cys  Thr Ala  Ala Cys Cys
             1220                1225                1230

Gly Thr  Gly Gly Ala Cys  Ala Ala Gly Ala  Gly Cys  Ala Gly Gly
             1235                1240                1245

Thr Gly  Gly Cys Ala Gly  Gly Ala Gly Gly  Gly Ala  Ala Ala Thr
             1250                1255                1260

Gly Thr  Cys Thr Thr Cys  Thr Cys Ala Thr  Gly Cys  Thr Cys Cys
             1265                1270                1275

Gly Thr  Gly Ala Thr Gly  Cys Ala Thr Gly  Ala Gly  Gly Cys Thr
             1280                1285                1290

Cys Thr  Gly Cys Ala Cys  Ala Ala Cys Cys  Ala Cys  Thr Ala Cys
             1295                1300                1305

Ala Cys  Ala Cys Ala Gly  Ala Ala Gly Ala  Gly Cys  Cys Thr Cys
             1310                1315                1320

Thr Cys  Cys Cys Thr Gly  Thr Cys Thr Cys  Thr Gly  Gly Gly Thr
             1325                1330                1335

Ala Ala  Ala
             1340

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Ala Ser Gln Asp Val Gly Thr Ala Val Ala
1               5                   10

<210> SEQ ID NO 12
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 12

Trp Ala Ser Thr Arg His Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Tyr Asn Ser Tyr Pro Leu Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gln Asp Val Gly Thr Ala
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ala Ser
1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Asn Ser Tyr Pro Leu
1               5

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
```

```
                  20                  25                  30

Val Ala Trp Tyr Leu Gln Lys Pro Gly Gln Ser Pro Gln Leu Leu Ile
            35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105

<210> SEQ ID NO 18
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcacccttta ccatcagtag cctggaagct    240
gaagatgctg caacatatta ctgtcagcag tataacagct atcctctcac gttcggccaa     300
gggaccaagg tggaaatcaa a                                                321

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
            35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcaccttta ccatcagtag cctggaagct     240
gaagatgctg caacatatta ctgtcagcag tataacagct atcctctcac gttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Thr Phe Thr Thr Tyr Trp Met His
1               5                   10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Tyr Trp Met His
1               5

<210> SEQ ID NO 23
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 23

Asn Ile Tyr Pro Gly Thr Gly Gly Ser Asn Phe Asp Glu Lys Phe Lys
1               5                   10                  15

Asn

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Thr Thr Gly Thr Gly Ala Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Tyr Thr Phe Thr Thr Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Pro Gly Thr Gly Gly
1               5

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
                20                  25                  30

Trp Met His Trp Val Arg Gln Ala Thr Gly Gln Gly Leu Glu Trp Met
            35                  40                  45

Gly Asn Ile Tyr Pro Gly Thr Gly Gly Ser Asn Phe Asp Glu Lys Phe
        50                  55                  60

Lys Asn Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 28
<211> LENGTH: 351
<212> TYPE: DNA
<213> ORGANISM: Artificial Sequence
<220> FEATURE:
<223> OTHER INFORMATION: Description of Artificial Sequence: Synthetic
      polynuceotide

<400> SEQUENCE: 28
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata agtctactag caccgcctat     240
atggaactgt ctagcctgag atcagaggac accgccgtct actactgcac taggtggact     300
accggcacag gcgcctactg gggtcaaggc actaccgtga ccgtgtctag c               351

<210> SEQ ID NO 29
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

```
Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 30
<211> LENGTH: 1329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Ala Gly Gly Thr Gly Cys Ala Gly Cys Thr Gly Gly Thr Gly Cys
1               5                   10                  15

Ala Gly Thr Cys Ala Gly Gly Cys Gly Cys Gly Ala Ala Gly Thr
            20                  25                  30

Gly Ala Ala Gly Ala Ala Gly Cys Cys Cys Gly Gly Cys Gly Ala Gly
        35                  40                  45

Thr Cys Ala Cys Thr Gly Ala Gly Ala Ala Thr Thr Ala Gly Cys Thr
50                  55                  60

Gly Thr Ala Ala Ala Gly Gly Thr Thr Cys Ala Gly Gly Cys Thr Ala
65                  70                  75                  80

Cys Ala Cys Cys Thr Thr Cys Ala Cys Thr Ala Cys Thr Ala Cys
                85                  90                  95

Thr Gly Gly Ala Thr Gly Cys Ala Cys Thr Gly Gly Gly Thr Cys Cys
```

```
            100                 105                 110

Gly Cys Cys Ala Gly Gly Cys Thr Ala Cys Cys Gly Gly Thr Cys Ala
        115                 120                 125

Ala Gly Gly Cys Cys Thr Cys Gly Ala Gly Thr Gly Gly Ala Thr Gly
    130                 135                 140

Gly Gly Thr Ala Ala Thr Ala Thr Cys Thr Ala Cys Cys Cys Cys Gly
145                 150                 155                 160
Gly Cys Ala Cys Cys Gly Gly Cys Gly Gly Cys Thr Cys Thr Ala Ala
                165                 170                 175

Cys Thr Thr Cys Gly Ala Cys Gly Ala Gly Ala Ala Gly Thr Thr Thr
            180                 185                 190
Ala Ala Gly Ala Ala Thr Ala Gly Ala Gly Thr Gly Ala Cys Thr Ala
        195                 200                 205

Thr Cys Ala Cys Cys Gly Cys Cys Gly Ala Thr Ala Ala Gly Thr Cys
    210                 215                 220

Thr Ala Cys Thr Ala Gly Cys Ala Cys Cys Gly Cys Cys Thr Ala Thr
225                 230                 235                 240
Ala Thr Gly Gly Ala Ala Cys Thr Gly Thr Cys Thr Ala Gly Cys Cys
                245                 250                 255

Thr Gly Ala Gly Ala Thr Cys Ala Gly Ala Gly Gly Ala Cys Ala Cys
            260                 265                 270
Cys Gly Cys Cys Gly Thr Cys Thr Ala Cys Thr Ala Cys Thr Gly Cys
        275                 280                 285

Ala Cys Thr Ala Gly Gly Thr Gly Gly Ala Cys Thr Ala Cys Cys Gly
    290                 295                 300

Gly Cys Ala Cys Ala Gly Gly Cys Gly Cys Cys Thr Ala Cys Thr Gly
305                 310                 315                 320

Gly Gly Gly Thr Cys Ala Ala Gly Gly Cys Ala Cys Thr Ala Cys Cys
                325                 330                 335

Gly Thr Gly Ala Cys Cys Gly Thr Gly Thr Cys Thr Ala Gly Cys Gly
            340                 345                 350

Cys Thr Ala Gly Cys Ala Cys Thr Ala Ala Gly Gly Gly Cys Cys Cys
        355                 360                 365

Gly Thr Cys Cys Gly Thr Gly Thr Thr Cys Cys Cys Cys Cys Thr Gly
    370                 375                 380

Gly Cys Ala Cys Cys Thr Thr Gly Thr Ala Gly Cys Cys Gly Gly Ala
385                 390                 395                 400

Gly Cys Ala Cys Thr Ala Gly Cys Gly Ala Ala Thr Cys Cys Ala Cys
                405                 410                 415

Cys Gly Cys Thr Gly Cys Cys Cys Thr Cys Gly Gly Cys Thr Gly Cys
            420                 425                 430

Cys Thr Gly Gly Thr Cys Ala Ala Gly Gly Ala Thr Thr Ala Cys Thr
        435                 440                 445

Thr Cys Cys Cys Gly Gly Ala Gly Cys Cys Cys Gly Thr Gly Ala Cys
    450                 455                 460

Cys Gly Thr Gly Thr Cys Cys Thr Gly Gly Ala Ala Cys Ala Gly Cys
465                 470                 475                 480

Gly Gly Ala Gly Cys Cys Cys Thr Gly Ala Cys Cys Thr Cys Cys Gly
                485                 490                 495

Gly Ala Gly Thr Gly Cys Ala Cys Ala Cys Cys Thr Thr Cys Cys Cys
            500                 505                 510

Cys Gly Cys Thr Gly Thr Gly Cys Thr Gly Cys Ala Gly Ala Gly Cys
        515                 520                 525
```

```
Thr Cys Cys Gly Gly Cys Thr Gly Thr Ala Cys Thr Cys Gly Cys
    530                 535                 540
Thr Gly Thr Cys Gly Thr Cys Gly Gly Thr Gly Thr Cys Ala Cys
545                 550                 555                 560
Gly Gly Thr Gly Cys Cys Thr Thr Cys Ala Thr Cys Thr Ala Gly Cys
                    565                 570                 575
Cys Thr Gly Gly Gly Thr Ala Cys Ala Ala Gly Ala Cys Cys Thr
                580                 585                 590
Ala Cys Ala Cys Thr Thr Gly Cys Ala Ala Cys Gly Thr Gly Gly Ala
    595                 600                 605
Cys Cys Ala Cys Ala Ala Gly Cys Cys Thr Thr Cys Cys Ala Ala Cys
    610                 615                 620
Ala Cys Thr Ala Ala Gly Gly Thr Gly Gly Ala Cys Ala Ala Gly Cys
625                 630                 635                 640
Gly Cys Gly Thr Cys Gly Ala Ala Thr Cys Gly Ala Ala Gly Thr Ala
                    645                 650                 655
Cys Gly Gly Cys Cys Ala Cys Cys Gly Thr Gly Cys Cys Cys Gly
                    660                 665                 670
Cys Cys Thr Thr Gly Thr Cys Cys Gly Cys Gly Cys Cys Gly Gly
                    675                 680                 685
Ala Gly Thr Thr Cys Cys Thr Cys Gly Gly Cys Gly Gly Thr Cys Cys
    690                 695                 700
Cys Thr Cys Gly Gly Thr Cys Thr Thr Thr Cys Thr Gly Thr Thr Cys
705                 710                 715                 720
Cys Cys Ala Cys Cys Gly Ala Ala Gly Cys Cys Ala Ala Gly Gly
                    725                 730                 735
Ala Cys Ala Cys Thr Thr Thr Gly Ala Thr Gly Ala Thr Thr Thr Cys
    740                 745                 750
Cys Cys Gly Cys Ala Cys Cys Cys Thr Gly Ala Ala Gly Thr Gly
                    755                 760                 765
Ala Cys Ala Thr Gly Cys Gly Thr Gly Gly Thr Cys Gly Thr Gly
    770                 775                 780
Ala Cys Gly Thr Gly Thr Cys Ala Cys Ala Gly Gly Ala Ala Gly Ala
785                 790                 795                 800
Thr Cys Cys Gly Gly Ala Gly Gly Thr Gly Cys Ala Gly Thr Thr Cys
                    805                 810                 815
Ala Ala Thr Thr Gly Gly Thr Ala Cys Gly Thr Gly Ala Thr Gly
    820                 825                 830
Gly Cys Gly Thr Cys Gly Ala Gly Gly Thr Gly Cys Ala Cys Ala Ala
    835                 840                 845
Cys Gly Cys Cys Ala Ala Ala Ala Cys Cys Ala Ala Gly Cys Cys Gly
    850                 855                 860
Ala Gly Gly Gly Ala Gly Gly Ala Gly Cys Ala Gly Thr Thr Cys Ala
865                 870                 875                 880
Ala Cys Thr Cys Cys Ala Cys Thr Thr Ala Cys Cys Gly Cys Gly Thr
    885                 890                 895
Cys Gly Thr Gly Thr Cys Cys Gly Thr Cys Thr Gly Ala Cys Gly
                    900                 905                 910
Gly Thr Gly Cys Thr Gly Cys Ala Cys Ala Gly Gly Ala Cys Thr
                    915                 920                 925
Gly Gly Cys Thr Gly Ala Ala Cys Gly Gly Gly Ala Ala Gly Gly Ala
                    930                 935                 940
```

```
Gly Thr Ala Cys Ala Ala Gly Thr Gly Cys Ala Ala Gly Thr Gly
945                 950                 955                 960

Thr Cys Cys Ala Ala Cys Ala Ala Gly Gly Gly Ala Cys Thr Thr Cys
                965                 970                 975

Cys Thr Ala Gly Cys Thr Cys Ala Ala Thr Cys Gly Ala Ala Ala
            980                 985                 990

Gly Ala Cys Cys Ala Thr Cys Thr Cys Gly Ala Ala Ala Gly Cys Cys
        995                 1000                1005

Ala Ala Gly Gly Gly Ala Cys Ala Gly Cys Cys Cys Cys Gly Gly
    1010                1015                1020

Gly Ala Ala Cys Cys Cys Ala Ala Gly Thr Gly Thr Ala Thr
    1025                1030                1035

Ala Cys Cys Cys Thr Gly Cys Cys Ala Cys Cys Gly Ala Gly Cys
    1040                1045                1050

Cys Ala Gly Gly Ala Ala Gly Ala Ala Ala Thr Gly Ala Cys Thr
    1055                1060                1065

Ala Ala Gly Ala Ala Cys Cys Ala Ala Gly Thr Cys Thr Cys Ala
    1070                1075                1080

Thr Thr Gly Ala Cys Thr Thr Gly Cys Cys Thr Gly Thr Gly
    1085                1090                1095

Ala Ala Gly Gly Gly Cys Thr Cys Thr Ala Cys Cys Cys Ala
    1100                1105                1110

Thr Cys Gly Gly Ala Thr Ala Thr Cys Gly Cys Cys Gly Thr Gly
    1115                1120                1125

Gly Ala Ala Thr Gly Gly Ala Gly Thr Cys Cys Ala Ala Cys
    1130                1135                1140

Gly Gly Cys Cys Ala Gly Cys Cys Gly Gly Ala Ala Ala Ala Cys
    1145                1150                1155

Ala Ala Cys Thr Ala Cys Ala Ala Gly Ala Cys Cys Ala Cys Cys
    1160                1165                1170

Cys Cys Thr Cys Cys Gly Gly Thr Gly Cys Thr Gly Gly Ala Cys
    1175                1180                1185

Thr Cys Ala Gly Ala Cys Gly Gly Ala Thr Cys Cys Thr Thr Cys
    1190                1195                1200

Thr Thr Cys Cys Thr Cys Thr Ala Cys Thr Cys Gly Cys Gly Gly
    1205                1210                1215

Cys Thr Gly Ala Cys Cys Gly Thr Gly Gly Ala Thr Ala Ala Gly
    1220                1225                1230

Ala Gly Cys Ala Gly Ala Thr Gly Gly Cys Ala Gly Gly Ala Gly
    1235                1240                1245

Gly Gly Ala Ala Ala Thr Gly Thr Gly Thr Thr Cys Ala Gly Cys
    1250                1255                1260

Thr Gly Thr Thr Cys Thr Gly Thr Gly Ala Thr Gly Cys Ala Thr
    1265                1270                1275

Gly Ala Ala Gly Cys Cys Cys Thr Gly Cys Ala Cys Ala Ala Cys
    1280                1285                1290

Cys Ala Cys Thr Ala Cys Ala Cys Thr Cys Ala Gly Ala Ala Gly
    1295                1300                1305

Thr Cys Cys Cys Thr Gly Thr Cys Cys Cys Thr Cys Thr Cys Cys
    1310                1315                1320

Cys Thr Gly Gly Gly Ala
    1325
```

```
<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Ser Ser Gln Ser Leu Leu Asp Ser Gly Asn Gln Lys Asn Phe Leu
1               5                   10                  15

Thr

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Ala Ser Thr Arg Glu Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Asn Asp Tyr Ser Tyr Pro Tyr Thr
1               5

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Gln Ser Leu Leu Asp Ser Gly Asn Gln Lys Asn Phe
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ala Ser
1

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 36

Asp Tyr Ser Tyr Pro Tyr
1               5

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 38
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg taaagcccct aagctgctga tctactgggc ctctactaga     180
gaatcaggcg tgccctctag gtttagcggt agcggtagtg gcaccgactt caccttcact     240
atctctagcc tgcagcccga ggatatcgct acctactact gtcagaacga ctatagctac     300
ccctacacct tcggtcaagg cactaaggtc gagattaag                            339

<210> SEQ ID NO 39
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

```
Gly Asn Gln Lys Asn Phe Leu Thr Trp Tyr Gln Gln Lys Pro Gly Lys
             35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Phe Thr
 65                  70                  75                  80

Ile Ser Ser Leu Gln Pro Glu Asp Ile Ala Thr Tyr Tyr Cys Gln Asn
                 85                  90                  95

Asp Tyr Ser Tyr Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 40
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg taaagcccct aagctgctga tctactgggc ctctactaga     180
gaatcaggcg tgccctctag gtttagcggt agcggtagtg gcaccgactt caccttcact     240
atctctagcc tgcagcccga ggatatcgct acctactact gtcagaacga ctatagctac     300
ccctacacct tcggtcaagg cactaaggtc gagattaagc gtacggtggc cgctcccagc     360
gtgttcatct tccccccag cgacgagcag ctgaagagcg gcaccgccag cgtggtgtgc     420
ctgctgaaca acttctaccc ccggaggcc aaggtgcagt ggaaggtgga caacgccctg     480
cagagcggca acagccagga gagcgtcacc gagcaggaca gcaaggactc cacctacagc     540
ctgagcagca ccctgaccct gagcaaggcc gactacgaga gcataaggt gtacgcctgc     600 gaggtgaccc accagggcct gtccagcccc gtgaccaaga gcttcaacag gggcgagtgc     660

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
                20                  25                  30

Gly Asn Gln Lys Asn Phe Leu Thr Trp Tyr Gln Gln Lys Pro Gly Gln
            35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 42
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg tcaagcccct agactgctga tctactgggc ctctactaga     180
gaatcaggcg tgccctctag gtttagcggt agcggtagtg gcaccgactt caccttcact     240
atctctagcc tggaagccga ggacgccgct acctactact gtcagaacga ctatagctac     300
ccctacacct tcggtcaagg cactaaggtc gagattaag                             339

<210> SEQ ID NO 43
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
                20                  25                  30

Gly Asn Gln Lys Asn Phe Leu Thr Trp Tyr Gln Gln Lys Pro Gly Gln
            35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

```
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 44
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gagatcgtcc tgactcagtc acccgctacc ctgagcctga gccctggcga gcgggctaca      60
ctgagctgta aatctagtca gtcactgctg gatagcggta atcagaagaa cttcctgacc     120
tggtatcagc agaagcccgg tcaagcccct agactgctga tctactgggc ctctactaga     180
gaatcaggcg tgccctctag gtttagcggt agcggtagtg gcaccgactt caccttcact     240
atctctagcc tggaagccga ggacgccgct acctactact gtcagaacga ctatagctac     300
ccctacacct tcggtcaagg cactaaggtc gagattaagc gtacggtggc cgctcccagc     360
gtgttcatct tccccccccag cgacgagcag ctgaagagcg gcaccgccag cgtggtgtgc     420
ctgctgaaca acttctaccc ccgggaggcc aaggtgcagt ggaaggtgga caacgccctg     480
cagagcggca cagccagga gagcgtcacc gagcaggaca gcaaggactc cacctacagc     540
ctgagcagca ccctgaccct gagcaaggcc gactacgaga gcataaggt gtacgcctgc     600 gaggtgaccc accagggcct gtccagcccc gtgaccaaga gcttcaacag gggcgagtgc     660

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
acctactgga tgcac                                                       15

<210> SEQ ID NO 46
<211> LENGTH: 51
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
```
aatatctacc ccggcaccgg cggctctaac ttcgacgaga agtttaagaa t            51

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
tggactaccg gcacaggcgc ctac                                          24

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
ggctacacct tcactaccta c                                             21

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
taccccggca ccggcggc                                                 18

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
aaatctagtc agtcactgct ggatagcggt aatcagaaga acttcctgac c            51

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
tgggcctcta ctagagaatc a                                             21

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
cagaacgact atagctaccc ctacacc                                       27

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 53
agtcagtcac tgctggatag cggtaatcag aagaacttc                          39

<210> SEQ ID NO 54
<211> LENGTH: 9
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 54 tgggcctct                                                            9

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 55
gactatagct acccctac                                                 18

<210> SEQ ID NO 56
<211> LENGTH: 440
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 56

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr

```
                145                 150                 155                 160
Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 57
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 58
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Tyr Met Tyr Trp Val Arg Gln Ala Pro Gly Gln Gly Leu Glu Trp Met
         35                  40                  45

Gly Gly Ile Asn Pro Ser Asn Gly Gly Thr Asn Phe Asn Glu Lys Phe
     50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205
```

```
Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 59
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
```

```
                115                 120                 125
Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 60
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 61
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```